US012767934B2

(12) United States Patent
Attar et al.

(10) Patent No.: US 12,767,934 B2
(45) Date of Patent: Oct. 20, 2026

(54) VACCINES BASED ON MUTANT CALR AND JAK2 AND THEIR USES

(71) Applicant: Janssen Biotech, Inc., Horsham, PA (US)

(72) Inventors: Ricardo Attar, Lawrenceville, NJ (US); Jason Dehart, San Diego, CA (US); Selina Khan, Leiden (NL); Vinod Krishna, Philadelphia, PA (US); Jenifer Lum, Castro Valley, CA (US); Christian Maine, San Diego, CA (US); Barbara Sanders, Amsterdam (NL); Manuel Alejandro Sepulveda, West Windsor, NJ (US); Patrick Wilkinson, Collegeville, PA (US); Roland Zahn, Rijnsburg (NL)

(73) Assignee: Janssen Biotech, Inc., Horsham, PA (US)

( * ) Notice: Subject to any disclaimer, the term of this patent is extended or adjusted under 35 U.S.C. 154(b) by 331 days.

(21) Appl. No.: 18/663,981

(22) Filed: May 14, 2024

(65) Prior Publication Data

US 2024/0294884 A1 Sep. 5, 2024

Related U.S. Application Data

(62) Division of application No. 17/097,458, filed on Nov. 13, 2020, now Pat. No. 12,018,289.

(60) Provisional application No. 62/936,846, filed on Nov. 18, 2019, provisional application No. 62/936,841, filed on Nov. 18, 2019.

(51) Int. Cl.

| | |
|---|---|
| ***C12N 7/00*** | (2006.01) |
| ***A61K 39/00*** | (2006.01) |
| ***A61K 45/06*** | (2006.01) |
| ***C12N 15/86*** | (2006.01) |

(52) U.S. Cl.

CPC ........ *C12N 7/00* (2013.01); *A61K 39/001162* (2018.08); *A61K 45/06* (2013.01); *C12N 15/86* (2013.01); *A61K 2039/505* (2013.01); *C12N 2750/14111* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,603,112 | A | 7/1986 | Paoletti et al. |
| 4,769,330 | A | 9/1988 | Paoletti et al. |
| 4,772,848 | A | 9/1988 | Hummel |
| 4,837,028 | A | 6/1989 | Allen |
| 5,100,587 | A | 3/1992 | Clough et al. |
| 5,179,993 | A | 1/1993 | Bak et al. |
| 5,185,146 | A | 2/1993 | Altenburger |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,559,099 | A | 9/1996 | Wickham et al. |
| 5,571,698 | A | 11/1996 | Ladner et al. |
| 5,580,717 | A | 12/1996 | Dower et al. |
| 5,595,897 | A | 1/1997 | Midoux et al. |
| 5,744,166 | A | 4/1998 | Illum |
| 5,747,323 | A | 5/1998 | Darlix et al. |
| 5,837,511 | A | 11/1998 | Falck-Pedersen et al. |
| 5,846,782 | A | 12/1998 | Wickham et al. |
| 5,851,806 | A | 12/1998 | Kovesdi et al. |
| 5,885,793 | A | 3/1999 | Griffiths et al. |
| 5,891,690 | A | 4/1999 | Massie |
| 5,965,541 | A | 10/1999 | Wickham et al. |
| 5,969,108 | A | 10/1999 | Mccafferty et al. |
| 5,972,707 | A | 10/1999 | Roy et al. |
| 5,976,567 | A | 11/1999 | Wheeler et al. |
| 5,981,225 | A | 11/1999 | Kochanek et al. |
| 5,981,501 | A | 11/1999 | Wheeler et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,025,337 | A | 2/2000 | Truong et al. |

(Continued)

FOREIGN PATENT DOCUMENTS

| | | |
|---|---|---|
| EP | 0901463 A1 | 3/1999 |
| EP | 0919627 A2 | 6/1999 |

(Continued)

OTHER PUBLICATIONS

Qin et al., "Relationship between CALR gene mutations and development of myeloproliferative neoplasms", Cancer Progress, vol. 17, No. 07, Apr. 10, 2019, pp. 776-779.

(Continued)

*Primary Examiner* — Allison M Fox

*Assistant Examiner* — Alyssa G Weston

(74) *Attorney, Agent, or Firm* — BakerHostetler

(57) ABSTRACT

Provided are vaccines, polypeptides and polynucleotides based on mutant CALR and JAK2 sequences, vectors, host cells, viruses, and methods of making and using them. The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises a plurality of administrations of any of the compositions comprising polynucleotides, polypeptides or vectors disclosed herein.

25 Claims, 26 Drawing Sheets

Specification includes a Sequence Listing.

(56) References Cited

U.S. PATENT DOCUMENTS

| | | | |
|---|---|---|---|
| 6,040,174 | A | 3/2000 | Imler et al. |
| 6,113,913 | A | 9/2000 | Brough et al. |
| 6,150,584 | A | 11/2000 | Kucherlapati et al. |
| 6,172,197 | B1 | 1/2001 | Mccafferty et al. |
| 6,207,195 | B1 | 3/2001 | Walsh et al. |
| 6,218,370 | B1 | 4/2001 | Bischoff et al. |
| 6,348,584 | B1 | 2/2002 | Hodgson et al. |
| 6,440,442 | B1 | 8/2002 | Ehrhard et al. |
| 6,521,404 | B1 | 2/2003 | Griffiths et al. |
| 6,534,484 | B1 | 3/2003 | Wheeler et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,586,410 | B1 | 7/2003 | Wheeler et al. |
| 6,593,081 | B1 | 7/2003 | Griffiths et al. |
| 6,673,901 | B2 | 1/2004 | Koide |
| 6,815,432 | B2 | 11/2004 | Wheeler et al. |
| 6,818,749 | B1 | 11/2004 | Kashmiri et al. |
| 7,270,811 | B2 | 9/2007 | Bout et al. |
| 7,329,731 | B2 | 2/2008 | Jakobsen et al. |
| 7,569,664 | B2 | 8/2009 | Jakobsen et al. |
| 7,709,226 | B2 | 5/2010 | Foote |
| 7,781,199 | B2 | 8/2010 | Vainchenker et al. |
| 8,007,781 | B2 | 8/2011 | Wu et al. |
| 8,163,293 | B2 | 4/2012 | Chaplin |
| 8,268,329 | B2 | 9/2012 | Chaplin et al. |
| 8,313,740 | B2 | 11/2012 | Delcayre et al. |
| 8,377,688 | B2 | 2/2013 | Delcayre et al. |
| 8,394,385 | B2 | 3/2013 | Hausmann et al. |
| 8,748,356 | B2 | 6/2014 | Raghunathan |
| 8,940,290 | B2 | 1/2015 | Roy et al. |
| 9,133,264 | B2 | 9/2015 | Blankenstein et al. |
| 9,371,570 | B2 | 6/2016 | Kralovics et al. |
| 9,593,077 | B2 | 3/2017 | Payne et al. |
| 9,617,560 | B2 | 4/2017 | Brough et al. |
| 9,624,292 | B2 | 4/2017 | Voss et al. |
| 9,750,801 | B2 | 9/2017 | Barouch et al. |
| 9,790,256 | B2 | 10/2017 | Bunnik et al. |
| 9,884,075 | B2 | 2/2018 | Bethune et al. |
| 10,010,592 | B2 | 7/2018 | Thess et al. |
| 10,035,832 | B2 | 7/2018 | Schlom et al. |
| 10,350,275 | B2 | 7/2019 | Aguilar-Cordova |
| 10,441,643 | B2 | 10/2019 | Pulido et al. |
| 10,512,662 | B2 | 12/2019 | Deng et al. |
| 10,532,067 | B2 | 1/2020 | Geall et al. |
| 10,548,930 | B2 | 2/2020 | Deng et al. |
| 10,640,786 | B2 | 5/2020 | Barry et al. |
| 10,736,962 | B2 | 8/2020 | Deng et al. |
| 10,781,169 | B2 | 9/2020 | Payne et al. |
| 10,973,892 | B2 | 4/2021 | Lauterbach et al. |
| 11,793,843 | B2 | 10/2023 | Bachman et al. |
| 2001/0049136 | A1 | 12/2001 | Imler et al. |
| 2010/0216708 | A1 | 8/2010 | Jacobs et al. |
| 2010/0255056 | A1 | 10/2010 | Jacobs et al. |
| 2010/0261620 | A1 | 10/2010 | Almagro et al. |
| 2015/0079091 | A1 | 3/2015 | Kralovics et al. |
| 2016/0122396 | A1 | 5/2016 | Bunnik et al. |
| 2016/0130319 | A1 | 5/2016 | Li |
| 2016/0271239 | A1 | 9/2016 | Mandl et al. |
| 2017/0106065 | A1 | 4/2017 | Foy et al. |
| 2017/0266270 | A1 | 9/2017 | Mandl et al. |
| 2018/0000912 | A1 | 1/2018 | Meruelo et al. |
| 2018/0028626 | A1 | 2/2018 | Slos et al. |
| 2018/0064803 | A1 | 3/2018 | Tomaka et al. |
| 2018/0104359 | A1 | 4/2018 | Kamrud |
| 2018/0171340 | A1 | 6/2018 | Kamrud et al. |
| 2018/0251852 | A1 | 9/2018 | Kralovics et al. |
| 2018/0311269 | A1 | 11/2018 | Lobb et al. |
| 2018/0340944 | A1 | 11/2018 | Han et al. |
| 2019/0000948 | A1 | 1/2019 | Mccurry et al. |
| 2019/0093085 | A1 | 3/2019 | Tufaro et al. |
| 2019/0328857 | A1 | 10/2019 | Andersen et al. |
| 2019/0343942 | A1 | 11/2019 | Fotin-Mleczek et al. |
| 2019/0350993 | A1 | 11/2019 | Cai |
| 2019/0351040 | A1 | 11/2019 | Valiante et al. |
| 2020/0061174 | A1 | 2/2020 | Kalla et al. |
| 2020/0121774 | A1 | 4/2020 | Harris et al. |
| 2020/0138923 | A1 | 5/2020 | Silvestre et al. |
| 2020/0148742 | A1 | 5/2020 | Grandi et al. |
| 2020/0171151 | A1 | 6/2020 | Yeung |
| 2020/0197500 | A1 | 6/2020 | Blair et al. |
| 2020/0222478 | A1 | 7/2020 | Bachman et al. |
| 2020/0239906 | A1 | 7/2020 | Roeth et al. |
| 2020/0299725 | A1 | 9/2020 | Beissert et al. |
| 2020/0306352 | A1 | 10/2020 | Hochrein et al. |
| 2020/0330534 | A1 | 10/2020 | Delgoffe et al. |
| 2020/0339959 | A1 | 10/2020 | Merghoub et al. |
| 2021/0015878 | A1 | 1/2021 | Larson et al. |
| 2021/0046130 | A1 | 2/2021 | Jia et al. |
| 2021/0222133 | A1 | 7/2021 | Attar et al. |

FOREIGN PATENT DOCUMENTS

| | | | |
|---|---|---|---|
| EP | 1230354 | A2 | 8/2002 |
| EP | 3494985 | A1 | 6/2019 |
| EP | 3721899 | A1 | 10/2020 |
| JP | 2016-537012 | A | 12/2016 |
| JP | 2019-517544 | A | 6/2019 |
| WO | 88/01649 | A1 | 3/1988 |
| WO | 90/04036 | A1 | 4/1990 |
| WO | 90/07861 | A1 | 7/1990 |
| WO | 92/01047 | A1 | 1/1992 |
| WO | 92/22653 | A1 | 12/1992 |
| WO | 94/13804 | A1 | 6/1994 |
| WO | 95/01447 | A1 | 1/1995 |
| WO | 95/24221 | A1 | 9/1995 |
| WO | 96/02655 | A1 | 2/1996 |
| WO | 96/17070 | A1 | 6/1996 |
| WO | 96/19240 | A1 | 6/1996 |
| WO | 96/27677 | A2 | 9/1996 |
| WO | 96/40964 | A2 | 12/1996 |
| WO | 97/04119 | A1 | 2/1997 |
| WO | 97/35996 | A1 | 10/1997 |
| WO | 98/00524 | A1 | 1/1998 |
| WO | 98/26048 | A1 | 6/1998 |
| WO | 98/34910 | A1 | 8/1998 |
| WO | 98/37916 | A1 | 9/1998 |
| WO | 98/39411 | A1 | 9/1998 |
| WO | 98/44001 | A1 | 10/1998 |
| WO | 99/45962 | A1 | 9/1999 |
| WO | 00/50573 | A1 | 8/2000 |
| WO | 2000/070071 | A1 | 11/2000 |
| WO | 01/30382 | A1 | 5/2001 |
| WO | 01/30847 | A1 | 5/2001 |
| WO | 01/36615 | A2 | 5/2001 |
| WO | 02/12281 | A2 | 2/2002 |
| WO | 2002/043478 | A2 | 6/2002 |
| WO | 2002/066630 | A1 | 8/2002 |
| WO | 2004/044176 | A2 | 5/2004 |
| WO | 2005/046621 | A2 | 5/2005 |
| WO | 2005/048957 | A2 | 6/2005 |
| WO | 2005/051991 | A2 | 6/2005 |
| WO | 2005/071093 | A2 | 8/2005 |
| WO | 2007/047653 | A2 | 4/2007 |
| WO | 2007/101792 | A1 | 9/2007 |
| WO | 2007/104792 | A2 | 9/2007 |
| WO | 2009/006479 | A2 | 1/2009 |
| WO | 2009/065546 | A1 | 5/2009 |
| WO | 2009/127060 | A1 | 10/2009 |
| WO | 2010/086189 | A2 | 8/2010 |
| WO | 2010/132867 | A1 | 11/2010 |
| WO | 2011/068810 | A1 | 6/2011 |
| WO | 2012/006369 | A2 | 1/2012 |
| WO | 2012/006372 | A1 | 1/2012 |
| WO | 2012/006376 | A2 | 1/2012 |
| WO | 2012/006378 | A1 | 1/2012 |
| WO | 2012/030901 | A1 | 3/2012 |
| WO | 2012/031043 | A1 | 3/2012 |
| WO | 2012/089225 | A1 | 7/2012 |
| WO | 2012/089338 | A1 | 7/2012 |
| WO | 2012/172277 | A1 | 12/2012 |
| WO | 2013/006825 | A1 | 1/2013 |
| WO | 2013/006838 | A1 | 1/2013 |
| WO | 2013/006842 | A2 | 1/2013 |

(56) References Cited

FOREIGN PATENT DOCUMENTS

| | | | |
|---|---|---|---|
| WO | 2013/033563 | A1 | 3/2013 |
| WO | 2013/116778 | A2 | 8/2013 |
| WO | 2014/127917 | A1 | 8/2014 |
| WO | 2014/186596 | A2 | 11/2014 |
| WO | 2015/036599 | A1 | 3/2015 |
| WO | 2015/069571 | A1 | 5/2015 |
| WO | 2015/069770 | A1 | 5/2015 |
| WO | 2015/077624 | A1 | 5/2015 |
| WO | 2015/078856 | A1 | 6/2015 |
| WO | 2015/123496 | A1 | 8/2015 |
| WO | 2015/164674 | A1 | 10/2015 |
| WO | 2015/175334 | A2 | 11/2015 |
| WO | 2015/175340 | A1 | 11/2015 |
| WO | 2015/176033 | A1 | 11/2015 |
| WO | 2015/192068 | A1 | 12/2015 |
| WO | 2016/046357 | A1 | 3/2016 |
| WO | 2016/087514 | A1 | 6/2016 |
| WO | 2016/128542 | A1 | 8/2016 |
| WO | 2016/170176 | A1 | 10/2016 |
| WO | 2016/172505 | A2 | 10/2016 |
| WO | 2016/184822 | A1 | 11/2016 |
| WO | 2016/197067 | A1 | 12/2016 |
| WO | 2016/203025 | A1 | 12/2016 |
| WO | 2017/020026 | A1 | 2/2017 |
| WO | 2017/070110 | A1 | 4/2017 |
| WO | 2017/070618 | A1 | 4/2017 |
| WO | 2017/080920 | A1 | 5/2017 |
| WO | 2017/095486 | A1 | 6/2017 |
| WO | 2017/095487 | A1 | 6/2017 |
| WO | 2017/147554 | A2 | 8/2017 |
| WO | 2017/180770 | A1 | 10/2017 |
| WO | 2017/182634 | A1 | 10/2017 |
| WO | 2017/201325 | A1 | 11/2017 |
| WO | 2017/201350 | A1 | 11/2017 |
| WO | 2017/201352 | A1 | 11/2017 |
| WO | 2017/205810 | A1 | 11/2017 |
| WO | 2017/211371 | A2 | 12/2017 |
| WO | 2017/220499 | A1 | 12/2017 |
| WO | 2018/014008 | A1 | 1/2018 |
| WO | 2018/033254 | A2 | 2/2018 |
| WO | 2018/046803 | A1 | 3/2018 |
| WO | 2018/075235 | A1 | 4/2018 |
| WO | 2018/081480 | A1 | 5/2018 |
| WO | 2018/083220 | A2 | 5/2018 |
| WO | 2018/093907 | A1 | 5/2018 |
| WO | 2018/098362 | A1 | 5/2018 |
| WO | 2018/106615 | A2 | 6/2018 |
| WO | 2018/107011 | A1 | 6/2018 |
| WO | 2018/144082 | A1 | 8/2018 |
| WO | 2018/146205 | A1 | 8/2018 |
| WO | 2018/148381 | A1 | 8/2018 |
| WO | 2018/161092 | A1 | 9/2018 |
| WO | 2018/167320 | A1 | 9/2018 |
| WO | 2018/187356 | A2 | 10/2018 |
| WO | 2018/236904 | A1 | 12/2018 |
| WO | 2019/008111 | A1 | 1/2019 |
| WO | 2019/012082 | A1 | 1/2019 |
| WO | 2019/012091 | A1 | 1/2019 |
| WO | 2019/014665 | A1 | 1/2019 |
| WO | 2019/023566 | A1 | 1/2019 |
| WO | 2019/046377 | A1 | 3/2019 |
| WO | 2019/086615 | A1 | 5/2019 |
| WO | 2019/094396 | A1 | 5/2019 |
| WO | 2019/115816 | A1 | 6/2019 |
| WO | 2019/134048 | A1 | 7/2019 |
| WO | 2019/135086 | A1 | 7/2019 |
| WO | 2019/139987 | A1 | 7/2019 |
| WO | 2019/143949 | A2 | 7/2019 |
| WO | 2019/147925 | A1 | 8/2019 |
| WO | 2019/152922 | A1 | 8/2019 |
| WO | 2019/191780 | A1 | 10/2019 |
| WO | 2019/213550 | A1 | 11/2019 |
| WO | 2019/219851 | A1 | 11/2019 |
| WO | 2019/226939 | A1 | 11/2019 |
| WO | 2019/226941 | A1 | 11/2019 |
| WO | 2019/232103 | A1 | 12/2019 |
| WO | 2020/003126 | A1 | 1/2020 |
| WO | 2020/014539 | A1 | 1/2020 |
| WO | 2020/025642 | A1 | 2/2020 |
| WO | 2020/056424 | A1 | 3/2020 |
| WO | 2020/070303 | A1 | 4/2020 |
| WO | 2020/072371 | A1 | 4/2020 |
| WO | 2020/073045 | A1 | 4/2020 |
| WO | 2020/079234 | A1 | 4/2020 |
| WO | 2020/096640 | A2 | 5/2020 |
| WO | 2020/097291 | A1 | 5/2020 |
| WO | 2020/097393 | A1 | 5/2020 |
| WO | 2020/099614 | A1 | 5/2020 |
| WO | 2020/104531 | A1 | 5/2020 |
| WO | 2020/121273 | A1 | 6/2020 |
| WO | 2020/123912 | A1 | 6/2020 |
| WO | 2020/131586 | A2 | 6/2020 |
| WO | 2020/143634 | A1 | 7/2020 |
| WO | 2020/150152 | A1 | 7/2020 |
| WO | 2020/154189 | A1 | 7/2020 |
| WO | 2020/205412 | A1 | 10/2020 |
| WO | 2020/243719 | A1 | 12/2020 |
| WO | 2020/247547 | A1 | 12/2020 |

OTHER PUBLICATIONS

Ayyagari et al., "Design of a multi-epitope-based vaccine targeting M-protein of SARS-CoV2: an immunoinformatics approach", J. of Biomol. Struct. and Dyn., Nov. 30, 2020, 15 pages.

Schuhmacher et al., "R&D efficiency of leading pharmaceutical companies—A 20-year analysis", Drug Discovery Today, Aug. 2021, vol. 26, No. 8, 1784-1789.

Gigoux et al., P156, "Developing a cross-reactive heteroclitic peptide cancer vaccine targeting poorly immunogenic mutant calreticulin in myeloproliferative neoplasms", 33rd Annual Meeting & Pre-Conference Programs of the Society for Immunotherapy of Cancer, 2018, Journal for ImmunoTherapy of Cancer, 2018, 6(Suppl 1): 114, 1-398.

Ahl et al., "Enhancement of the in vivo circulation lifetime of L-a-distearoylphosphatidylcholine liposomes: importance of liposomal aggregation versus complement opsonization", Biochim. Biophys. Acta, 1997, vol. 1329, pp. 370-382.

Akimaru et al., "Formulation and antitumor efficacy of liposomal-caprylated-TNF-SAM2.", Cytokines Mol. Ther., 1995, vol. 1, No. 3, pp. 197-210.

Altschul et al., "BLAST—(see, for example), in Basic Local Alignment Search Tool", J. Mol. Biol., 1993, vol. 215, pp. 403-410.

Alving et al., "Liposomes As Carriers Of Peptide Antigens: Induction Of Antibodies And Cytotoxic T Lymphocytes To Conjugated And Unconjugated Peptides", Immunol. Rev., 1995, vol. 145, pp. 5-31.

Amato et al., "Evaluation of MVA-5T4 As A Novel Immunotherapeutic Vaccine In Colorectal, Renal And Prostate Cancer", Future Oncol., 2012, vol. 8, No. 3, pp. 231-237.

Anonymous: "Calr Exon 9 Mutant Peptide Vaccine to Patients With CALR-mutant Myeloproliferative Neoplasms: NCT03566446", Retrieved from https://clinicaltrials.gov/ct2/show/NCT03566446, Jun. 25, 2018, pp. 1-5.

Arber et al., "The 2016 Revision To The World Health Organization Classification Of Myeloid Neoplasms And Acute Leukemia", Blood, 2016, vol. 127, No. 20, pp. 2391-2405.

Balligand et al., "Pathologic Activation Of Thrombopoietin Receptor And JAK2-STAT5 Pathway By Frameshift Mutants Of Mouse Calreticulin", Leukemia, Aug., 2016, vol. 30, No. 8, pp. 1775-1778.

Barbui et al., "Survival And Disease Progression In Essential Thrombocythemia Are Significantly Influenced By Accurate Morphologic Diagnosis: An International Study", J Clin Oncol., 2011, vol. 29, No. 23, pp. 3179-3184.

Barosi et al., "International Working Group For Myelofibrosis Research And Treatment (IWGMRT). Proposed Criteria For The Diagnosis Of Post-Polycythemia Vera And Post-Essential Thrombocythemia Myelofibrosis: A Consensus Statement From The International Working Group For Myelofibrosis Research And Treatment", Leukemia, 2008, vol. 22, No. 2, pp. 437-438.

(56) References Cited

OTHER PUBLICATIONS

Barosi et al., "Revised Response Criteria For Polycythemia Vera And Essential Thrombocythemia: An ELN And IWG-MRT Consensus Project", Blood, 2013, vol. 121, No. 23, pp. 4778-4781.
Behr et al., "Efficient Gene Transfer Into Mammalian Primary Endocrine Cells With Lipopolyamine-Coated DNA", Proc. Natl. Acad. Sci. USA, 1989, vol. 86, pp. 6982-6986.
Bendjama et al., "Modified Vaccinia Virus Ankara-Based Vaccines In The Era Of Personalized Immunotherapy Of Cancer", Hum Vaccin Immunother., 2017, vol. 13, No. 9, pp. 1997-2003.
Bozkus et al., "Immune Checkpoint Blockade Enhances Shared Neoantigen-Induced T-cell Immunity Directed against Mutated Calreticulin in Myeloproliferative Neoplasms", Cancer Discov. 2019, vol. 9, pp. 1192-1207.
Brahmer et al., "Society For Immunotherapy Of Cancer (SITC) Clinical Practice Guideline On Immune Checkpoint Inhibitor-Related Adverse Events", J Immunother Cancer, Jun. 2021, vol. 9, No. 6, e00243, pp. 1-33.
Cervantes et al., "Three-Year Efficacy, Safety, And Survival Findings From Comfortii, A Phase 3 Study Comparing Ruxolitinib With Best Available Therapy For Myelofibrosis", Blood, 2013, vol. 122, No. 25, pp. 4047-4053.
Chachoua et al., "Thrombopoietin Receptor Activation By Myeloproliferative Neoplasm Associated Calreticulin Mutants", Blood, Mar. 2016, vol. 127, No. 10, pp. 1325-1335.
Chamanza et al., "Incidences and Range of Spontaneous Findings in Control Cynomolgus Monkeys (*Macaca fascicularis*) Used in Toxicity Studies", Toxicol Pathol., 2010, vol. 38, No. 4, pp. 642-657.
ClinicalTrials.gov. NCT04041310: Nous-209 genetic vaccine for the treatment of microsatellite unstable solid tumors. https://clinicaltrials.gov/ct2/show/NCT04041310. Accessed Mar. 19, 2021.
Colby et al., "Safety And Immunogenicity Of Ad26 And MVA Vaccines In Acutely Treated HIV And Effect On Viral Rebound After Antiretroviral Therapy Interruption", Nat Med., 2020, vol. 26, No. 4, pp. 498-501.
Danos et al., "Safe and Efficient Generation Of Recombinant Retroviruses With Amphotropic And Ecotropic Host Ranges", Proc. Natl. Acad. Sci. USA, 1988, vol. 85, pp. 6460-6464.
Demaria et al., "Phase 1 Open-Label Trial Of Intravenous Administration Of MVA-BN-brachyury-TRICOM Vaccine In Patients With Advanced Cancer", J. Immunother Cancer, Sep. 2021, vol. 9, No. 9, e003238, pp. 1-12.
Emanuel et al., "Myeloproliferative Neoplasm (MPN) Symptom Assessment Form Total Symptom Score: Prospective International Assessment Of An Abbreviated Symptom Burden Scoring System Among Patients With Mpns", J Clin. Oncol., 2012, vol. 30, No. 33, pp. 4098-4103.
Excler et al., "HIV-1 Vaccines: Challenges And New Perspectives", Hum Vaccin Immunother, 2014, vol. 10, No. 6, pp. 1734-1746.
Expert Hematology Panel (EHP), "Guidance from the Expert Hematology Panel (EHP) on Covid-19 Vaccine-induced Immune Thrombocytopenia and Thrombosis (VITT)", Updated Guidance on Management. Version 2.2, Issued Aug. 31, 2021. https://b-s-h.org.uk/media/20499/guidance-version-22-20210903.pdf. Accessed Nov. 29, 2021.
Feigner et al., "Lipofection: A Highly Efficient, Lipid-Mediated DNA-Transfection Procedure", Proc. Natl. Acad. Sci. USA, 1987, vol. 84, pp. 7413-7417.
Felgner et al., "Cationic Lipid-Mediated Transfection in Mammalian Cells: Lipofection", Methods, 1993, vol. 5, pp. 63-68.
Gangat et al., "DIPSS Plus: A Refined Dynamic International Prognostic Scoring System For Primary Myelofibrosis That Incorporates Prognostic Information From Karyotype, Platelet Count, And Transfusion Status", J. Clin. Oncol., 2011, vol. 29, pp. 392-397.
Gao et al., "A Novel Cationic Reagent for Efficient Transfection of Mammalian Cells", Biochemical and Biophysical Research Comms., 1991, vol. 179, pp. 280-285.
Garcia et al., "Safety and Efficacy of Decitabine Plus Ipilimumab in Relapsed or Refractory MDS/AML in the Post-BMT or Transplant Naïve Settings", Blood, 2020, vol. 136, No. S1, pp. 15-17.
Garcia-Manero et al., "A Phase II Study of Nivolumab or Ipilimumab with or without Azacitidine for Patients with Myelodysplastic Syndrome (MDS)", Blood, 2018, vol. 132, Supplement 1, 465, pp. 1-4.
Geall et al., "Nonviral Delivery Of Self-Amplifying RNA Vaccines", PNAS, 2012, vol. 109, 14604-14609.
Gilboa et al., "Retroviral Gene Transfer: Applications to Human Therapy", Adv. Exp. Med. Biol., 1988, vol. 241, pp. 29-33.
Goding, "Monoclonal Antibodies: Principles and Practice", Academic Press, 1986, pp. 59-103.
Gorchakov et al., "A New Role For NS Polyprotein Cleavage In Sindbis Virus Replication", J. Virol., 2008, vol. 82, No. 13, pp. 6218-6231.
Graham et al., "Characteristics of a Human Cell Line Transformed by DNA from Human Adenovirus Type 5", Gen. Virol., 1977, vol. 36, pp. 59-72.
Grauslund et al., "Therapeutic Cancer Vaccination with a Peptide Derived From the Calreticulin Exon 9 Mutations Induces Strong Cellular Immune Responses in Patients With CALR-Mutant Chronic Myeloproliferative Neoplasms", Front Oncol. 2021, vol. 11, No. 637420, pp. 1-17.
Guglielmelli et al., "MIPSS-70: Mutation-Enhanced International Prognostic Score System for Transplantation-Age Patients with Primary Myelofibrosis", J. Clin. Oncol., 2018, vol. 36, pp. 310-318.
Gulley et al., "Phase III Trial of PROSTVAC in Asymptomatic or Minimally Symptomatic Metastatic Castration-Resistant Prostate Cancer", J Clin Oncol., 2019, vol. 37, No. 13, pp. 1051-1061.
Guo et al., "Vaccinia virus-mediated cancer immunotherapy: cancer vaccines and oncolytics", J Immunother Cancer, 2019, vol. 7, No. 6, pp. 1-21.
Gwaltney et al., "Development Of A Harmonized Patient-Reported Outcome Questionnaire To Assess Myelofibrosis Symptoms In Clinical Trials", Leuk Res. 2017, vol. 59, pp. 26-31.
Haensler et al., "Polyamidoamine Cascade Polymers Mediate Efficient Transfection of Cells in Culture", Bioconjugate Chem., 1993, vol. 4, pp. 372-379.
Handlos et al., "Therapeutic Cancer Vaccination With a Peptide Derived From the Calreticulin Exon 9 Mutations Induces Strong Cellular Immune Responses in Patients With CALR-Mutant Chronic Myeloproliferative Neoplasms", Front. 2021 Oncol., vol. 11, Article 637420, pp. 1-17.
Harrison et al., "Long-term findings from COMFORT-II, A Phase 3 Study Of Ruxolitinib Vs Best Available Therapy For Myelofibrosis", Leukemia, 2016, vol. 30, No. 8, pp. 1701-1707.
Hodge et al., "Multiple Costimulatory Modalities Enhance CTL Avidity", J Immunol., 2005, vol. 174, No. 10, pp. 5994-6004.
Hoganson, et al., "Development of a Stable Adenoviral Vector Formulation", Mar. 2002, BioProcessing, vol. 1, No. 1, 43-48.
Holman et al., "Viral Vectors. Vaccines for Biodefense and Emerging and Neglected Diseases", 2009, vol. 7, pp. 77-91.
Holmstrom et al., "High Frequencies Of Circulating Memory T Cells Specific For Calreticulin Exon 9 Mutations In Healthy Individuals" , Blood Cancer Journal, vol. 9, No. 2, Jan. 2019, pp. 1-14.
Holmström et al., "The CALR Exon 9 Mutations are Shared Neoantigens In Patients With CALR Mutant Chronic Myeloproliferative Neoplasms", Leukemia, Dec. 2016, vol. 30, No. 12, pp. 2413-2416.
Holmström et al., "The Calreticulin (CALR) exon 9 Mutations Are Promising Targets For Cancer Immune Therapy", Leukemia, Feb. 2018, vol. 32, No. 2, pp. 429-437.
Holmström et al., "The JAK2V617F Mutation Is A Target For Specific T Cells In The JAK2V617F-Positive Myeloproliferative Neoplasms", Leukemia, Feb. 2017, vol. 31, No. 2, pp. 495-498.
Hosse et al., "A New Generation of Protein Display Scaffolds for Molecular Recognition", Protein Sci., 2006, vol. 15, pp. 14-27.
Juliano, "The Effect Of Particle Size And Change On The Clearance Rates Of Liposomes And Liposome Encapsulated Drugs", Biochem. Biophys. Res. Commun., 1975, vol. 63, pp. 651-658.
Kantoff et al., "Sipuleucel-T immunotherapy for castration-resistant prostate cancer", N. England J. Med., 2010, vol. 363, No. 5, pp. 411-422.

(56) References Cited

OTHER PUBLICATIONS

Khan et al., "Immunoinformatics Approaches To Explore Helicobacter Pylori Proteome (Virulence Factors) To Design B And T Cell Multi-Epitope Subunit Vaccine", Scientific Reports, 2019, vol. 9, pp. 1-13.
Kim et al., "Enhancement of Protein Expression By Alphavirus Replicons By Designing Self-Replicating Subgenomic RNAs", PNAS, 2014, vol. 111, pp. 10708-10713.
Klampfl et al., "Somatic Mutations Of Calreticulin In Myeloproliferative Neoplasms", New Engl. J. Med., Dec. 19, 2013, vol. 369, No. 25, pp. 2379-2390.
Kohler et al., "Continuous Cultures of Fused Cells Secreting Antibody of Predefined Specificity", Nature, 1975, vol. 256, pp. 495-497.
Krougliak et al., "Development of Cell Lines Capable of Complementing E1, E4 and Protein 1x Defective Adenovirus Type 5 Mutants", Human Gene Ther., 1995, vol. 6, pp. 1575-1586.
Lacout et al., "Expression in Murine Hematopoietic Cells Leads To MPD Mimicking Human PV With Secondary Myelofibrosis", Blood, Sept. 1, 2006, vol. 108, No. 5, pp. 1652-1660.
Larkin et al., "Combined nivolumab and ipilimumab or monotherapy in untreated melanoma", N. Engl. J. Med., 2015, vol. 373, No. 1, pp. 23-34.
Levey et al., "Using standardized serum creatinine values in the modification of diet in renal disease study equation for estimating glomerular filtration rate", Ann Intern Med., 2006, vol. 145, No. 4, pp. 247-254.
Lim et al., "Frequent CALR Exon 9 Alterations In JAK2 V617F-Mutated Essential Thrombocythemia Detected By High-Resolution Melting Analysis", Blood Cancer Journal, 2015, vol. 5, pp. 1-4.
Liu et al., "Bayesian optimal interval designs for phase I clinical trials", J R Stat Soc Ser C Appl Stat., 2015, vol. 64, No. 3, pp. 507-523.
Ljungberg et al., "Self-Replicating Alphavirus RNA Vaccines", Expert Review of Vaccines, 2015, vol. 14, pp. 177-194.
Lopata et al., "High Level Trasient Expression Of A Chloramphenicol Acetyl Transferase Gene By DEAE-Dextran Mediated DNA Transfection Coupled With A Dimethyl Sulfoxide Or Glycerol Shock Treatment", Nucleic Acid Res., 1984, vol. 12, pp. 5707-5717.
Lusky, et al., "In Vitro and In Vivo Biology of Recombinant Adenovirus Vectors with E1, E1/E2A, or E1/E4 Deleted.", J. Viral., Mar. 1998, vol. 72, No. 3, pp. 2022-2032.
Markowitz et al., "Construction Of Use Of A Safe And Efficient Amphotropic Packaging Cell Line", Virol., 1988, vol. 167, pp. 400-406.
Masarova et al., "The Rationale for Immunotherapy in Myeloproliferative Neoplasms", Current Hematologic Malignancy Reports, vol. 14, No. 4, Jun. 21, 2019, pp. 310-327.
Mayr et al., "Vaccination Against Pox Diseases Under Immunosuppressive Conditions", Dev. Biol. Stand., 1978, vol. 41, pp. 225-234.
Mclachlan et al., "Evaluation In Vitro And In Vivo Of Cationic Liposome-Expression Construct Complexes For Cystic Fibrosis Gene Therapy", Gene Therapy, 1995, vol. 2, No. 9, pp. 614-622.
Meisinger-Henschel et al., "Genomic Sequence Of Chorioallantois Vaccinia Virus Ankara, The Ancestor Of Modified Vaccinia Virus Ankara", J. Gen. Virol., 2007, vol. 88, pp. 3249-3259.
Mendonca et al., "Adenoviral vector vaccine platforms in the SARS-CoV-2 pandemic", NPJ Vaccines, 2021, vol. 6, No. 97, pp. 1-14.
Mesa et al., "Comparison of placebo and best available therapy for the treatment of myelofibrosis in the phase 3 COMFORT studies", Haematologica, 2014, vol. 99, No. 2, pp. 292-298.
Mesa et al., Myeloproliferative Neoplasms, Version 2.2017, Journal of the National Comprehensive Cancer Network, vol. 14, No. 12, Dec. 2016, pp. 1572-1611.
Meyer et al., "Mapping of deletions in the genome of the highly attenuated vaccinia virus MVA and their influence on virulence", J. Gen. Virol., vol. 72, 1991, pp. 1031-1038.
Meyer, H. et al., "Mapping of deletions in the genome of the highly attenuated vaccinia virus MVA and their influence on virulence", J. Gen. Virol. 72, 1991, 1031-1038.
Miller et al., "Improved Retroviral Vectors for Gene Transfer and Expression", BioTechniques, 1989, vol. 7, pp. 980-990.
Mosteller, "Simplified calculation of body-surface area", N. England J. Med., 1987, vol. 317, No. 17, pp. 1098-1098.
Mudireddy et al., "Prefibrotic versus overtly fibrotic primary myelofibrosis: clinical, cytogenetic, molecular and prognostic comparisons", Br J Haematol, 2018, vol. 182, pp. 594-597.
Newberry et al., "Clonal evolution and outcomes in myelofibrosis after ruxolitinib discontinuation", Blood, 2017, vol. 130, No. 9, pp. 1125-1131.
Nicaise et al., "Affinity Transfer by CDR Grafting on a Nonimmunoglobulin Scaffold", Protein Sci., 2004, vol. 13, pp. 1882-1891.
Nygren et al., "Scaffolds for Engineering Novel Binding Sites in Proteins", Curr. Opin. Struc. Biol., 1997, vol. 7, pp. 463-469.
Oken et al., "Toxicity and response criteria of the Eastern Cooperative Oncology Group", Am J Clin Oncol., 1982, vol. 5, No. 6, pp. 649-655.
Overman et al., Initial Results from a Phase I Study of NOUS-209, an Off-the-Shelf Viral Vectored Immunotherapy Encoding 209 Shared Frame Shift Peptide Neoantigens, with Pembrolizumab, for the Treatment of Tumors with a Deficiency in Mismatch Repair/ Microsatellite Instability. Abstract 1004P presented at European Society for Medical Oncology (ESMO) 2021.
Padlan, "A Possible Procedure for reducing the Immunogenicity of antibody Variable Domains while Preserving their Ligand-Binding Properties", Mol. Immunol., 1991, vol. 28, pp. 489-499.
Passamonti et al., "A clinical-molecular prognostic model to predict survival in patients with post polycythemia vera and post essential thrombocythemia myelofibrosis", Leukemia, 2017, vol. 31, pp. 2726-2731.
Passamonti et al., "A dynamic prognostic model to predict survival in primary myelofibrosis: a study by the IWG-MRT (International Working Group for Myeloproliferative Neoplasms Research and Treatment)", Blood, 2010, vol. 115, No. 9, pp. 1703-1708.
Piccini et al., "[34] Vaccinia Virus as an Expression Vector", Methods of Enzymology, 1987, vol. 153, pp. 545-563.
Porpaczy et al., "Aggressive B-cell lymphomas in patients with myelofibrosis receiving JAK1/2 inhibitor therapy", Blood, 2018, 132(7), 694-706.
Rahja et al., "Gastrointestinal adverse events associated with immune checkpoint inhibitor therapy", Gastroenterol Rep (Oxf)., 2019, vol. 8, No. 1, pp. 25-30.
Rocha et al., "Pedroto I. Management of Gastrointestinal Toxicity from Immune Checkpoint Inhibitor", Port J Gastroenterol., 2019, vol. 26, pp. 268-274.
Sadoff et al., "Interim Results of a Phase 1-2a Trial of Ad26. COV2.S Covid19 Vaccine", N. England J. Med., 2021, vol. 384, No. 19, pp. 1824-1835.
Sato et al., "Histopathology of incidental findings in cynomolgus monkeys (*Macaca fascicularis*) used in toxicity studies", J. Toxicol Pathol., 2012, vol. 25, No. 1, pp. 63-101.
Schieber et al., "Myelofibrosis in 2019: moving beyond JAK2 inhibition", Blood Cancer J., 2019, vol. 9, No. 9, 74.
Selby et al., "Preclinical Development of Ipilimumab and Nivolumab Combination Immunotherapy: Mouse Tumor Models, In Vitro Functional Studies, and Cynomolgus Macaque Toxicology", PLoS One, 2016, vol. 11, No. 9, e0161779.
Sharma et al., "The future of immune checkpoint therapy", Science, 2015, vol. 348, No. 6230, pp. 56-61.
Shaw et al., "Immunology of Adenoviral Vectors in Cancer Therapy", Mol Ther Methods Clin Dev., 2019, vol. 15, pp. 418-429.
Singh et al., "Development of PROSTVAC immunotherapy in prostate cancer", Future Oncol., 2015, vol. 11, No. 15, pp. 2137-2148.
Skerra, "Alternative Non-Antibody Scaffolds for Molecular Recognition", Curr. Opin. Biotechnol., 2007, vol. 18, pp. 295-304.
Spivak, "The chronic myeloproliferative disorders: clonality and clinical heterogeneity", Semin Hematol., 2004, vol. 41, Suppl. 3, pp. 1-5.

(56) References Cited

OTHER PUBLICATIONS

Sun et al., "An enhanced immune response against G250, induced by a heterologous DNA prime-protein boost vaccination, using polyethyleneimine as a DNA vaccine adjuvant", Mol. Med. Rep., 2014, vol. 10, No. 5, pp. 2657-2662.
Swerdlow et al., "WHO Classification of Tumours of Haematopoietic and Lymphoid Tissues", Lyon, France: IARC, 2008, pp. 885-887.
Szoka, "Comparative Properties and Methods of Preparation of Lipid Vesicles (Liposomes)l", Ann. Rev. Biophys. Bioeng., 1980, vol. 9, pp. 467-508.
Talpaz et al., "A Newly Approved Treatment For Patients With Myeloproliferative Neoplasmassociated Myelofibrosis", Leukemia, 2021, vol. 35, pp. 1-17.
Tapia et al., "Use of ChAd3-EBO-Z Ebola Virus Vaccine In Malian And US Adults And Boosting Of Malian Adults With MVA-BN-Filo: A Phase 1, Single-Blind, Randomised Trial, A Phase 1b, Open-Label And Double-Blind, Dose-Escalation Trial, And A Nested, Randomised, Double-Blind, Placebo-Controlled Trial", Lancet Infect Dis., 2016, vol. 16, No. 1, pp. 31-42.
Taylor et al., "Mechanisms of Immune Suppression By Interleukin-10 And Transforming Growth Factor-Beta: The Role Of T Regulatory Cells", Immunology, 2006, vol. 117, No. 4, pp. 433-442.
Tefferi et al., "MIPSS70+ Version 2.0: Mutation And Karyotype-Enhanced International Prognostic Scoring System For Primary Myelofibrosis", J Clin Oncol., 2018, vol. 36, pp. 1769-1770.
Tefferi et al., "Revised Cytogenetic Risk Stratification In Primary Myelofibrosis: Analysis Based On 1002 Informative Patients", Leukemia, 2018, vol. 32, pp. 1189-1199.
Tefferi et al., "Revised response criteria for myelofibrosis: International Working Group-Myeloproliferative Neoplasms Research and Treatment (IWG-MRT) and European LeukemiaNet (ELN) consensus report", Blood, 2013, vol. 122, No. 8, pp. 1395-1398.
Tefferi, "Primary Myelofibrosis: 2017 Update On Diagnosis, Risk-Stratification, And Management", Am J Hematol., 2016, vol. 91, No. 12, pp. 1262-1271.
Toribio et al., "An RNA Trapping Mechanism In Alphavirus Mrna Promotes Ribosome Stalling And Translation Initiation", Nucleic Acids Res., May 2016, vol. 44, No. 9, pp. 4368-4380.
Vainchenker et al., "JAK/STAT Signaling In Hematological Malignancies", Oncogene, May 2013, vol. 32, No. 21, pp. 2601-2613.
Ventoso, "Adaptive Changes in Alphavirus mRNA Translation Allowed Colonization of Vertebrate Hosts", J. Virol., Sep. 2012, vol. 86, pp. 9484-9494.
Verstovsek et al., "A Double-Blind, Placebo-Controlled Trial Of Ruxolitinib For Myelofibrosis", N Engl J Med., 2012, vol. 366, No. 9, pp. 799-807.
Vinay et al., "Immune Evasion In Cancer: Mechanistic Basis And Therapeutic Strategies", Semin Cancer Biol., 2015, 35 Suppl, pp. S185-S198.
Wang, et al., "A Packaging Cell Line For Propagation Of Recombinant Adenovirus Vectors Containing Two Lethal Gene-Region Deletions", Gene Ther., 1995, vol. 2, pp. 775-783.
Yeh et al., "Efficient Dual Transcomplementation of Adenovirus E1 and E4 Regions from a 293-Derived Cell Line Expressing a Minimal E4 Functional Unit", J. Virol., 1996, vol. 70, pp. 559-565.
Yetter et al., "Estimating Splenic vol. Sonographic Measurements Correlated with Helical CT Determination", AJR Am J Roentgenol., 2003, vol. 181, No. 6, pp. 1615-1620.
Zeidan et al., "A Multi-center Phase I Trial of Ipilimumab in Patients with Myelodysplastic Syndromes following Hypomethylating Agent Failure", Clin Cancer Res., 2018, vol. 24, No. 15, pp. 3519-3527.
Zhao et al., "Safety and Efficacy of Therapeutic Cancer Vaccines Alone or in Combination with Immune Checkpoint Inhibitors in Cancer Treatment", Front Pharmacol., 2019, vol. 10, No. 1184, pp. 1-11.

VACCINES BASED ON MUTANT CALR AND JAK2 AND THEIR USES

CROSS-REFERENCE TO RELATED APPLICATIONS

This application is a divisional of U.S. application Ser. No. 17/097,458, filed on Nov. 13, 2020, which claims priority to U.S. Provisional Application No. 62/936,841, filed on Nov. 18, 2019, and U.S. Provisional Application No. 62/936,846, filed on Nov. 18, 2019, the disclosures of each of which are hereby incorporated by reference in their entireties.

SEQUENCE LISTING

The instant application contains a Sequence Listing which has been submitted electronically in XML format and is hereby incorporated by reference in its entirety. The XML copy, created on Apr. 15, 2024, is named 103693.004237_SL.txt and is 111,658 bytes in size.

FIELD

Provided are vaccines, polypeptides and polynucleotides based on mutant calreticulin (CALR) and Janus Kinase 2 (JAK2) sequences, vectors, host cells, viruses, and methods of making and using them.

BACKGROUND

The classical myeloproliferative neoplasms (MPNs), also called BCR-ABL-MPNs, are the most frequent diseases among the myeloproliferative disorders. MPNs are characterized by excessive production of terminally differentiated blood cells that are fully functional. Classical MPNs have been classified into three entities: polycythemia vera (PV), essential thrombocythemia (ET), and primary myelofibrosis (PMF), which have frequent disease-related complications, such as venous and arterial thrombosis, hemorrhages, and transformation to acute myeloid leukemia (AML). All MPN entities arise from a single somatically mutated hematopoietic stem cell (HSC) that clonally expands and gives rise to virtually all myeloid cells, and B and NK cells. The clonal expansion of the MPN HSC is accompanied by single- or multi-lineage hyperplasia.

PV is characterized not only by an excess of erythrocytes and predominant erythroid lineage involvement but is also associated with a variable hyperplasia of the megakaryocytic/granulocytic lineages. ET is characterized by an increased platelet count with a megakaryocytic hyperplasia, whereas PMF is a more heterogeneous disorder, defined by the presence of bone marrow fibrosis (specifically excess of collagen fibers) and megakaryocytic hyperplasia. Myeloproliferation in PMF initially predominates in the bone marrow and later expands to extramedullary sites, such as the spleen. Diagnosis at disease onset is often challenging, but a 2016 revision of the World Health Organization (WHO) diagnostic criteria for MPN is helping to define both the molecular, clinical, and symptomatic presentation of MPN. However, in many patients, progression of ET and PV to secondary myelofibrosis (MF) is observed. Furthermore, boundaries between these three disorders cannot be well established, especially between ET and PMF. Thus, transitional entities may emerge describing disease states such as prefibrotic PMF (or early PMF) that displays an ET phenotype at diagnosis with typical bone marrow histology, but with a high probability of progression to MF and worse prognosis than true ET.

More than 50% of patients with MPNs harbor the JAK2V617F mutation. In addition, mutations in exon 9 of the calreticulin (CALR) gene are found in approximately 60% of patients with JAK2 wild type essential thrombocytemia (ET) or primary myelofibrosis (PMF).

In 2005, a G to T somatic mutation at Nucleotide 1849, in Exon 14 of JAK2 was discovered. This mutation, results in the substitution of valine to phenylalanine at Codon 617 (V617F) in the pseudokinase domain of JAK2. This mutation can be found in around 70% of myeloproliferative neoplasms (MPNs): 95% of polycythemia vera (PV) and 50% to 60% of ET and PMF. JAK2V617F often undergoes a transition from heterozygosity to homozygosity due to occurrence of mitotic recombination resulting in copy-neutral loss of heterozygosity along a variable size region on the short arm of Chromosome 9 (9pLOH). JAK2V617F arises in a multipotent hematopoietic progenitor, is present in all myeloid lineages, and can be also detected in lymphoid cells, mainly B and natural killer (NK) cells and more rarely and later in disease in T cells. J AK2V617F is mainly restricted to classical MPNs with the exception of refractory anemia with ring sideroblasts and thrombocytosis (RARS T). However, JAK2V617F has been detected at very low level (lower than 1%) in the normal population, including in a neonate. It is one of the most frequent mutations found in the clonal hematopoiesis associated with aging (clonal hematopoiesis of indeterminate potential). Presence of JAK2V71F mutations leads to constitutive activation of signal transducer and activator of transcription (STAT) signaling leading to increased cell proliferation, activation, and autocrine/paracrine release. JAK2V617F mutation has also been identified in patients with cardiovascular indications.

In 2013, frameshift mutations in Exon 9 of the CALR gene were identified in essential thrombocythemia (ET) and primary myelofibrosis (PMF) patients that were negative for the V617F mutation in the JAK2 gene (JAK2V617F) and for mutations in the thrombopoietin receptor (MPL) gene. Over 50 frameshift mutations were identified, with >85% leading to an identical 44-amino-acid-mutant C terminal tail. Mutation of the C terminal tail removes a KDEL motif (SEQ ID NO: 55) leading to loss of endoplasmic reticulum (ER) retention and translocation to the cell surface membrane. Additionally, the mutant version of CALR has a positively charged C terminal tail that disrupts Ca2+ binding and that limits canonical function. The two most frequent CALR mutations correspond to a 52 bp deletion (p.L367fs*46), also called Type 1, and a 5 bp insertion (p.K385fs*47), also called Type 2. There are great differences in the frequency between Type 1 and Type 2 mutations in ET and PMF: in ET, Type 1 and Type 2 mutations are closely distributed (55% versus 35%), whereas in PMF, Type 1 are largely predominant (75% versus 15%) Altogether, these results indicate that mutant CALR is an oncogenic driver and that CALRmut induces transformation through the MPL-JAK2-STAT signaling pathway.

MPN patients have high symptom burden, life-threatening complications, and risk of progression to acute leukemia while also having limited treatment options. MPN patient treatments are best divided into the categories of observation, medical therapies, and allogeneic stem cell transplantation (allo-SCT). Medical therapies themselves fall into the categories of cytoreductive agents, single-agent JAK inhibitors, and the immunomodulatory agent interferon (IFN)-α. The current standard of care, and only approved therapeutic, specifically for patients with MPN, is the small-molecule JAK1/2 inhibitor JAKAFI® (ruxolitinib). JAKAFI® (ruxolitinib) was the first targeted US food and drug administration (FDA)-approved medication for intermediate to high risk PMF and post-polycythemia vera myelofibrosis (PPV-MF) and post-essential thrombocythemia myelofibrosis (PET-MF) but has also gained approval in both the PV and graft-versus-host disease (GVHD) patient population more recently. Efficacy was established in the COMFORT-I and COMFORT-II studies and showed significant reduction in spleen size as the primary endpoint. However, discontinuation due to loss of response, disease progression and treatment-related adverse events involved about 50% of the patients at 3 years and 75% at 5 years. JAKAFI® (ruxolitinib) therapy has also been associated with increased risk for aggressive B-cell lymphoma in MF patients. Indeed, in a study of 107 MF patients that discontinued JAKAFI® (ruxolitinib) treatment, the medium overall survival was just 14 months. Although there is a subset of patients that may derive a survival benefit with JAKAFI® (ruxolitinib) use, the majority of MPN patients continue to progress in their disease.

SUMMARY

The disclosure provides a polypeptide comprising at least two or more epitope sequences of the following: Janus kinase 2 (JAK2) epitope of SEQ ID NO: 6 (FCGDENILV), JAK2 epitope of SEQ ID NO: 5. (VLNYGVCFC), JAK2 epitope of SEQ ID NO: 4 (KLSHKH LVLNYGVCFCGDENILVQEFVKFG), calreticulin (CALR) epitope of SEQ ID NO: 1 (MKDKQDEEQRTRRMMRTKMRMRRMRRTRRKMRRKMSPARPRTSCREACLQGWTE) and CALR epitope of SEQ ID NO: 2 (EEAEDNCRRMMRTK).

The disclosure also provides a polypeptide comprising two or more repeats of SEQ ID NO: 6. In some embodiments, the polypeptide comprises 2, 3, 4, 5, or more than 5 repeats of SEQ ID NO: 6 separated by a linker sequence such as AAY, RR or DPP, HHAA (SEQ ID NO: 56), HHA, HHL, RKSYL (SEQ ID NO: 57), RKSY (SEQ ID NO: 58), SSL, or REKR (SEQ ID NO: 59).

The disclosure also provides a polypeptide of SEQ ID NO:28 (FCGDENILVAA YFCGDENILV) comprising two polypeptides of SEQ ID NO: 6 linked by the non-natural linker sequence AAY.

The disclosure also provides polynucleotides encoding for the polypeptides disclosed herein and vectors comprising the polynucleotides encoding for the polypeptides disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, comprising administering to a subject in need thereof any of the polynucleotides, polypeptides or vectors disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises a plurality of administrations of any of the compositions comprising polynucleotides, polypeptides or vectors disclosed herein.

The disclosure also provides administering an anti-CTLA-4 antibody, an anti-PD-1 or an anti-PD-L1 antibody in combination with any of the compositions comprising polynucleotides, polypeptides or vectors disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises administering two or more times to a subject in need thereof a vector comprising a polynucleotide encoding JAK2 epitope of SEQ ID NO: 6 (FCGDENILV), JAK2 epitope of SEQ ID NO: 5 (VLNYGVCFC), CALR epitope of SEQ ID NO: 1 (MKDKQDEEQRTRRMMRTKMRMRRMRRTRRKMRRKMSPARPRTSCRE ACLQGWTE) and CALR epitope of SEQ ID NO: 2 (EEAEDNCRRMMRTK); wherein the vector is Ad26, GAd20, MVA or a self-replicating RNA.

In some embodiments, the method of inducing an immune response and the methods of treating, preventing, reducing a risk of onset or delaying the onset of a clinical condition characterized by an expression of JAK2V617F or CALR exon 9 mutant, or both JAK2V617F and CALR exon 9 mutant, comprises administering two or more times to a subject in need thereof a vector comprising a polynucleotide encoding a polypeptide comprising two or more repeats of SEQ ID NO: 6; wherein the vector is Ad26, GAd20, MVA or a self-replicating RNA.

The disclosure also provides methods for treating or preventing a myeloproliferative disease in a subject, wherein the method comprises administering two or more times to a subject in need thereof a vector comprising a polynucleotide encoding JAK2 epitope of SEQ ID NO: 6 (FCGDENILV), JAK2 epitope of SEQ ID NO: 5 (VLNYGVCFC), CALR epitope of SEQ ID NO: 1 (MKDKQDEEQRTRRMMRTKMRMRRMRRTRRKMRRKMSPARPRTSCREAC LQGWTE) and CALR epitope of SEQ ID NO: 2 (EEAEDNCRRMMRTK); wherein the vector is Ad26, GAd20, MVA or a self-replicating RNA.

Autologous CD8 T cells were added to dendritic cells 24 hours post infection. Dendritic and T cell s were co-cultured for 11 days and restimulated with a 9mer peptide specific to either mutJAK2 epitope 1 (SEQ ID NO: 5) or epitope 2 (SEQ ID NO:6).

Figure 5:
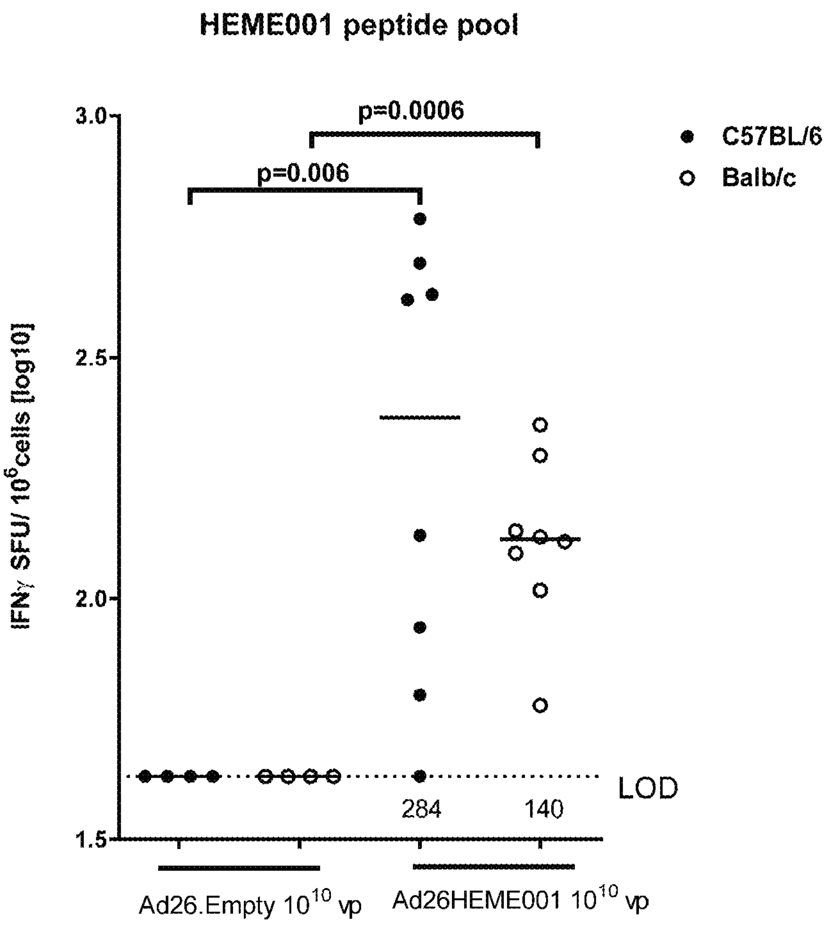

FIG. 5 shows IFN-γ ELISpot responses in splenocytes from C57BL6 or Balb/c mice immunized IM with Ad26HEME001 (LS_CALR_JAK2-30mer, SEQ ID NO: 11) (n=8/group) or Ad26.Empty (n=4) at a dose of $10^{10}$ VP, at 2 weeks post immunization. Splenocytes were stimulated overnight with a 15-mer peptide pool spanning the HEME001 sequence. The number of IFN-γ SFU per $10^6$ splenocytes was determined by ELISpot. The mean response per group is indicated with a horizontal line. The dotted lines indicate the background of the assay defined as the 95% percentile of SFU observed in non-stimulated splenocytes (43 SFU/$10^6$ cells). Statistical analysis was done using Wilcoxon Rank Sum test, values below 43 SFU/$10^6$ cells were set to this cut-off. VP, virus particle; LOD, limit of detection.

Figure 6:
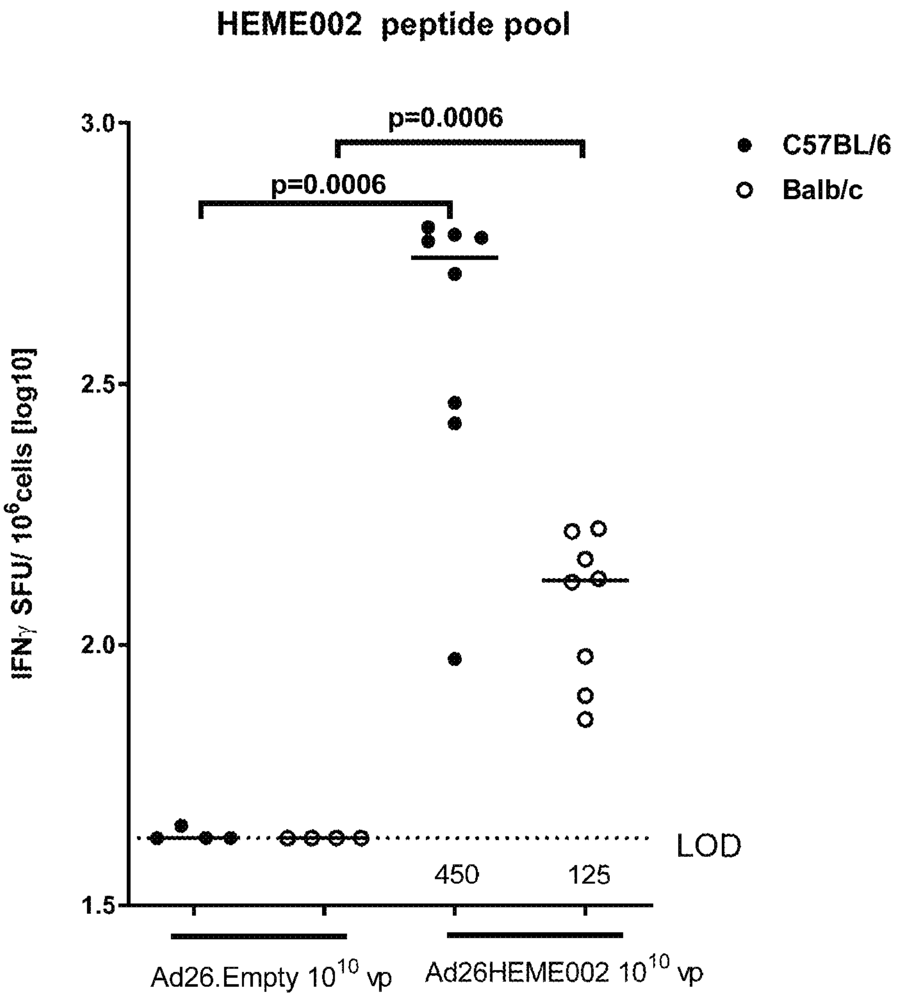

FIG. 6 shows IFN-γ ELISpot responses in splenocytes from C57BL6 or Balb/c mice immunized IM with Ad26HEME002 (LS_CALR_JAK2-2×9mer, SEQ ID NO: 10) (n=8/group) or Ad26.Empty (n=4) at a dose of $10^{10}$ VP, at 2 weeks post immunization. Splenocytes were stimulated overnight with a 15-mer peptide pool spanning the HEME002 sequence. The number of IFN-γ SFU per $10^6$ splenocytes was determined by ELISpot. The mean response per group is indicated with a horizontal line. The dotted lines indicate the background of the assay defined as the 95% percentile of SFU observed in non-stimulated splenocytes (43 SFU/$10^6$ cells). Statistical analysis was done using Wilcoxon Rank Sum test, values below 43 SFU/$10^6$ cells were set to this cut-off. VP, virus particle; LOD, limit of detection.

Figure 7:
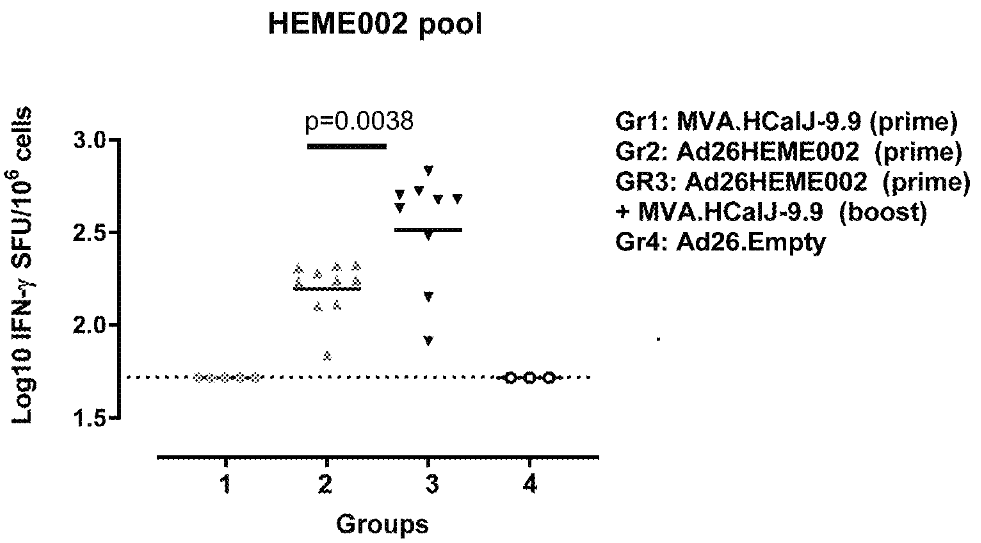

FIG. 7 shows IFN-γ ELISpot responses in splenocytes from C57BL6 mice immunized IM with Ad26HEME002 (LS_CALR_JAK2-2×9mer, SEQ ID NO: 10), MVA-HCalJ-9.9 (TCE_CALR_JAK2-2×9mer, SEQ ID NO: 26), or Ad26.Empty (n=10/group, except for Group 1 [MVA-HCalJ-9.9] which had 5 animals and Group 10 [Ad26.Empty] which had 3 animals). At Week 4, splenocytes were stimulated overnight with a peptide pool spanning the sequence of Ad26HEME002. The number of IFN-γ SFU per $10^6$ splenocytes was determined by ELISpot. The geometric mean response per group is indicated with a horizontal line. The dotted lines in the graphs indicate the background of the assay defined as the 95% percentile of SFU observed in non-stimulated splenocytes. For difference testing comparing Ad26HEME002 prime-only with Ad26HEME002 prime immunization and boost with MVA-HCalJ-9.9, an ANOVA was performed on $\log_{10}$-transformed ELISpot data. Values below 52 SFU/$10^6$ cells were set as cut-off. The horizontal bars correspond to the mean of each group. Gr: group.

Figure 8:
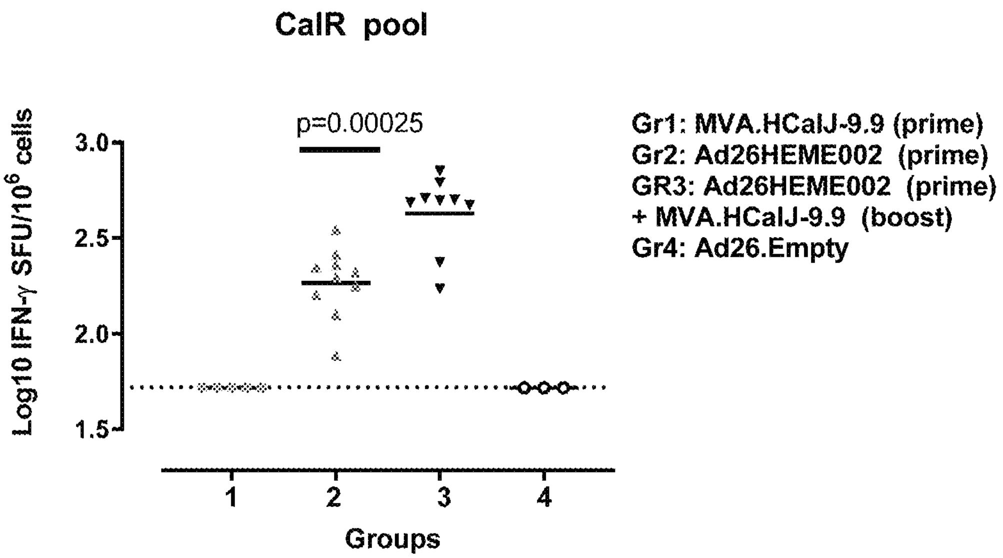

FIG. 8 shows IFN-γ ELISpot responses in splenocytes from C57BL6 mice immunized IM with Ad26HEME002 (LS_CALR_JAK2-2×9mer; SEQ ID NO: 10), MVA-HCalJ-9.9 (TCE_CALR_JAK2-2×9mer; SEQ ID NO: 26), or Ad26.Empty (n=10/group, except for Group 1 [MVA-HCalJ-9.9] which had 5 animals and Group 4 [Ad26.Empty] which had 3 animals). At Week 4, splenocytes were stimulated overnight with a peptide pool spanning CALRmut sequence. The number of IFN-γ SFU per $10^6$ splenocytes was determined by ELISpot. The geometric mean response per group is indicated with a horizontal line. The dotted lines in the graphs indicate the background of the assay defined as the 95% percentile of SFU observed in non-stimulated splenocytes. For difference testing comparing Ad26HEME002 prime-only with Ad26HEME002 prime immunization and boost with MVA-HCalJ-9.9, an ANOVA was performed on $\log_{10}$-transformed ELISpot data. Values below 52 SFU/$10^6$ cells were set as cut-off. The horizontal bars correspond to the mean of each group. Gr: group.

Figure 9:
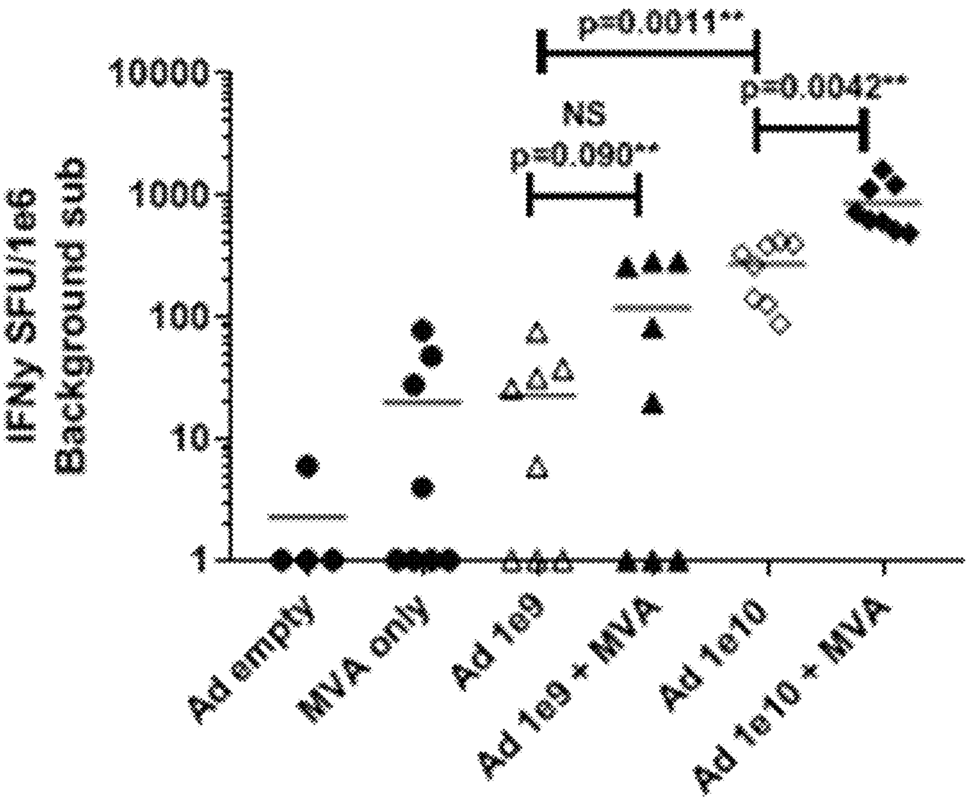

FIG. 9 shows IFN-γ ELISpot responses in splenocytes from Balb/c mice immunized IM with Ad26HEME002 (LS_CALR_JAK2-2×9mer; SEQ ID NO: 10), MVA-HCalJ-9.9 (TCE_CALR_JAK2-2×9mer; SEQ ID NO: 26), or Ad26.Empty (n=8/group). At Week 4, splenocytes were isolated and stimulated overnight with a peptide pool spanning the sequence of HEME002. The number of IFN-γ SFU per $10^6$ splenocytes was determined by ELISpot. The mean response per group is indicated with a horizontal line. Each individual data point is background subtracted using splenocytes not stimulated overnight with peptide to assess background SFU/$10^6$ splenocytes. For difference testing comparing Ad26HEME002 prime-only with Ad26HEME002 prime immunization and boost with MVA-HCalJ-9.9, an unpaired t-test with Welches correct (unequal SD) was run to assess statistical significance. SFU: spot-forming unit; Ad empty: Ad26.Empty; MVA only: MVA-HCalJ-9.9 (TCE_CALR_JAK2-2×9mer; SEQ ID NO: 26); Ad: Ad26HEME002 (LS_CALR_JAK2-2×9mer; SEQ ID NO: 10).

Figure 10:
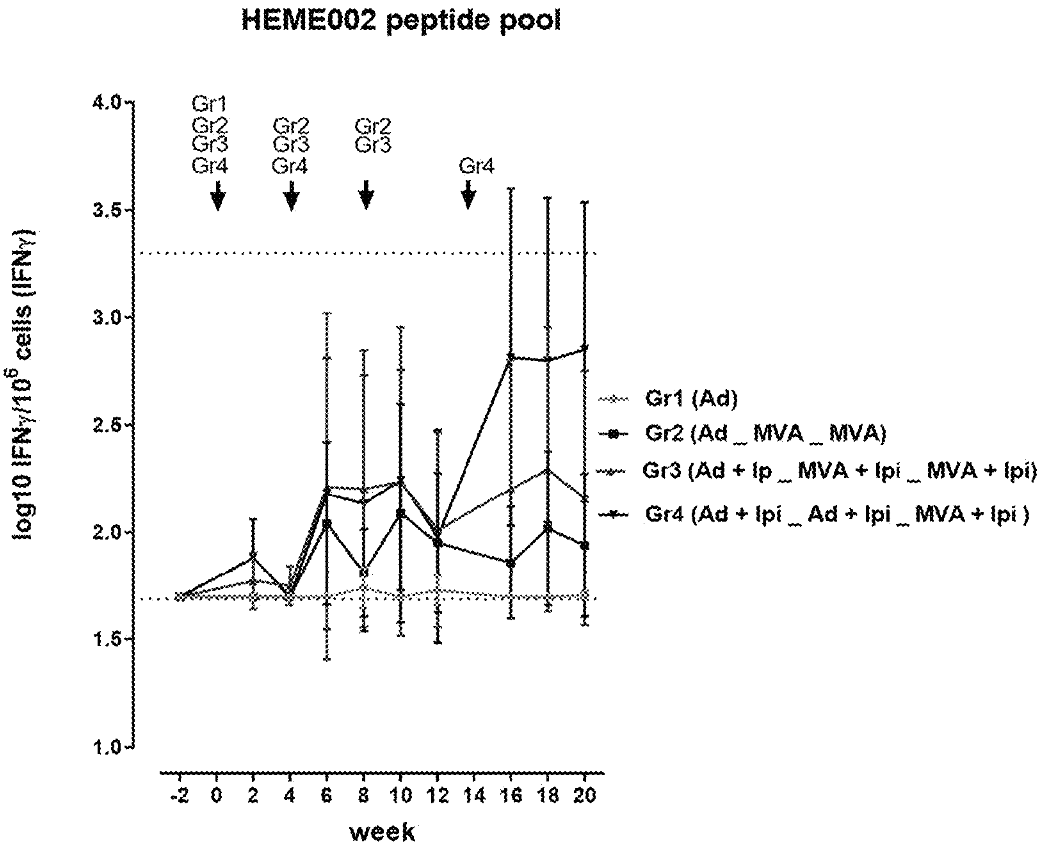

FIG. 10 shows the kinetic of induction of IFN-7-producing human HEME002-specific T-cells in non-human primates immunized with Ad26HEME002,LS_CALR_JAK2-2×9mer; SEQ ID NO: 10 (Ad) and/or MVA-HCalJ-9.9 TCE_CALR_JAK2-2×9mer; SEQ ID NO: 26 (MVA) alone or in combination with YERVOY® (ipilimumab) (Ipi) over time measured by ELISpot. Human HEME002-specific T-cell responses per $10^6$ PBMC were measured over time. Assay positivity was defined as SFU/$10^6$ cells of background subtracted response >50 SFU/$10^6$ cells and SFU/$10^6$ cells of background subtracted response >2× medium response. Values failing the assay positivity criteria were adjusted to 50 SFU/$10^6$ cells. Shown are the $\log_{10}$-transformed data. The lower dotted line was set at 50 SFU/$10^6$ cells and corresponds to the LOD, whereas the upper dotted line was set at 2,000 SFU/$10^6$ cells and corresponds to the ULOQ. The arrows points refer to the time of immunization per group. The arrow bars are standard deviations. LOD: lower limit of detection; ULOQ: upper limit of quantitation. Gr: Group. Groups from the top of the graph: Top line: Gr4; second line from the top: Gr3, third line from the top: Gr2, fourth line from the top: Gr1.

Figure 11:
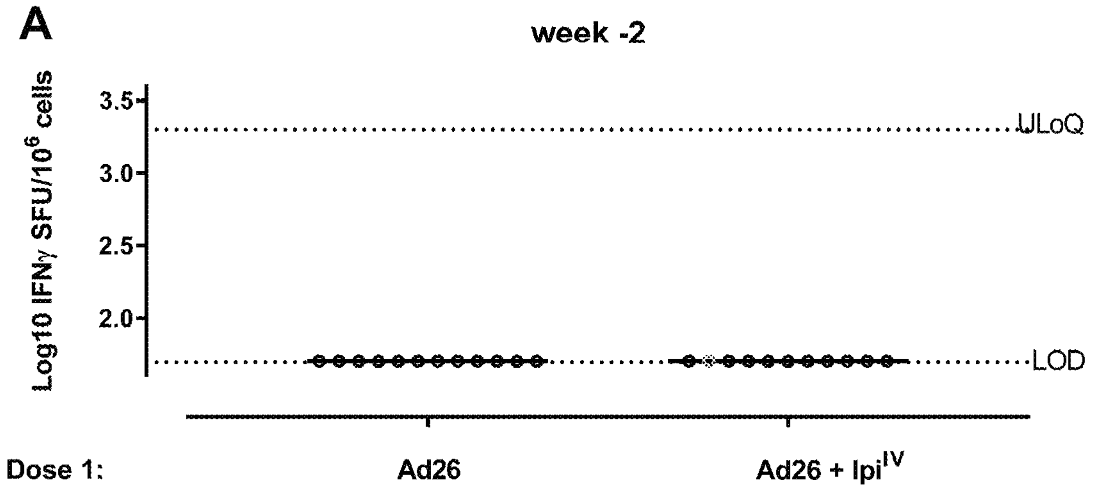

FIG. 11 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY® (ipilimumab) (Ipi) per group at Week −2 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have $p<0.05$. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.

Figure 12:
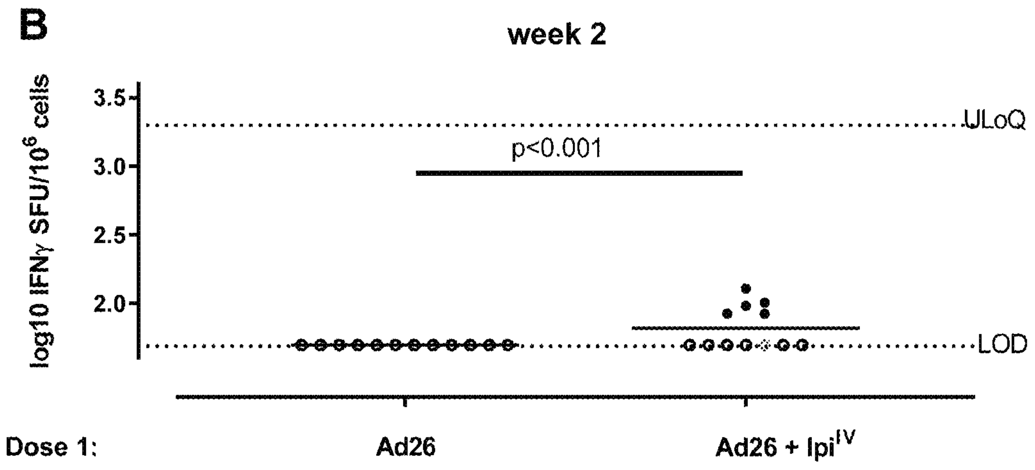

FIG. 12 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY® (ipilimumab) (Ipi) per group at Week 2 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have $p<0.05$. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.

Figure 13:
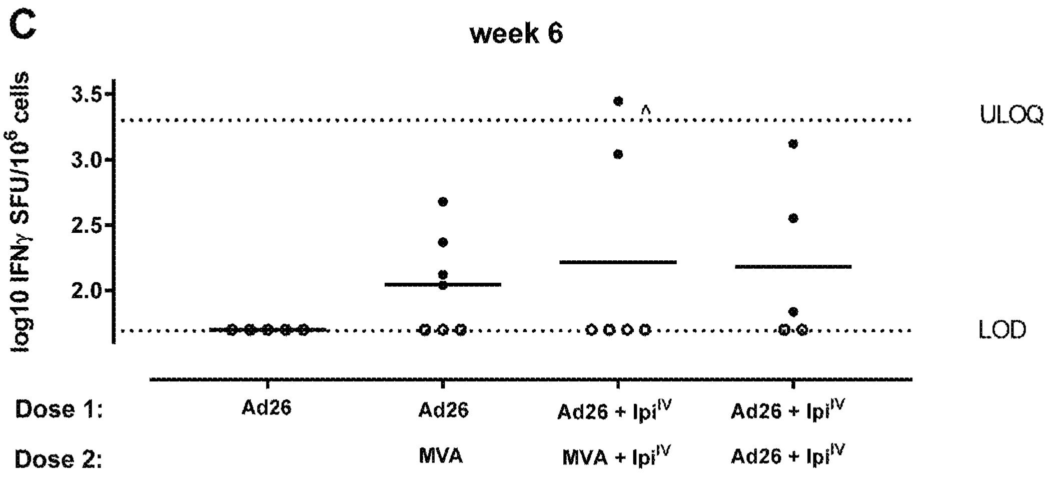

FIG. 13 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY® (ipilimumab) (Ipi) per group at Week 6 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have $p<0.05$. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.

Figure 14:
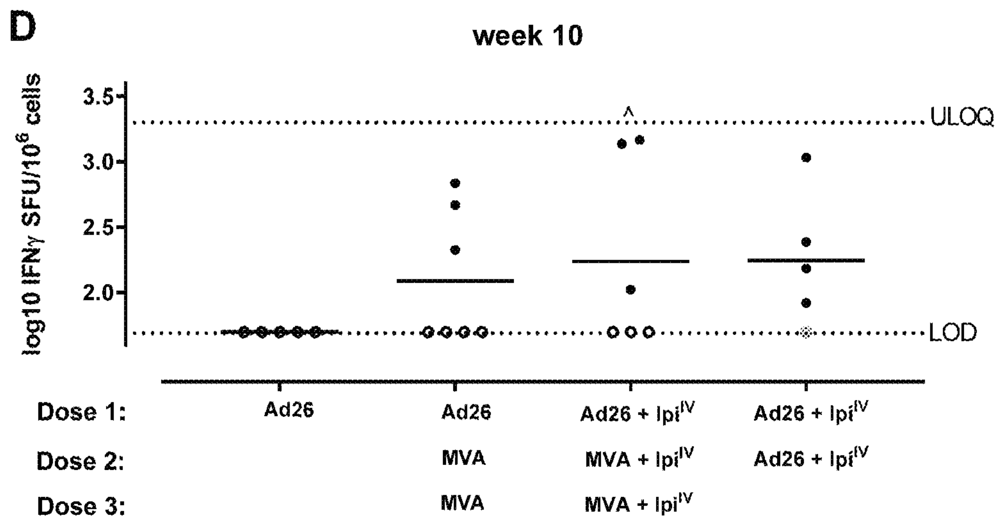

FIG. 14 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY® (ipilimumab) (Ipi) per group at Week 10 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have $p<0.05$. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.

Figure 15:
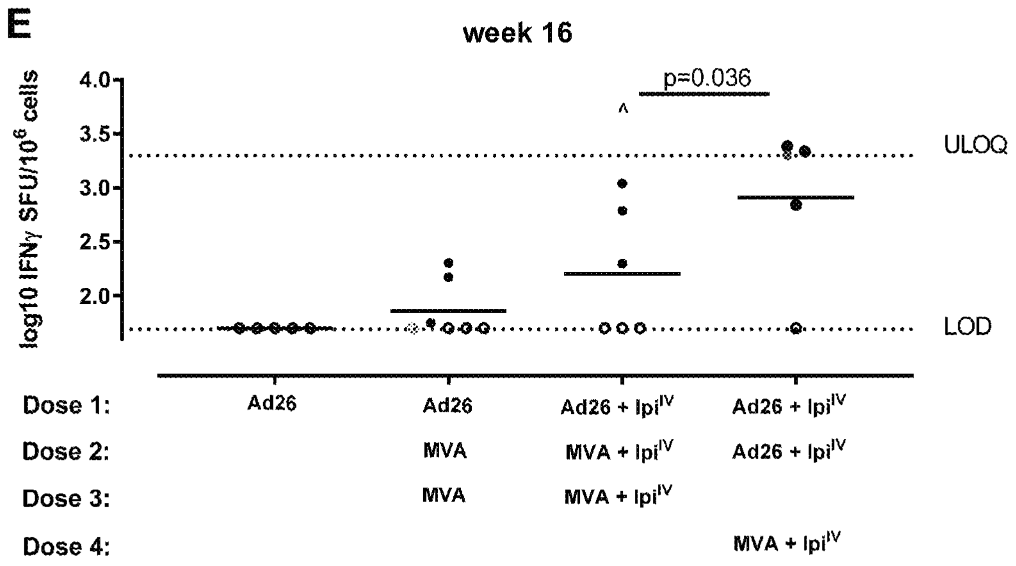

FIG. 15 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY® (ipilimumab) (Ipi) per group at Week 16 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have $p<0.05$. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.

Figure 16:
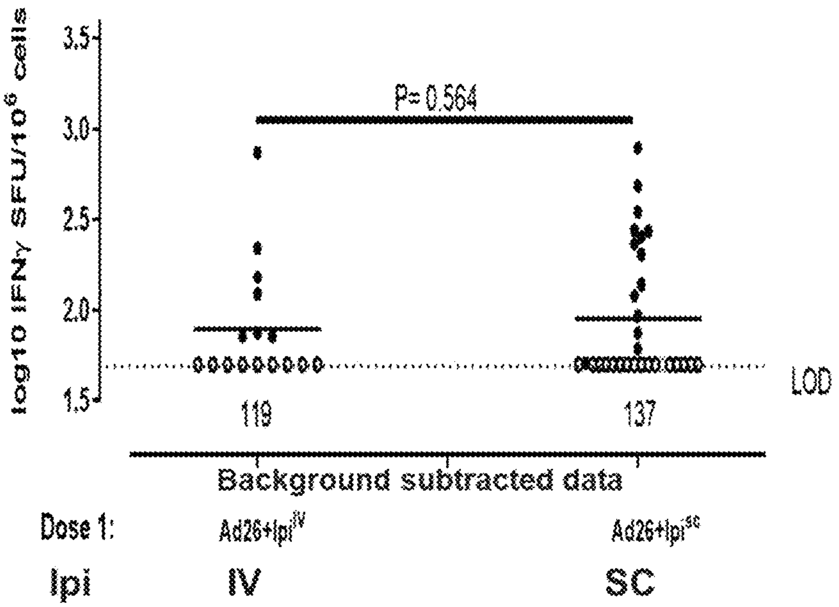

FIG. 16 shows that anti-CTLA4 antibody Ipilimumab administered SC is equal to IV at priming antigen specific T cell responses in NHP. Ipilimumab was dosed at 3 mg/kg IV or SC at time of vector immunization. IFNγ producing cells from 250K cynomolgus PBMCs were stimulated overnight with mutCALR specific peptides and analyzed by Elipot. mutCALR peptide response was calculated based on mutCALR specific response—background. The bar indicates the group mean. Statistical analysis was performed on the complete data set, using a Tobit model with Likelihood ratio tests and applying a Bonferroni adjustment, Significant responses have $p<0.05$.

Figure 17:
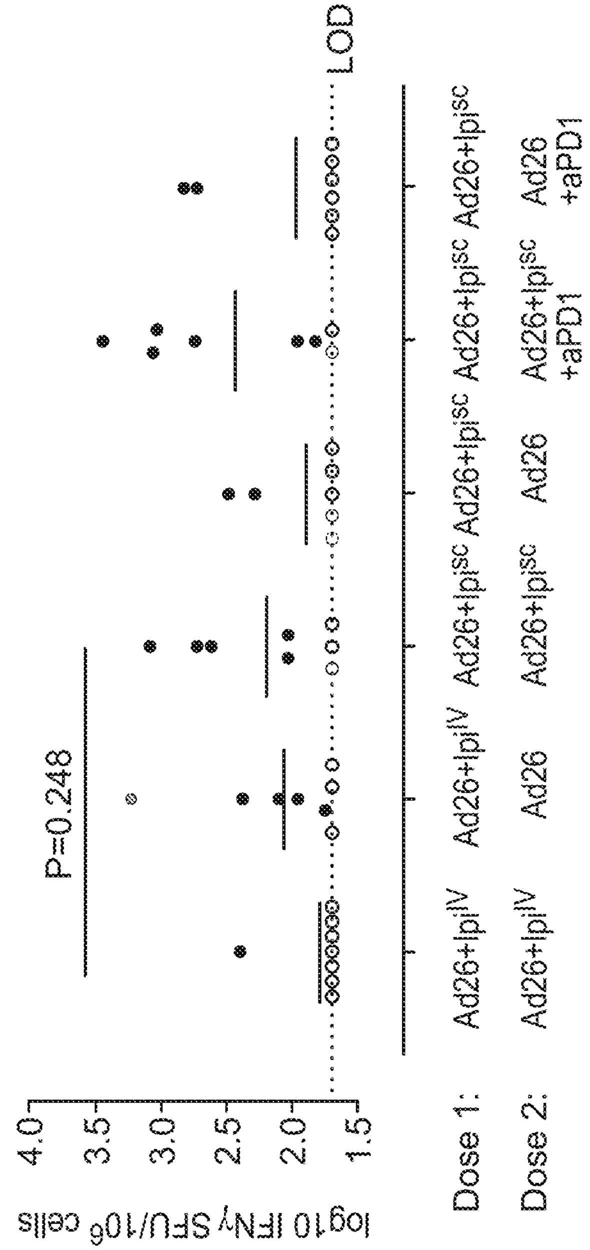

FIG. 17 shows that the inclusion of ani-PD-1 antibody (Nivolumab 10 mg/kg IV) starting at week 4 to Ad/Ad/MVA+either 1 dose (Group 6) or 2 doses (group 5) of ipilimumab (SC) improves magnitude of mutCALR specific T cell response compared to animals dosed with Ad/Ad/MVA+ipilimumab (SC) alone. Ad26: Ad26HEME002, LS_CALR_JAK2-2×9mer, SEQ ID NO: 10; Ipi; ipilimumab; aPD1: Nivolumab.

Figure 18A:
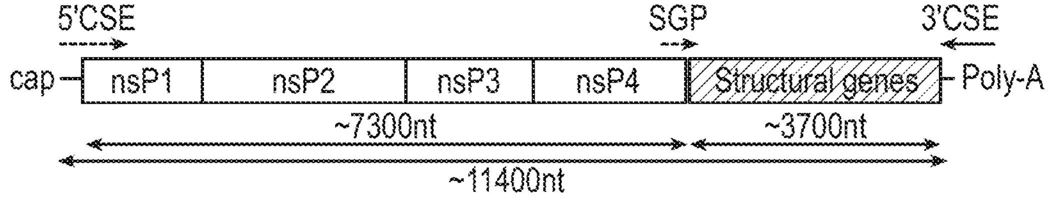

FIG. 18A shows the schematic representation of the alphavirus genome of the Semliki Forest virus, a positive-sensed, single-stranded RNA that encodes the non-structural polyproteins (nsP1-nsP4; replicase) at the 5'-end and the structural genes (capsid and glycoproteins) at the 3'-end.

Figure 18B:
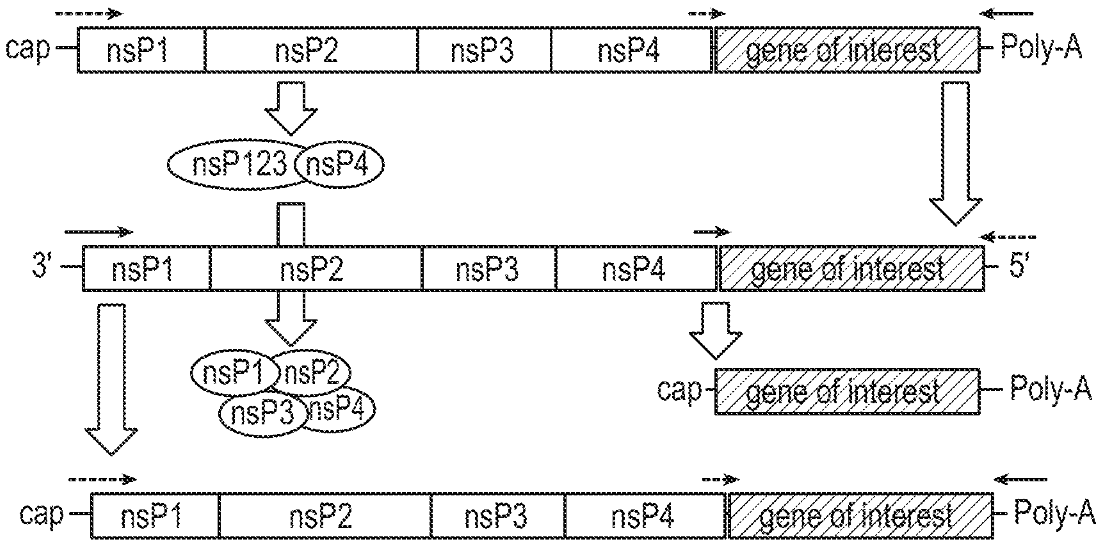

FIG. 18B shows the schematic representation of an exemplary self-replicating RNA molecule (replicon) derived from alphavirus replicons, where viral structural genes are replaced by gene of interest under the transcriptional control of a subgenomic promoter (SGP). Conserved sequence elements (CSE) at the 5' and 3'-end act as promoters for minus-strand and positive-strand RNA transcription. After the replicon is delivered into a cell, the non-structural polyprotein precursor (nsP1234) is translated from in vitro transcribed replicon. nsP1234 is at early stages auto-proteolytically processed to the fragments nsP123 and nsP4, which transcribes negative-stranded copies of the replicon. Later, nsP123 is completely processed to single proteins, which assemble to the (+) strand replicase to transcribe new positive-stranded genomic copies, as well as (+) stranded subgenomic transcripts that code for the gene of interest. Subgenomic RNA as well as new genomic RNA is capped and poly-adenylated. Inactive promoters are dotted arrows; active promoters are lined arrows.

Figure 19:
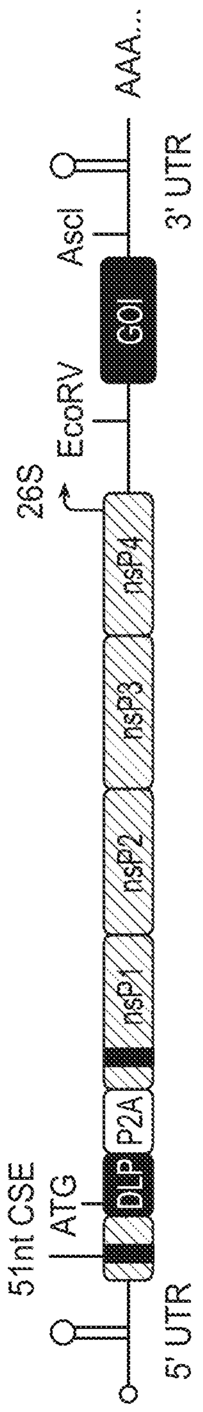

FIG. 19 is a schematic illustration of an exemplary self-amplifying RNA derived from an alphavirus that contains a 5'-cap, nonstructural genes (NSP1-4), 26S subgenomic promoter (grey arrow), the gene of interest (GOI), and a 3'-polyadenylated tail. The illustration also shows the 2A ribosome skipping element (P2A) and the duplicated first 193 nucleotides of nsP1 downstream of the 5'-UTR and upstream of the DLP except for the start codon.

Figure 20:
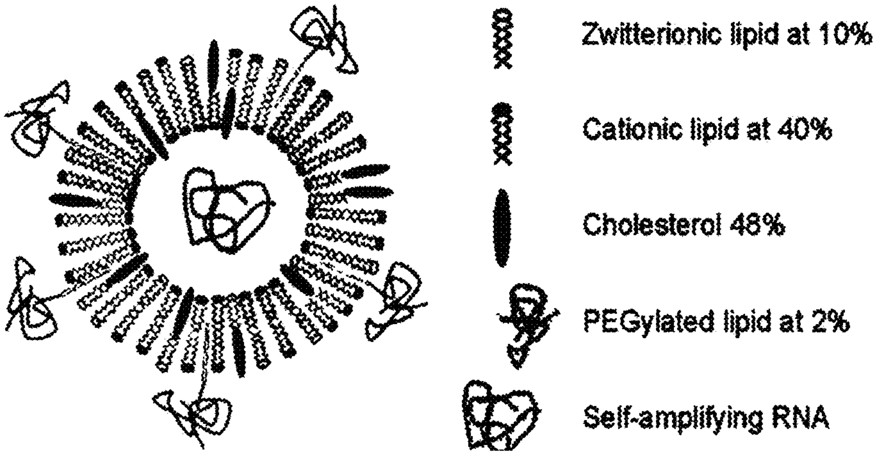

FIG. 20 is a schematic illustration of an exemplary lipid nanoparticle (LNP) encapsulating self-amplifying RNA, with the percent molar ratios of lipid components as indicated (Geall et al., PNAS, 2012, 109:14604-14609).

Figure 21A:
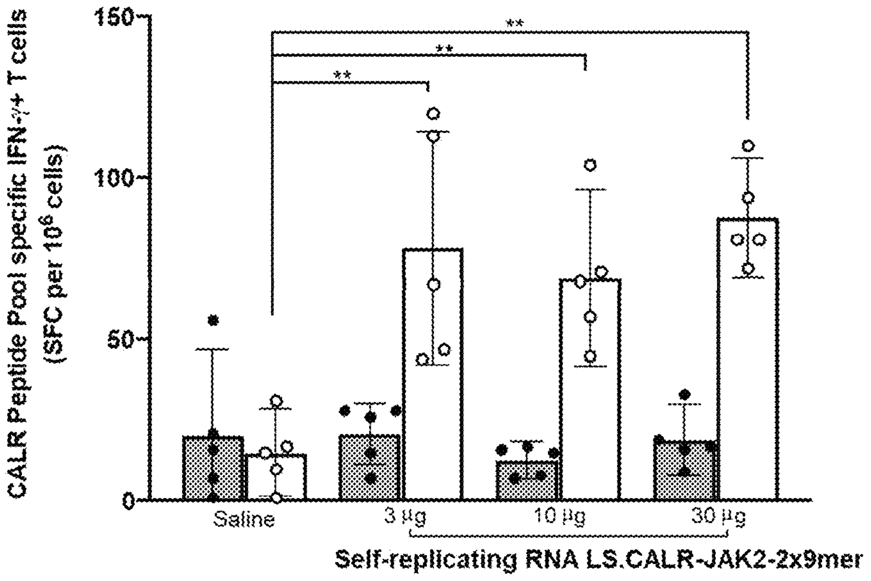

FIG. 21A shows self-replicating RNA LS.CALR-JAK2-2×9mer primes anti-CALR CD4 T cell responses. The data shows IFNγ production by splenocytes restimulated with an overlapping CALR peptide library (unfilled bars) or DMSO (grey bars) as measured by ELISpot.

Figure 21B:
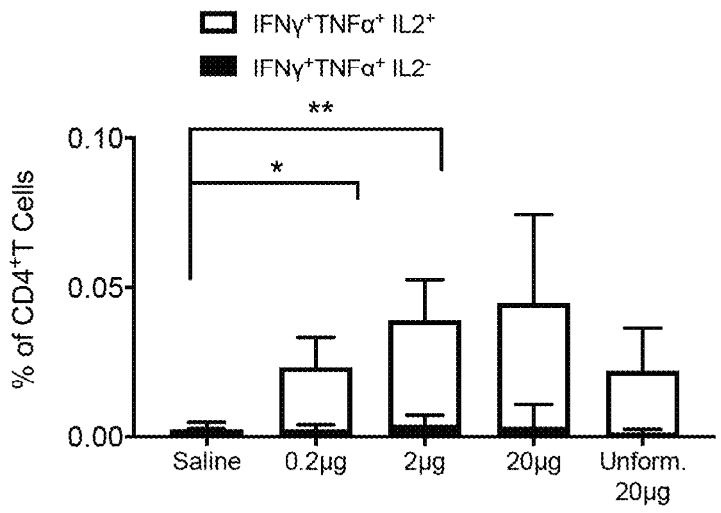

FIG. 21B shows self-replicating RNA LS.CALR-JAK2-2×9mer primes anti-CALR CD4 T cell responses. The data shows IFNγ, TNFα and IL-2 production of splenocytes restimulated with overlapping CALR peptides measured by flow cytometry. Symbols represent individual mice (n=5), bars represent mean with SD. **$p<0.01$, Mann-Whitney test.

Figure 22A:
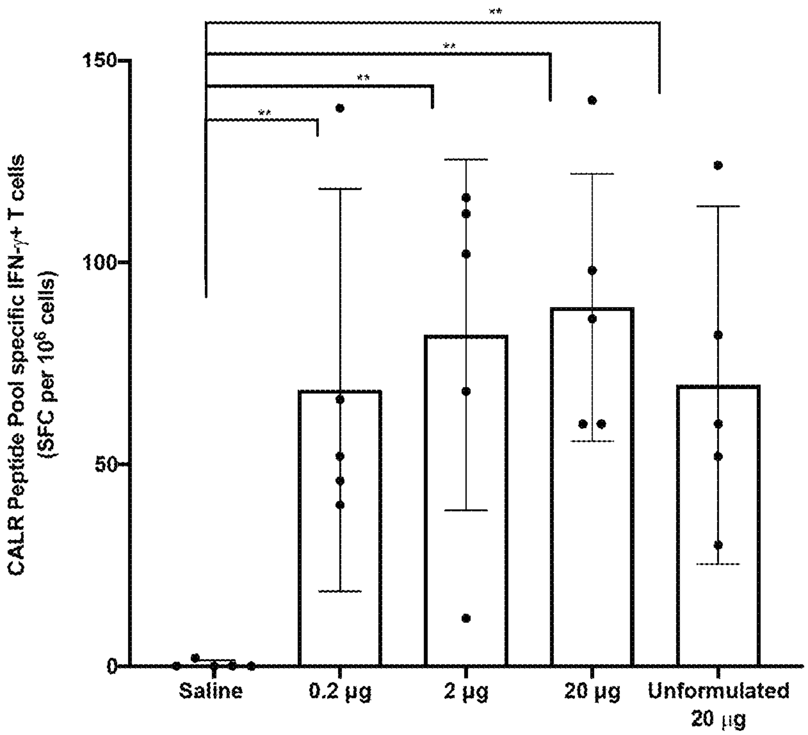

FIG. 22A shows lipid nanoparticle formulated self-replicating RNA LS.CALR-JAK2-2×9mer priming anti-CALR CD4 T cell responses. Balb/c mice were immunized with the indicated doses of LNP formulated self-replicating RNA LS.CALR-JAK2-2×9mer, as well as the unformulated version at 20 μg, and 14 days later spleens were analyzed. The figure shows IFNγ production by splenocytes restimulated with an overlapping CALR peptide library (DMSLO background subtracted) as measured by ELISpot.

Figure 22B:
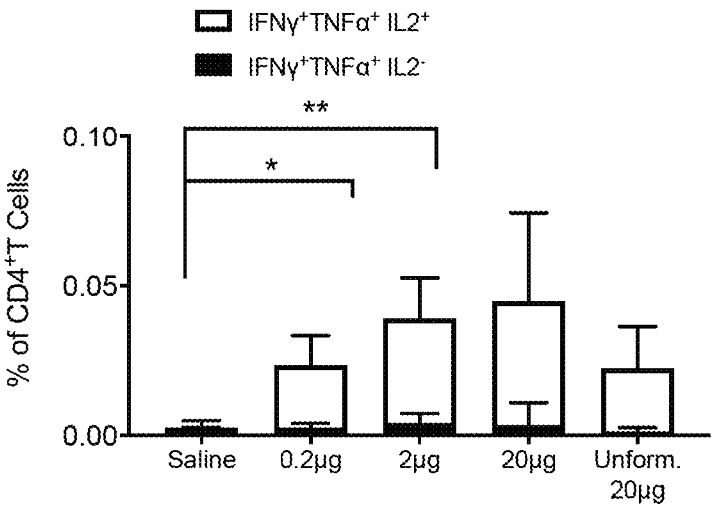

FIG. 22B shows lipid nanoparticle formulated self-replicating RNA LS.CALR-JAK2-2×9mer priming anti-CALR CD4 T cell responses. The data shows IFNγ, TNFα and IL-2 production of splenocytes restimulated with overlapping CALR peptides measured by flow cytometry. Symbols represent individual mice (n=5), bars represent mean with SD.*$p<0.05$, **$p<0.01$, Mann-Whitney test.

Figure 23A:
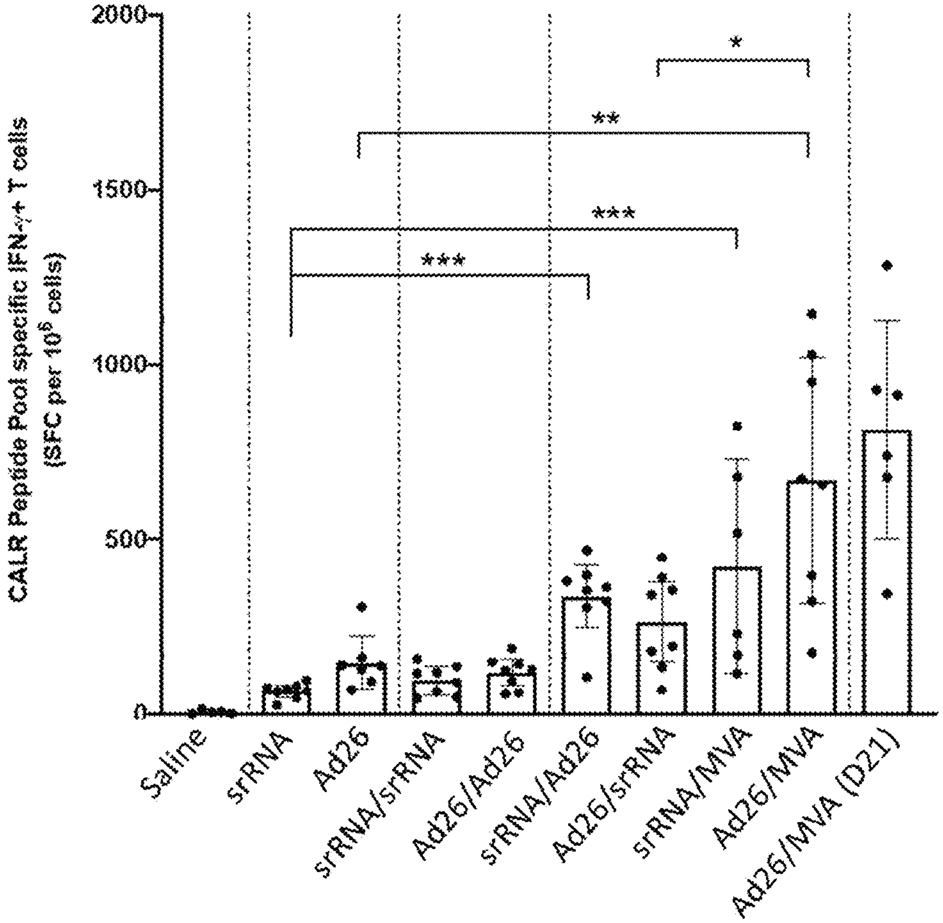

FIG. 23A shows vaccine regimens boosting anti-CALR CD4 T cell responses. Balb/c mice were primed then boosted with various combinations of Ad26, self-replicating RNA molecule (replicon) or MVA as indicated in the figure then spleens were analyzed. The figure shows IFNγ production by splenocytes restimulated with an overlapping CALR peptide library (DMSO background subtracted) as measured by ELISpot.

Figure 23B:
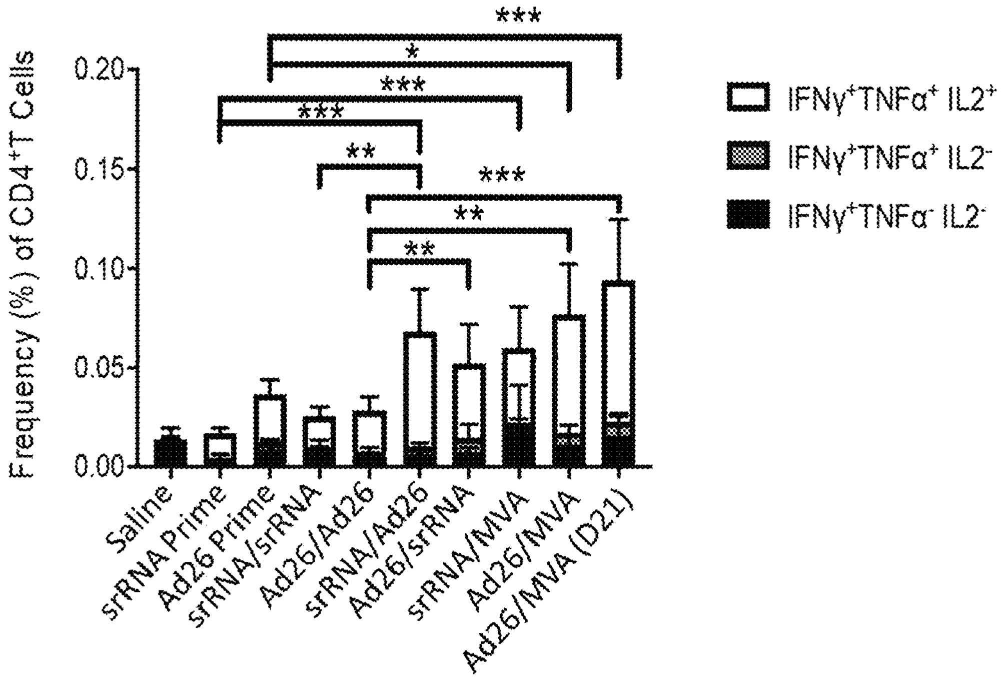

FIG. 23B shows vaccine regimens boosting anti-CALR CD4 T cell responses. The data shows IFNγ, TNFα and IL-2 production of splenocytes restimulated with overlapping CALR peptides measured by flow cytometry. Symbols represent individual mice, bars represent mean with SD. *$p<0.05$, $p<0.01$, *$p<0.001$ Mann-Whitney test.

DETAILED DESCRIPTION

Definitions

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Adjuvant" and "immune stimulant" are used interchangeably herein and are defined as one or more substances that cause stimulation of the immune system. In this context, an adjuvant is used to enhance an immune response to the vaccines of the disclosure.

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Antigen presenting cell" (APC) refers to any cell that presents on its surface an antigen in association with a major histocompatibility complex molecule, either MHC class I or MHC class II molecule, or both.

"Antibody" refers to an immunoglobulin molecule including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649, Int. Pat. Publ. No. WO1994/13804 or Int. Pat. Publ. No. WO1992/01047.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"CALR" refers to human calreticulin. Human CALR protein comprises an amino acid sequence as shown for example in UniProt accession number P27797.

"Downstream loop" or "DLP motif" refers to a polynucleotide sequence comprising at least one RNA stem-loop, which when placed downstream of a start codon of an open reading frame (ORF) provides increased translation the ORF compared to an otherwise identical construct without the DLP motif.

"Enhance" or "induce" when in reference to an immune response refers to increasing the scale and/or efficiency of an immune response or extending the duration of the immune response. The terms are used interchangeably with "augment".

"Epitope sequence" as used herein, refers to a part of a polypeptide or an amino acid sequence, for example a part of the primary, secondary, tertiary, or quaternary structure of the polypeptide or an amino acid sequence, that is recognized by the immune system, for example antibodies, B cells (e.g., B lymphocytes) and/or T cells.

"Expression vector" refers to a vector that can be utilized in a biological system or in a reconstituted biological system to direct the translation of a polypeptide encoded by a polynucleotide sequence present in the expression vector.

"Facilitator element" refers to any polynucleotide or polypeptide element that is operably linked to a polynucleotide or a polypeptide, and include promoters, enhancers, polyadenylation signals, stop codons, protein tags, such as histidine tag, and the like.

"Heterologous" refers to two or more polynucleotides or two or more polypeptides that are not found in the same relationship to each other in nature.

"Immunogenic fragment" refers to a polypeptide that is recognized by cytotoxic T lymphocytes, helper T lymphocytes or B cells when the fragment is in complex with MHC class I or MHC class II molecules.

"In-frame" refers to the reading frame of codons in a first polynucleotide being the same as the reading frame of codons in a second polynucleotide which are joined together to form a polynucleotide. In-frame polynucleotide encodes a polypeptide encoded by both the first polynucleotide and the second polynucleotide.

"Immunogenic" refers to a polypeptide that comprises one or more immunogenic fragments.

"Immune response" refers to any response to an immunogenic polypeptide or polynucleotide or fragment by the immune system of a vertebrate subject. Exemplary immune responses include local and systemic cellular as well as humoral immunity, such as cytotoxic T lymphocyte (CTL) responses, including antigen-specific induction of CD8+ CTLs, helper T-cell responses including T-cell proliferative responses and cytokine release, and B-cell responses including antibody response.

"In combination with" means that two or more therapeutic agents are be administered to a subject together in a mixture, concurrently as single agents or sequentially as single agents in any order.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"JAK2" refers to human Janus kinase 2. Human JAK2 protein comprises an amino acid sequence as shown for example in UniPort accession number 0060674.

"Mutant CALR" refers to CALR harboring one or more exon 9 mutations.

"Mutant JAK2" refers to JAK2 harboring V617F mutation.

"Non-naturally occurring" refers to a molecule that does not exist in nature.

"Operatively linked" sequences refers to both expression control sequences that are contiguous with the nucleic acid sequences that they regulate and regulatory sequences that act in trans, or at a distance to control the regulated nucleic acid sequence.

"Philadelphia chromosome" or "Ph" refers to a well-known chromosomal translocation between chromosomes 9 and 22, resulting in the oncogenic BCR-ABL gene fusion with constitutively active tyrosine kinase activity. The translocation results in a portion of the BCR gene from chromosome 22q11 becoming fused with a portion of the ABL gene from chromosome 9q34, and is designated as t(9; 22)(q34; q11) under the International System for Human Cytogenetic Nomenclature (ISCN). Depending on the precise location of the fusion, the molecular weight of the resulting fusion protein can range from 185 to 210 kDa. "Philadelphia chromosome" refers to all BCR-ABL fusion proteins formed due the (9; 22)(q34; q11) translocation.

"Polynucleotide" refers to a molecule comprising a chain of nucleotides covalently linked by a sugar-phosphate backbone or other equivalent covalent chemistry. Examples of polynucleotides include RNA and DNA.

"Polypeptide" or "protein" refers to a molecule that comprises at least two amino acid residues linked by a peptide bond to form a polypeptide.

"Prevent", "preventing", "prevention", or "prophylaxis" of a disease or disorder means preventing that a disorder occurs in subject.

"Prime-boost" or "prime-boost regimen" refers to a method of treating a subject involving priming a T-cell response with a first vaccine followed by boosting the immune response with a second vaccine. The first vaccine and the second vaccine are typically distinct. These prime-boost immunizations elicit immune responses of greater height and breadth than can be achieved by priming and boosting with the same vaccine. The priming step initiates memory cells and the boost step expands the memory response. Boosting can occur once or multiple times.

"Recombinant" refers to polynucleotides, polypeptides, vectors, viruses and other macromolecules that are prepared, expressed, created or isolated by recombinant means.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Replicon" refers to a viral nucleic acid that is capable of directing the generation of copies of itself and includes RNA as well as DNA. For example, double-stranded DNA versions of arterivirus genomes can be used to generate a single-stranded RNA transcript that constitutes an arterivirus replicon. Generally, a viral replicon contains the complete genome of the virus.

"RNA replicon" (or "self-replicating RNA", or "self-replicating RNA molecule" or "srRNA") refer to RNA molecule which contains all of the genetic information required for directing its own amplification or self-replicating within a permissive cell. To direct its own replication, the RNA molecule: 1) encodes polymerase, replicase, or other proteins which may interact with viral or host cell-derived proteins, nucleic acids or ribonucleoproteins to catalyze the RNA amplification process; and 2) contains cis-acting RNA sequences required for replication and transcription of the replicon-encoded RNA. Self-replicating RNA molecule is typically derived from the genomes of positive strand RNA viruses and can be used as a basis of introducing foreign sequences to host cells by replacing viral sequences encoding structural or non-structural genes or inserting the foreign sequences 5' or 3' of the sequences encoding the structural or non-structural genes. Foreign sequences may be introduced into the subgenomic regions of alphaviruses. Self-replicating RNA molecule may be packaged into recombinant virus particles, such as recombinant alphavirus particles or alternatively delivered to the host using lipid nanoparticles (LNP). Self-replicating RNA may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. Self-replicating RNAs are described, for example, in WO2017/180770, WO2018/075235, and WO2019143949A2.

"Specifically binds", "specific binding", "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant (KD) of about 1×10−7 M or less, for example about 5×10−8 M or less, about 1×10−8 M or less, about 1×10−9 M or less, about 1×10−10 M or less, about 1×10−11 M or less, or about 1×10−12 M or less, typically with the KD that is at least one hundred fold less than its KD for binding to a non-specific antigen (e.g., BSA, casein). In the context of the molecules described herein, "specific binding" refers to binding of the proteinaceous molecule to the CALR/JAK2 mutant polypeptides, CALR mutant polypeptides or JAK2 mutant polypeptides alone or in complex with HLA without detectable binding to a wild-type CALR or JAK2 alone or in complex with HLA.

"Subgenomic RNA" refers to an RNA molecule of a length or size which is smaller than the genomic RNA from which it was derived. The viral subgenomic RNA can be transcribed from an internal promoter, whose sequences reside within the genomic RNA or its complement. Transcription of a subgenomic RNA can be mediated by viral-encoded polymerase(s) associated with host cell-encoded proteins, ribonucleoprotein(s), or a combination thereof. Numerous RNA viruses generate subgenomic mRNAs (sgRNAs) for expression of their 3'-proximal genes. The viral subgenomic RNA can be transcribed from an internal promoter, whose sequences reside within the genomic RNA or its complement. Transcription of a subgenomic RNA can be mediated by viral-encoded polymerase(s) associated with host cell-encoded proteins, ribonucleoprotein(s), or a combination thereof.

"Subgenomic replicon" refers to a viral nucleic acid that contains something less than the full complement of genes and other features of the viral genome, yet is still capable of directing the generation of copies of itself. For example, the sub-genomic replicons of arterivirus may contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subject have previously had the disorder, or limiting or preventing recurrence of symptoms in subjects that were previously symptomatic for the disorder.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the subject.

"Vaccine" refers to a composition that comprises one or more immunogenic polypeptides, polynucleotides encoding immunogenic polypeptides or fragments, vectors comprising polynucleotides encoding immunogenic polypeptides, or any combination thereof intentionally administered to induce acquired immunity in the recipient (e.g. subject).

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Viral vector" refers to a vector construct that includes at least one polynucleotide element of viral origin and has the capacity to be packaged into a viral vector particle.

"Variant", "mutant" or "altered" refers to a polypeptide or a polynucleotide that differs from a reference polypeptide or a reference polynucleotide by one or more modifications, for example one or more substitutions, insertions or deletions.

Polypeptides

Disclosed herein are polypeptides comprising epitope sequences of mutant CALR and mutant JAK2 that may elicit an immune response in a subject. In some embodiments, the polypeptide may comprise at least two or more epitope sequences selected from the group consisting of:

CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;

CALR epitope of SEQ ID NO: 2 (EEAEDN-CRRMMRTK) or having at least 90% sequence identity to SEQ ID NO: 2;

JAK2 epitope of SEQ ID NO: 4 (KLSHKHLVLNYGVCFCGDENILVQEFVKFG) or having at least 90% sequence identity to SEQ ID NO: 4;

JAK2 epitope of SEQ ID NO: 5 (VLNYGVCFC) or at least 90% sequence identity to SEQ ID NO: 5;

JAK2 epitope of SEQ ID NO: 6 (FCGDENILV) or having at least 90% sequence identity to SEQ ID NO: 6; and combinations thereof.

In some embodiments, the disclosure provides a polypeptide comprising epitope sequences of CALR epitope of SEQ ID NO: 1 or having at least 90% sequence identity to SEQ ID NO: 1; CALR epitope of SEQ ID NO: 2 or having at least 90% sequence identity to SEQ ID NO: 2; and JAK2 epitope of SEQ ID NO: 4 or having at least 90% sequence identity to SEQ ID NO: 4. The epitope sequences of SEQ ID NO: 1, 2, and 4 may be present in any order and can be separated by a linker. Exemplary linker sequences include AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the disclosure provides a polypeptide comprising epitope sequences of Janus kinase 2 (JAK2) epitope of SEQ ID NO: 6 or having at least 90% sequence identity to SEQ ID NO: 6, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 1, and 2 may be present in any order and can be separated by a linker. Exemplary linker sequences include AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the disclosure also provides a polypeptide comprising epitope sequences of Janus kinase 2 (JAK2) epitope of SEQ ID NO: 6 or having at least 90% sequence identity to SEQ ID NO: 6, JAK2 epitope of SEQ ID NO: 5 or having at least 90% sequence identity to SEQ ID NO: 5, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 5, 1, and 2 may be present in any order and can be separated by a linker, such as AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

The disclosure also provides a polypeptide comprising amino acid sequences of one or more of the following: SEQ ID NO: 12, SEQ ID NO: 10, SEQ ID NO: 13, SEQ ID NO: 11, SEQ ID NO: 3, SEQ ID NO: 4, SEQ ID NO: 6, SEQ ID NO: 7, SEQ ID NO: 28, SEQ ID NO: 31, or an immunogenic fragment thereof.

In some embodiments, the disclosure provides a polypeptide comprising an amino acid sequence of SEQ ID NO: 3 or having at least 90% sequence identity, or at least 95% sequence identity, or at least 99% sequence identity to SEQ ID NO: 3.

In some embodiments, the disclosure provides a polypeptide comprising an amino acid sequence of SEQ ID NO: 4 or having at least 90% sequence identity, or at least 95% sequence identity, or at least 99% sequence identity to SEQ ID NO: 4.

In some embodiments, the disclosure provides a polypeptide comprising an amino acid sequence of SEQ ID NO: 7 or having at least 90% sequence identity, or at least 95% sequence identity, or at least 99% sequence identity to SEQ ID NO: 7.

In some embodiments, the disclosure provides a polypeptide comprising an amino acid sequence of SEQ ID NO: 9 or having at least 90% sequence identity, or at least 95% sequence identity, or at least 99% sequence identity to SEQ ID NO: 9.

In some embodiments, the disclosure provides a polypeptide comprising an amino acid sequence of SEQ ID NO: 10 or having at least 90% sequence identity, or at least 95% sequence identity, or at least 99% sequence identity to SEQ ID NO: 10.

In some embodiments, the disclosure provides a polypeptide comprising an amino acid sequence of SEQ ID NO: 11 or having at least 90% sequence identity, or at least 95% sequence identity, or at least 99% sequence identity to SEQ ID NO: 11.

In some embodiments, the disclosure provides a polypeptide comprising an amino acid sequence of SEQ ID NO: 12 or having at least 90% sequence identity, or at least 95% sequence identity, or at least 99% sequence identity to SEQ ID NO: 12.

In some embodiments, the disclosure provides a polypeptide comprising an amino acid sequence of SEQ ID NO: 13 or having at least 90% sequence identity, or at least 95% sequence identity, or at least 99% sequence identity to SEQ ID NO: 13.

In some embodiments, the disclosure provides a polypeptide comprising an amino acid sequence of SEQ ID NO: 14 or having at least 90% sequence identity, or at least 95% sequence identity, or at least 99% sequence identity to SEQ ID NO: 14.

In some embodiments, the disclosure provides a polypeptide comprising an amino acid sequence of SEQ ID NO: 15 or having at least 90% sequence identity, or at least 95% sequence identity, or at least 99% sequence identity to SEQ ID NO: 15.

In some embodiments, the disclosure provides a polypeptide comprising an amino acid sequence of SEQ ID NO: 28 or having at least 90% sequence identity, or at least 95% sequence identity, or at least 99% sequence identity to SEQ ID NO: 28.

In some embodiments, the disclosure provides a polypeptide comprising an amino acid sequence of SEQ ID NO: 31 or having at least 90% sequence identity, or at least 95% sequence identity, or at least 99% sequence identity to SEQ ID NO: 31.

In some embodiments, the polypeptide comprises a polypeptide comprising an amino acid sequence of SEQ ID NO: 6 or having at least 90% sequence identity, or at least 95% sequence identity, or at least 99% sequence identity to SEQ ID NO: 6. The disclosure also provides a polypeptide comprising two or more repeats of SEQ ID NO: 6. In some embodiments, the polypeptide comprises 2, 3, 4, 5, or more than 5 repeats of SEQ ID NO: 6. In some embodiments, the repeats of SEQ ID NO: 6 can be separated by a linker. Exemplary linker sequences include AAY, RR or DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the linkers disclosed herein may comprise a protease cleavage site such that the polypeptides may be cleaved in vivo in a subject into peptide fragments comprising epitope sequences, resulting in improved immune response.

In some embodiments, the polypeptides of the disclosure may further comprise a leader sequence or T-cell enhancer sequence (TCE) at the N-terminus. Leader sequences can increase the expression and/or increase immunological response. Exemplary leader sequences include the a chain of the TCR receptor of $T^2$ lymphocytes (HAVT20) (MACPGFLWALVISTC LEFSMA; SEQ ID NO: 8), a ubiquitin signal sequence (Ubiq) (MQIFVKTLTGKTITLEVEP SDTIENVKAKIQDKEGIPPDQQRLIF-AGKQLEDGRTLSDYNIQKESTLHLVLRLRGV; SEQ ID NO: 54), or a T cell enhancer (TCE) sequence, such as a peptide fragment of length of 28 aa from the mandarin fish invariant chain (MGQKEQIHTLQKNSERMSKQL-TRSSQAV; SEQ ID NO: 29). It is believed that the leader sequences may help in increasing an immune response to the epitopes disclosed herein.

Polynucleotides

The disclosure also provides polynucleotides that encode any of the polypeptides disclosed herein.

In some embodiments, the polynucleotide encodes a polypeptide that comprises at least two or more epitope sequences selected from the group consisting of:

- CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;
- CALR epitope of SEQ ID NO: 2 (EEAEDN-CRRMMRTK) or having at least 90% sequence identity to SEQ ID NO: 2;
- JAK2 epitope of SEQ ID NO: 4 (KLSHKHLVLNYGVCFCGDENILVQEFVKFG) or having at least 90% sequence identity to SEQ ID NO: 4;
- JAK2 epitope of SEQ ID NO: 5 (VLNYGVCFC) or at least 90% sequence identity to SEQ ID NO: 5;
- JAK2 epitope of SEQ ID NO: 6 (FCGDENILV) or having at least 90% sequence identity to SEQ ID NO: 6; and combinations thereof.

In some embodiments, the disclosure provides a polynucleotide encoding a polypeptide comprising epitope sequences of CALR epitope of SEQ ID NO: 1 or having at least 90% sequence identity to SEQ ID NO: 1; CALR epitope of SEQ ID NO: 2 or having at least 90% sequence identity to SEQ ID NO: 2; and JAK2 epitope of SEQ ID NO: 4 or having at least 90% sequence identity to SEQ ID NO: 4. The epitope sequences of SEQ ID NO: 1, 2, and 4 may be present in any order and can be separated by a linker.

In some embodiments, the disclosure provides a polynucleotide encoding a polypeptide comprising epitope sequences of Janus kinase 2 (JAK2) epitope of SEQ ID NO: 6 (FCGDENILV) or having at least 90% sequence identity to SEQ ID NO: 6, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 1, and 2 may be present in any order and can be separated by a linker.

In some embodiments, the disclosure provides a polynucleotide encoding a polypeptide comprising epitope sequences of Janus kinase 2 (JAK2) epitope of SEQ ID NO: 6 or having at least 90% sequence identity to SEQ ID NO: 6, JAK2 epitope of SEQ ID NO: 5 or having at least 90% sequence identity to SEQ ID NO: 5, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 5, 1, and 2 may be present in any order and can be separated by a linker.

In some embodiments, the isolated polynucleotide encodes a polypeptide comprising an amino acid sequence of SEQ ID NO: 3 or having at least 90% sequence identity, or at least 95% sequence identity, or at least 99% sequence identity to SEQ ID NO: 3.

In some embodiments, the isolated polynucleotide encodes a polypeptide comprising an amino acid sequence of SEQ ID NO: 4 or having at least 90% sequence identity, or at least 95% sequence identity, or at least 99% sequence identity to SEQ ID NO: 4.

In some embodiments, the isolated polynucleotide encodes a polypeptide comprising an amino acid sequence of SEQ ID NO: 7 or having at least 90% sequence identity, or at least 95% sequence identity, or at least 99% sequence identity to SEQ ID NO: 7.

In some embodiments, the isolated polynucleotide encodes a polypeptide comprising an amino acid sequence of SEQ ID NO: 12 or having at least 90% sequence identity, or at least 95% sequence identity, or at least 99% sequence identity to SEQ ID NO: 12.

In some embodiments, the isolated polynucleotide encodes a polypeptide comprising an amino acid sequence of SEQ ID NO: 13 or having at least 90% sequence identity, or at least 95% sequence identity, or at least 99% sequence identity to SEQ ID NO: 13.

In some embodiments, the isolated polynucleotide encodes a polypeptide comprising an amino acid sequence of SEQ ID NO: 6 or having at least 90% sequence identity, or at least 95% sequence identity, or at least 99% sequence identity to SEQ ID NO: 6.

The disclosure also provides an isolated polynucleotide encoding a polypeptide comprising two or more repeats of SEQ ID NO: 6. In some embodiments, the polynucleotide encodes for a polypeptide comprising 2, 3, 4, 5, or more than 5 repeats of SEQ ID NO: 6. In some embodiments, the repeats of SEQ ID NO: 6 can be separated by a linker.

In some embodiments, the polynucleotide is selected from the group consisting of:

- a nucleic acid sequence of SEQ ID NO: 16 or having at least 90% sequence identity, or at least 95% sequence identity, or at least 99% sequence identity to SEQ ID NO: 16;
- a nucleic acid sequence of SEQ ID NO: 17 or having at least 90% sequence identity, or at least 95% sequence identity, or at least 99% sequence identity to SEQ ID NO: 17;
- a nucleic acid sequence of SEQ ID NO: 18 or having at least 90% sequence identity, or at least 95% sequence identity, or at least 99% sequence identity to SEQ ID NO: 18;
- a nucleic acid sequence of SEQ ID NO: 19 or having at least 90% sequence identity, or at least 95% sequence identity, or at least 99% sequence identity to SEQ ID NO: 19;

- a nucleic acid sequence of SEQ ID NO: 20 or having at least 90% sequence identity, or at least 95% sequence identity, or at least 99% sequence identity to SEQ ID NO: 20;
- a nucleic acid sequence of SEQ ID NO: 21 or having at least 90% sequence identity, or at least 95% sequence identity, or at least 99% sequence identity to SEQ ID NO: 21;
- a nucleic acid sequence of SEQ ID NO: 22 or having at least 90% sequence identity, or at least 95% sequence identity, or at least 99% sequence identity to SEQ ID NO: 22;
- a nucleic acid sequence of SEQ ID NO: 26 or having at least 90% sequence identity, or at least 95% sequence identity, or at least 99% sequence identity to SEQ ID NO: 26; and
- a nucleic acid sequence of SEQ ID NO: 27 or having at least 90% sequence identity, or at least 95% sequence identity, or at least 99% sequence identity to SEQ ID NO: 27.

In some embodiments, the polynucleotide comprises DNA.

In some embodiments, the polynucleotide comprises RNA.

In some embodiments, RNA is mRNA or self-replicating RNA.

In some embodiments, the polynucleotide comprises a promoter, an enhancer, a polyadenylation site, a Kozak sequence, a stop codon, or any combination thereof.

Methods of generating polynucleotides of the disclosure are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Vectors

The disclosure also provides vectors comprising any of the polynucleotides disclosed herein. The disclosure also provides vectors comprising a polynucleotide encoding for any of the polypeptides disclosed herein.

In some embodiments, the vector comprises a polynucleotide encoding a polypeptide that comprises at least two or more epitope sequences selected from the group consisting of:

- CALR epitope of SEQ ID NO: 1 (MKDKQDEEQRTRRMMRTKMRMRRMRR TRRKMRRKMSPARPRTSCREACLQGWTE) or having at least 90% sequence identity to SEQ ID NO: 1;
- CALR epitope of SEQ ID NO: 2 (EEAEDNCRRMMRTK) or having at least 90% sequence identity to SEQ ID NO: 2;
- JAK2 epitope of SEQ ID NO: 4 (KLSHKHLVLNYGVCFCGDENILVQEFVKFG) or having at least 90% sequence identity to SEQ ID NO: 4;
- JAK2 epitope of SEQ ID NO: 5 (VLNYGVCFC) or at least 90% sequence identity to SEQ ID NO: 5;
- JAK2 epitope of SEQ ID NO: 6 (FCGDENILV) or having at least 90% sequence identity to SEQ ID NO: 6; and combinations thereof.

The vector may be a vector intended for expression of the polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors or artificial chromosomes.

Suitable vectors that may be used are—Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia).

The disclosure provides an expression vector comprising the polynucleotide of the disclosure. The disclosure also provides an expression vector comprising the polynucleotide encoding for the polypeptide of the disclosure.

The disclosure also provides a viral vector comprising any of the polynucleotides of the disclosure.

The disclosure also provides a viral vector comprising a polynucleotide encoding any of the polypeptides of the disclosure.

Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), Great ape adenovirus vectors (GAd), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, and bacterial spores.

In some embodiments, the viral vector is derived from adenovirus, poxvirus, alphavirus, adeno-associated virus, retrovirus or a self-replicating RNA molecule.

Adenoviral Vectors

In some embodiments, the viral vector is derived from an adenovirus.

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (*Pan*), Gorilla (*Gorilla*), Orangutan (*Pongo*), Bonobo (*Pan paniscus*) and common chimpanzee (*Pan troglodytes*). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus (GAd) vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in SEQ ID NO: 1 of Int. Pat. Publ. No. WO2007/104792. An exemplary genome sequence of Ad35 is found in FIG. 6 of Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

Adenovirus vectors are engineered to comprise at least one functional deletion or a complete removal of a gene product that is essential for viral replication, such as one or more of the adenoviral regions E1, E2 and E4, therefore rendering the adenovirus to be incapable of replication. The deletion of the E1 region may comprise deletion of EIA, EIB 55K or EIB 21K, or any combination thereof. Replication deficient adenoviruses are propagated by providing the proteins encoded by the deleted region(s) in trans by the producer cell by utilizing helper plasmids or engineering the produce cell to express the required proteins. Adenovirus vectors may also have a deletion in the E3 region, which is dispensable for replication, and hence such a deletion does not have to be complemented. The adenovirus vector of the disclosure may comprise a functional deletion or a complete removal of the E1 region and at least part of the E3 region. The adenovirus vector of the disclosure may further comprise a functional deletion or a complete removal of the E4 region and/or the E2 region. Suitable producer cells that can be utilized are human retina cells immortalized by E1, e.g. 911 or PER.C6 cells (see, e.g., U.S. Pat. No. 5,994,128), E1-transformed amniocytes (See, e.g., EP 1230354), E1-transformed A549 cells (see e.g. Int. Pat. Publ. No. WO1998/39411, U.S. Pat. No. 5,891,690). Exemplary vectors that may be used are Ad26 comprising a functional E1 coding region that is sufficient for viral replication, a deletion in the E3 coding region and a deletion in the E4 coding region, provided that E4 open reading frame 6/7 is not deleted (see e.g. U.S. Pat. No. 9,750,801)

In some embodiments, the adenovirus vector is a human adenovirus (Ad) vector. In some embodiments, the Ad vector is derived from Ad5. In some embodiments, the Ad vector is derived from Ad11. In some embodiments, the Ad vector is derived from Ad7. In some embodiments, the Ad vector is derived from Ad26. In some embodiments, the Ad vector is derived from Ad34. In some embodiments, the Ad vector is derived from Ad35. In some embodiments, the Ad vector is derived from Ad48. In some embodiments, the Ad vector is derived from Ad49. In some embodiments, the Ad vector is derived from Ad50.

In some embodiments, the adenovirus vector is a great ape adenovirus (GAd) vector. In some embodiments, the GAd vector is derived from GAd20. In some embodiments, the GAd vector is derived from GAd19. In some embodiments, the GAd vector is derived from GAd21. In some embodiments, the GAd vector is derived from GAd25. In some embodiments, the GAd vector is derived from GAd26. In some embodiments, the GAd vector is derived from GAd27. In some embodiments, the GAd vector is derived from GAd28. In some embodiments, the GAd vector is derived from GAd29. In some embodiments, the GAd vector is derived from GAd30. In some embodiments, the GAd vector is derived from GAd31. In some embodiments, the GAd vector is derived from ChAd3. In some embodiments, the GAd vector is derived from ChAd4. In some embodiments, the GAd vector is derived from ChAd5. In some embodiments, the GAd vector is derived from ChAd6. In some embodiments, the GAd vector is derived from ChAd7. In some embodiments, the GAd vector is derived from ChAd8. In some embodiments, the GAd vector is derived from ChAd9. In some embodiments, the GAd vector is derived from ChAd9. In some embodiments, the GAd vector is derived from ChAd10. In some embodiments, the GAd vector is derived from ChAd11. In some embodiments, the GAd vector is derived from ChAd16. In some embodiments, the GAd vector is derived from ChAd17. In some embodiments, the GAd vector is derived from ChAd19. In some embodiments, the GAd vector is derived from ChAd20. In some embodiments, the GAd vector is derived from ChAd22. In some embodiments, the GAd vector is derived from ChAd24. In some embodiments, the GAd vector is derived from ChAd26. In some embodiments, the GAd vector is derived from ChAd30. In some embodiments, the GAd vector is derived from ChAd31. In some embodiments, the GAd vector is derived from ChAd32. In some embodiments, the GAd vector is derived from ChAd31. In some embodiments, the GAd vector is derived from ChAd33. In some embodiments, the GAd vector is derived from ChAd37. In some embodiments, the GAd vector is derived from ChAd38. In some embodiments, the GAd vector is derived from ChAd44. In some embodiments, the GAd vector is derived from ChAd55. In some embodiments, the GAd vector is derived from ChAd63. In some embodiments, the GAd vector is derived from ChAd68. In some embodiments, the GAd vector is derived from ChAd73. In some embodiments, the GAd vector is derived from ChAd82. In some embodiments, the GAd vector is derived from ChAd83. GAd19-21 and GAd25-31 are described in Int. Pat. Publ. No. WO2019/008111 and represents strains with high immunogenicity and no pre-existing immunity in the general human population. The polynucleotide sequence of GAd20 genome is disclosed in Int. Pat. Publ. No. WO2019/008111.

The polynucleotides of the disclosure may be inserted into a site or region (insertion region) in the vector that does not affect virus viability of the resultant recombinant virus. The polynucleotides of the disclosure may be inserted into the deleted E1 region in parallel (transcribed 5' to 3') or anti-parallel (transcribed in a 3' to 5' direction relative to the vector backbone) orientation. In addition, appropriate transcriptional regulatory elements that are capable of directing expression of the polypeptide or the polypeptide of the disclosure in the mammalian host cells that the vector is being prepared for use may be operatively linked to the polypeptide or the polypeptide of the disclosure.

Recombinant adenoviral particles may be prepared and propagated according to any conventional technique in the field of the art (e.g., Int. Pat. Publ. No. WO1996/17070) using a complementation cell line or a helper virus, which supplies in trans the missing viral genes necessary for viral replication. The cell lines 293, PER.C6, E1 A549 and 911 are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and Int. Pat. Publ. No. WO1997/04119). The adenoviral particles may be recovered from the culture supernatant but also from the cells after lysis and optionally further purified according to standard techniques (e.g., chromatography, ultracentrifugation, as described in Int. Pat. Publ. No. WO1996/27677, Int. Pat. Publ. No. WO1998/00524, Int. Pat. Publ. No. WO1998/26048 and Int. Pat. Publ. No. WO2000/50573). The construction and methods for propagating adenoviral vectors are also described in for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

Provided herein is a viral vector comprising any of the polynucleotides of the disclosure, wherein the vector is derived from hAd26 (also referred to has Ad26).

In some embodiments, the Ad26 vector comprises a polynucleotide of SEQ ID NO: 16 or having at least 90% sequence identity, or at least 95% sequence identity, or at least 99% sequence identity to SEQ ID NO: 16.

In some embodiments, the Ad26 vector comprises a polynucleotide of SEQ ID NO: 17 or having at least 90% sequence identity, or at least 95% sequence identity, or at least 99% sequence identity to SEQ ID NO: 17.

In some embodiments, the Ad26 vector comprises a polynucleotide of SEQ ID NO: 18 or having at least 90% sequence identity, or at least 95% sequence identity, or at least 99% sequence identity to SEQ ID NO: 18.

In some embodiments, the Ad26 vector comprises a polynucleotide of SEQ ID NO: 19 or having at least 90% sequence identity, or at least 95% sequence identity, or at least 99% sequence identity to SEQ ID NO: 19.

In some embodiments, the Ad26 vector comprises a polynucleotide of SEQ ID NO: 20 or having at least 90% sequence identity, or at least 95% sequence identity, or at least 99% sequence identity to SEQ ID NO: 20.

In some embodiments, the Ad26 vector comprises a polynucleotide of SEQ ID NO: 21 or having at least 90% sequence identity, or at least 95% sequence identity, or at least 99% sequence identity to SEQ ID NO: 21.

In some embodiments, the Ad26 vector comprises a polynucleotide of SEQ ID NO: 22 or having at least 90% sequence identity, or at least 95% sequence identity, or at least 99% sequence identity to SEQ ID NO: 22.

In some embodiments, the Ad26 vector comprises a polynucleotide of SEQ ID NO: 23 or having at least 90% sequence identity, or at least 95% sequence identity, or at least 99% sequence identity to SEQ ID NO: 23.

In some embodiments, the Ad26 vector comprises a polynucleotide of SEQ ID NO: 24 or having at least 90% sequence identity, or at least 95% sequence identity, or at least 99% sequence identity to SEQ ID NO: 24.

In some embodiments, the Ad26 vector comprises a polynucleotide of SEQ ID NO: 25 or having at least 90% sequence identity to SEQ ID NO: 25.

In some embodiments, the Ad26 vector comprises a polynucleotide of SEQ ID NO: 26 or having at least 90% sequence identity, or at least 95% sequence identity, or at least 99% sequence identity to SEQ ID NO: 26.

In some embodiments, the Ad26 vector comprises a polynucleotide of SEQ ID NO: 27 or having at least 90% sequence identity, or at least 95% sequence identity, or at least 99% sequence identity to SEQ ID NO: 27.

In some embodiments, the Ad26 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the Ad26 vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the Ad26 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the Ad26 vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the Ad26 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the Ad26 vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the Ad26 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the Ad26 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the Ad26 vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the Ad26 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the Ad26 vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the Ad26 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the Ad26 vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the Ad26 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the Ad26 vector comprises a polynucleotide encoding an amino acid sequence of SEQ ID NO: 31 or having at least 90% sequence identity, or at least 95% sequence identity, or at least 99% sequence identity to SEQ ID NO: 31.

Provided herein is a viral vector comprising any of the polynucleotides of the disclosure, wherein the vector is derived from GAd20.

In some embodiments, the GAd20 vector comprises a polynucleotide of SEQ ID NO: 16 or having at least 90% sequence identity, or at least 95% sequence identity, or at least 99% sequence identity to SEQ ID NO: 16.

In some embodiments, the GAd20 vector comprises a polynucleotide of SEQ ID NO: 17 or having at least 90% sequence identity, or at least 95% sequence identity, or at least 99% sequence identity to SEQ ID NO: 17.

In some embodiments, the GAd20 vector comprises a polynucleotide of SEQ ID NO: 18 or having at least 90% sequence identity, or at least 95% sequence identity, or at least 99% sequence identity to SEQ ID NO: 18.

In some embodiments, the GAd20 vector comprises a polynucleotide of SEQ ID NO: 19 or having at least 90% sequence identity, or at least 95% sequence identity, or at least 99% sequence identity to SEQ ID NO: 19.

In some embodiments, the GAd20 vector comprises a polynucleotide of SEQ ID NO: 20 or having at least 90% sequence identity, or at least 95% sequence identity, or at least 99% sequence identity to SEQ ID NO: 20.

In some embodiments, the GAd20 vector comprises a polynucleotide of SEQ ID NO: 21 or having at least 90% sequence identity, or at least 95% sequence identity, or at least 99% sequence identity to SEQ ID NO: 21.

In some embodiments, the GAd20 vector comprises a polynucleotide of SEQ ID NO: 22 or having at least 90% sequence identity, or at least 95% sequence identity, or at least 99% sequence identity to SEQ ID NO: 22.

In some embodiments, the GAd20 vector comprises a polynucleotide of SEQ ID NO: 23 or having at least 90% sequence identity, or at least 95% sequence identity, or at least 99% sequence identity to SEQ ID NO: 23.

In some embodiments, the GAd20 vector comprises a polynucleotide of SEQ ID NO: 24 or having at least 90% sequence identity, or at least 95% sequence identity, or at least 99% sequence identity to SEQ ID NO: 24.

In some embodiments, the GAd20 vector comprises a polynucleotide of SEQ ID NO: 25 or having at least 90% sequence identity, or at least 95% sequence identity, or at least 99% sequence identity to SEQ ID NO: 25.

In some embodiments, the GAd20 vector comprises a polynucleotide of SEQ ID NO: 26 or having at least 90% sequence identity, or at least 95% sequence identity, or at least 99% sequence identity to SEQ ID NO: 26.

In some embodiments, the GAd20 vector comprises a polynucleotide of SEQ ID NO: 27 or having at least 90% sequence identity, or at least 95% sequence identity, or at least 99% sequence identity to SEQ ID NO: 27.

In some embodiments, the GAd20 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the GAd20 vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the GAd20 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the GAd20 vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the GAd20 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the GAd20 vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the GAd20 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the GAd20 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the GAd20 vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the GAd20 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the GAd20 vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the GAd20 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the GAd20 vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the GAd20 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the GAd20 vector comprises a polynucleotide encoding an amino acid sequence of SEQ ID NO: 31 or having at least 90% sequence identity, or at least 95% sequence identity, or at least 99% sequence identity to SEQ ID NO: 31.

Poxvirus Vectors

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC or Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (Meyer et al., *J. Gen. Virol.,* 72: 1031-1038 (1991) and U.S. Pat. No. 10,035,832). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007.) Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). It was shown in a variety of animal models that the resulting MVA was significantly avirulent (Mayr, A. & Danner, K. Vaccination against pox diseases under immunosuppressive conditions, Dev. Biol. Stand. 41: 225-34, 1978). Being that many passages were used to attenuate MVA, there are a number of different strains or isolates, depending on the passage number in CEF cells, such as MVA 476 MG/14/78, MVA-571, MVA-572, MVA-574, MVA-575 and MVA-BN. MVA 476 MG/14/78 is described for example in Int. Pat. Publ. No. WO2019/115816A1. MVA-572 strain was deposited at the European Collection of Animal Cell Cultures ("ECACC"), Health Protection Agency, Microbiology Services, Porton Down, Salisbury SP4 OJG, United Kingdom ("UK"), under the deposit number ECACC 94012707 on Jan. 27, 1994. MVA-575 strain was deposited at the ECACC under deposit number ECACC 00120707 on Dec. 7, 2000; MVA-Bavarian Nordic ("MVA-BN") strain was deposited at the ECACC under deposit number V00080038 on Aug. 30, 2000. The genome sequences of MVA-BN and MVA-572 are available at GenBank (Accession numbers DQ983238 and DQ983237, respectively). The genome sequences of other MVA strains can be obtained using standard sequencing methods.

Vectors and viruses of the disclosure may be derived from any MVA strain or further derivatives of the MVA strain. A further exemplary MVA strain is deposit VR-1508, deposited at the American Type Culture collection (ATCC), Manassas, Va. 20108, USA.

Derivatives of MVA refer to viruses exhibiting essentially the same characteristics as the parent MVA but exhibiting differences in one or more parts of their genomes.

In some embodiments, the MVA vector is derived from MVA 476 MG/14/78. In some embodiments, the MVA vector is derived from MVA-571. In some embodiments, the MVA vector is derived from MVA-572. In some embodiments, the MVA vector is derived from MVA-574. In some embodiments, the MVA vector is derived from MVA-575. In some embodiments, the MVA vector is derived from MVA-BN.

The polynucleotide of the disclosure may be inserted into a site or region (insertion region) in the MVA vector that does not affect virus viability of the resultant recombinant virus. Such regions can be readily identified by testing segments of virus DNA for regions that allow recombinant formation without seriously affecting virus viability of the recombinant virus. The thymidine kinase (TK) gene is an insertion region that may be used and is present in many viruses, such as in all examined poxvirus genomes. Additionally, MVA contains 6 natural deletion sites, each of which may be used as insertion sites (e.g. deletion I, II, III, IV, V, and VI; see e.g. U.S. Pat. Nos. 5,185,146 and 6,440,442). One or more intergenic regions (IGR) of the MVA may also be used as an insertion site, such as IGRs IGR07/08, IGR 44/45, IGR 64/65, IGR 88/89, IGR 136/137, and IGR 148/149 (see e.g. U.S. Pat. Publ. No. 2018/0064803). Additional suitable insertion sites are described in Int. Pat. Publ. No. WO2005/048957.

Recombinant poxviral particles such as rMVA are prepared as described in the art (Piccini, et al., 1987, Methods of Enzymology 153: 545-563; U.S. Pat. Nos. 4,769,330; 4,772,848; 4,603,112; 5,100,587 and 5,179,993). In an exemplary method, the DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences. rMVA particles may be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

Provided herein is a viral vector comprising any of the polynucleotides of the disclosure, wherein the vector is derived from MVA.

In some embodiments, the MVA vector comprises a polynucleotide of SEQ ID NO: 16 or having at least 90% sequence identity, or at least 95% sequence identity, or at least 99% sequence identity to SEQ ID NO: 16.

In some embodiments, the MVA vector comprises a polynucleotide of SEQ ID NO: 17 or having at least 90% sequence identity, or at least 95% sequence identity, or at least 99% sequence identity to SEQ ID NO: 17.

In some embodiments, the MVA vector comprises a polynucleotide of SEQ ID NO: 18 or having at least 90% sequence identity, or at least 95% sequence identity, or at least 99% sequence identity to SEQ ID NO: 18.

In some embodiments, the MVA vector comprises a polynucleotide of SEQ ID NO: 19 or having at least 90% sequence identity, or at least 95% sequence identity, or at least 99% sequence identity to SEQ ID NO: 19.

In some embodiments, the MVA vector comprises a polynucleotide of SEQ ID NO: 20 or having at least 90% sequence identity, or at least 95% sequence identity, or at least 99% sequence identity to SEQ ID NO: 20.

In some embodiments, the MVA vector comprises a polynucleotide of SEQ ID NO: 21 or having at least 90% sequence identity, or at least 95% sequence identity, or at least 99% sequence identity to SEQ ID NO: 21.

In some embodiments, the MVA vector comprises a polynucleotide of SEQ ID NO: 22 or having at least 90% sequence identity, or at least 95% sequence identity, or at least 99% sequence identity to SEQ ID NO: 22.

In some embodiments, the MVA vector comprises a polynucleotide of SEQ ID NO: 23 or having at least 90% sequence identity, or at least 95% sequence identity, or at least 99% sequence identity to SEQ ID NO: 23.

In some embodiments, the MVA vector comprises a polynucleotide of SEQ ID NO: 24 or having at least 90% sequence identity, or at least 95% sequence identity, or at least 99% sequence identity to SEQ ID NO: 24.

In some embodiments, the MVA vector comprises a polynucleotide of SEQ ID NO: 25 or having at least 90% sequence identity, or at least 95% sequence identity, or at least 99% sequence identity to SEQ ID NO: 25.

In some embodiments, the MVA vector comprises a polynucleotide of SEQ ID NO: 26 or having at least 90% sequence identity, or at least 95% sequence identity, or at least 99% sequence identity to SEQ ID NO: 26.

In some embodiments, the MVA vector comprises a polynucleotide of SEQ ID NO: 27 or having at least 90% sequence identity, or at least 95% sequence identity, or at least 99% sequence identity to SEQ ID NO: 27.

In some embodiments, the MVA vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the MVA vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the MVA vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the MVA vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the MVA vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the MVA vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the MVA vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the MVA vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the MVA vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the MVA vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the MVA vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the MVA vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the MVA vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the MVA vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the MVA vector comprises a polynucleotide encoding an amino acid sequence of SEQ ID NO: 31 or having at least 90% sequence identity, or at least 95% sequence identity, or at least 99% sequence identity to SEQ ID NO: 31.

Self-Replicating RNA Molecules

Self-replicating RNA may be derived from alphavirus. Alphaviruses may belong to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

The self-replicating RNA molecules can be derived from alphavirus genomes, meaning that they have some of the structural characteristics of alphavirus genomes, or similar to them. The self-replicating RNA molecules can be derived from modified alphavirus genomes.

Self-replicating RNA molecules may be derived from Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV).

In some embodiments, the alphavirus-derived self-replicating RNA molecule is a Venezuelan equine encephalitis virus (VEER).

The self-replicating RNA molecules can contain RNA sequences from (or amino acid sequences encoded by) a wild-type New World or Old World alphavirus genome. Any of the self-replicating RNA molecules disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome.

Self-replicating RNA molecules contain all of the genetic information required for directing their own amplification or self-replication within a permissive cell. To direct their own replication, self-replicating RNA molecules encode polymerase, replicase, or other proteins which may interact with viral or host cell-derived proteins, nucleic acids or ribonucleoproteins to catalyze the RNA amplification process; and contain cis-acting RNA sequences required for replication and transcription of the replicon-encoded RNA. Thus, RNA replication leads to the production of multiple daughter RNAs. These daughter RNAs, as well as collinear subgenomic transcripts, can be translated to provide in situ expression of a gene of interest, or can be transcribed to provide further transcripts with the same sense as the delivered RNA which are translated to provide in situ expression of the gene of interest. The overall results of this sequence of transcriptions is a huge amplification in the number of the introduced replicon RNAs and so the encoded gene of interest becomes a major polypeptide product of the cells.

There are two open reading frames (ORFs) in the genome of alphaviruses, non-structural (ns) and structural genes. The ns ORF encodes proteins (nsP1-nsP4) necessary for transcription and replication of viral RNA and are produced as a polyprotein and are the virus replication machinery. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome. An exemplary depiction of an alphavirus genome is shown in FIG. 18A.

Self-replicating RNA molecules can be used as basis of introducing foreign sequences to host cells by replacing viral sequences encoding structural genes or inserting the foreign sequences 5' or 3' of the sequences encoding the structural genes. They can be engineered to replace the viral structural genes downstream of the replicase, which are under control of a subgenomic promoter, by genes of interest (GOI), e.g. the polynucleotide encoding for the polypeptide of the disclosure. Upon transfection, the replicase which is translated immediately, interacts with the 5' and 3' termini of the genomic RNA, and synthesizes complementary genomic RNA copies. Those act as templates for the synthesis of novel positive-stranded, capped, and poly-adenylated genomic copies, and subgenomic transcripts (FIG. 18B). Amplification eventually leads to very high RNA copy numbers of up to $2\times10^1$ copies per cell. The result is a uniform and/or enhanced expression of a GOI (e.g. the polynucleotide encoding for the polypeptide of the disclosure) that can affect vaccine efficacy or therapeutic impact of a treatment. Vaccines based on self-replicating RNA molecules can therefore be dosed at very low levels due to the very high copies of RNA generated compared to conventional viral vector. One of the significant values of the compositions and methods disclosed herein is that vaccine efficacy can be increased in individuals that are in a chronic or acute state of immune activation.

The self-replicating RNA molecules of the disclosure comprising the RNA encoding for the CALR/JAK2 or JAK2 epitope 2 polypeptides of the disclosure may be utilized as therapeutics by delivering them to a subject having a myeloproliferative neoplasms using various technologies, including viral vectors as described herein or other delivery technologies as also described herein.

The disclosure provides a self-replicating RNA molecule containing all of the genetic information required for directing its own amplification or self-replication within a permissive cell.

The disclosure also provides a self-replicating RNA molecule that can be used as the basis of introducing foreign sequences to host cells (e.g. the CALR/JAK2 or the JAK2 epitope 2 polypeptides of the disclosure) by replacing viral sequences encoding structural genes.

Provided herein is a viral vector comprising any of the polynucleotides of the disclosure, wherein the vector is a self-replicating RNA molecule.

In some embodiments, the self-replicating RNA molecule comprises an RNA sequence derived from a polynucleotide of SEQ ID NO: 16 or having at least 90% sequence identity, or at least 95% sequence identity, or at least 99% sequence identity to SEQ ID NO: 16.

In some embodiments, the self-replicating RNA molecule comprises an RNA sequence derived from a polynucleotide of SEQ ID NO: 17 or having at least 90% sequence identity, or at least 95% sequence identity, or at least 99% sequence identity to SEQ ID NO: 17.

In some embodiments, the self-replicating RNA molecule comprises an RNA sequence derived from a polynucleotide of SEQ ID NO: 18 or having at least 90% sequence identity, or at least 95% sequence identity, or at least 99% sequence identity to SEQ ID NO: 18.

In some embodiments, the self-replicating RNA molecule comprises an RNA sequence derived from a polynucleotide of SEQ ID NO: 19 or having at least 90% sequence identity, or at least 95% sequence identity, or at least 99% sequence identity to SEQ ID NO: 19.

In some embodiments, the self-replicating RNA molecule comprises an RNA sequence derived from a polynucleotide of SEQ ID NO: 20 or having at least 90% sequence identity, or at least 95% sequence identity, or at least 99% sequence identity to SEQ ID NO: 20.

In some embodiments, the self-replicating RNA molecule comprises an RNA sequence derived from a polynucleotide of SEQ ID NO: 21 or having at least 90% sequence identity, or at least 95% sequence identity, or at least 99% sequence identity to SEQ ID NO: 21.

In some embodiments, the self-replicating RNA molecule comprises an RNA sequence derived from a polynucleotide of SEQ ID NO: 22 or having at least 90% sequence identity, or at least 95% sequence identity, or at least 99% sequence identity to SEQ ID NO: 22.

In some embodiments, the self-replicating RNA molecule comprises an RNA sequence derived from a polynucleotide of SEQ ID NO: 23 or having at least 90% sequence identity, or at least 95% sequence identity, or at least 99% sequence identity to SEQ ID NO: 23.

In some embodiments, the self-replicating RNA molecule comprises an RNA sequence derived from a polynucleotide of SEQ ID NO: 24 or having at least 90% sequence identity, or at least 95% sequence identity, or at least 99% sequence identity to SEQ ID NO: 24.

In some embodiments, the self-replicating RNA molecule comprises an RNA sequence derived from a polynucleotide of SEQ ID NO: 25 or having at least 90% sequence identity, or at least 95% sequence identity, or at least 99% sequence identity to SEQ ID NO: 25.

In some embodiments, the self-replicating RNA molecule comprises an RNA sequence derived from a polynucleotide of SEQ ID NO: 26 or having at least 90% sequence identity, or at least 95% sequence identity, or at least 99% sequence identity to SEQ ID NO: 26.

In some embodiments, the self-replicating RNA molecule comprises an RNA sequence derived from a polynucleotide of SEQ ID NO: 27 or having at least 90% sequence identity, or at least 95% sequence identity, or at least 99% sequence identity to SEQ ID NO: 27.

In some embodiments, the self-replicating RNA molecule comprises an RNA sequence encoding an amino acid sequence of SEQ ID NO: 1 or having at least 90% sequence identity, or at least 95% sequence identity, or at least 99% sequence identity to SEQ ID NO: 1.

In some embodiments, the self-replicating RNA molecule comprises an RNA sequence encoding an amino acid sequence of SEQ ID NO: 2 or having at least 90% sequence identity, or at least 95% sequence identity, or at least 99% sequence identity to SEQ ID NO: 2.

In some embodiments, the self-replicating RNA molecule comprises an RNA sequence encoding an amino acid sequence of SEQ ID NO: 3 or having at least 90% sequence identity, or at least 95% sequence identity, or at least 99% sequence identity to SEQ ID NO: 3.

In some embodiments, the self-replicating RNA molecule comprises an RNA sequence encoding an amino acid sequence of SEQ ID NO: 4 or having at least 90% sequence identity, or at least 95% sequence identity, or at least 99% sequence identity to SEQ ID NO: 4.

In some embodiments, the self-replicating RNA molecule comprises an RNA sequence encoding an amino acid sequence of SEQ ID NO: 5 or having at least 90% sequence identity, or at least 95% sequence identity, or at least 99% sequence identity to SEQ ID NO: 5.

In some embodiments, the self-replicating RNA molecule comprises an RNA sequence encoding an amino acid sequence of SEQ ID NO: 6 or having at least 90% sequence identity, or at least 95% sequence identity, or at least 99% sequence identity to SEQ ID NO: 6.

In some embodiments, the self-replicating RNA molecule comprises an RNA sequence encoding an amino acid sequence of SEQ ID NO: 7 or having at least 90% sequence identity, or at least 95% sequence identity, or at least 99% sequence identity to SEQ ID NO: 7.

In some embodiments, the self-replicating RNA molecule comprises an RNA sequence encoding an amino acid sequence of SEQ ID NO: 9 or having at least 90% sequence identity, or at least 95% sequence identity, or at least 99% sequence identity to SEQ ID NO: 9.

In some embodiments, the self-replicating RNA molecule comprises an RNA sequence encoding an amino acid sequence of SEQ ID NO: 10 or having at least 90% sequence identity, or at least 95% sequence identity, or at least 99% sequence identity to SEQ ID NO: 10.

In some embodiments, the self-replicating RNA molecule comprises an RNA sequence encoding an amino acid sequence of SEQ ID NO: 11 or having at least 90% sequence identity, or at least 95% sequence identity, or at least 99% sequence identity to SEQ ID NO: 11.

In some embodiments, the self-replicating RNA molecule comprises an RNA sequence encoding an amino acid sequence of SEQ ID NO: 12 or having at least 90% sequence identity, or at least 95% sequence identity, or at least 99% sequence identity to SEQ ID NO: 12.

In some embodiments, the self-replicating RNA molecule comprises an RNA sequence encoding an amino acid sequence of SEQ ID NO: 13 or having at least 90% sequence identity, or at least 95% sequence identity, or at least 99% sequence identity to SEQ ID NO: 13.

In some embodiments, the self-replicating RNA molecule comprises an RNA sequence encoding an amino acid sequence of SEQ ID NO: 14 or having at least 90% sequence identity, or at least 95% sequence identity, or at least 99% sequence identity to SEQ ID NO: 14.

In some embodiments, the self-replicating RNA molecule comprises an RNA sequence encoding an amino acid sequence of SEQ ID NO: 15 or having at least 90% sequence identity, or at least 95% sequence identity, or at least 99% sequence identity to SEQ ID NO: 15.

In some embodiments, the self-replicating RNA molecule comprises an RNA sequence encoding an amino acid sequence of SEQ ID NO: 31 or having at least 90% sequence identity, or at least 95% sequence identity, or at least 99% sequence identity to SEQ ID NO: 31.

Any of the above self-replicating RNA molecules can further comprise one or more of the following:

one or more nonstructural genes nsP1, nsP2, nsP3 and nsP4;

at least one of a DLP motif, a 5' UTR, a 3'UTR and a Poly A; and a subgenomic promoter.

In some embodiments, for example, the self-replicating RNA molecule can comprise one or more of the following:

one or more nonstructural genes nsP1, nsP2, nsP3 and nsP4;

at least one of a DLP motif, a 5' UTR, a 3'UTR and a Poly A; and a subgenomic promoter; and an RNA encoding for amino acids of SEQ ID NOs: 3, 4, 5, 6, 7, 9, 10, 11, 12, 13, 14, 15, or 31, and operably linked to the subgenomic promoter.

In some embodiments, the self-replicating RNA molecule comprises an RNA sequence encoding a protein or peptide; 5' and 3' alphavirus untranslated regions; RNA sequences encoding amino acid sequences derived from New World alphavirus VEEV nonstructural proteins nsP1, nsP2, nsP3 and nsP4; a sub-genomic promoter that is operably linked to and regulates translation of the RNA sequence encoding the protein; a 5' cap and a 3' poly-A tail; positive sense, single-stranded RNA; a DLP from Sindbis virus upstream of the non-structural protein 1 (nsP1); a 2A ribosome skipping element; and a nsp1 nucleotide repeat downstream of the 5'-UTR and upstream of the DLP.

In some embodiments, the self-replicating RNA molecules may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size.

Any of the above-disclosed self-replicating RNA molecules can further include a coding sequence for an autoprotease peptide (e.g., autocatalytic self-cleaving peptide), where the coding sequence for the autoprotease is optionally operably linked upstream to the second nucleic acid sequence.

Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro and in vivo eukaryotic systems. As such, the concept of autoproteases is available to one of skill in the art as many naturally occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequence for the autoprotease peptide is operably linked downstream of the DLP motif and upstream to the first and second polynucleotides.

In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

In some embodiments, the autoprotease peptide is selected from the group consisting of porcine teschovirus-1 2A (P2A), foot-and-mouth disease virus (FMDV) 2A (F2A), Equine Rhinitis A Virus (ERAV) 2A (E2A), Thosea asigna virus 2A (T2A), cytoplasmic polyhedrosis virus 2A (BmCPV2A), Flacherie Virus 2A (BmIFV2A), and a combination thereof.

In some embodiments, the autoprotease peptide is porcine teschovirus-1 2A (P2A).

The incorporation of the P2A peptide in the modified viral RNA replicons of the present disclosure allows release of protein encoded by GOI (e.g.CALR-JAK2 or JAK2 epitope 2 polypeptide of the disclosure) from the capsid-GOI fusion.

In some embodiments disclosed herein, the porcine teschovirus-1 2A (P2A) peptide sequence is engineered in-frame immediately after the DLP sequence and in-frame immediately upstream of all GOI.

Any of the above-disclosed self-replicating RNA molecules can further include a coding sequence downstream Loop (DLP) motif.

Some viruses have sequences capable of forming one or more stem-loop structures which regulate, for example increase, capsid gene expression. Viral capsid enhancer as used herein refers to a regulatory element comprising sequences capable of forming such stem-loop structures. In some examples, the stem-loop structures are formed by sequences within the coding sequence of a capsid protein and named Downstream Loop (DLP) sequence. As disclosed herein, these stem-loop structures or variants thereof can be used to regulate, for example increase, expression level of genes of interest. For example, these stem-loop structures or variants thereof can be used in a recombinant vector (e.g., in a heterologous viral genome) for enhancing transcription and/or translation of coding sequence operably linked downstream thereto.

Alphavirus replication in host cells is known to induce the double-stranded RNA-dependent protein kinase (PKR). PKR phosphorylates the eukaryotic translation initiation factor 2α (eIF2α). Phosphorylation of eIF2α blocks translation initiation of mRNA and in doing so keeps viruses from a completing a productive replication cycle. Infection of cells with Sindbis virus induces PKR that results in phosphorylation of eIF2α, yet the viral subgenomic mRNA is efficiently translated while translation of all other cellular mRNAs is restricted. The efficient translation of the viral subgenomic mRNA in Sindbis virus is made possible by the presence of a stable RNA hairpin loop (or DLP motif) located downstream of the wild type AUG initiator codon for the virus capsid protein (e.g., capsid enhancer). It has been reported that the DLP structure can stall a ribosome on the wild type AUG and this supports translation of the subgenomic mRNA without the requirement for functional eIF2α. Thus, subgenomic mRNAs of Sindbis virus (SINV) as well as of other alphaviruses are efficiently translated even in cells that have highly active PKR resulting in complete phosphorylation of eIF2α.

The DLP structure was first characterized in Sindbis virus (SINV) 26S mRNA and also detected in Semliki Forest virus (SFV). Similar DLP structures have been reported to be present in at least 14 other members of the Alphavirus genus including New World (for example, MAYV, UNAV, EEEV (NA), EEEV (SA), AURAV) and Old World (SV, SFV, BEBV, RRV, SAG, GETV, MIDV, CHIKV, and ONNV) members. The predicted structures of these Alphavirus 26S mRNAs were constructed based on SHAPE (selective 2'-hydroxyl acylation and primer extension) data (Toribio et al., Nucleic Acids Res. May 19; 44(9):4368-80, 2016), the content of which is hereby incorporated by reference). Stable stem-loop structures were detected in all cases except for CHIKV and ONNV, whereas MAYV and EEEV showed DLPs of lower stability (Toribio et al., 2016 supra). The highest DLP activities were reported for those Alphaviruses that contained the most stable DLP structures.

As an example, members of the Alphavirus genus can resist the activation of antiviral RNA-activated protein kinase (PKR) by means of the dowsntream loop (DLP) present within in viral 26S transcripts, which allows an eIF2-independent translation initiation of these mRNAs. The downstream loop (DLP), is located downstream from the AUG in SINV 26S mRNA and in other members of the Alphavirus genus.

In some embodiments, the nucleic acid molecules of the disclosure can include a coding sequence for a gene of interest (GOI) operably linked to DLP motif(s) and/or the coding sequence for the DLP motifs.

In some embodiments, the self-replicating RNA molecule of the disclosure comprises a downstream loop (DLP).

In some embodiments, the downstream loop (DLP) comprises at least one RNA-stem-loop.

In some instances, DLP activity depends on the distance between the DLP motif and the initiation codon AUG (AUGi). The AUG-DLP spacing in Alphavirus 26S mRNAs is tuned to the topology of the ES6S region of the ribosomal 18S rRNA in a way that allows the placement of the AUGi in the P site of the 40S subunit stalled by the DLP, allowing the incorporation of Met-tRNA without the participation of eIF2. In the case of Sindbis virus, the DLP motif is found in the first ~150 nt of the Sindbis subgenomic RNA. The hairpin is located downstream of the Sindbis capsid AUG initiation codon (AUG at nt 50 of the Sindbis subgenomic RNA) and results in stalling a ribosome such that the correct capsid gene AUG is used to initiate translation. Previous studies of sequence comparisons and structural RNA analysis revealed the evolutionary conservation of DLP in SINV and predicted the existence of equivalent DLP structures in many members of the Alphavirus genus (see e.g., Ventoso, J. Virol. 9484-9494, Vol. 86, September 2012).

Without being bound by any particular theory, it is believed that placing the DLP motif upstream of a coding sequence for any GOI typically results in a fusion-protein of N-terminal capsid amino acids that are encoded in the hairpin region to the GOI encoded protein because initiation occurs on the capsid AUG not the GOI AUG.

In some embodiments, the self-replicating RNA molecule comprises a downstream loop placed upstream of the non-structural protein 1 (nsP1).

In some embodiments, the downstream loop is placed upstream of the non-structural protein 1 (nsP1) and is joined to the nsP1 by a porcine teschovirus-1 2A (P2A) ribosome skipping element.

The DLP-containing self-replicating RNA of the disclosure can be useful in conferring a resistance to the innate immune system in a subject. Unmodified RNA replicons are sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform and/or enhanced expression of a GOI that can impact vaccine efficacy or therapeutic impact of a treatment.

The DLP motif of the self-replicating RNA of the disclosure can confer efficient mRNA translation in cellular environments where cellular mRNA translation is inhibited. When a DLP is linked with translation of a replicon vector's non-structural protein genes the replicase and transcriptase proteins are capable of initiating functional replication in PKR activated cellular environments. When a DLP is linked with translation of subgenomic mRNAs robust GOI expression is possible even when cellular mRNA is restricted due to innate immune activation. Accordingly, engineering self-replicating RNA that contain DLP structures to help drive translation of both non-structural protein genes and subgenomic mRNAs provides a powerful way to overcome innate immune activation.

Examples of a self-replicating RNA vector comprising a DLP motif are described in US Patent Application Publication US2018/0171340 and the International Patent Application Publication WO2018106615, the content of which is incorporated herein by reference in its entirety.

Any of the above-disclosed self-replicating RNA molecules can further comprise nonstructural genes nsP1, nsP2, nsP3 and/or nsP4. In some embodiments, the self-replicating RNA molecule does not encode a functional viral structural protein.

Alphavirus genomes encode non-structural proteins nsP1, nsP2, nsP3, and nsP4, which are produced as a single polyprotein precursor, sometimes designated P1234 (or nsP1-4 or nsP1234), and which is cleaved into the mature proteins through proteolytic processing (FIG. 18B). nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD). nsP4 is about 70 kDa in size and contains the core RNA-dependent RNA polymerase (RdRp) catalytic domain. After infection the alphavirus genomic RNA is translated to yield a P1234 polyprotein, which is cleaved into the individual proteins.

Alphavirus genomes also encode three structural proteins: the core nucleocapsid protein C, and the envelope proteins P62, and E1 that associate as a heterodimer. Structural proteins are under the control of a subgenomic promoter and can be replaced by gene of interests (GIO).

In some embodiments of the present disclosure, the self-replicating RNA can lack (or not contain) the sequence(s) of at least one (or all) of the structural viral proteins (e.g. nucleocapsid protein C, and envelope proteins P62, 6K, and E1). In these embodiments, the sequences encoding one or more structural genes can be substituted with one or more sequences such as, for example, a coding sequence for at least one protein or peptide (or other gene of interest (GOI)) e.g. the CALR/JAK2 polypeptides or JAK2 epitope 2 polypeptides of the disclosure.

In some embodiments, the self-replicating RNA lack sequences encoding alphavirus structural proteins; or do not encode alphavirus (or, optionally, any other) structural proteins. In some embodiments, the self-replicating RNA molecules are further devoided of a part or the entire coding region for one or more viral structural proteins. For example, the alphavirus expression system may be devoid of a portion of or the entire coding sequence for one or more of the viral capsid protein C, E1 glycoprotein, E2 glycoprotein, E3 protein and 6K protein.

In some embodiments, the self-replicating RNA molecule does not contain coding sequences for at least one of the structural viral proteins. In these instances, the sequences encoding structural genes can be substituted with one or more sequences such as, for example, a coding sequence for a GOI e.g., CALR/JAK2 or JAK2 epitope 2 polynucleotides of the disclosure FIG. 18.

The disclosure also provides a self-replicating RNA molecule comprising nonstructural genes nsP1, nsP2, nsP3 and nsP4, and wherein the self-replicating RNA molecule does not encode a functional viral structural protein.

In some embodiments, the disclosure provides a self-replicating RNA molecule comprising the coding sequence for at least one, at least two, at least three, or at least four nonstructural viral proteins (e.g. nsP1, nsP2, nsP3, nsP4). The nsP1, nsP2, nsP3, and nsP4 proteins encoded by the replicon are functional or biologically active proteins.

In some embodiments, the self-replicating RNA molecule includes the coding sequence for a portion of the at least one nonstructural viral protein. For example, the self-replicating RNA molecules can include about 10%, 20%, 30%, 40%, 50%, 60%, 70%, 80%, 90%, 95%, 100%, or a range between any two of these values, of the encoding sequence for the at least one nonstructural viral protein. In some embodiments, the self-replicating RNA molecule can include the coding sequence for a substantial portion of the at least one nonstructural viral protein. As used herein, a "substantial portion" of a nucleic acid sequence encoding a nonstructural viral protein comprises enough of the nucleic acid sequence encoding the nonstructural viral protein to afford putative identification of that protein, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993).

In some embodiments, the self-replicating RNA molecule can include the entire coding sequence for the at least one nonstructural protein. In some embodiments, the self-replicating RNA molecule comprises substantially all the coding sequence for the native viral nonstructural proteins. In certain embodiments, the one or more nonstructural viral proteins are derived from the same virus.

In some embodiments, the downstream loop DLP of the self-replicating RNA molecule placed upstream of the nonstructural protein 1 (nsP1) is derived from Sindbis virus.

In some embodiments, the self-replicating RNA molecule comprises nsP1, nsP2, nsP3 and nsP4 sequences derived from the Venezuelan equine encephalitis virus (VEEV) and a DLP motif derived from the Sindbis virus (SIN).

In some embodiments, the self-replicating RNA molecules also have an RNA sub-sequence encoding an amino acid sequence derived from an alphavirus nsP3 macro domain, and an RNA sub-sequence encoding an amino acid sequence derived from an alphavirus nsP3 central domain. The self-replicating RNA molecules can also have an RNA sub-sequence encoding an amino acid sequence derived entirely from an Old World alphavirus nsP3 hypervariable domain; or can have an amino acid sequence having a portion derived from a New World alphavirus nsP3 hypervariable domain, and a portion derived from an Old World alphavirus nsP3 hypervariable domain. i.e. the hyper variable domain (HVD) can be a hybrid or chimeric New World/Old World sequence.

In some embodiments, the self-replicating RNA molecules can have an RNA sequence encoding amino acid sequences derived from a wild type New World alphavirus nsP1, nsP2, nsP3 and nsP4 protein sequences. In other embodiments, the one or more nonstructural proteins are derived from different viruses.

In some embodiments, the self-replicating RNA molecule may have an RNA sequence encoding an nsP3 macro domain derived from a wild type alphavirus nsP3, and an nsP3 central domain derived from a wild type alphavirus nsP3. In various embodiments the macro and central domain(s) can both be derived from a New World wild type alphavirus nsP3 or can both be derived from an Old World wild type alphavirus nsP3 protein. In other embodiments, the macro domain can be derived from a New World wild type alphavirus macro domain and the central domain can be derived from an Old World wild type alphavirus central domain, or vice versa. The various domains can be of any sequence described herein.

In some embodiments, the self-replicating RNA molecule contains non VEEV nonstructural proteins nsP1, nsP2, nsP3 and nsP4.

The accumulated experimental evidence has demonstrated that replication/amplification of VEEV and other alphavirus genomes and their defective interfering (DI) RNAs is determined by three promoter elements: (i) the conserved 3'-terminal sequence element (3' CSE) and the following poly(A) tail; (ii) the 5' UTR, which functions as a key promoter element for both negative- and positive-strand RNA synthesis; and (iii) the 51-nt conserved sequence element (51-nt CSE), which is located in the nsP1-coding sequence and functions as an enhancer of alphavirus genome replication (Kim et al., PNAS, 2014, 111: 10708-10713, and references therein).

Any of the above-disclosed self-replicating RNA molecules can further include an unmodified 5' untranslated region (5'UTR).

Previous studies have demonstrated that during VEEV and Sindbis virus infections only a small portion of viral nonstructural proteins (nsPs) is colocalized with dsRNA replication intermediates. Thus, it appears that a large fraction of nsPs are not involved in RNA replication (Gorchakov R, et al. (2008) A new role for ns polyprotein cleavage in Sindbis virus replication. J Virol 82(13):6218-6231). This has provided an opportunity to exploit the under used ns proteins for amplification of the subgenomic RNAs encoding proteins of interest, which is normally transcribed from the subgenomic promoter and is not further amplified In some embodiments, a fragment of the nsP1 of the self-replicating RNA molecule of the disclosure is duplicated downstream of the 5'-UTR and upstream of the DLP.

In some embodiments the first 193 nucleotides of nsP1 are duplicated downstream of the 5' UTR and upstream of the DLP In some embodiment, a self-replicating RNA molecule comprises a modified 5' untranslated region (5'-UTR). For example, the modified 5'-UTR can comprise one or more nucleotide substitutions at position 1, 2, 4, or a combination thereof. Preferably, the modified 5'-UTR comprises a nucleotide substitution at position 2, more preferably, the modified 5'-UTR has a U→G substitution at position 2. Examples of such self-replicating RNA molecules are described in US Patent Application Publication US2018/0104359 and the International Patent Application Publication WO2018075235, the content of which is incorporated herein by reference in its entirety.

In some embodiments, the UTRs can be wild type New World or Old World alphavirus UTR sequences, or a sequence derived from any of them. The 5' UTR can be of any suitable length, such as about 60 nt or 50-70 nt or 40-80 nt. In some embodiments the 5' UTR can also have conserved primary or secondary structures (e.g. one or more stem-loop(s)) and can participate in the replication of alphavirus or of replicon RNA. The 3' UTR can be up to several hundred nucleotides, for example it can be 50-900 or 100-900 or 50-800 or 100-700 or 200 nt-700 nt. The '3 UTR also can have secondary structures, e.g. a step loop, and can be followed by a polyadenylate tract or poly-A tail.

The 5' and 3' untranslated regions can be operably linked to any of the other sequences encoded by the replicon. The UTRs can be operably linked to a promoter and/or sequence encoding a protein or peptide by providing sequences and spacing necessary for recognition and transcription of the other encoded sequences.

The GOI, e.g the CALR/JAK2 or the JAK2 epitope 2 polynucleotides of the disclosure can be expressed under the control of a subgenomic promoter. In certain embodiments, instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses. Subgenomic promoters range from 24 nucleotide (Sindbis virus) to over 100 nucleotides (Beet necrotic yellow vein virus) and are usually found upstream of the transcription start.

The self-replicating RNA molecules can have a 3' poly-A tail. It can also include a poly-A polymerase recognition sequence (e.g. AAUAAA) near its 3' end.

In those instances where the self-replicating RNA molecule is to be packaged into a recombinant alphavirus particle, it can contain one or more sequences, so-called packaging signals, which serve to initiate interactions with alphavirus structural proteins that lead to particle formation. In some embodiments, the alphavirus particles comprise RNA derived from one or more alphaviruses; and structural proteins wherein at least one of said structural proteins is derived from two or more alphaviruses.

In some embodiments, the self-replicating RNA molecule comprises a VEEV derived vector wherein the structural viral proteins (e.g. nucleocapsid protein C, and envelope proteins P62, 6K, and E1) are removed and replaced by the coding sequence of the CARL.JAK2 or the JAK2 epitope 2 polypeptides of the disclosure.

Other Viral Vectors and Recombinant Viruses

The viral vector comprising the polynucleotide of the disclosure may be derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{a}$ particles or copies of DNA in contrast to naked DNA doses of 50 μg or about $10^{15}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

The viral vector comprising the polynucleotide of the disclosure also include Retroviral vectors. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323).

The polynucleotides encoding the polypeptide of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Regulatory Elements

The polynucleotides encoding the polypeptides of the disclosure may be operably linked to one or more regulatory elements in the vector. The regulatory elements may comprise promoters, enhancers, polyadenylation signals, repressors and the like. As used herein, the term "operably linked" is to be taken in its broadest reasonable context and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499. Polyadenylation signals may be derived from SV40 or bovine growth hormone (BGH).

The self-replicating RNA vectors comprising the polynucleotide encoding the polypeptide of the disclosure can further comprise any regulatory elements to establish conventional function(s) of the vector, including but not limited to replication and expression of the polypeptide of the disclosure encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., the polypeptides of the disclosure) from a start codon to a stop codon. Regulatory elements of the expression cassette can be operably linked to a polynucleotide sequence encoding the polypeptides of interest. Any components suitable for use in an expression cassette described herein can be used in any combination and in any order to prepare vectors of the application.

The vector can comprise a promoter sequence, preferably within an expression cassette, to control expression of the polypeptides of the disclosure. The term "promoter" is used in its conventional sense and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including viral, bacterial, fungal, plants, insects, and animals. A promoter can be a homologous promoter (i.e., derived from the same genetic source as the vector) or a heterologous promoter (i.e., derived from a different vector or genetic source). Preferably, the promoter is located upstream of the polynucleotide encoding the polypeptides of the disclosure within an expression cassette. For example, in a self-replicating RNA, the promoter can be a subgenomic promoter for the alphavirus.

In a self-replicating RNA, the vector can further comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., the polypeptides of the disclosure) within an expression cassette of the vector. Enhancer sequences are regulatory DNA sequences that, when bound by transcription factors, enhance the transcription of an associated gene. An enhancer sequence is preferably located upstream of the polynucleotide sequence encoding the polypeptides of the disclosure, but downstream of a promoter sequence within an expression cassette of the vector.

Any enhancer sequence known to those skilled in the art in view of the present disclosure can be used.

Any of the components or sequences of the self-replicating RNA vector of the disclosure can be functionally or operably linked to any other of the components or sequences. The components or sequences of the self-replicating RNA molecule can be operably linked for the expression of the at least one protein or peptide (or biotherapeutic) in a host cell or treated organism and/or for the ability of the replicon to self-replicate.

A promoter or UTR operably linked to a coding sequence is capable of effecting the transcription and expression of the coding sequence when the proper enzymes are present. The promoter need not be contiguous with the coding sequence, so long as it functions to direct the expression thereof. Thus, an operable linkage between an RNA sequence encoding a protein or peptide and a regulatory sequence (for example, a promoter or UTR) is a functional link that allows for expression of the polynucleotide of interest. Operably linked can also refer to sequences such as the sequences encoding the RdRp (e.g. nsP4), nsP1-4, the UTRs, promoters, and other sequences encoding in the RNA replicon, are linked so that they enable transcription and translation of the biotherapeutic molecule and/or replication of the replicon. The UTRs can be operably linked by providing sequences and spacing necessary for recognition and translation by a ribosome of other encoded sequences.

A molecule is functional or biologically active if it performs at least 50% of the same activity as its natural (or wild type), corresponding molecule, but a functional molecule can also perform at least 60% or at least 70% or at least 90% or at least 95% or 100% of the same activity as its natural (or wild type) corresponding molecule. The self-replicating RNA molecules can also encode an amino acid sequence derived from or based on a wild type alphavirus amino acid sequence, meaning that they have at least 60% or at least 65% or at least 68% or at least 70% or at least 80% or at least 70% or at least 80% or at least 90% or at least 95% or at least 97% or at least 98% or at least 99% or 100% or 80-99% or 90-100% or 95-99% or 95-100% or 97-99% or 98-99% sequence identity with an amino acid sequence (which can be a corresponding sequence) encoded by a wild type RNA alphavirus genome, which can be a New World or Old World alphavirus genome. Sequences derived from other sequences can be up to 5% or up to 10% or up to 20% or up to 30% longer or shorter than the original sequence. In any of the embodiments the sequence identity can be at least 95% or at least 97% or at least 98% or at least 99% or 100% for any nucleotide sequence encoding (or amino acid sequence having) a G3BP or FXR binding site thereon. These sequences can also be up to 5% or up to 10% or up to 20% or up to 30% longer or shorter than the original sequence.

Host Cells

The disclosure also provides a host cell comprising any of the above vectors of the disclosure. In some embodiments, the host cell is prokaryotic or eukaryotic host cell. In some embodiments, the host cell is PER.C6, PER.C6 TetO, a chicken embryo fibroblast (CEF), CHO, HEK293, HT-1080, HKB-11, CAP, HuH-7, or Age1 cell line.

Compositions

The disclosure also provides compositions comprising any of the polynucleotides, any of the polypeptides, and any of the vectors disclosed herein. In some embodiments, the compositions may comprise a vector comprising any of the nucleotides disclosed herein, wherein the vector is selected from Ad26, GAd20, MVA, or a self-replicating RNA molecule.

Any of the compositions described above may comprise or may be formulated into a pharmaceutical composition comprising the composition and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

The composition may comprise one or more adjuvants. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine). Other non-limiting examples of adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be used include lectins, growth factors, cytokines, and lymphokines such as alpha-interferon, gamma interferon, platelet derived growth factor (PDGF), granulocyte-colony stimulating factor (GCSF), granulocyte macrophage colony stimulating factor (GMCSF), tumor necrosis factor (TNF), epidermal growth factor (EGF), IL-1, IL-2, IL-4, IL-6, IL-8, IL-10, IL-12 or TLR agonists, and particulate adjuvants (e g immunostimulatory complexes (ISCOMS).

Nanoparticles

In some embodiments, the compositions may comprise nanoparticles. Any of the polynucleotides of the disclosure may be attached to or in contact with nanoparticles for delivery to a subject. Delivery of any of the polynucleotides or polypeptides of the disclosure using nanoparticles may eliminate the need to include a virus or an adjuvant in the vaccine composition. The polynucleotides of the disclosure may be DNA or RNA. The nanoparticles may contain immune danger signals that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells.

The nanoparticles are typically from about 1 nm to about 100 nm in diameter, such as about 20 nm to about 40 nm. Nanoparticles with a mean diameter of 20 to 40 nm may facilitate uptake of the nanoparticle to the cytosol (see. e.g. WO2019/135086). Exemplary nanoparticles are polymeric nanoparticles, inorganic nanoparticles, liposomes, lipid nanoparticles (LNP), an immune stimulating complex (ISCOM), a virus-like particle (VLP), or a self-assembling protein. The nanoparticles may be calcium phosphate nanoparticles, silicon nanoparticles or gold nanoparticles. The polymeric nanoparticles may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene or one or more natural polymers such as a polysaccharide, for example pullulan, alginate, inulin, and chitosan. The use of a polymeric nanoparticles may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may also form hydrogel nanoparticles, hydrophilic three-dimensional polymer networks with favorable properties including flexible mesh size, large surface area for multivalent conjugation, high water content, and high loading capacity for antigens. Polymers such as Poly (L-lactic acid) (PLA), PLGA, PEG, and polysaccharides are suitable for forming hydrogel nanoparticles. Inorganic nanoparticles typically have a rigid structure and comprise a shell in which an antigen is encapsulated or a core to which the antigen may be covalently attached. The core may comprise one or more atoms such as gold (Au), silver (Ag), copper (Cu) atoms, Au/Ag, Au/Cu, Au/Ag/Cu, Au/Pt, Au/Pd or Au/Ag/Cu/Pd or calcium phosphate (CaP).

In some embodiments, the nanoparticles may be liposomes. Liposomes are typically formed from biodegradable, non-toxic phospholipids and comprise a self-assembling phospholipid bilayer shell with an aqueous core. Liposomes may be an unilamellar vesicle comprising a single phospholipid bilayer, or a multilamellar vesicle that comprises several concentric phospholipid shells separated by layers of water. As a consequence, liposomes may be tailored to incorporate either hydrophilic molecules into the aqueous core or hydrophobic molecules within the phospholipid bilayers. Liposomes may encapsulate polynucleotides or the polypeptides or fragments thereof of the disclosure within the core for delivery. Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. The liposomes may comprise a targeting molecule for targeting liposome complexes to a particular cell type. Targeting molecule may comprise a binding partner (e.g., a ligand or receptor) for a biomolecule (e.g., a receptor or ligand) on the surface of a blood vessel or a cell found in a target tissue. Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028). Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The self-replicating RNA molecules and/or compositions comprising the same can also be formulated as a nanoparticle using a combination of polymers, lipids, and/or other biodegradable agents, such as, but not limited to, calcium phosphate, polymers. Components can be combined in a core-shell, hybrid, and/or layer-by-layer architecture, to allow for fine-tuning of the nanoparticle so that delivery of the molecules and/or compositions of the disclosure can be enhanced.

In some embodiments, the nanoparticles can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powder like form. This film is covered with an aqueous solution of the polypeptide or polynucleotide and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium may comprise the nucleic acid at a concentration which is desired in the interior volume of the liposomes in the final liposome suspension. Suitable lipids that may be used to form multilamellar vesicles include DOTMA (Feigner, et al., 1987, Proc. Natl. Acad. Sci. USA 84: 7413-7-7417), DOGS or Transfectain™ (Behr, et al., 1989, Proc. Natl. Acad. Sci. USA 86: 6982-6986), DNERIE or DORIE (Feigner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

In some embodiments, the nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*).

In some embodiments, the nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

Other molecules suitable for complexing with the polynucleotides of the disclosure include cationic molecules, such as, polyamidoamine (Haensler and Szoka, 1993, Bioconjugate Chem. 4: 372-379), dendritic polylysine (Int. Pat. Publ. No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717).

In some embodiments, the self-replicating RNA molecule can be packaged or encapsulated in cationic molecules, such as, polyamidoamine (Haensler and Szoka, 1993, Bioconjugate Chem. 4: 372-379), dendritic polylysine (Int. Pat. Publ.

No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717), dendrimers (see, e.g., WO1996/19240), or polyethylenimine (PEI) (see, e.g., Sun et al., 2014, Mol Med Rep. 10(5):2657-2662).

The disclosed self-replicating RNA molecules and/or compositions comprising the self-replicating RNA molecules encoding any of the polypeptides of the disclosure can be encapsulated using one or more liposomes, lipoplexes, and/or lipid nanoparticles. Liposomes are artificially prepared vesicles which can primarily be composed of a lipid bilayer and can be used as a delivery vehicle for the administration of polynucleotides and self-replicating RNA molecules. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the polynucleotides and self-replicating RNA molecules disclosed herein.

The formation of liposomes can depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, the self-replicating RNA molecule is encapsulated in, bound to or adsorbed on a liposome, a lipoplex, a lipid nanoparticle, or combinations thereof, preferably the self-replicating RNA molecule is encapsulated in a lipid nanoparticle.

In some embodiments, the self-replicating RNA molecule encoding the any of the polypeptides of the disclosure can be fully encapsulated within the lipid portion of the particle, thereby protecting the RNA from nuclease degradation. "Fully encapsulated" means that the RNA is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In some embodiments, the self-replicating RNA molecules and/or compositions of the disclosure comprising the same can be formulated in a lipid vesicle which can have crosslinks between functionalized lipid bilayers. In some embodiments, the self-replicating RNA molecules and/or compositions of the disclosure can be formulated in a lipid-polycation complex. The formation of the lipid-polycation complex can be accomplished by methods known in the art. As a non-limiting example, the polycation can include a cationic peptide or a polypeptide such as, but not limited to, polylysine, polyornithine and/or polyarginine and the cationic peptides. In some embodiments, the self-replicating RNA molecules and/or compositions disclosed herein can be formulated in a lipid-polycation complex which can further include a neutral lipid such as, but not limited to, cholesterol or dioleoyl phosphatidylethanolamine (DOPE). The lipid nanoparticle formulation can be influenced by, but not limited to, the selection of the cationic lipid component, the degree of cationic lipid saturation, the nature of the PEGylation, ratio of all components and biophysical parameters such as size.

In some embodiments, the self-replicating RNA molecule disclosed herein is encapsulated in a lipid nanoparticle (LNP) as shown in FIG. 20. Lipid nanoparticles typically comprise four different lipids—an ionizable lipid, a neutral helper lipid, cholesterol, and a diffusible polyethylene glycol (PEG) lipid. LNPs are similar to liposomes but have slightly different function and composition. LNPs are designed toward encapsulating polynucleotides, such as DNA, mRNA, siRNA and sRNA. Traditional liposomes contain an aqueous core surrounded by one or more lipid bilayers. LNPs may assume a micelle-like structure, encapsulating polynucleotides in a non-aqueous core. LNPs typically contain a cationic lipid, a non-cationic lipid, and a lipid that prevents aggregation of the particle (e.g., a PEG-lipid conjugate). LNPs are useful for systemic applications, as they exhibit extended circulation lifetimes following intravenous (i.e.) injection and accumulate at distal sites (e.g., sites physically separated from the administration site). The LNPs may have a mean diameter of about 50 nm to about 150 nm, such as about 60 nm to about 130 nm, or about 70 nm to about 110 nm, or about 70 nm to about 90 nm, and are substantially nontoxic. Preparation of polynucleotide loaded LNPs are disclosed in, e.g., U.S. Pat. Nos. 5,976,567; 5,981,501; 6,534,484; 6,586,410; 6,815,432; and PCT Publication No. WO 96/40964. Polynucleotide containing LNPs are described for example in WO2019/191780.

In some embodiments, the lipid nanoparticles comprise a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may encapsulate at least 1, 2, 3, 4, 5, 6, 7, 8, 9, 10, or more self-replicating RNA molecules that encode for one or more polypeptides.

In some embodiments, the LNP formulations comprising a polycationic composition can be used for the delivery of the self-replicating RNA molecules described herein in vivo and/or ex vitro. The disclosure further provides a LNP formulations comprising a cationic lipid.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the pKa of the cationic lipid and is substantially neutral at a pH above the pKa. The cationic lipids may also be termed titratable cationic lipids. In some embodiments, the cationic lipids comprise: a protonatable tertiary amine (e.g., pH-titratable) head group; C18 alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DIen-C2K-DMA, γ-DLen-C2K-DMA, DLin-M-C2-DMA (also known as MC2), DLin-M-C3-DMA (also known as MC3) and (DLin-MP-DMA)(also known as 1-B11).

The disclosure also provides an encapsulated self-replicating RNA molecule, wherein the cationic lipid comprises a protonatable tertiary amine. In some embodiments, the cationic lipid is di((Z)-non-2-en-1-yl) 8,8'-((((2-(dimethylamino)ethyl)thio)carbonyl)azanediyl) dioctanoate.

In some embodiments, the cationic lipid compounds are relatively non-cytotoxic. The cationic lipid compounds may be biocompatible and biodegradable. The cationic lipid may have a pKa in the range of approximately 5.5 to approximately 7.5, more preferably between approximately 6.0 and approximately 7.0.

The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the self-replicating RNA molecule to be delivered, they can be synthesized from commercially available starting materials; and/or they are pH responsive and can be engineered with a desired pKa.

Lipid nanoparticle formulations can be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and can be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain. The lipid particles may comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g, HO-PEG-S, HO-PEG-S-NHS, HO-PEG-NH2).

The PEG moiety of the PEG-lipid conjugates described herein may comprise an average molecular weight ranging from 550 daltons to 10,000 daltons. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof. In some embodiments, the PEG conjugated lipid is a DMG-PEG-2000.

The self-replicating RNA molecules can also be formulated in a particle comprising non-cationic lipids. Suitable non-cationic lipids include, for example, neutral uncharged, zwitterionic, or anionic lipids capable of producing a stable complex. Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoylo-leoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), phosphatidylethanolamine phosphatidylethanolamine phosphatidylethanolamine phosphatidylethanolamine, phosphatidylethanolamine, phosphatidylethanolaminedipalmitoyl-dimyristoyl-distearoyl-monomethyl-dimethyl-dielaidoyl-stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5a-cholestanol, 5a-coprostanol, cholesteryl-(2'-hydroxy)-ethyl ether, cholesteryl-(4'-hydroxy)-butyl ether, and 6-ketocholestanol; non-polar analogues such as 5a-cholestane, cholestenone, 5a-cholestanone, 5a-cholestanone, and cholesteryl decanoate; and mixtures thereof. In preferred embodiments, the cholesterol derivative is a polar analogue such as cholesteryl-(4'-hydroxy)-butyl ether. In some embodiments, the phospholipid is DSPC. In some embodiments, the non-cationic lipid present in lipid particles comprises or consists of a mixture of one or more phospholipids and cholesterol or a derivative thereof. In some embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, LNPs may comprise 30-70% cationic lipid compound, 0-60% cholesterol, 0-30% phospholipid, and 1-10% polyethylene glycol (PEG).

In some embodiments, the cationic lipid, zwitterion lipid, cholesterol and conjugated lipid are combined in a molar ratio of 50:7:40:3, respectively in the lipid nanoparticle In some embodiments, the LNP formulations described herein can additionally comprise a permeability enhancer molecule.

In some embodiments, the nanoparticle formulations can be a carbohydrate nanoparticle comprising a carbohydrate carrier and self-replicating RNA molecule. As a non-limiting example, the carbohydrate carrier can include, but is not limited to, an anhydride-modified phytoglycogen or glycogen-type material, phtoglycogen octenyl succinate, phytoglycogen beta-dextrin, and anhydride-modified phytoglycogen beta-dextrin.

Kits

The disclosure also provides a kit comprising one or more compositions, one or more polynucleotides, one or more polypeptides or one or more vectors of the disclosure. The disclosure also provides a kit comprising one or more recombinant viruses of the disclosure. The kits may be used to facilitate performing the methods described herein. In some embodiments, the kit further comprises reagents to facilitate entry of the vaccines of the disclosure into a cell, such as lipid-based formulations or viral packaging materials.

In some embodiments, the kit comprises one or more Ad26 vectors comprising any of the polynucleotides of the disclosure. In some embodiments, the kit comprises one or more MVA vectors comprising any of the polynucleotides of the disclosure. In some embodiments, the kit comprises one or more GAd20 vectors comprising any of the polynucleotides of the disclosure. In some embodiments, the kit comprises one or more self-replicating RNA molecules comprising any of the polynucleotides of the disclosure.

In some embodiments, the kit comprises an Ad26 vector of the disclosure and a MVA vector of the disclosure. In some embodiments, the kit comprises a GAd20 vector of the disclosure and a MVA vector of the disclosure. In some embodiments, the kit comprises an Ad26 vector of the disclosure and a Gad20 vector of the disclosure. In some embodiments, the kit comprises a self-replicating RNA molecule of the disclosure and a Gad20 vector of the disclosure. In some embodiments, the kit comprises a self-replicating RNA molecule of the disclosure and a MVA vector of the disclosure. In some embodiments, the kit comprises a self-replicating RNA molecule of the disclosure and an Ad26 vector of the disclosure. In some embodiments, the kit comprises one or more polynucleotides of the disclosure. In some embodiments, the kit comprises one or more polypeptides of the disclosure. In some embodiment, the kit comprises one or more cells of the disclosure.

Other Molecules

Peptide-HLA Complex

The disclosure also provides a protein complex comprising human leukocyte antigen (HLA) and a polypeptide comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 9, SEQ ID NO: 10, SEQ ID NO: 11, SEQ ID NO: 11, SEQ ID NO:12, SEQ ID NO:13, SEQ ID NO:14, SEQ ID NO:15, SEQ ID NO:28, SEQ ID NO: 31, or a fragment thereof.

In some embodiments, the fragment is an immunogenic fragment of any of the polypeptides disclosed herein. In some embodiments, the fragment is between about 6 and 25 amino acids long. In some embodiments, the fragment is about 6 amino acids long. In some embodiments, the fragment is about 7 amino acids long. In some embodiments, the fragment is about 8 amino acids long. In some embodiments, the fragment is about 9 amino acids long. In some embodiments, the fragment is about 10 amino acids long. In some embodiments, the fragment is about 11 amino acids long. In some embodiments, the fragment is about 12 amino acids long. In some embodiments, the fragment is about 13 amino acids long. In some embodiments, the fragment is about 14 amino acids long. In some embodiments, the fragment is about 15 amino acids long. In some embodiments, the fragment is about 16 amino acids long. In some embodiments, the fragment is about 17 amino acids long. In some embodiments, the fragment is about 18 amino acids long. In some embodiments, the fragment is about 19 amino acids long. In some embodiments, the fragment is about 20 amino acids long. In some embodiments, the fragment is about 21 amino acids long. In some embodiments, the fragment is about 22 amino acids long. In some embodiments, the fragment is about 23 amino acids long. In some embodiments, the fragment is about 24 amino acids long. In some embodiments, the fragment is about 25 amino acids long.

In some embodiments, HLA is class I HLA or class II HLA.

In some embodiments, HLA is HLA-A*02:01, HLA-A*03:01, HLA-B*07:02 and HLA-C*07:02, or any combination thereof.

In some embodiments, the protein complex is conjugated to a detection agent or a cytotoxic agent.

The disclosure also provides an isolated proteinaceous molecule that specifically binds the polypeptide of the disclosure or the complex of the HLA and the polypeptide.

Proteinaceous Molecules

In some embodiments, the proteinaceous molecule is an antibody, an alternative scaffold, a chimeric antigen receptor (CAR) or a T cell receptor (TCR).

In some embodiments, the proteinaceous molecule is an antibody.

In some embodiments, the proteinaceous molecule is an alternative scaffold.

In some embodiments, the proteinaceous molecule is a chimeric antigen receptor (CAR).

In some embodiments, the proteinaceous molecule is a T cell receptor (TCR).

Binding of the proteinaceous molecule to the polypeptide or the peptide-HLA complex of the disclosure may be determined experimentally using any suitable method. Such methods may utilize ProteOn XPR36, Biacore 3000 or KinExA instrumentation, ELISA or competitive binding assays known to those skilled in the art. The measured binding may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. "Insubstantial" refers to binding that is 100-fold less when compared to the measured binding of the proteinaceous molecule to the polypeptides or HLA/peptide the disclosure.

Antibodies

Antibodies binding the polypeptides or HLA/peptide complexes may be generated using known methods. For example, the hybridoma method of Kohler and Milstein, Nature 256:495, 1975 may be used to generate monoclonal antibodies. In the hybridoma method, a mouse or other host animal, such as a hamster, rat or monkey, is immunized with one or more polypeptides or fragments thereof, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding and affinity.

Various host animals may be used to produce the antibodies. For example, Balb/c mice, rats or chickens may be used to generate antibodies containing the VH/VL pair, and llama and alpaca may be used to generated heavy chain only (VHH) antibodies using standard immunization protocols. The antibodies made in non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) and superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or any combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www.trianni_com) and Ablexis (www_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions. The antibodies of the disclosure may be isolated for example from phage display library expressing antibody heavy and light chain variable regions as polypeptides with bacteriophage pIX coat protein. The libraries may be screened for phage binding to the desired antigen and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081.

Preparation of immunogenic antigens and monoclonal antibody production may be performed using any suitable technique, such as recombinant protein production or by chemical synthesis of peptides. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Alternative Scaffolds

Alternative scaffolds (also referred to as antibody mimetics) that bind the polypeptides or HLA/peptide complexes may be generated using various scaffolds known in the art and described herein. Alternative scaffolds may be monobodies, designed to incorporate the fibronectin type III domain (Fn3) of fibronectin or tenascin as a protein scaffold (U.S. Pat. Nos. 6,673,901; 6,348,584) or synthetic FN3 domains such as tencon as described in U.S. Pat. Publ. No. 2010/0216708 and U.S. Pat. Pub. No. 2010/0255056. Additional alternative scaffolds comprise Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. Alternative scaffolds are single chain polypeptidic frameworks that contains a highly structured core associated with variable domains of high conformational tolerance allowing insertions, deletions, or other substitutions within the variable domains. Libraries introducing diversity to one or more variable domains, and in some instances to the structured core, may be generated using known protocols and the resulting libraries may be screened for binding to the neoantigen of the disclosure, and the identified binders may be further characterized for their specificity using known methods. Alternative scaffold may be derived from Protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, A., "Alternative Non-Antibody Scaffolds for Molecular Recognition," *Curr. Opin. Biotechnol.* 18:295-304 (2005); Hosse et al., "A New Generation of Protein Display Scaffolds for Molecular Recognition," *Protein Sci.* 15:14-27 (2006); Nicaise et al., "Affinity Transfer by CDR Grafting on a Nonimmunoglobulin Scaffold," *Protein Sci.* 13:1882-1891 (2004); Nygren and Uhlen, "Scaffolds for Engineering Novel Binding Sites in Proteins," *Curr. Opin. Struc. Biol.* 7:463-469 (1997).

Chimeric Antigen Receptors (CAR)

CARs may be generated that bind the polypeptides or HLA/peptide complexes. Chimeric antigen receptors (CARs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

The CAR typically comprises an extracellular domain that binds the antigen, an optional linker, a transmembrane domain, and a cytosolic domain comprising a costimulatory domain and/or a signaling domain.

The extracellular domain of the CAR may contain any polypeptide that binds the desired antigen. The extracellular domain may comprise a scFv, a portion of an antibody or an alternative scaffold. The CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of the CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD19, IL2R beta, IL2R gamma, IL7R a, ITGA1, VLA1, CD49a, ITGA4, IA4, CD49D, ITGA6, VLA-6, CD49f, ITGAD, CDI 1d, ITGAE, CD103, ITGAL, CDI 1a, LFA-1, ITGAM, CDI 1b, ITGAX, CDI 1c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMF1), CD152 (CTLA4), CD223 (LAG3), CD270 (HVEM), CD278 (ICOS), DAP10, LAT, NKD2C SLP76, TRIM, and ZAP70.

The intracellular signaling domain of the CAR may be derived from the signaling domains of for example CD3ζ, CD3ε, CD22, CD79a, CD66d or CD39. "Intracellular signaling domain," refers to the part of the CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of the CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin.

Exemplary CARs that may be used are for example CAR that contains an extracellular domain that binds HLA in complex with a fragment of the CALR/JAK2 polypeptides of the disclosure, CD8 transmembrane domain and CD3ζ signaling domain. Other exemplary CARs contain CD8 or CD28 transmembrane domain, CD28, 41BB or OX40 costimulatory domain and CD3ζ signaling domain.

The CARs are generated by standard molecular biology techniques. The extracellular domain that binds the desired antigen may be derived from antibodies or their antigen binding fragments generated using the technologies described herein.

T-Cell Receptor (TCR)

TCRs may be generated that bind the HLA/peptide complexes of the disclosure. The TCRs may be identified based on T-cell binding to the HLA/peptide complex, followed by sequencing of the TCR. The identified TCR may be identified from αβ T cells. The identified TCRs may be further engineered to improve their affinity, stability, solubility or the like. For example, TCRs may be cysteine stabilized, expressed as soluble TCRs, as single chain TCRs, as fusion with N-terminal or C-terminal epitope tags, engineered to improve stability with mutations in hydrophobic core, such as positions 11, 13, 19, 21, 53, 76, 89, 91 or 94 of the a chain, domain swapped with a and p chain variable and/or constant domains swapped as described in U.S. Pat. Nos. 7,329,731, 7,569,664, 9,133,264, 9,624,292, US2016/0130319 and U.S. Pat. No. 9,884,075.

Methods of Using any of the Compositions Herein

Provided herein are methods for treating a subject with the compositions disclosed herein. The methods provided herein comprise administering any of the polynucleotides, polypeptides, vectors, and compositions of the disclosure. The polynucleotides, polypeptides, vectors, compositions and administration regimens of the disclosure may be used to treat, prevent or reduce the risk of a clinical condition.

In some embodiments, the clinical condition is a cancer, a myeloproliferative disease, or a cardiovascular disease.

In some embodiments, the clinical condition is a cancer selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

In some embodiments, the clinical condition is a myeloproliferative disease selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

In some embodiments, the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis or a clonal hematopoiesis.

In some embodiments, the subject is Philadelphia chromosome negative. In some embodiments, the subject is treatment naïve. In some embodiments, the subject has become or is suspected to become resistant or refractory to one or more anti-cancer therapeutic. In some embodiments, the subject is not eligible for stem cell transplantation. In some embodiments, the subject has been treated with stem cell transplantation.

In some embodiments, a method of treating, preventing, reducing a risk of onset or delaying the onset of a clinical condition characterized by an expression of JAK2V617F and/or CALR exon 9 mutant in a subject comprises administering to the subject in need thereof any of the compositions disclosed herein, and wherein the administration comprises one or more administrations of the composition. In some embodiments, the clinical condition is a cancer, a myeloproliferative disease, or a cardiovascular disease.

In some embodiments, a method of inducing an immune response in a subject carrying JAK2V617F and/or CALR exon 9 mutation comprises administering to the subject in need thereof any of the compositions disclosed herein, and wherein the administration comprises one or more administrations of the composition.

In some embodiments, a method of treating or preventing a myeloproliferative disease in a subject comprises administering to the subject in need thereof any of the compositions disclosed herein, and wherein the administration comprises one or more administrations of the composition. In some embodiments, the myeloproliferative disease is selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

In some embodiments, a method of treating cancer in a subject comprises administering to the subject in need thereof any of the compositions disclosed herein, and wherein the administration comprises one or more administrations of the composition. In some embodiments, the cancer is selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

In some embodiments, a method of treating a cardiovascular disease in a subject comprises administering to the subject in need thereof a composition comprising any of the compositions disclosed herein, and wherein the administration comprises one or more administrations of the composition. In some embodiments, the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis, and a clonal hematopoiesis.

In some embodiments, the methods disclosed herein comprise administering to the subject in need thereof a composition comprising a polypeptide that comprises at least two or more epitope sequences or a polynucleotide encoding a polypeptide that comprises at least two or more epitope sequences or a vector comprising a polynucleotide encoding for a polypeptide that comprises at least two or more epitope sequences, wherein the epitope sequences are selected from:

CALR epitope of SEQ ID NO: 1 (MKDKQDEEQRTRRMMRTKMRMRRMRR TRRKMRRKMSPARPRTSCREACLQGWTE) or having at least 90% sequence identity to SEQ ID NO: 1;

CALR epitope of SEQ ID NO: 2 (EEAEDNCRRMMRTK) or having at least 90% sequence identity to SEQ ID NO: 2;

JAK2 epitope of SEQ ID NO: 4 (KLSHKHLVLNYGVCFCGDENILVQEFVKFG) or having at least 90% sequence identity to SEQ ID NO: 4;

JAK2 epitope of SEQ ID NO: 5 (VLNYGVCFC) or at least 90% sequence identity to SEQ ID NO: 5;

JAK2 epitope of SEQ ID NO: 6 (FCGDENILV) or having at least 90% sequence identity to SEQ ID NO: 6; and combinations thereof.

In any of the methods disclosed herein, the composition that is administered to a subject may comprise a vector selected from an adenovirus vector, an alphaviral vector, a poxvirus vector, an adeno-associated virus vector, a retrovirus vector, a self-replicating RNA molecule, and a combination thereof. In some embodiments, the vector is selected from Ad26 vector, MVA vector, GAd20 vector, a self-replicating RNA molecule, and combinations thereof.

In some embodiments, the methods disclosed herein comprise one or more administrations of the compositions provided in the disclosure. For example, the method comprises a first administration followed by a second administration, with a time period between the two administrations.

In some embodiments, the first administration and the second administration may comprise the same or different compositions. For example, the first administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the second administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration and the second administration are administered once in a lifetime of the subject. In some embodiments, first administration and the second administration are administered two or more times in the lifetime of the subject.

In some embodiments, the time period between the first administration and the second administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the first administration and the second administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the first administration and the second administration is about 2 weeks.

In some embodiments, the time period between the first administration and the second administration is about 4 weeks.

In some embodiments, the first administration and the second administration constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following examples are provided to further describe some of the embodiments disclosed herein. The examples are intended to illustrate, not to limit, the disclosed embodiments. In some embodiments, the first administration and second administration can comprise any combination of vectors provided in Table 1 or any combination of epitopes provided in Table 2 below.

TABLE 1

Vector composition in first and second administration

| First administration | Second administration |
|---|---|
| Ad26 | MVA |
| Ad26 | GAd20 |
| Ad26 | Self-replicating RNA molecule |
| Ad26 | Ad26 |
| MVA | Ad26 |
| MVA | GAd20 |
| MVA | Self-replicating RNA molecule |
| MVA | MVA |
| GAd20 | Ad26 |
| GAd20 | MVA |
| GAd20 | Self-replicating RNA molecule |
| GAd20 | GAd20 |
| Self-replicating RNA molecule | Ad26 |
| Self-replicating RNA molecule | MVA |
| Self-replicating RNA molecule | GAd20 |
| Self-replicating RNA molecule | Self-replicating RNA molecule |

TABLE 2

Epitopes present in the vector composition of the first and second administration.

| Vaccine cohort | First administration | SEQ ID NO: | Second administration | SEQ ID NO: |
|---|---|---|---|---|
| 1 | CALR1 epitope 1 and 2 + JAK2 epitope 2 | 1, 2, 6 | CALR1 epitope 1 and 2 + JAK2 epitope 2 | 1, 2, 6 |
| 2 | CALR1 epitope 1 and 2 + JAK2 epitope 2 | 1, 2, 6 | CALR1 epitope 1 and 2 + JAK2 epitope 2 + JAK2 epitope 1 | 1, 2, 6, 5 |
| 3 | CALR-JAK2-2x9mer | 12 | CALR-JAK2-2x9mer | 12 |
| 4 | CALR-JAK2-30mer | 13 | CALR-JAK2-30mer | 13 |
| 5 | LS_CALR-JAK2-2x9mer | 10 | LS_CALR-JAK2-2x9mer | 10 |
| 6 | LS_CALR-JAK2-2x9mer | 10 | TCE_CALR-JAK2-2x9mer | 31 |
| 7 | LS_CALR-JAK2-30mer | 11 | LS_CALR-JAK2-30mer | 11 |
| 8 | TCE_CALR-JAK2-2x9mer | 31 | TCE_CALR-JAK2-2x9mer | 31 |
| 9 | JAK2 epitope 2 | 6 | JAK2 epitope 2 | 6 |
| 10 | CALR-JAK2-2x9mer | 12 | JAK2 epitope 2 | 6 |
| 11 | CALR-JAK2-30mer | 13 | JAK2 epitope 2 | 6 |
| 9 | JAK2epitope2.AAY. JAK2epitope2 | 28 | JAK2epitope2.AAY. JAK2epitope2 | 28 |

TABLE 2-continued

Epitopes present in the vector composition of the first and second administration.

| Vaccine cohort | First administration | SEQ ID NO: | Second administration | SEQ ID NO: |
|---|---|---|---|---|
| 10 | CALR-JAK2-2x9mer | 12 | JAK2epitope2.AAY. JAK2epitope2 | 28 |
| 11 | CALR-JAK2-30mer | 13 | JAK2epitope2.AAY. JAK2epitope2 | 28 |

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ II) NO: 2, and JAK2 epitope of SEQ II) NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26 vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Third Administration

In some embodiments, any of the methods disclosed herein may further comprise a third administration. For example, the method may comprise a first administration, a second administration, followed by a third administration, with a time period between each administration.

In some embodiments, the first administration, second administration, and third administration may comprise the same or different compositions. For example, the first administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the second administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the third administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration, the second administration, and the third administration are administered once in a lifetime of the subject. In some embodiments, the first, second, and third administration are administered two or more times in the lifetime of the subject.

In some embodiments, the time period between the second administration and the third administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the second administration and the third administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the second administration and the third administration is about 6 weeks.

In some embodiments, the time period between the second administration and the third administration is about 8 weeks.

In some embodiments, the first administration, second administration, and third administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following examples are provided to further describe some of the embodiments disclosed herein. The first, second, and third administrations used in the methods disclosed herein can comprise any combination of the epitopes and compositions provided in Table 3 and Table 4 below.

TABLE 3

Epitopes present in the vector composition of first, second, and third administration

| Vaccine cohort | First administration | SEQ ID NO: | Second administration | SEQ IDs NO: | Third administration | SEQ ID NO: |
|---|---|---|---|---|---|---|
| 1 | CALR1 epitope 1 and 2 + JAK2 epitope 2 | 1, 2, 6 | CALR1 epitope 1 and 2 + JAK2 epitope 2 | 1, 2, 6 | CALR1 epitope 1 and 2 + JAK2 epitope 2 | 1, 2, 6 |
| 2 | CALR1 epitope 1 and 2 + JAK2 epitope 2 | 1, 2, 6 | CALR1 epitope 1 and 2 + JAK2 epitope 2 + JAK2 epitope 1 | 1, 2, 6, 5 | CALR1 epitope 1 and 2 + JAK2 epitope 2 + JAK2 epitope 1 | 1, 2, 6, 5 |
| 3 | CALR-JAK2-2x9mer | 12 | CALR-JAK2-2x9mer | 12 | CALR-JAK2-2x9mer | 12 |
| 4 | CALR-JAK2-30mer | 13 | CALR-JAK2-30mer | 13 | CALR-JAK2-30mer | 13 |
| 5 | LS_CALR-JAK2-2x9mer | 10 | LS_CALR-JAK2-2x9mer | 10 | LS_CALR-JAK2-2x9mer | 10 |
| 6 | LS_CALR-JAK2-2x9mer | 10 | TCE_CALR-JAK2-2x9mer | 31 | TCE_CALR-JAK2-2x9mer | 31 |
| 7 | LS_CALR-JAK2-30mer | 11 | LS_CALR-JAK2-30mer | 11 | LS_CALR-JAK2-30mer | 11 |
| 8 | TCE_CALR-JAK2-2x9mer | 31 | TCE_CALR-JAK2-2x9mer | 31 | TCE_CALR-JAK2-2x9mer | 31 |
| 9 | JAK2 epitope 2 | 6 | JAK2 epitope 2 | 6 | JAK2 epitope 2 | 6 |

TABLE 4

Vector composition in first, second and third administration

| First administration | Second administration | Thrid administration |
|---|---|---|
| Ad26 | Ad26 | Ad26 |
| Ad26 | Ad26 | MVA |
| Ad26 | Ad26 | GAd20 |
| Ad26 | Ad26 | Self-replicating RNA molecule |
| Ad26 | MVA | Ad26 |
| Ad26 | MVA | MVA |
| Ad26 | MVA | GAd20 |
| Ad26 | MVA | Self-replicating RNA molecule |
| Ad26 | GAd20 | Ad26 |
| Ad26 | GAd20 | MVA |
| Ad26 | GAd20 | GAd20 |
| Ad26 | GAd20 | Self-replicating RNA molecule |
| Ad26 | Self-replicating RNA molecule | Ad26 |
| Ad26 | Self-replicating RNA molecule | MVA |
| Ad26 | Self-replicating RNA molecule | GAd20 |
| Ad26 | Self-replicating RNA molecule | Self-replicating RNA molecule |
| MVA | Ad26 | Ad26 |

TABLE 4-continued

Vector composition in first, second and third administration

| First administration | Second administration | Thrid administration |
|---|---|---|
| MVA | Ad26 | MVA |
| MVA | Ad26 | GAd20 |
| MVA | Ad26 | Self-replicating RNA molecule |
| MVA | MVA | Ad26 |
| MVA | MVA | MVA |
| MVA | MVA | GAd20 |
| MVA | MVA | Self-replicating RNA molecule |
| MVA | GAd20 | Ad26 |
| MVA | GAd20 | MVA |
| MVA | GAd20 | GAd20 |

TABLE 4-continued

Vector composition in first, second and third administration

| First administration | Second administration | Thrid administration |
|---|---|---|
| MVA | GAd20 | Self-replicating RNA molecule |
| MVA | Self-replicating RNA molecule | Ad26 |
| MVA | Self-replicating RNA molecule | MVA |
| MVA | Self-replicating RNA molecule | GAd20 |
| MVA | Self-replicating RNA molecule | Self-replicating RNA molecule |
| GAd20 | Ad26 | Ad26 |
| GAd20 | Ad26 | MVA |
| GAd20 | Ad26 | GAd20 |
| GAd20 | Ad26 | Self-replicating RNA molecule |
| GAd20 | MVA | Ad26 |
| GAd20 | MVA | MVA |
| GAd20 | MVA | GAd20 |
| GAd20 | MVA | Self-replicating RNA molecule |
| GAd20 | GAd20 | Ad26 |
| GAd20 | GAd20 | MVA |

TABLE 4-continued

| Vector composition in first, second and third administration | | |
|---|---|---|
| First administration | Second administration | Third administration |
| GAd20 | GAd20 | GAd20 |
| GAd20 | GAd20 | Self-replicating RNA molecule |
| GAd20 | Self-replicating RNA molecule | Ad26 |
| GAd20 | Self-replicating RNA molecule | MVA |
| GAd20 | Self-replicating RNA molecule | GAd20 |
| GAd20 | Self-replicating RNA molecule | Self-replicating RNA molecule |
| Self-replicating RNA molecule | Ad26 | Ad26 |
| Self-replicating RNA molecule | Ad26 | MVA |
| Self-replicating RNA molecule | Ad26 | GAd20 |
| Self-replicating RNA molecule | Ad26 | Self-replicating RNA molecule |
| Self-replicating RNA molecule | MVA | Ad26 |
| Self-replicating RNA molecule | MVA | MVA |
| Self-replicating RNA molecule | MVA | GAd20 |
| Self-replicating RNA molecule | MVA | Self-replicating RNA molecule |
| Self-replicating RNA molecule | GAd20 | Ad26 |
| Self-replicating RNA molecule | GAd20 | MVA |
| Self-replicating RNA molecule | GAd20 | GAd20 |
| Self-replicating RNA molecule | GAd20 | Self-replicating RNA molecule |
| Self-replicating RNA molecule | Self-replicating RNA molecule | Ad26 |
| Self-replicating RNA molecule | Self-replicating RNA molecule | MVA |
| Self-replicating RNA molecule | Self-replicating RNA molecule | GAd20 |
| Self-replicating RNA molecule | Self-replicating RNA molecule | Self-replicating RNA molecule |

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule;

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule; and a third administration comprising a third composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Fourth Administration

In some embodiments, any of the methods disclosed herein may further comprise a fourth administration. For example, the method may comprise a first administration, a second administration, a third administration, and a fourth administration, with a time period between each administration. In some embodiments, the first administration, second administration, third administration, and fourth administration may comprise same or different compositions.

For example, the fourth administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration, the second administration, the third administration, and the fourth administration are administered once in a lifetime of the subject. In some embodiments, the first, second, third, and the fourth administration are administered two or more times in the lifetime of the subject.

In some embodiments, the time period between the third administration and the fourth administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the third administration and the fourth administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the third administration and the fourth administration is about 4 weeks.

In some embodiments, the time period between the third administration and the fourth administration is about 8 weeks.

In some embodiments, the first administration, second administration, third administration, and the fourth administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Maintenance Administration

In some embodiments, the method further comprises administering to the subject a composition at regular intervals during the treatment cycles, and may continue even after the treatment cycles have ended. For example, the composition may be administered to a subject every month during the treatment regimen, and may continue for additional 6 months. In some embodiments, the composition may be administered between two treatment cycles. In some embodiments, the composition may be any of the compositions disclosed herein, such as a composition comprising a vector selected from Ad26 vector, GAd20 vector, MVA vector or self-replicating RNA molecule encoding the epitope sequences Dose and Route of Administration In some embodiments, the compositions comprising adenovirus vectors is administered at a dose from about $1\times10^4$ IFU (Infectious Unit) to about $1\times10^{12}$ IFU per dose, about $1\times10^4$ IFU to about $1\times10^{11}$ IFU per dose, about $1\times10^4$ IFU to about $1\times10^{10}$ IFU per dose, about $1\times10^4$ IFU to about $1\times10^9$ IFU per dose, about $1\times10^4$ IFU to about $1\times10^8$ IFU per dose, or about $1\times10^4$ IFU to about $1\times10^6$ IFU per dose.

In some embodiments, the compositions comprising adenovirus vectors is administered at a dose from about $1\times10^6$ VP (viral particles) to about $1\times10^{14}$ VP per dose, about $1\times10^6$ VP to about $1\times10^{12}$ VP per dose, about $1\times10^6$ VP to about $1\times10^{10}$ VP per dose, about $1\times10^6$ VP to about $1\times10^8$ VP per dose, or about $1\times10^6$ VP to about $1\times10^7$ VP per dose.

In some embodiments, a composition comprising Ad26 vector is administered at about $1\times10^{10}$ IFU per dose. In some embodiments, a composition comprising Ad26 vector is administered at about $1\times10^{11}$ IFU per dose. In some embodiments, a composition comprising Ad26 vector is administered at about $1\times10^{10}$ VP per dose. In some embodiments, a composition comprising Ad26 vector is administered at about $1\times10^{11}$ VP per dose.

In some embodiments, a composition comprising GAd20 vector is administered at about $1\times10^8$ IFU per dose. In some embodiments, a composition comprising GAd20 vector is administered at about $1\times10^{10}$ IFU per dose. In some embodiments, a composition comprising GAd20 vector is administered at about $1\times10^{10}$ VP per dose. In some embodiments, a composition comprising GAd20 vector is administered at about $1\times10^{11}$ VP per dose.

In some embodiments, the compositions comprising poxvirus vectors is administered at dose from about $1\times10^4$ IFU (Infectious Unit) to about $1\times10^{12}$ IFU per dose, about $1\times10^4$ IFU to about $1\times10^{11}$ IFU per dose, about $1\times10^4$ IFU to about $1\times10^{10}$ IFU per dose, about $1\times10^4$ IFU to about $1\times10^9$ IFU per dose, about $1\times10^4$ IFU to about $1\times10^8$ IFU per dose, or about $1\times10^4$ IFU to about $1\times10^6$ IFU per dose.

In some embodiments, a composition comprising MVA vector is administered from about $1\times10^8$ IFU per dose. In some embodiments, a composition comprising MVA vector is administered from about $1\times10^{10}$ IFU per dose.

In some embodiments, the compositions comprising self-replicating RNA molecule is administered at a dose from about 1 microgram to about 100 microgram, about 1 microgram to about 90 micrograms, about 1 microgram to about 80 microgram, about 1 microgram to about 70 micrograms, about 1 microgram to about 60 micrograms, about 1 microgram to about 50 micrograms, about 1 microgram to about 40 micrograms, about 1 microgram to about 30 micrograms, about 1 microgram to about 20 micrograms, about 1 microgram to about 10 micrograms, or about 1 microgram to about 5 micrograms of the self-replicating RNA molecule.

In some embodiments, the compositions disclosed herein may be administered to a subject by a variety of routes such as subcutaneous, topical, oral and intramuscular. Administration of the compositions may be accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present disclosure also has the objective of providing suitable topical, oral, systemic and parenteral formulations for use in the methods of prophylaxis and treatment.

In some embodiments, intramuscular administration of the vaccine composition can be achieved by using a needle. An alternative is the use of a needleless injection device to administer the composition (using, e.g., Biojector™) or a freeze-dried powder containing the vaccine composition. For intravenous, cutaneous or subcutaneous injection, or injection at the site of affliction, the composition may be the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against the mutant CALR and/or mutant JAK2 before development of clinical symptoms. The compositions of the disclosure are administered to a subject, giving rise to an immune response in the subject. The amount of the composition able to in induce a detectable immune response is defined to be an "immunologically effective dose." The compositions of the disclosure may induce a humoral as well as a cell-mediated immune response. In a typical embodiment, the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In one exemplary regimen, the composition comprising adenovirus vector is administered (e.g., intramuscularly) in a volume ranging between about 100 μL to about 10 ml containing concentrations of about $10^4$ to $10^{12}$ virus particles/ml. The adenovirus vector composition may be administered in a volume ranging between 0.25 and 1.0 ml, such as in a volume of 0.5 ml.

In one exemplary regimen, the composition comprising MVA vector is administered (e.g., intramuscularly) in a volume ranging between about 100 μl to about 10 ml of saline solution containing a dose of about $1\times10^7$ $TCID_{50}$ to $1\times10^9$ $TCID_{50}$ (50% Tissue Culture Infective Dose) or Inf.U. (Infectious Unit). The MVA vector composition may be administered in a volume ranging between 0.25 and 1.0 ml.

Second Therapeutic Agent

In some embodiments, the methods disclosed herein further comprise administering a second therapeutic agent. In some embodiments, the second therapeutic is an immunostimulating agent, a chemotherapeutic agent, an antibiotic, a checkpoint inhibitor, or a cellular therapy.

In some embodiments, the second therapeutic is selected from CTLA-4 antibody, CTLA4 ligand, a PD-1 axis inhibitor, PD-L1 axis inhibitor, a TLR agonist, a CD40 agonist, an OX40 agonist, hydroxyurea, ruxolitinib, fedratinib, a 41BB agonist, aa CD28 agonist, a STING antagonist, a RIG-1 antagonist, TCR-T therapy, CAR-T therapy, FLT3 ligand, aluminum sulfate, BTK inhibitor, a JAK inhibitor, CD38 antibody, CDK inhibitor, CD33 antibody, CD37 antibody, CD25 antibody, GM-CSF inhibitor, IL-2, IL-15, IL-7, CD3 redirection molecules, pomalimib, IFNγ, IFNα, TNFα, VEGF antibody, CD70 antibody, CD27 antibody, BCMA antibody or a GPRC5D antibody, and combinations thereof.

In some embodiments, the second therapeutic is a checkpoint inhibitor selected from pilimumab, cetrelimab, pembrolizumab, nivolumab, sintilimab, cemiplimab, toripalimab, camrelizumab, tislelizumab, dostralimab, spartalizumab, prolgolimab, balstilimab, budigalimab, sasanlimab, avelumab, atezolizumab, durvalumab, envafolimab, or iodapolimab, or any combination thereof.

In some embodiments, the second therapeutic is the JAK inhibitor.

In some embodiments, the second therapeutic agent may be administered in combination with a first composition of the first administration or a second composition of the second administration or a third composition of the third administration, or a fourth composition of the fourth administration.

In some embodiments, the anti-CTLA-4 antibody is combined with any of the first, or the second, or the third, or the fourth administration of the composition of the disclosure.

In some embodiments, the anti-PD-1 or anti-PD-L1 antibody is combined with any of the first, or the second, or the third, or the fourth administration of the composition of the disclosure.

In some embodiments, the checkpoint inhibitors are administered at as dose of about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, or about 250 to about 300 mg/kg.

EXAMPLES

Example 1: Identification of JAK2 V617F Epitope 2 and In-Silico Immunogenicity Assessment of JAK2 V617F Epitopes A 17mer sequence of the JAK2 protein with the V617F mutation as the central residue, and all 9-mers of contiguous amino acids that are contained in this 17mer sequence, were generated. In-silico predictions of the binding affinity of these 9-mers to common HLA-A and HLA-B alleles was predicted using netMHCpan4.0. Binding predictions were categorized into three categories of weak binding (predicted affinity >500 nM); moderate binding (predicted affinity between 50 nM to 500 nM), and strong binding (predicted affinity <50 nM) to commonly occurring HLA-A alleles. 9-mer JAK2 epitope 1 of SEQ ID NO: 5 (VLNYGVCFC) and a novel 9-mer JAK2 epitope 2 of SEQ ID NO: 6 (FCGDENILV) were selected from this analysis for further experimental follow-up. The peptide of SEQ ID NO: 6 has not been previously described as being an immunogenic JAK2 fragment. The predicted binding affinity of JAK2 epitope 2 shown in Table 5 is lower than the binding of JAK2 epitope 1.

TABLE 5

Affinity of JAK2 epitope 2.

| Allele | Binding affinity nM | Binding Rank |
|---|---|---|
| HLA-A01:01 | 22680 | 11 |
| HLA-A02:01 | 2878 | 7 |
| HLA-A03:01 | 42208 | 84 |
| HLA-A24:02 | 41245 | 52 |
| HLA-B07:02 | 40322 | 66 |
| HLA-B08:01 | 35548 | 69 |
| HLA-B15:01 | 38417 | 76 |
| HLA-B27:05 | 40573 | 84 |
| HLA-B40:01 | 39076 | 44 |

Binding categories are non-binders = rank > 2.0; moderate binders = rank between 0.5 to 2.0; strong binders = Rank < 0.5.

Example 2: Mutant JAK2 Versus Wild-Type JAK2 Epitope Immunogenicity in Disease Patient Samples PBMCs were isolated from Essential thrombocythemia (ET) or Primary Myelofibrosis (PMF) patients with a confirmed JAK617F mutation. Individual Class-I-associated mutJAK2 or wild-type JAK2 peptides were exogenously administered at 5 μg/ml concentration to 250,000 PBMCs on day 0. Cells were cultured for 10 days in the presence on 10 IU/ml of human IL-2 and 10 ng/ml of human IL-15, and subsequently evaluated for frequency of mutant or wild-type JAK2 antigen-specific T cells by peptide-pulse recall and intracellular staining flow cytometry analysis for IFNγ and TNFα producing CD8+ T cells. An antigen specific response was considered positive if the frequency of IFNγ/TNFα+ CD8+ T cells was three-fold greater compared to cells treated cells with DMSO only on Day 0 and greater than 0.1%. Results are summarized in Table 6.

TABLE 6

| Disease | Donor Number | Control viral antigens CEF response | Mutant JAK2 epitope 2 | Mutant JAK2 epitope 1 | Wild Type JAK2 epitope 2 | Wild Type JAK2 epitope 1 |
|---|---|---|---|---|---|---|
| PMF | 120174174 | Yes | Yes (30%) | No | No | No |
| PMF | 120250311 | Yes | No | No | No | No |
| PMF | 120800910 | No | No | No | No | No |
| PMF | 120800936 | Yes | Yes (0.63%) | Yes (0.62%) | No | No |
| PMF | 120817869 | Yes | No | No | No | No |
| ET | 120708928 | Yes | No | No | No | No |
| ET | 120815833 | Yes | Yes (30.6%) | No | No | Yes (1.3%) |
| ET | 120824685 | Yes | No | No | No | No |

YES indicates a 3-fold increase in frequency of IFNγ/TNFα + CD8+ T cells compared to DMSO only stimulated cells for each donor. The parentheses indicate the actual frequency of IFNγ/TNFα + CD8+ T cells.

Figure 1:
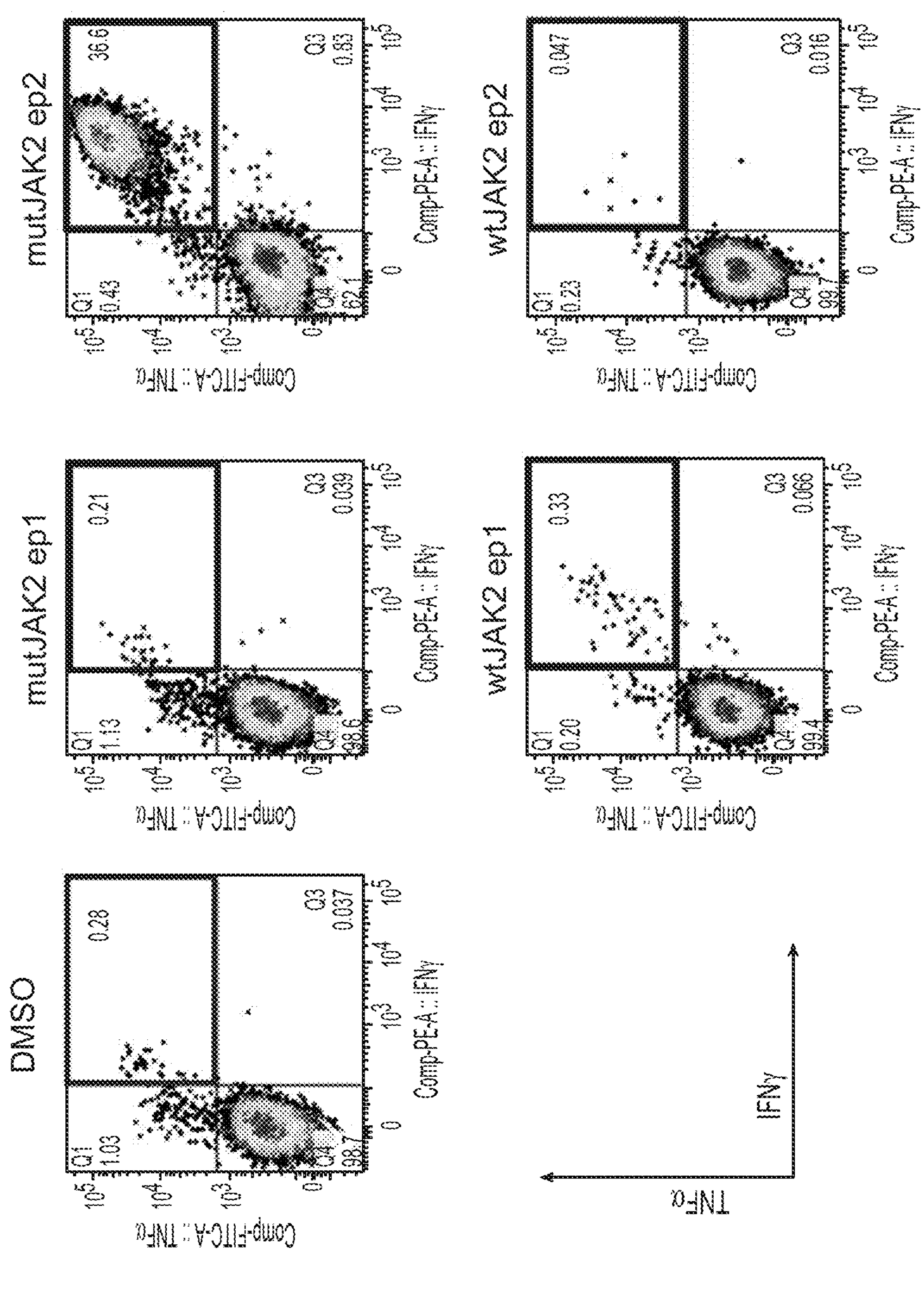
FIG. 1 shows JAK2 V617F+ HLA A02:01+ MPN donor T-cell response to mutJAK2 class I epitopes 1 and 2.

FIG. 1 shows the immunogenicity of JAK2 epitope 1 and JAK2 epitope 2 in disease patient samples compared to the wild-type sequences of the same epitope regions. The corresponding wild-type peptide sequences for mutJAK2 Epitopes I and II were also evaluated and shown to have similar responses as DMSO control.

Example 3: Design and Generation of the CALR.JAK2 Polynucleotides and Polypeptides for Ad26 and MVA Expression To select a vaccine composition that resulted in good antigen expression and T-cell activation, a series of CALR.JAK2 polynucleotides and polypeptides were designed and tested.

CALR Type 1 and Type 2 mutations were included into the polynucleotide. Based on in silico T cell epitope prediction and HLA binding studies, a 54-mer peptide (SEQ ID NO: 1) of the CALR mutant Type 1 and a truncated 14-mer peptide (SEQ ID NO: 2) of the CALR mutant Type 2 protein was included into the polynucleotide. The CARL portion of the polynucleotide encodes the amino acid sequence shown in SEQ ID NO: 3. To ensure good intracellular processing of all proteins, the individual peptides were connected by AAY (ala-ala-tyr) linkers that promote proteasomal cleavage.

Also based on in silico T cell epitope prediction and HLA binding studies, two distinct JAK2 peptides, a 30-mer peptide (SEQ ID NO: 4) or two 9-mer peptides (SEQ ID NO: 5 or SEQ ID NO: 6) were included, each of which containing the V617F mutation. The peptide of SEQ ID NO: 6 has not been described earlier as being an immunogenic JAK2 fragment.

To ensure good intracellular processing of all proteins, the individual peptides were also connected by AAY (ala-ala-tyr) linkers that promote proteasomal cleavage. SEQ ID NO: 7 represents the amino acid sequence of the JAK2 two 9-mers separated by the AAY linker.

Two different constructs were designed in which the CALR portions were identical, but the JAK2 portion was either the 30-mer peptide or the two 9-mer peptides. These two different transgenes were designed with either no leader sequence (LS), a HAVT20 LS (MACPGFLWALVIST-CLEFSMA; SEQ ID NO: 8), or a ubiquitin signal (Ubiq) (MQIFVKTLTGKTITLEVEPSDTIENVKAKIQDKEG-IPPDQQRLIFAGKQLEDGRTLSDYNI QKESTLHLVLRLRGV; SEQ ID NO: 54) at the N-terminus. The constructs are listed in Table 3. The HAVT20 LS should direct the transgene into the ER, whereas the ubiquitin sequence targets the proteasome. This could result in different levels of expression of the TG between the constructs. In addition, a construct encoding only the sequence from two mutant CALR proteins was generated, which was used as a control for the expression of the CALR protein. The protein and polynucleotide sequence of the transgenes are shown in Table 7. The polynucleotide sequences shown were optimized for adenovirus expression.

TABLE 7

Constructs for adenovirus expression

| Construct name | Mutant CALR sequences | JAK2 mutant sequences |
|---|---|---|
| LS_CALR | CALR mutant Type 1, truncated<br>CALR mutant Type 2 | none |
| LS_CALR_JAK2-2x9mer | CALR mutant Type 1, truncated<br>CALR mutant Type 2 | 2x9-mer |
| LS_CALR_JAK2-30mer | CALR mutant Type 1, truncated<br>CALR mutant Type 2 | 30-mer |
| CALR_JAK2-2x9mer | CALR mutant Type 1, truncated<br>CALR mutant Type 2 | 2x9-mer |
| CALR_JAK2-30mer | CALR mutant Type 1, truncated<br>CALR mutant Type 2 | 30-mer |
| Ubiq_CALR_JAK2-2x9mer | CALR mutant Type 1, truncated<br>CALR mutant Type 2 | 2×9-mer |
| Ubiq_CALR_JAK2-30mer | CALR mutant Type 1, truncated<br>CALR mutant Type 2 | 30-mer |

LS: leader sequence; Ubiq: ubiquitin

TABLE 8

CALR.JAK2 polypeptide SEQ ID and polynucleotide SEQ ID NOs

| construct name | Protein SEQ ID NO: | Polynucleotide SEQ ID NO: |
|---|---|---|
| LS_CALR | 9 | 16 |
| LS_CALR_JAK2-2x9mer | 10 | 17 |
| LS_CALR_JAK2-30mer | 11 | 18 |
| CALR_JAK2-2x9mer | 12 | 19 |
| CALR_JAK2-30mer | 13 | 20 |
| Ubiq_CALR_JAK2-2x9mer | 14 | 21 |
| Ubiq_CALR_JAK2-30mer | 15 | 22 |

The CALR.JAK2 constructs were cloned into pUC57 shuttle plasmid using standard methods for adenovirus expression. The expression cassette consisted of a tetracycline operator (TetO)-containing cytomegalovirus (CMV) promoter, to allow use in combination with the PER.C6 TetR cell line, a Kozak sequence, the CALR.JAK2 polynucleotide and the simian virus 40 (SV40) polyadenylation signal flanked by Ad26-specific sequences outside the expression cassette. These flanking Ad26-specific sequences were homologous to the Ad26 backbone plasmid sequence to ensure plasmid generation by homologous recombination. The sequence was human-gene optimized for enhanced transgene expression.

To test CALR.JAK2 expression by these different constructs, HEK293 cells were transfected with the respective DNA plasmids and expression in cell lysates was examined by Western blot 72 hours post transfection. In addition, proteasome activity was inhibited by adding proteasome inhibitor MG132 4 hours before collecting the samples to examine the effect on the transgene expression. All constructs expressed the CALR.JAK2 epitopes and the highest expression was observed for the constructs with the HAVT20 LS. Proteasome inhibition modestly enhanced transgene expression by the constructs with a ubiquitin signal, but this difference could not be quantified by Western blot. Based on the CALR.JAK2 expression data, the two constructs with the HATV20 leader sequence (LS) were selected for production of adenovirus, i.e., Ad26.LS_CALR_JAK2-30mer (Ad26HEME001) and Ad26.LS_CALR_JAK2-2×9mer (Ad26HEME002). In addition, Ad26-LS-CALR (AD26HEME003) was produced to serve as a possible control. The polynucleotide sequence of Ad26HEME001 containing the tetracycline operator (TetO)-containing cytomegalovirus (CMV) promoter, a Kozak sequence, CALR,JAK2 and the simian virus 40 (SV40) polyadenylation signal is shown in SEQ ID NO: 23. The polynucleotide sequence of the Ad26HEME002 containing the tetracycline operator (TetO)-containing cytomegalovirus (CMV) promoter, a Kozak sequence, CALR.JAK2 and the simian virus 40 (SV40) polyadenylation signal is shown in SEQ ID NO: 24.

To select the cell line for Ad26HEME001 and Ad26HEME002 production, virus rescue-ability was measured by transfection of viral genome DNA in PER.C6® compared to PER.C6 TetR cells. Cytopathic effect (CPE) and plaque formation (together showing rescue-ability) were comparable between the Ad26HEME001 and Ad26HEME002 constructs (Table 9). In summary, both constructs showed full CPE within 8 days on PER.C6 TetR, but not on PER.C6® cells. Ad26HEME001 and Ad26HEME002 showed about 13 and about 11 plaques respectively on PER.C6® cells and >100 plaques on PER.C6 TetR cells for co-easy transfections at Day 8. This indicated that the rescue-ability was inhibited on PER.C6® cells. Adenoviral vectors that are difficult to rescue have limited productivity characteristics and have a high risk on deletions and mutations in the transgene expression cassette. Based on these results, PER.C6 TetR was selected as cell line for virus production of Ad26HEME001 and Ad26HEME002. Ad26HEME003 was also produced on PER.C6 TetR cells.

TABLE 9

| | Full CPE PER.C6 ®/ PER.C6 TetR | # plaques PER.C6 ®/ PER.C6 TetR |
|---|---|---|
| Ad26HEME001 | No CPE/<8 days | 13/>100 |
| Ad26HEME002 | No CPE/<8 days | 11/>100 |

Example 4: Generation of Ad26HEME001 and Ad26HEME002

Research batches were generated from cells transfected with single-genome pAd26HEME001 (pAd26.LS_CALR_JAK2-30mer), pAd26HEME002 (pAd26.LS_CALR_JAK2-2×9mer), and pAd26HEME003 (pAd26.LS_CALR) plasmids.

The pUC57 plasmid DNA, was used to clone the Ad26 Early Region 1 (E1) TG expression cassette into the pAd26 backbone to generate the pAd26HEME001, pAd26HEME002, and pAd26HEME003 plasmids. The E1 region in the pAd26 backbone was deleted to render the vector replication-incompetent in non-complementing cells such as human cells. In addition, a part of the Ad26 Early Region 3 (E3) region was removed (ΔE3) to create sufficient space in the viral genome for insertion of foreign antigens, and the Ad26 Early Region 4 (E4) open reading frame (orf) 6 was exchanged by the adenovirus Type 5 (Ad5) homologue to enable production of replication-incompetent Ad26 vectors in Ad5-E1-complementing cell lines like HEK293, PER.C6®, and HER96 cells. The pAd26 backbone was linearized by using a unique restriction site (AsiSI) in the region in which the TG cassette was later introduced. Both ends of this linearized plasmid contained overlapping sequences homologous to the Ad26-specific sequences present at the outsides of the E1 transgene expression cassette. This enabled plasmid generation by cloning the transgene cassette into the pAd26 backbone using homologous recombination techniques. The complete plasmid sequences were verified.

To generate the Ad26HEME001, Ad26HEME002, and Ad26HEME003 vectors, the plasmids were transfected into PER.C6 TetR cells. Virus was amplified on PER.C6 TetR cells, purified, and tested for integrity and identity of the adenovirus genome and correct expression of the TG.

Batch Generation and Characterization

One Ad26HEME001, two Ad26HEME002, and one Ad26HEME003 research batches were generated and characterized for assessment of infectivity, transgene expression, batch genetic stability, and relative productivity in suspension PER.C6 (sPER.C6) TetR cells. All research batches were generated on adherent PER.C6 TetR cells. Batch quality was characterized by expression of the encoded antigen under non-replicating conditions, the number of virus particles (VP) and infectious units (IU).

All produced research batches showed expression of the encoded antigen as shown by Western blot and all batches had low VP/IU ratios. The research batch of Ad26HEME001 showed a VP/IU ratio of 29. The two research batches of Ad26HEME002 showed a VP/IU ratio of 5, and Ad26HEME003 showed a VP/IU ratio of 8. Both genetic stability and productivity are important for the feasibility to scale-up production of adenoviral vectors to clinical trial material (CTM) or commercial scale. The risk for genetic instability as defined by changes in the vector genome and outgrowth of a population with undesired properties during propagation in the production cell line can be assessed by propagation of several virus populations at small scale. For all research batches, genetic stability was assessed on the final batch material, by identity polymerase chain reaction (ID PCR) for the transgene region, E3 gene region, and E4 gene region. In addition, the polymerase chain reaction (PCR) product of the transgene region was sequenced. All research batches were found to be genetically stable.

Productivity (as defined by titers of VP/mL) was assessed in small-scale experiments by comparing the vaccine candidate vector to respective benchmark controls, of which performance in the 10 L process intensified (PIN)-bioreactor is known. In brief, sPER.C6 TetR cells were transduced with 70, 300, and 900 VP/cell of purified research batch material and two Ad26 benchmark controls. Ad26HEME001, Ad26HEME002, and Ad26HEME003 showed comparable productivity to the standard control at 70, 300, and 900 VP/cell, indicating that all three vectors are good producers (controls showed expected outcome) with ~$10^{11}$ VP/ml produced after 2-3 days in culture.

The polynucleotide sequence of Ad26HEME002 vector including the various elements is shown in SEQ ID NO: 24 and the amino acid sequences encoded by them is shown is SEQ ID NO: 10.

Example 5: Generation of MVA.CALRJAK2 and GAd20.CALRJAK2 Construct

Amino acid sequence for CALR.JAK2 transgene was converted into nucleotide sequence based on the human codon usage. Termination motifs for the MVA vector (TTTITnT) were avoided. BamH1 restriction site and a KOZAK sequence were then added upstream the nucleotide sequence. Two STOP codons followed by Asc1 restriction site were added downstream the nucleotide sequence. A T cell enhancer (TCE) polynucleotide encoding a small peptide fragment with length of 28 aa from the mandarin fish invariant chain (SEQ ID NO: 29) was placed at the N-terminus of the transgene. Preclinical data has shown this sequence to increase the immunological response of the viral vector. The synthesis of the transgene was performed using known methods.

The MVA transgene cloned under the control of the vaccinia P7.5 early/late promoter (SEQ ID NO: 32) was inserted by homologous recombination into the deletion III locus of MVA (FlankIII-1 and -2 regions) and the recombinant virus particles were produced using known methods.

The GAd20 transgene was subcloned into a shuttle plasmid between CMV promoter with two TetO repeats and a BGH polyA via EcoRI-Not1 restriction sites. The resulting expression cassette was transferred into the GAd20 genome by homologous recombination in suitable *E. coli* strains, transformed with the CMV-transgene-BGH DNA fragment and with a construct carrying the GAd20 genome. Recombination involved CMV and BGH as homology arms, that were already present in the GAd20 construct in place of the E1 deletion (insertion site of the transgene). Recombinant GAd20 vectors were then rescued by transfection of the E1 complementing, TetR expressing M9 cells and amplified by subsequent re-infection of fresh M9 cells. MVA and GAd20 vectors expressing the polypeptide TCE_CALR_JAK2-2× 9mer (SEQ ID NO: 31) (HCalJ-9.9) were generated using know methods.

Example 6: Ad26.CALR.JAK2 Vectors Express, Process and Present Antigen to Autologous T Cells The purpose of this study was to test human antigen-presenting cells (APCs) capacity to process and present the vaccine's neoantigens and mount T-cell responses.

Frozen vials of autologous $CD1c^+$ DCs and autologous $CD4^+/CD8^+$ T cells were isolated via magnetic bead negative selection. $CD1c^+$ DCs were infected at a multiplicity of infection (MOI) of 50,000 VP overnight with Ad26HEME002 or Ad5HEME002 (Ad5 vector engineered to express the LS_CALR_JAK2-2×9mer transgene). At 18 to 24 hours post infection, identical donor autologous T cells were mixed with $CD1c^+$ DCs at a 10:1 ratio. Human IL-15 at 10 ng/mL was added to culture on Day 0 and half media changes with 2×IL-15 and IL-2 (10 IU/mL) were performed every 2 to 3 days until Day 11. On Day 11, peptides corresponding to CALRmut, JAK2V617F, or Adeno Hexon protein (positive control) were added to DC/T-cell culture overnight together with protein transport inhibitors. The resulting cultures were stained for T-cell markers (CD4, CD8, CD3) and markers of activated T cells (IFN-γ, TNF-α) and analyzed by flow cytometry. Increased IFN-γ and TNF-α staining after overnight stimulation of peptides on Day 11 indicated expansion of CALRmutant, and/or JAK2V617F antigen specific T cells specifically due to Ad26/Ad5-HEME002-driven transgene expression. A 3-fold increase in IFN-γ and TNF-α double-positive CD8 T cells over Ad26/Ad5 empty vector was considered a positive response. Exclusion criteria were (i) Adeno Hexon responses below 0.5% IFN-γ and TNF-α double-positive T cells, or (ii) <1% viral antigen (adeno CEF construct) IFN-γ and TNF-α double-positive T cells; in which case the experiment was considered suboptimal and the negative response was likely a technical failure of the donor or the experimental set up.

Figure 2:
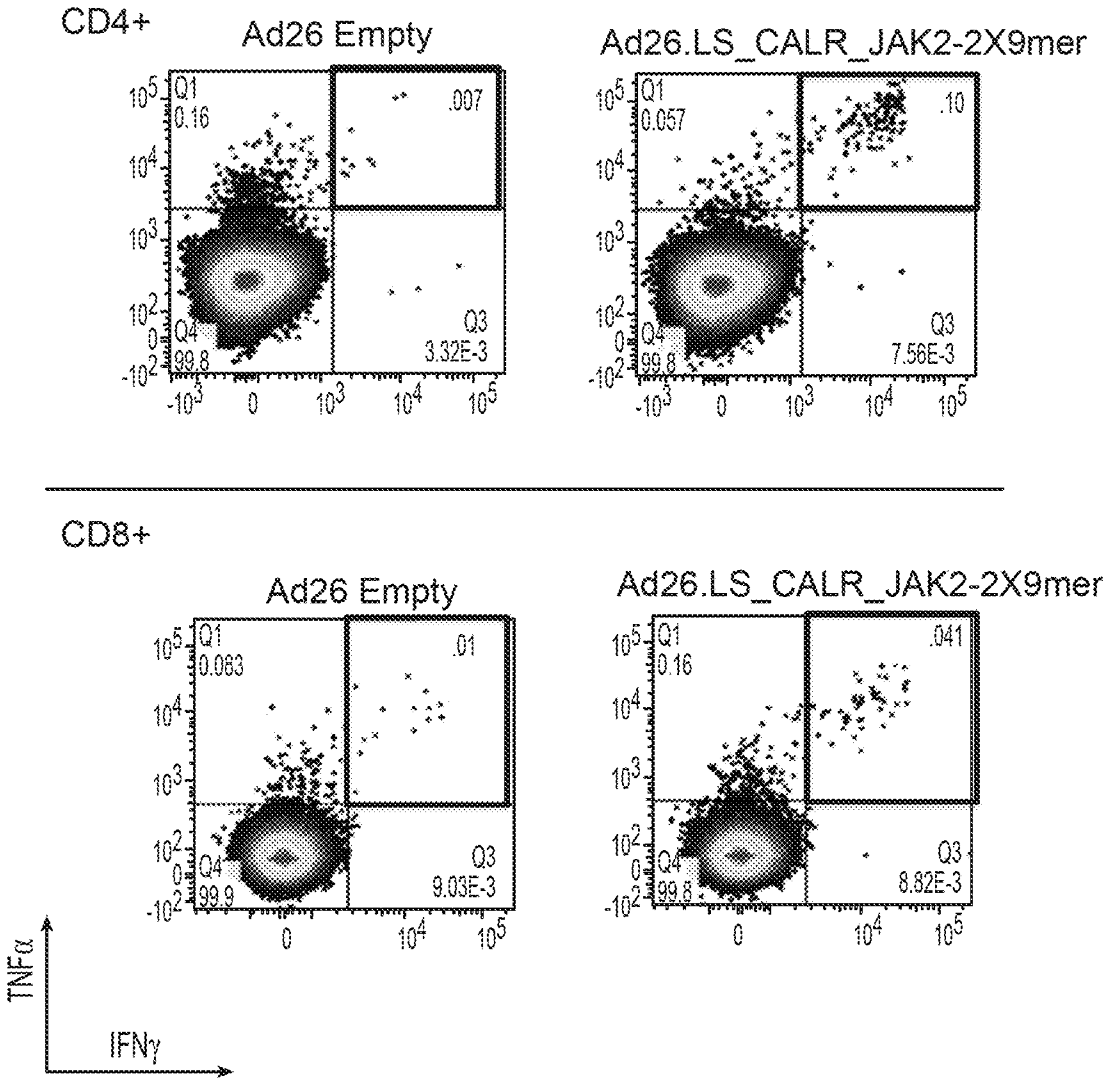
FIG. 2 shows flow cytometry intracellular cytokine staining for IFN-γ/TNF-α response from both CD4+ and CD8+ T cells. Normal donor dendritic cells were infected with adenovirus 26 vectors containing either an empty vector or a polynucleotide encoding for LS_CALR.JAK2 2×9mer of SEQ ID NO: 10. Autologous CD4/CD8 T cells were added to dendritic cells 24 hours post infection. Dendritic and T cell s were co-cultured for 11 days and restimulated with a pool of peptides specific mutCALR.
Figure 3:
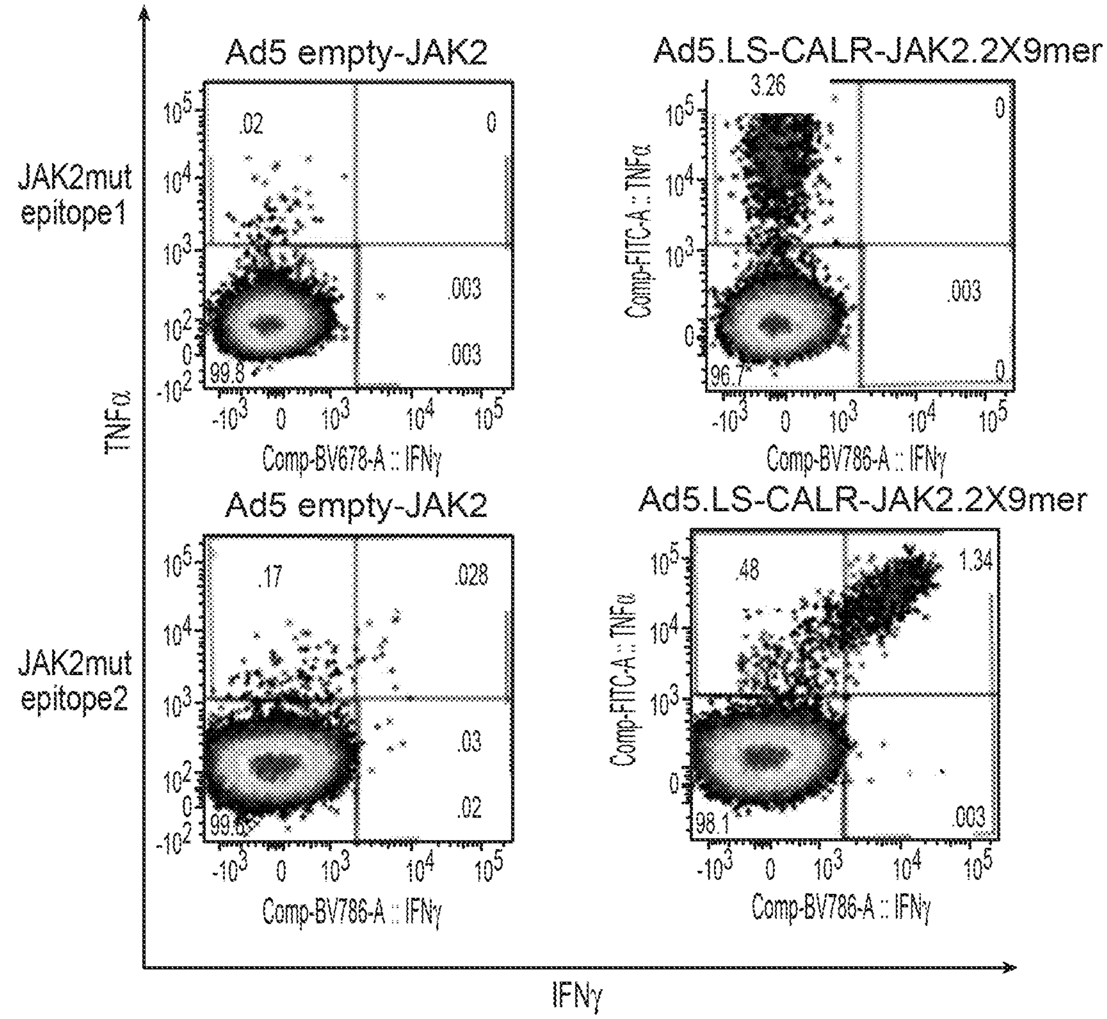
FIG. 3 shows flow cytometry intracellular cytokine staining for IFN-γ/TNF-α response from CD8+ T cells. Normal donor dendritic cells were infected with adenovirus 5 vectors containing either an empty vector or a polynucleotide encoding for LS_CALR/JAK2 2×9mer of SEQ ID NO: 10. Autologous CD8 T cells were added to dendritic cells 24 hours post infection. Dendritic and T cell s were co-cultured for 11 days and restimulated with 9mer peptides specific to either muJAK2 epitope 1 (SEQ ID NO: 5) or epitope 2 (SEQ ID NO: 6).
Figure 4:
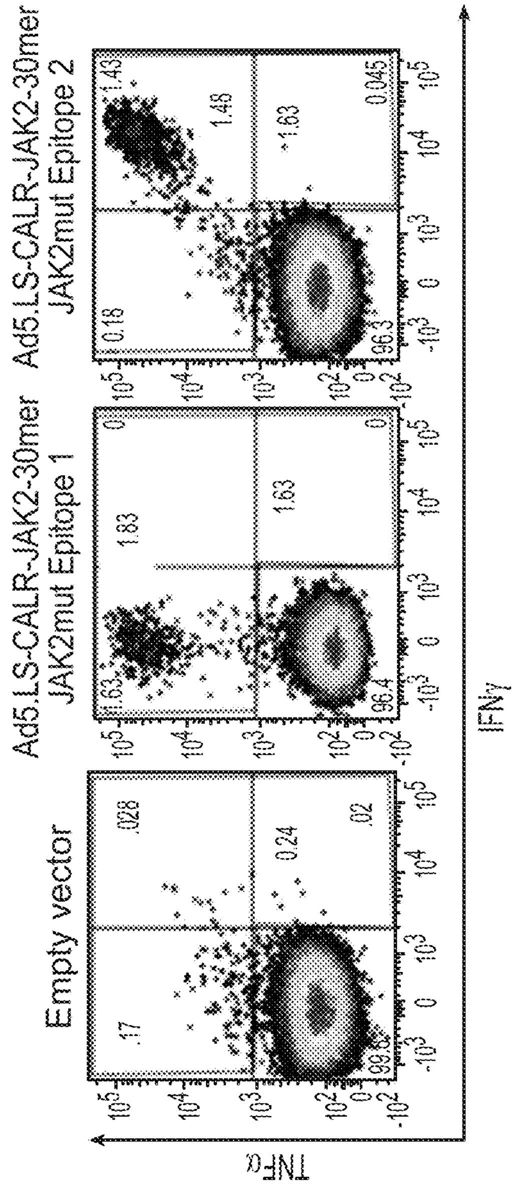
FIG. 4 shows flow cytometry intracellular cytokine staining for IFN-γ/TNF-α response from CD8+ T cells. Normal donor dendritic cells were infected with adenovirus 5 vectors containing either an empty vector or a polynucleotide encoding for LS_CALR.JAK2-30mer (SEQ ID NO: 11).

A total of 24 unique healthy donor cells were screened. FIG. 2 shows a representative result of screening on one donor for CALRmutant specific T cell responses. In the experiment, the cells were gated on live/CD3+/CD8+ cells and IFN-γ and TNF-α staining assessed. Both CD8 (class I) and CD4 (class II) responses were observed after infection. The experiments were conducted across 3 independent analyses and the frequency of response was similar across the experiments, about 35% regardless wheatear Ad26 or Ad5 was used. FIG. 3 shows that both JAK2 epitopes included into the vaccine (SEQ ID NO: 5 (VLNYGVCFC); epitope 1 in FIG. 3 and SEQ ID NO: 6; FCGDENILV epitope 2 in FIG. 3) are immunogenic. FIG. 4 shows a representative result of screening one donor for JAK2 mutant specific T cell responses. The data demonstrated that both JAK2 mutant neoepitopes were processed from the vaccine transgene sequence indicating that these epitopes can be presented by cancer cells. The HLA types of all tested donors are shown in Table 10.

TABLE 10

| Donor | HLA A1 | HLA B1 | HLA C1 | HLA A2 | HLA B2 | HLA C2 |
|---|---|---|---|---|---|---|
| 2480 | 03:01 | 15:03 | 2:10 | 23:01 | 44:02 | 05:01 |
| 013B | 01:01 | 07:02 | 07:01 | 03:01 | 08:01 | 07:02 |
| 4384 | 24:02 | 35:01 | 04:01 | 30:01 | 42:01 | 07:01 |
| 118 | 02:01 | 14:02 | 1:01 | 68:02:00 | 27:05 | 8:02 |
| 676 | 1:01 | 08:01 | 3:04 | 32:01:00 | 15:01 | 7:01 |
| 274 | 03:01 | | | | | |
| 3942 | 02:02 | 08:01 | 03:04 | 03:01 | | 07:02 |
| 240 | 03:01 | 15:03 | 02:10 | 23:01 | 44:02:00 | 5:01 |
| 644 | 03:01 | 07:02 | 06:02 | 66:01:00 | 13:02 | 7:02 |
| 359 | 1:01 | 07:02 | 7:01 | 03:01 | 08:01 | 7:01 |
| 538 | 02:01 | 27:05 | 1:02 | 03:01 | 38:01:00 | 12:03 |

Example 7: Ad26.CALR.JAK2 Vectors Express Induced Cellular Responses in Mice

The purpose of the study was to test if the T-cell responses induced by Ad26-containing Ad26HEME001 or A26HEME002 were higher than that induced by the empty Ad26 vector using IFN-γ enzyme-linked immunospot assay (ELISpot), and to select the optimal mouse strain for further immunogenicity studies.

The C57BL/6 and Balb/c mouse strains were tested for this immunogenicity study as epitope prediction analysis showed that potential CD8 T-cell epitopes were present in these mice strains. Mice were injected with a dose of $10^{10}$ VP/mouse of Ad26HEME001 or Ad26HEME002, or an Ad26 not encoding a transgene (Ad26.Empty). 15-mer overlapping peptide pools spanning the Ad26HEME001 or Ad26HEME002 insert were used to assess the cellular immune response 14 days after a prime vaccination (IFN-γ ELISpot). The experimental groups are shown in Table 11.

TABLE 11

| Group | Animal nr | Description of groups | Mouse strain |
|---|---|---|---|
| 1a | 4 | Ad26.Empty dose $10^{10}$ VP | C57BL/6 |
| 1b | 4 | Ad26.Empty dose $10^{10}$ VP | Balb/c |
| 2 | 8 | Ad26HEME001 dose $10^{10}$ VP | C57BL/6 |
| 3 | 8 | Ad26HEME002 dose $10^{10}$ VP | C57BL/6 |
| 4 | 8 | Ad26HEME001 dose $10^{10}$ VP | Balb/c |
| 5 | 8 | Ad26HEME002 dose $10^{10}$ VP | Balb/c |

An insert-specific T-cell response was elicited 14 days after the prime, in C57BL/6 and Balb/c mice as measured by IFN-γ ELISpot, and there was a significantly higher immune-response induced in animals immunized with Ad26HEME001 (FIG. 5) or Ad26HEME002 (FIG. 6) over that induced by Ad26.Empty-immunized animals. No cellular immune response was detected against the LS peptide (data not shown). There was no significant difference between the immune response induced by the two vectors when looking across mouse strain. Similarly, there was no significant difference between the immune response towards the HEME001 peptide pool induced by Balb/c and C57BL/6 when looking across the vaccine candidates. There was a significant difference between the immune response towards the HEME002 peptide pool induced by Balb/c and C57BL/6 when looking across the vaccine candidates.

Example 8: Ad26.CALRJAK2 and MVA.CALRJAK2 Vectors Induce Cellular Responses in Mice The purpose of these studies was to determine if a modified vaccinia Ankara (MVA) vector encoding HCaJ-9.9 (i.e., MVA-HCaJ-9.9, MVAHEME002) could boost the immune response induced by a prime immunization with Ad26HEME002 in Balb/c mice. The Balb/c mouse strain was selected based on the data described in Example 7 where less variation was seen with the Balb/c mouse strain compared to the C57BL/6 mouse strain.

In the first study, Ad26HEME002 was dosed $10^{10}$ VP and MVA-HCaJ-9.9 was dosed $10^{7}$ IU. At Week 0, mice were immunized by IM injection with Ad26HEME002; half of the animals did not receive a boost immunization (Group 2) and half of the animals were boosted at Week 3 with MVA-HCaJ-9.9 (Group 3). Another group of mice were immunized (prime) with MVA-HCalJ-9.9 at Week 3 (Group 1). Control mice were primed at Week 0 with Ad26.Empty (Group 4). At Week 4, all animals were sacrificed and splenocytes were stimulated with 15-mer overlapping peptide pools spanning the Ad26HEME002 insert, or a peptide pool covering the CALR sequence in the insert, or 9-mers covering the two JAK2 9-mer sequences. The induction of IFN-γ-producing cells was measured by IFN-γ ELISpot. Table 12 shows the various experimental groups.

TABLE 12

| Group | Animal nr | Description of groups |
|---|---|---|
| 1 (#5) | 5 | MVA-HCalJ-9.9 dose $10^{7}$ IU |
| 2 (#7) | 10 | Ad26HEME002 dose $10^{10}$ VP |
| 3 (#8) | 10 | Ad26HEME002 dose $10^{10}$ VP/ MVA-HCalJ-9.9 dose $10^{7}$ IU |
| 4 (#9) | 3 | Ad26.Empty dose $10^{10}$ VP |

All animals immunized with either Ad26HEME002 alone or in combination with MVA-HCalJ-9.9 boost developed IFN-7-producing cells upon stimulation with a peptide pool made up of 15mer peptides overlapping by 11 amino acids and covering the entire HEME002 (LS_CALR.JAK2.2× 9mer) (FIG. 7) or a mutCALR peptide pool consisting of 15mer peptides overlapping by 11 amino acids and covering only the mutCALR portion of HEME002 (FIG. 8). In contrast no induction of cytokine-producing cells was detected upon stimulation with the two 9-mer JAK2 peptides (data not shown). Importantly, a boost with MVA-HCalJ-9.9 after prime immunization with Ad26HEME002 (Group 3) induced a significantly higher response than animals only primed at Week 0 with Ad26HEME002 (Group 2) (HEME002 peptide pool: p=0.038; CALRmut peptide pool:

p=0.00025; ANOVA). In conclusion, ELISpot data showed that MVA was able to boost the insert-specific cellular immune response induced by a prime immunization with Ad26HEME002.

In the second study, Ad26HEME002 was dosed $10^9$ VP or $10^{10}$ VP and MVA-HCalJ-9.9 was dosed $10^7$ IU. At Week 0, mice were immunized by IM injection with Ad26HEME002 followed by boost at Week 3 with MVA-HCalJ-9.9. At Week 4, all animals were sacrificed and splenocytes were stimulated with 15-mer overlapping peptide pools spanning the Ad26HEME002 insert, or a peptide pool covering the CALR sequence in the insert, or 9-mers covering the two JAK2 9-mer sequences. The induction of IFN-7-producing cells was measured by IFN-γ ELISpot. Ad26HEME002 prime at $1\times10^{10}$ VP followed by MVA-HCalJ-9.9 boost at 1×107 plaque-forming units (pfu) resulted in a statistically significant increase in IFN-γ when compared to Ad26.Empty vector at $1\times10^{10}$ VP alone (3.2-fold increase, p=0.0042). In contrast, no significant change in IFN-γ was observed at a lower dose of Ad26HEME002 prime at $1\times10^9$ VP followed by MVA-HCalJ-9.9 boost at $1\times10^7$ pfu (p=0.090). Increased IFN-γ-producing splenocytes were observed with 1×1010 VP Ad26HEME002 compared to $1\times10^9$ VP dosing. FIG. 9 shows the results of the experiment.

Example 9: Immunogenicity of Ad26HEME002 and MVA-HCaJ 9.9 in Non-Human Primates (NHP)

The primary aim of the study was to determine whether vaccination with Ad26HEME002 and MVA-HCalJ-9.9 induces CALR- and/or JAK2-specific T-cell responses that were higher in magnitude and duration than vaccination with Ad26HEME002 alone in NHP. The secondary aim was to evaluate if an anti-CTLA-4 monoclonal antibody i.e., YERVOY® (ipilimumab) ([Ipi]) in combination with Ad26HEME002 and MVA-HCalJ-9.9 is capable of enhancing the immune responses. In addition, an explorative objective was to evaluate if anti-CTLA-4 antibodies in combination with homologues two-regimen dosing of Ad26HEME002 was able to enhance the insert-specific T-cell responses compared to Ad26HEME002 one-regimen dosing.

Cynomolgus macaques were immunized IM with Ad26HEME002 and/or MVA-HCalJ-9.9 alone or in combination with Ipi (10 mg/kg intravenously [IV]) according to schedule shown in Table 13. Briefly, NHPs were immunized with Ad26HEME002 ($5\times10^{10}$ VP, IM) alone (Group 1 and Group 2) or in combination with Ipi 10 mg/kg IV (Group 3 and Group 4). Animals were boosted at Week 4 and 8 with MVA-HCalJ-9.9 alone ($10^8$ IU, IM, Group 2) or MVA-HCalJ-9.9 in combination with Ipi 10 mg/kg IV (Group 3), or animals were boosted with Ad26HEME002 in combination with Ipi at Week 4 followed by a dosing at Week 14 with MVA-HCalJ-9.9 in combination with Ipi 10 mg/kg IV (Group 4), or animals did not receive any boost (Group 1). Animals were bled at various time points and PBMCs and serum were isolated for immunological assays. The induction of immune responses to CALRmut or JAK2 was evaluated in PBMCs at various time points during the study by IFN-γ ELISpot using peptide pools spanning either CALRmut or JAK2 2×9-mer insert sequence, the leader sequence, or the whole insert (HEME002; CALR_JAK2-2×9mer).

TABLE 13

| | Animal | Immunization | | | | Ipi |
|---|---|---|---|---|---|---|
| Group | nr | (Week 0) | (Week 4) | (Week 8) | (Week 14) | mg/kg IV |
| 1 | 5 | Ad26HEME002 ($5\times10^{10}$ VP) | NA | NA | NA | NA |
| 2 | 7 | Ad26HEME002 ($5\times10^{10}$ VP) | MVA-HCalJ-9.9 ($10^8$ IU) | MVA-HCalJ-9.9 ($10^8$ IU) | NA | NA |
| 3 | 7a | Ad26HEME002 ($5\times10^{10}$ VP) | MVA-HCalJ-9.9 ($10^8$ IU) | MVA-HCalJ-9.9 ($10^8$ IU) | NA | 10 |
| 4 | 5 | Ad26HEME002 ($5\times10^{10}$ VP) | Ad26HEME002 ($5\times10^{10}$ VP) | NA | MVA-HCalJ-9.9 ($10^8$ IU) | 10 |

Ipi, ipilimumab; nr, number; VP, viral particles; IU, infectious units; IV, intravenously; PBMC, peripheral blood mononuclear cell.

High non-specific background responses were seen in a few of the animals at various time points across the study, which may obscure the interpretation of particularly low responses. All animals were included in the data set.

There was no detectable immune response to the JAK2 or the leader sequence peptide pools at any of the measured time point (data not shown). The magnitude and responder rate measured to CALR and CALR_JAK2-2×9mer (HEME002) peptide pools was very similar and therefore only the CALR_JAK2-2×9mer (HEME002) data set is shown. FIG. 10 shows the kinetic of induction of IFN-γ-producing human HEME002-specific T-cells across the four groups. A single Ad26HEME002 immunization did not elicit detectable IFN-γ-producing cells to the HEME002 peptide pool in any of the animals (FIG. 10). In contrast, low, but detectable HEME002-specific IFN-γ-producing cells were detected in 5 out of 12 animals immunized with Ad26HEME002 in combination with Ipi (Group 3 and Group 4 combined) at Week 2 (FIG. 12) and 4 (data not shown) and this immune response was significantly higher than that detected in animals dosed with Ad26HEME002 only (p<0.001).

An immune response to CALR_JAK2-2×9mer (HEME002) was seen from Week 6 onward in animals dosed with Ad26HEME002 and MVA-HCalJ-9.9. There was only minor change in the responder rate (3-4 out of 7 animals) whether the animals had received one dose (FIG. 13) or two doses (FIG. 14) of MVA-HCalJ-9.9. Of the responding animals, the mean magnitude of HEME002 immune response ranged from 129 to 453 SFU/$10^6$ cells (FIG. 13-15). FIG. 11 shows the immune response at −2 weeks of the study (i.e. 2 weeks prior to first dose). FIG. 12 shows the immune response at 2 weeks. FIG. 13 shows the immune response at week 6. FIG. 14 shows the immune response at week 10. FIG. 15 shows the immune response at week 16. Animals dosed with MVA-HCalJ-9.9 in combination with Ipi at Week 4 and at Week 8 (Group 3) had an increase in the magnitude of the HEME002-specific immune response compared to after the Ad26HEME002 immunization (average mean response of responding animals: 93 SFU/$10^6$ cells at Week 2, 1,945 SFU/$10^6$ cells at Week 6, and 983 SFU/$10^6$ cells at Week 10), while there was no increase in the overall responder rate comparing before and after MVA dosing.

There was an increase in the magnitude of IFN-γ-producing cells following two doses with Ad26HEME002 in combination with Ipi compared to a single dosing with Ad26HEME002 in combination with Ipi (Group 4): average mean HEME002 response of responding animals of 93 SFU/$10^6$ cells at Week 2 (post first dosing) and 580 SFU/$10^6$ cells at Week 6 (post second dosing). At Week 14, Group 4 received a dosing with MVA-HCalJ-9.9 in combination with Ipi, which resulted in a 4.6-fold increase in the average mean response of responding animals (400 SFU/$10^6$ cells at Week 12 and 1,827 SFU/$10^6$ cells at Week 16; Tobit on change score p<0.001), whereas no change in the responder rate was seen. Of the responding animals, only minor contraction of the immune response was seen, with an average response of 1,698 SFU/$10^6$ cells for HEME002 at Week 20 (6 weeks post dosing with MVA-HCalJ-9.9+Ipi) (Group 4).

An analysis of area under the curve (AUC; Tobit with Bonferroni correction) for the HEME002 immune response was done for the following time windows: (i) Week 2 to Week 20, (ii) Week 2 to Week 12, and (iii) Week 16 to Week 20. Due to the high variation and high amount of censored values, there was no statistically significant difference found when comparing the AUC for Group 1 and Group 2, or AUC for Group 2 and Group 3 (FIG. 10). In contrast, there was a significant difference in the AUC for the HEME002 response when comparing Group 3 and Group 4 for the time window Week 16 to 20 (p=0.029). Animal #3002 (sample #14) was euthanized on Day 43. Animal #4003 (sample #22) Week 16 showed wells which were too numerous to count, and this sample was set at 2,000 SFU/$10^6$ cells and was also used for statistical analysis.

The nonclinical studies demonstrate that the produced Ad26 and MVA vectors expressing CALRmut and JAK2 2×9-mer fusion protein was able to give rise to T-cell activation in vitro and induce a cellular immune response in mice and NHP.

Example 10: MutCALR/MutJAK2 Construct Study, Dosing, and Scheduling

The primary aim of the study was to compare subcutaneous (SC) versus IV administration of antiCTLA4 antibody in combination with an Ad/Ad/MVA vaccine. The aim was also to evaluate multi dosing of anti-CTLA4 antibody versus single dose in combination with an Ad/Ad/MVA vaccine. The secondary aim was to evaluate if the combination of the anti-CTLA-4 monoclonal antibody i.e., YERVOY® (ipilimumab) ([Ipi]) with an anti PD-1 antibody (Nivolumab) is able to further enhance a specific T cell response.

The anti-CLTA4 antibody was administered SC at the same time as Ad26 vaccination localized to the Ad26 injection. Alternatively, anti-CTLA4 antibody was IV infused over time immediately after Ad26 administration. SC administration of anti-CTLA4 antibody was compared to IV administration at 3 mg/kg per animal. At week 2 analysis 16 animals received anti CTLA4 IV (3 mg/kg) and 31 animals had received anti CTLA4 (3 mg/kg) via SC administration. Similar number of responding animals 7/16 (44%) and 13/31 (42%) were observed in IV and SC administered anti CTLA4 administered cohorts respectively. Additionally, the average magnitude of response was not significantly different as determined by Tobit LRT analysis, with Bonferroni correction, p<0.05 (FIG. 16. Table 14).
Table 14.

Inclusion of anti αPD-1 antibody (Nivolumab 10 mg/kg IV) starting at week 4 to Ad/Ad/MVA+ipilimumab improves the magnitude of mutCALR specific T cell response (FIG. 17). The mutCALR peptide response was calculated based on mutCALR specific response—background. Week 6 Preliminary ELISpot analysis also indicate that multiple doses with anti αCTLA4 antibody and Ad/Ad/MVA dosing regimen is superior than a single dose (FIG. 17).

TABLE 14

| Group | Prime/ Boost Day 0 and Day 28 | Boost' Day 84 | IO Agent Day 0 | Day 28 | Day 84 | Day 29 start every 28 days |
|---|---|---|---|---|---|---|
| 1 | Ad26/Ad26 | MVA | aCTLA4 3mpk iv | aCTLA4 3mpk iv | aCTLA4 3mpk iv | — |
| 2 | Ad26/Ad26 | MVA | aCTLA4 3mpk iv | | | — |
| 3 | Ad26/Ad26 | MVA | aCTLA4 3mpk sc | aCTLA4 3mpk sc | aCTLA4 3mpk sc | — |
| 4 | Ad26/Ad26 | MVA | aCTLA4 3mpk sc | | | — |
| 5 | Ad26/Ad26 | MVA | aCTLA4 3mpk sc | aCTLA4 3mpk sc | aCTLA4 3mpk sc | aPD1 10mpk IV |
| 6 | Ad26/Ad26 | MVA | aCTLA4 3mpk sc | | | aPD1 10mpk IV |

IV, intravenously; sc, sub cutaneous.

Example 11: Generation of Self-Replicating RNA CALR_JAK2-2×9 Construct

The LS_CALR.JAK2-2×9mer polynucleotide was cloned into a self-replicating RNA.

The TC-83 strain of Venezuelan Equine Encephalitis Virus (VEEV) genome sequence served as the base sequence used to construct the replicon of the invention. This sequence was modified by placing the Downstream LooP (DLP) from Sindbis virus upstream of the non-structural protein 1 (nsP1) with the two joined by a 2A ribosome skipping element from porcine teschovirus-1. The first 193 nucleotides of nsP1 were duplicated downstream of the 5' UTR and upstream of the DLP except for the start codon, which was mutated to TAG. This insured all regulatory and secondary structures necessary for replication were maintained but prevented translation of this partial nsp1 sequence. The structural genes were removed and EcoR V and Asc I restriction sites were placed downstream of the subgenomic promoter as a multiple cloning site (MCS) to facilitate insertion of any gene of interest (FIG. 19). The LS_CALR_JAK2-2×9mer was inserted in the cloning site. The transgene was synthesized as a dsDNA fragment by IDT with 40 bp of homology to the MCS at their 5' and 3' ends and cloned into the VEEV derived self-replicating RNA vector digested with EcoRV and AscI using NEB HiFi DNA assembly master mix (cat #E2621S).

The polynucleotide sequence of the full self-replicating RNA plasmid is shown in SEQ ID NO: 33. The polynucleotide sequence of the T7 terminator is shown in SEQ ID NO: 34. The polynucleotide sequence of the AmpR promoter is shown in SEQ ID NO: 35. The polynucleotide sequence of the minimal 26S promoter is shown in SEQ ID NO: 36. The polynucleotide sequence of the T7 promoter is shown in SEQ ID NO: 37. The polynucleotide sequence of the Poly A site is shown in SEQ ID NO: 38. The polynucleotide sequence of the Alpha 5' replication sequence from nsP1 is shown SEQ ID NO: 39. The polynucleotide sequence of the DLP SEQ is shown in ID NO: 40. The polynucleotide sequence of P2A is shown in SEQ ID NO: 41. The polynucleotide sequence of Bom is shown in SEQ ID NO:42. The polynucleotide sequence of the DLP nsp ORF is shown in SEQ ID NO: 43. The polynucleotide sequence of nsP2 is shown in SEQ ID NO: 44. The polynucleotide sequence of nsP4 is shown is SEQ ID NO: 45. The polynucleotide sequence of nsP3 is shown in SEQ ID NO: 46. The polynucleotide sequence of the nsP1 is shown in SEQ ID NO: 47. The polynucleotide sequence of KanR is shown is SEQ ID NO: 48. The polynucleotide sequence of Rop is shown in SEQ ID NO: 49. The polynucleotide sequence of the 5'UTR is shown in SEQ ID NO: 50. The polynucleotide sequence of the 3'UTR is shown in SEQ ID NO: 51.

Example 12: srRNA.CALR/JAK2 Replicon RNA Platform Induces Cellular Responses in Mice The purpose of these studies was to determine if a self-replicating RNA molecule encoding CALR_JAK2-2×9mer could prime immune responses in Balb/c mice. The Balb/c mouse strain was selected based on the data described in Example 7 where less variation was seen with the Balb/c mouse strain compared to the C57BL/6 mouse strain.

In the first study, a self-replication RNA encoding LS_CALR_JAK2-2×9mer (srRNA.CALR/JAK2)) was dosed at 3, 10 and 30 μg. At Week 0, Balb/c mice were immunized by IM injection with srRNA.CALR/JAK2 at the indicated doses (3, 10 and 30 μg) and a control group was injected with saline. At Week 2, all animals were sacrificed and splenocytes were stimulated with 15-mer overlapping peptide (SEQ ID NO: 3) pools covering the CALR sequence in the insert, or 9-mers covering the two JAK2 9-mer sequences (SEQ ID NO:7). The induction of IFN-γ-producing cells was measured by IFN-γ ELISpot. CD8 and CD4 polyfunctional T cell responses were determined by measuring the production of IFN-γ, TNFα and IL-2 by flow cytometry. Table 15 shows the various experimental groups.

TABLE 15

| Group | Animal nr | Description of groups |
|---|---|---|
| 1 | 5 | Saline |
| 2 | 5 | srRNA.CALR/JAK2 3 μg |
| 3 | 5 | srRNA.CALR/JAK2 10 μg |
| 4 | 5 | srRNA.CALR/JAK2 30 μg |

All animals immunized with srRNA.CALR/JAK2 developed IFNγ-producing cells upon stimulation with peptides covering CALRmut sequence (FIG. 21A), in contrast no induction of cytokine-producing cells was detected upon stimulation with the two 9-mer JAK2 peptides (SEQ ID NO: 5 and 6) (data not shown). Intracellular flow cytometry showed that the anti-CALR response is CD4 driven and is polyfunctional at all doses tested (FIG. 21B).

Self-replicating RNA molecules in the first study were injected naked into the animals. For the second study we formulated the self-replication RNA molecule in a lipid nanoparticle (LNP) and performed a similar study outlined in Table 16. Similar to the first study, all animals immunized with srRNA.CALR/JAK2 developed IFNγ-producing cells upon stimulation with peptides covering CALRmut sequence (FIG. 22A), in contrast no induction of cytokine-producing cells was detected upon stimulation with the two 9-mer JAK2 peptides (SEQ ID NO: 5 and 6) (data not shown). Intracellular flow cytometry showed that the anti-CALR response is CD4 driven and is polyfunctional at all doses tested in both unformulated and LNP-formulated versions (FIG. 22B).

TABLE 16

| Group | Animal nr | Description of groups |
|---|---|---|
| 1 | 5 | Saline |
| 2 | 5 | srRNA.CALR/JAK2 0.2 μg LNP formulated |
| 3 | 5 | srRNA.CALR/JAK2 2 μg LNP formulated |
| 4 | 5 | srRNA.CALR/JAK2 20 μg LNP formulated |
| 5 | 5 | srRNA.CALR/JAK2 20 μg unformulated |

In the third study we tested srRNA.CALR/JAK2 in combination with two other vaccine platforms, Ad26 and MVA to determine whether heterologous prime/boost regimens increase anti-CALR T cell function. All platforms encoded the CALR_JAK2-2×9mer construct. On week 0, Balb/c mice were injected with saline, Ad26HEME002 ($10^{10}$ PFU) or srRNA/CALR.JAK2 (20 μg). On week 4 mice were injected with either Ad26HEME002, MVA-HCalJ-9.9 ($10^{7}$ PFU) or srRNA.CALR/JAK2 and spleens were analyzed one week post boost (see experimental design below, Table 17). A control group was added to bridge to historical data using Ad26/MVA with a 3 week prime/boost interval and spleen analysis 2 weeks post boost. Spleens were analyzed by ELISpot and ICS as described above using overlapping CALR peptides.

TABLE 17

| Group | Animal nr | Description of groups |
|---|---|---|
| 1 | 5 | Saline |
| 2 | 8 | srRNA prime only |
| 3 | 8 | Ad26 prime only |
| 4 | 8 | srRNA/srRNA |
| 5 | 8 | Ad26/Ad26 |
| 6 | 8 | srRNA/Ad26 |
| 7 | 8 | Ad26/srRNA |
| 8 | 8 | srRNA/MVA |
| 9 | 8 | Ad26/MVA |
| 10 | 6 | Ad26/MVA 3 week interval |

The addition of Ad26 or MVA boost to the self-replicating RNA prime resulted in statistically significant boosts according to IFNγELISpot ($p<0.001$, 5.1 and 6.5 fold increase respectively). The addition of self-replicating RNA as a boosting agent following Ad26 prime resulted in a 1.7 fold increase over Ad26 prime alone (not statistically significant) (FIG. 23A). Intracellular cytokine staining shows that following self-replication RNA prime, the addition of Ad26 and/or MVA as a boost results in statistically significant increases in polyfunctional IFNγ+TNFα+IL-2+CD4 T cells ($p<00.001$, 4.9 and 3.6 fold increase respectively). Boosting with self-replicating RNA following Ad26 prime leads to a 2-fold increase in polyfunctional triple cytokine positive T cells over Ad26 prime alone (not statistically significant) (FIG. 23B).

Example 13. Immunogenicity of srRNA.CALR/JAK2 and MVA-HCalJ-9.9 in Non-Human Primates (NHP)

The primary aim of this study will be to determine whether vaccination with srRNA.CALR/JAK2 and MVA- HCalJ-9.9 induces antigen specific T-cell responses that are higher in magnitude and duration than vaccination with srRNA.CALR/JAK2 alone in NHP. The secondary aim is to evaluate if an anti-CTLA-4 monoclonal antibody i.e., YERVOY® (ipilimumab) ([Ipi]) in combination with srRNA-.CALR/JAK2 and MVA-HCalJ-9.9 can enhance the vaccine induced immune response. In addition, an explorative objective is to evaluate if anti-PD-1 monoclonal antibodies OPDIVO® (nivolumab) in combination with vaccine regimen and anti-CTLA-4 antibody is comparable or increases insert-specific T-cell responses compared to animals dosed without anti-PD-1. Cynomolgus macaques are immunized IM with srRNA.CALR/JAK2, and/or MVA-HCalJ-9.9 alone or in combination with Ipi (3 mg/kg sub cutaneous [SC]) or in combination with Nivolumab (10 mg/kg intravenous [IV] according to schedule shown in Table 18. Briefly, NHPs will be immunized with srRNA.CALR/JAK2 and MVA-HCalJ-9.9 in combination with Ipi 3 mg/kg SC (Group 2) or in combination with Ipi 3 mg/kg SC and Nivolumab IV 10 mg/kg IV (Group 4). Animals are bled at various time points and PBMCs and serum are isolated for immunological assays. The induction of immune responses specific to CALR antigens are evaluated in PBMCs at various time points during the study by IFNγ ELISpot using peptide pools comprised of 15mer overlapping peptides corresponding to the entire CALR insert sequence.

The srRNA.CALR/JAK2 vaccine is expected to elicit an antigen specific T cell response that can be further increased when administered as a regimen in combination with MVA-HCalJ-9.9. Use of immune checkpoint blockade monoclonal antibodies anti-CTLA-4 and/or anti PD-1 antibodies in combination with srRNA.CALR/JAK2 and MVA-HCalJ-9.9 will lead to higher magnitude, quality, and more durable antigen specific T cell response.

TABLE 18

| Group | Day 0/28 | Day 70 | Anti-CTLA-4 mAb | Anti-PD-1 mAb |
|---|---|---|---|---|
| 1 | srRNA/srRNA | MVA | — | — |
| 2 | srRNA/srRNA | MVA | 0, 28, 70 | — |
| 3 | srRNA/srRNA | MVA | 0, 28, 70 | 29, 57, 84, 113 |

Example 14. Immunogenicity of GAd.CALR.JAK2 and Continuous Presentation of srRNA.CALR/JAK2 in Non-Human Primates (NHP)

The primary aim of this study is to confirm that vaccination with GAd20.CALR.JAK2 induces antigen specific T-cell responses in combination with anti-CTL-4 antibody and MVA or sRNA. The study is also designed to determine whether vaccination with srRNA.CALR/JAK2 increases T-cell when combined with GAd20 or GAD20/MVA and whether srRNA can be used in place of MVA. The objective of this study is also to evaluated whether GAD20/MVA/srRNA in combination with antiCTLA4 antibody can induce antigen specific T cell responses greater than GAD20/MVA/srRNA alone. Addition of a srRNA.CALR/JAK2 vector to an GAd20/MVA vaccine as a triple combination is expected to drive greater and more durable antigen specific T cell responses in cancer patients.

The second aim of this study is to assess srRNA-.CALR.JAK2 multi-dose regimen capacity to eliminate the need of anti CTL-4 antibody, completely or after administration of MVA. In addition, the study is constructed to determine if srRNA can be administered multiple times (monthly) to continually increase or maintain antigen specific T cell responses. The highest and most durable levels of anti-mutCALR/mutJAK2 targeted T cells generated will require continuous neo-antigen presentation by a vector not susceptible to Ab-mediated neutralization resulting in malignant clone clearance and clinical benefit for MPN patients. One potential advantage of a self-replicating RNA based vaccine is the lack of vector specific immunity developed. Absence of vector specific immune response can allow for repeated administration of the self-replicating RNA without diminishment of antigen presentation due to an inability of the self-replicating RNA based vaccine to generate neutralizing antibodies specific to the vector. Multi-dose regimens are tested to evaluate if srRNA.CALR/JAK2 can maintain an antigen specific T cell response by administration on a monthly intramuscular dosing schedule.

For this study, cynomolgus macaques are immunized according to schedule shown in Table 19. Animals are bled at various time points and PBMCs and serum are isolated for immunological assays. The induction of immune responses specific to CALR antigens are evaluated in PBMCs at various time points during the study by IFNγ ELISpot using peptide pools comprised of 15mer overlapping peptides corresponding to the entire CALR insert sequence Administration of srRNA.CALR/JAK2 after GAd20/MVA immunization will allow for continued boosting to prolonge antigen specific T cell response independent or in combination with CPI administration. Multi dose srRNA-.CALR/JAK2 self-replication RNA based regimens are expected to elicit higher magnitude of T cell responses with a longer duration.

TABLE 19

| Group | Description of Groups |
|---|---|
| 1 | GAd20/MVA/srRNA |
| 2 | GAd20/MVA/srRNA/srRNA |
| 3 | GAd20/srRNA/srRNA/srRNA |
| 4 | GAD20/GAD20/MVA + anti CTLA4 antibody 3 mg/kg IV |
| 5 | GAD20/GAD20/MVA/srRNA/srRNA/srRNA + anti CTLA4 antibody 3 mg/kg IV |
| 6 | GAD20/GAD20/srRNA/srRNA/srRNA/srRNA + anti CTLA4 antibody 3 mg/kg IV |
| 4 | GAD20/GAD20/srRNA/srRNA/srRNA/srRNA |

EMBODIMENTS

The following list of embodiments is intended to complement, rather than displace or supersede, the previous descriptions.

Embodiment 1. A polypeptide comprising at least two or more epitope sequences selected from the group consisting of:

MKDKQDEEQRTRRMMRTKMRMRRMRRTRRKMRRKMSPARPRTSCREACLQG WTE (SEQ ID NO: 1) or at least 90% sequence identity to SEQ ID NO: 1;

EEAEDNCRRMMRTK (SEQ ID NO: 2) or at least 90% sequence identity to SEQ ID NO: 2;

KLSHKHLVLNYGVCFCGDENILVQEFVKFG (SEQ ID NO: 4) or at least 90% sequence identity to SEQ ID NO: 4;

VLNYGVCFC (SEQ ID NO: 5) or at least 90% sequence identity to SEQ ID NO: 5;

FCGDENILV (SEQ ID NO: 6) or at least 90% sequence identity to SEQ ID NO: 6; and combinations thereof.

Embodiment 2. The polypeptide of embodiment 1, wherein the polypeptide comprises the epitope sequences:

MKDKQDEEQRTRRMMRTKMRMRRMRR-TRRKMRRKMSPARPRTSCREACLQG WTE (SEQ ID NO: 1) or at least 90% sequence identity to SEQ ID NO: 1;

EEAEDNCRRMMRTK (SEQ ID NO: 2) or at least 90% sequence identity to SEQ ID NO: 2;

VLNYGVCFC (SEQ ID NO: 5) or at least 90% sequence identity to SEQ ID NO: 5; and

FCGDENILV (SEQ ID NO: 6) or at least 90% sequence identity to SEQ ID NO: 6.

Embodiment 3. The polypeptide of embodiment 1, wherein the polypeptide comprises the epitope sequences:

MKDKQDEEQRTRRMMRTKMRMRRMRR-TRRKMRRKMSPARPRTSCREACLQG WTE (SEQ ID NO: 1) or at least 90% sequence identity to SEQ ID NO: 1;

EEAEDNCRRMMRTK (SEQ ID NO: 2) or at least 90% sequence identity to SEQ ID NO: 2; and KLSHKHLVLNYGVCFCGDENILVQEFVKFG (SEQ ID NO: 4) or at least 90% sequence identity to SEQ ID NO: 4.

Embodiment 4. The polypeptide of embodiment 1, wherein the polypeptide comprises the epitope sequences:

MKDKQDEEQRTRRMMRTKMRMRRMRR-TRRKMRRKMSPARPRTSCREACLQG WTE (SEQ ID NO: 1) or at least 90% sequence identity to SEQ ID NO: 1; and EEAEDNCRRMMRTK (SEQ ID NO: 2) or at least 90% sequence identity to SEQ ID NO: 2.

Embodiment 5. The polypeptide of any one of embodiments 1-4, further comprising a leader sequence at N terminus selected from:

```
                                          (SEQ ID NO: 8)
MACPGFLWALVISTCLEFSMA;

                                         (SEQ ID NO: 54)
MQIFVKTLTGKTITLEVEPSDTIENVKAKIQDKEGIPPDQQRLIFAGKQL

EDGRTLSDYNIQKESTLHLVLRLRGV;
and

                                         (SEQ ID NO: 29)
MGQKEQIHTLQKNSERMSKQLTRSSQAV.
```

Embodiment 6. The polypeptide of any of embodiments 1-5, wherein the epitope sequences are connected to each other by a linker sequence.

Embodiment 7. The polypeptide of embodiment 6, wherein the linker sequence is selected from AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

Embodiment 8. The polypeptide of embodiment 6, wherein the linker sequence comprises a protease cleavage site.

Embodiment 9. The polypeptide of embodiment 1, wherein the polypeptide is selected from:

an amino acid sequence of SEQ ID NO: 3 or having at least 90% sequence identity to SEQ ID NO: 3;

an amino acid sequence of SEQ ID NO: 7 or having at least 90% sequence identity to SEQ ID NO: 7;

an amino acid sequence of SEQ ID NO: 9 or having at least 90% sequence identity to SEQ ID NO: 9;

an amino acid sequence of SEQ ID NO: 10 or having at least 90% sequence identity to SEQ ID NO: 10;

an amino acid sequence of SEQ ID NO: 11 or having at least 90% sequence identity to SEQ ID NO: 11;

an amino acid sequence of SEQ ID NO: 12 or having at least 90% sequence identity to SEQ ID NO: 12;

an amino acid sequence of SEQ ID NO: 13 or having at least 90% sequence identity to SEQ ID NO: 13;

an amino acid sequence of SEQ ID NO:14 or having at least 90% sequence identity to SEQ ID NO: 14;

an amino acid sequence of SEQ ID NO: 15 or having at least 90% sequence identity to SEQ ID NO: 15; and an amino acid sequence of SEQ ID NO: 31 or having at least 90% sequence identity to SEQ ID NO: 31.

Embodiment 10. A polynucleotide encoding a polypeptide of any one of embodiments 1-9.

Embodiment 11. The polynucleotide of embodiment 10, wherein the polynucleotide is selected from the group consisting of:

a nucleic acid sequence of SEQ ID NO: 16 or having at least 90% sequence identity to SEQ ID NO: 16;

a nucleic acid sequence of SEQ ID NO: 17 or having at least 90% sequence identity to SEQ ID NO: 17;

a nucleic acid sequence of SEQ ID NO: 18 or having at least 90% sequence identity to SEQ ID NO: 18;

a nucleic acid sequence of SEQ ID NO: 19 or having at least 90% sequence identity to SEQ ID NO: 19;

a nucleic acid sequence of SEQ ID NO: 20 or having at least 90% sequence identity to SEQ ID NO: 20;

a nucleic acid sequence of SEQ ID NO: 21 or having at least 90% sequence identity to SEQ ID NO: 21;

a nucleic acid sequence of SEQ ID NO: 22 or having at least 90% sequence identity to SEQ ID NO: 22;

a nucleic acid sequence of SEQ ID NO: 26 or having at least 90% sequence identity to SEQ ID NO: 26; and a nucleic acid sequence of SEQ ID NO: 27 or having at least 90% sequence identity to SEQ ID NO: 27.

Embodiment 12. A vector comprising a polynucleotide of embodiment 10 or embodiment 11.

Embodiment 13. The vector of embodiment 12, wherein the vector is selected from an adenovirus vector, an alphaviral vector, a poxvirus vector, an adeno-associated virus vector, a retrovirus vector, a self-replicating RNA molecule, and a combination thereof.

Embodiment 14. The vector of embodiment 13, wherein the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Embodiment 15. The vector of embodiment 13, wherein the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Embodiment 16. The vector of embodiment 12, wherein the vector is the adenovirus vector comprising a polynucleotide encoding any one of the polypeptides of one of embodiments 1-9.

Embodiment 17. The vector of embodiment 12, wherein the vector is the self-replicating RNA molecule comprising a polynucleotide encoding any one of the polypeptides of any one of embodiments 1-9.

Embodiment 18. The vector of embodiment 12, wherein the vector is Ad26 comprising a polynucleotide encoding a polypeptide of SEQ ID NO: 10 or having at least 90% sequence identity to SEQ ID NO: 10.

Embodiment 19. The vector of embodiment 12, wherein the vector is MVA vector comprising a polynucleotide encoding a polypeptide of SEQ ID NO: 31 or having at least 90% sequence identity to SEQ ID NO: 31.

Embodiment 20. The vector of embodiment 12, wherein the vector is GAd20 comprising a polynucleotide encoding a polypeptide of SEQ ID NO: 31 or having at least 90% sequence identity to SEQ ID NO: 31.

Embodiment 21. The vector of embodiment 12, wherein the vector is a self-replicating RNA molecule comprising a polynucleotide encoding a polypeptide of SEQ ID NO: 12 or having at least 90% sequence identity to SEQ ID NO: 12.

Embodiment 22. A pharmaceutical composition comprising a polypeptide of any one of embodiments 1-9.

Embodiment 23. A pharmaceutical composition comprising a polynucleotide any one of embodiments 10 and 11.

Embodiment 24. A pharmaceutical composition comprising a vector of any one of embodiments 12-21.

Embodiment 25. The pharmaceutical composition of embodiment 24, wherein the vector is selected from an Ad26 vector, a MVA vector, a GAd20 vector, a self-replicating RNA molecule, and combinations thereof.

Embodiment 26. A method of treating, preventing, reducing a risk of onset or delaying the onset of a clinical condition characterized by an expression of JAK2V617F and/or CALR exon 9 mutant in a subject comprising administering to the subject in need thereof a pharmaceutical composition of any one of embodiments 22-25.

Embodiment 27. A method of inducing an immune response in a subject carrying JAK2V617F and/or CALR exon 9 mutation comprising administering to the subject in need thereof a pharmaceutical composition of any one of embodiments 22-25.

Embodiment 28. A method of treating or preventing a myeloproliferative disease in a subject comprising administering to the subject in need thereof a pharmaceutical composition of any one of embodiments 22-25.

Embodiment 29. A method of treating cancer in a subject comprising administering to the subject in need thereof a pharmaceutical composition of any one of embodiments 22-25.

Embodiment 30. A method of treating a cardiovascular disease in a subject comprising administering to the subject in need thereof a pharmaceutical composition of any one of embodiments 22-25.

Embodiment 31. A method of treating, preventing, reducing a risk of onset or delaying the onset of a clinical condition characterized by an expression of JAK2V617F and/or CALR exon 9 mutant in a subject comprising administering to the subject in need thereof a composition comprising a vector comprising a polynucleotide encoding at least two or more epitope sequences selected from the group consisting of:

CALR epitope of SEQ ID NO: 1 or having at least 90% sequence identity to SEQ ID NO: 1;

CALR epitope of SEQ ID NO: 2 or having at least 90% sequence identity to SEQ ID NO: 2;

JAK2 epitope of SEQ ID NO: 4 or having at least 90% sequence identity to SEQ ID NO: 4;

JAK2 epitope of SEQ ID NO: 5 or at least 90% sequence identity to SEQ ID NO: 5;

JAK2 epitope of SEQ ID NO: 6 or having at least 90% sequence identity to SEQ ID NO: 6; and combinations thereof, and wherein the administration comprises one or more administrations of the composition.

Embodiment 32. A method of inducing an immune response in a subject carrying JAK2V617F and/or CALR exon 9 mutation comprising administering to the subject in need thereof a composition comprising a vector comprising a polynucleotide encoding at least two or more epitope sequences selected from the group consisting of:

CALR epitope of SEQ ID NO: 1 or having at least 90% sequence identity to SEQ ID NO: 1;

CALR epitope of SEQ ID NO: 2 or having at least 90% sequence identity to SEQ ID NO: 2;

JAK2 epitope of SEQ ID NO: 4 or having at least 90% sequence identity to SEQ ID NO: 4;

JAK2 epitope of SEQ ID NO: 5 or at least 90% sequence identity to SEQ ID NO: 5;

JAK2 epitope of SEQ ID NO: 6 or having at least 90% sequence identity to SEQ ID NO: 6; and combinations thereof, and wherein the administration comprises one or more administrations of the composition.

Embodiment 33. A method of treating or preventing a myeloproliferative disease in a subject comprising administering to the subject in need thereof a composition comprising a vector comprising a polynucleotide encoding at least two or more epitope sequences selected from the group consisting of:

CALR epitope of SEQ ID NO: 1 or having at least 90% sequence identity to SEQ ID NO: 1;

CALR epitope of SEQ ID NO: 2 or having at least 90% sequence identity to SEQ ID NO: 2;

JAK2 epitope of SEQ ID NO: 4 or having at least 90% sequence identity to SEQ ID NO: 4;

JAK2 epitope of SEQ ID NO: 5 or at least 90% sequence identity to SEQ ID NO: 5;

JAK2 epitope of SEQ ID NO: 6 or having at least 90% sequence identity to SEQ ID NO: 6; and combinations thereof, and wherein the administration comprises one or more administrations of the composition.

Embodiment 34. The method of embodiment 33, wherein the myeloproliferative disease is selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

Embodiment 35. A method of treating cancer in a subject comprising administering to the subject in need thereof a composition comprising a vector comprising a polynucleotide encoding at least two or more epitope sequences selected from the group consisting of:

CALR epitope of SEQ ID NO: 1 or having at least 90% sequence identity to SEQ ID NO: 1;

CALR epitope of SEQ ID NO: 2 or having at least 90% sequence identity to SEQ ID NO: 2;

JAK2 epitope of SEQ ID NO: 4 or having at least 90% sequence identity to SEQ ID NO: 4;

JAK2 epitope of SEQ ID NO: 5 or at least 90% sequence identity to SEQ ID NO: 5;

JAK2 epitope of SEQ ID NO: 6 or having at least 90% sequence identity to SEQ ID NO: 6; and combinations thereof, and wherein the administration comprises one or more administrations of the composition.

Embodiment 36. The method of embodiment 35, wherein the cancer is selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

Embodiment 37. A method of treating a cardiovascular disease in a subject comprising administering to the subject in need thereof a composition comprising a vector comprising a polynucleotide encoding at least two or more epitope sequences selected from the group consisting of:

CALR epitope of SEQ ID NO: 1 or having at least 90% sequence identity to SEQ ID NO: 1;

CALR epitope of SEQ ID NO: 2 or having at least 90% sequence identity to SEQ ID NO: 2;

JAK2 epitope of SEQ ID NO: 4 or having at least 90% sequence identity to SEQ ID NO: 4;

JAK2 epitope of SEQ ID NO: 5 or at least 90% sequence identity to SEQ ID NO: 5;

JAK2 epitope of SEQ ID NO: 6 or having at least 90% sequence identity to SEQ ID NO: 6; and combinations thereof, and wherein the administration comprises one or more administrations of the composition.

Embodiment 38. The method of embodiment 37, wherein the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis, and a clonal hematopoiesis.

Embodiment 39. The method of any one of embodiments 31-38, wherein the vector is selected from an adenovirus vector, an alphaviral vector, a poxvirus vector, an adeno-associated virus vector, a retrovirus vector, a self-replicating RNA molecule, and a combination thereof.

Embodiment 40. The method of any one of embodiments 31-39, wherein the vector is selected from Ad26 vector, MVA vector, GAd20 vector, a self-replicating RNA molecule, and combinations thereof.

Embodiment 41. The method of any one of embodiments 31-39, wherein the vector is an Ad26 vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 42. The method of any one of embodiments 31-39, wherein the vector is a GAd20 vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 43. The method of any one of embodiments 31-39, wherein the vector is a MVA vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 44. The method of any one of embodiments 31-39, wherein the vector is a self-replicating RNA molecule comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and Janus kinase 2 (JAK2) epitope of SEQ ID NO: 6.

Embodiment 45. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

Embodiment 46. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

Embodiment 47. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector.

Embodiment 48. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector.

Embodiment 49. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 50. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 51. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 52. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 53. The method of any one of embodiments 31-52, further comprising administering a second therapeutic agent selected from a CTLA-4 antibody, a PD-1 antibody, a PD-L1 antibody, a TLR agonist, a CD40 agonist, an OX40 agonist, hydroxyurea, ruxolitinib, fedratinib, a 41BB agonist, a CD28 agonist, FLT3 ligand, aluminum sulfate, a BTK inhibitor, a JAK inhibitor, a CD38 antibody, a CDK inhibitor, a CD33 antibody, a CD37 antibody, a CD25 antibody, a GM-CSF inhibitor, IL-2, IL-15, IL-7, IFNγ, IFNα, TNFα, a VEGF antibody, a CD70 antibody, a CD27 antibody, a BCMA antibody, a GPRC5D antibody, and combinations thereof.

Embodiment 54. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector; and wherein the treatment cycle further comprising administering a checkpoint inhibitor selected from an anti CTLA-4 antibody, a PD-1 antibody, and a PD-L1 antibody, in combination with the first, second, and/or third composition.

Embodiment 55. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 56. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 57. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 58. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 58. The method of any one of embodiments 31-44, comprising one or more treatment cycles, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Embodiment 59. The method of any one of embodiments 31-44, comprising one or more treatment cycles, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a third administration comprising a third composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule; and wherein the treatment cycle further comprising administering a checkpoint inhibitor selected from an anti CTLA-4 antibody, a PD-1 antibody, and a PD-L1 antibody, in combination with the first, second, and/or third composition.

SEQUENCE LISTING

| SEQ ID NO: | Epitope | Sequence |
|---|---|---|
| 1 | CALR epitope I | MKDKQDEEQRTRRMMRTKMRMRRMRRTRRKMRRKMSPARPRTSCREACLQGWTE |
| 2 | CALR epitope II | EEAEDNCRRMMRTK |
| 3 | CALR epitope I-AAY-CALR epitope II | MKDKQDEEQRTRRMMRTKMRMRRMRRTRRKMRRKMSPARPRTSCREACLQGWTEA AYEEAEDNCRRMMRTK |
| 4 | JAK2 30mer epitope | KLSHKHLVLNYGVCFCGDENILVQEFVKFG |
| 5 | JAK2 epitope 1 | VLNYGVCFC |
| 6 | JAK2 epitope 2 | FCGDENILV |
| 7 | 2X9mer JAK2 | VLNYGVCFCAAYFCGDENILV |
| 8 | HAVt20 Leader sequence (LS) | MACPGFLWALVISTCLEFSMA |
| 9 | LS_CALR (HEME003) | MACPGFLWALVISTCLEFSMAMKDKQDEEQRTRRMMRTKMRMRRMRRTRRKMRRK MSPARPRTSCREACLQGWTEAAYEEAEDNCRRMMRTK |
| 10 | LS_CALR_JAK2-2x9mer (HEME002) | MACPGFLWALVISTCLEFSMAMKDKQDEEQRTRRMMRTKMRMRRMRRTRRKMRRK MSPARPRTSCREACLQGWTEAAYEEAEDNCRRMMRTKAAYVLNYGVCFCAAYFCGD ENILV |
| 11 | LS_CALR_JAK2-30mer (HEME001) | MACPGFLWALVISTCLEFSMAMKDKQDEEQRTRRMMRTKMRMRRMRRTRRKMRRK MSPARPRTSCREACLQGWTEAAYEEAEDNCRRMMRTKAAYKLSHKHLVLNYGVCFC GDENILVQEFVKFG |
| 12 | CALR_JAK2-2x9mer | MKDKQDEEQRTRRMMRTKMRMRRMRRTRRKMRRKMSPARPRTSCREACLQGWTEA AYEEAEDNCRRMMRTKAAYVLNYGVCFCAAYFCGDENILV |
| 13 | CALR_JAK2-30mer | MKDKQDEEQRTRRMMRTKMRMRRMRRTRRKMRRKMSPARPRTSCREACLQGWTEA AYEEAEDNCRRMMRTKAAYKLSHKHLVLNYGVCFCGDENILVQEFVKFG |
| 14 | Ubiq_CALR_JAK2-2x9mer | MQIFVKTLTGKTITLEVEPSDTIENVKAKIQDKEGIPPDQQRLIFAGKQLEDGRTLSDYNI QKESTLHLVLRLRGVRKDKQDEEQRTRRMMRTKMRMRRMRRTRRKMRRKMSPARP RTSCREACLQGWTEAAYEEAEDNCRRMMRTKAAYVLNYGVCFCAAYFCGDENILV |
| 15 | Ubiq_CALR_JAK2-30mer | MQIFVKTLTGKTITLEVEPSDTIENVKAKIQDKEGIPPDQQRLIFAGKQLEDGRTLSDYNI QKESTLHLVLRLRGVRKDKQDEEQRTRRMMRTKMRMRRMRRTRRKMRRKMSPARP RTSCREACLQGWTEAAYEEAEDNCRRMMRTKAAYKLSHKHLVLNYGVCFCGDENIL VQEFVKFG |
| 16 | LS_CALR | ATGGCATGCCCAGGCTTCCTGTGGGCCCTGGTCATCAGCACCTGTCTGGAGTTTTCC ATGGCCATGAAGGACAAGCAGGATGAGGAGCAGCGGACCCGGAGAATGATGAGG ACAAAGATGCGCATGAGGCGCATGCGGAGAACAAGGCGCAAGATGCGGAGAAAG ATGTCTCCAGCAAGGCCTAGAACCAGCTGCAGGGAGGCATGTCTGCAGGGATGGA CAGAGGCAGCATACGAGGAGGCAGAGGACAACTGCAGGCGCATGATGAGGACCA AG |

-continued

SEQUENCE LISTING

| SEQ ID NO: | Epitope | Sequence |
|---|---|---|
| 17 | LS_CALR_JAK2-2x9mer | ATGGCATGCCCAGGCTTCCTGTGGGCCCTGGTCATCAGCACCTGTCTGGAGTTTTCC<br>ATGGCCATGAAGGACAAGCAGGATGAGGAGCAGCGGACCCGGAGAATGATGAGG<br>ACAAAGATGCGCATGAGGCGCATGCGGAGAACAAGGCGCAAGATGCGGAGAAAG<br>ATGTCTCCAGCAAGGCCTAGAACCAGCTGCAGGGAGGCATGTCTGCAGGGATGGA<br>CAGAGGCAGCATACGAGGAGGCAGAGGACAACTGCAGGCGCATGATGAGGACCA<br>AGGCCGCCTACGTGCTGAATTATGGCGTGTGCTTCTGTGCCGCCTATTTTTGTGGCG<br>ATGAGAACATCCTGGTG |
| 18 | LS_CALR_JAK2-30mer | ATGGCATGCCCAGGCTTCCTGTGGGCCCTGGTCATCAGCACCTGTCTGGAGTTTTCC<br>ATGGCCATGAAGGACAAGCAGGATGAGGAGCAGCGGACCCGGAGAATGATGAGG<br>ACAAAGATGCGCATGAGGCGCATGCGGAGAACAAGGCGCAAGATGCGGAGAAAG<br>ATGTCTCCAGCAAGGCCTAGAACCAGCTGCAGGGAGGCATGTCTGCAGGGATGGA<br>CAGAGGCAGCATACGAGGAGGCAGAGGACAACTGCAGGCGCATGATGAGGACCA<br>AGGCCGCCTACAAGCTGAGCCACAAGCACCTGGTGCTGAACTATGGCGTGTGCTTC<br>TGTGGCGATGAGAATATCCTGGTGCAGGAGTTCGTGAAGTTTGGC |
| 19 | CALR_JAK2-2x9mer for Ad26 | ATGAAGGACAAGCAGGATGAGGAGCAGCGGACCCGGAGAATGATGAGGACAAAG<br>ATGCGCATGAGGCGCATGCGGAGAACAAGGCGCAAGATGCGGAGAAAGATGTCTC<br>CAGCAAGGCCTAGAACCAGCTGCAGGGAGGCATGTCTGCAGGGATGGACAGAGGC<br>AGCATACGAGGAGGCAGAGGACAACTGCAGGCGCATGATGAGGACCAAGGCCGCC<br>TACGTGCTGAATTATGGCGTGTGCTTCTGTGCCGCCTATTTTTGTGGCGATGAGAAC<br>ATCCTGGTG |
| 20 | CALR_JAK2-30mer | ATGAAGGACAAGCAGGATGAGGAGCAGCGGACCCGGAGAATGATGAGGACAAAG<br>ATGCGCATGAGGCGCATGCGGAGAACAAGGCGCAAGATGCGGAGAAAGATGTCTC<br>CAGCAAGGCCTAGAACCAGCTGCAGGGAGGCATGTCTGCAGGGATGGACAGAGGC<br>AGCATACGAGGAGGCAGAGGACAACTGCAGGCGCATGATGAGGACCAAGGCCGCC<br>TACAAGCTGAGCCACAAGCACCTGGTGCTGAACTATGGCGTGTGCTTCTGTGGCGA<br>TGAGAATATCCTGGTGCAGGAGTTCGTGAAGTTTGGC |
| 21 | Ubiq_CALR_JAK2-2x9mer | ATGCAGATCTTCGTGAAGACCCTGACAGGCAAGACCATCACACTGGAGGTGGAGC<br>CCTCCGACACCATCGAGAACGTGAAGGCCAAGATCCAGGACAAGGAGGGCATCCC<br>CCCTGATCAGCAGCGGCTGATCTTTGCCGGCAAGCAGCTGGAGGACGGCAGAACCC<br>TGTCTGATTACAATATCCAGAAGGAGAGCACACTGCACCTGGTGCTGCGGCTGAGA<br>GGCGTGAGGAAGGACAAGCAGGATGAGGAGCAGCGCACCCGGAGAATGATGCGG<br>ACAAAGATGAGAATGAGGCGCATGCGGAGAACCAGGCGCAAGATGCGGAGAAAG<br>ATGAGCCCAGCAAGGCCACGCACCTCCTGCAGGGAGGCATGTCTGCAGGGATGGA<br>CAGAGGCAGCCTATGAGGAGGCCGAGGACAACTGCAGGCGCATGATGCGGACAAA<br>GGCCGCCTACGTGCTGAATTATGGCGTGTGCTTCTGTGCCGCCTATTTTTGTGGCGA<br>TGAGAACATCCTGGTG |
| 22 | Ubiq_CALR_JAK2-30mer | ATGCAGATCTTCGTGAAGACCCTGACAGGCAAGACCATCACACTGGAGGTGGAGC<br>CCTCCGACACCATCGAGAACGTGAAGGCCAAGATCCAGGACAAGGAGGGCATCCC<br>CCCTGATCAGCAGCGGCTGATCTTTGCCGGCAAGCAGCTGGAGGACGGCAGAACCC<br>TGTCTGATTACAATATCCAGAAGGAGAGCACACTGCACCTGGTGCTGCGGCTGAGA<br>GGCGTGAGGAAGGACAAGCAGGATGAGGAGCAGCGCACCCGGAGAATGATGCGG<br>ACAAAGATGAGAATGAGGCGCATGCGGAGAACCAGGCGCAAGATGCGGAGAAAG<br>ATGAGCCCAGCAAGGCCACGCACCTCCTGCAGGGAGGCATGTCTGCAGGGATGGA<br>CAGAGGCAGCCTATGAGGAGGCCGAGGACAACTGCAGGCGCATGATGCGGACAAA<br>GGCCGCCTACAAGCTGTCTCACAAGCACCTGGTGCTGAACTATGGCGTGTGCTTCT<br>GTGGCGATGAGAATATCCTGGTGCAGGAGTTCGTGAAGTTTGGCTGATAA |
| 23 | polynucleotide sequence of the Ad26HEME001 transgene containing the tetracycline operator (TetO)-containing cytomegalovirus (CMV) promoter, a Kozak sequence and the transgene and the simian virus 40 (SV40) polyadenylation signal | TCAATATTGGCCATTAGCCATATTATTCATTGGTTATATAGCATAAATCAATATTGG<br>CTATTGGCCATTGCATACGTTGTATCCATATCATAATATGTACATTTATATTGGCTC<br>ATGTCCAACATTACCGCCATGTTGACATTGATTATTGACTAGTTATTAATAGTAATC<br>AATTACGGGGTCATTAGTTCATAGCCCATATATGGAGTTCCGCGTTACATAACTTAC<br>GGTAAATGGCCCGCCTGGCTGACCGCCCAACGACCCCCGCCCATTGACGTCAATAA<br>TGACGTATGTTCCCATAGTAACGCCAATAGGGACTTTCCATTGACGTCAATGGGTG<br>GAGTATTTACGGTAAACTGCCCACTTGGCAGTACATCAAGTGTATCATATGCCAAG<br>TACGCCCCCTATTGACGTCAATGACGGTAAATGGCCCGCCTGGCATTATGCCCAGT<br>ACATGACCTTATGGGACTTTCCTACTTGGCAGTACATCTACGTATTAGTCATCGCTA<br>TTACCATGGTGATGCGGTTTTGGCAGTACATCAATGGGCGTGGATAGCGGTTTGAC<br>TCACGGGGATTTCCAAGTCTCCACCCCATTGACGTCAATGGGAGTTTGTTTTGGCAC<br>CAAAATCAACGGGACTTTCCAAAATGTCGTAACAACTCCGCCCCATTGACGCAAAT<br>GGGCGGTAGGCGTGTACGGTGGGAGGTCTATATAAGCAGAGCTCTCCCTATCAGTG<br>ATAGAGATCTCCCTATCAGTGATAGAGATCGTCGACGAGCTCGTTTAGTGAACCGT<br>CAGATCGCCTGGAGACGCCATCCACGCTGTTTTGACCTCCATAGAAGACACCGGGA<br>CCGATCCAGCCTCCGCGGCCGGGAACGGTGCATTGGATCTAGAGCCACCATGGCAT<br>GCCCAGGCTTCCTGTGGGCCCTGGTCATCAGCACCTGTCTGGAGTTTTCCATGGCCA<br>TGAAGGACAAGCAGGATGAGGAGCAGCGGACCCGGAGAATGATGAGGACAAAGA<br>TGCGCATGAGGCGCATGCGGAGAACAAGGCGCAAGATGCGGAGAAAGATGTCTCC<br>AGCAAGGCCTAGAACCAGCTGCAGGGAGGCATGTCTGCAGGGATGGACAGAGGCA<br>GCATACGAGGAGGCAGAGGACAACTGCAGGCGCATGATGAGGACCAAGGCCGCCT<br>ACAAGCTGAGCCACAAGCACCTGGTGCTGAACTATGGCGTGTGCTTCTGTGGCGAT |

-continued

SEQUENCE LISTING

| SEQ ID NO: | Epitope | Sequence |
|---|---|---|
| | | GAGAATATCCTGGTGCAGGAGTTCGTGAAGTTTGGCTGATAAGGTACCATCCGAAC TTGTTTATTGCAGCTTATAATGGTTACAAATAAAGCAATAGCATCACAAATTTCACA AATAAAGCATTTTTTTCACTGCATTCTAGTTGTGGTTTGTCCAAACTCATCAATGTA TCTTATCATGTCT |
| 24 | polynucleotide sequence of the Ad26HEME002 transgene containing the tetracycline operator (TetO)-containing cytomegalovirus (CMV) promoter, a Kozak sequence and the transgene and the simian virus 40 (SV40) polyadenylation signal | TCAATATTGGCCATTAGCCATATTATTCATTGGTTATATAGCATAAATCAATATTGG CTATTGGCCATTGCATACGTTGTATCCATATCATAATATGTACATTTATATTGGCTC ATGTCCAACATTACCGCCATGTTGACATTGATTATTGACTAGTTATTAATAGTAATC AATTACGGGGTCATTAGTTCATAGCCCATATATGGAGTTCCGCGTTACATAACTTAC GGTAAATGGCCCGCCTGGCTGACCGCCCAACGACCCCCGCCCATTGACGTCAATAA TGACGTATGTTCCCATAGTAACGCCAATAGGGACTTTCCATTGACGTCAATGGGTG GAGTATTTACGGTAAACTGCCCACTTGGCAGTACATCAAGTGTATCATATGCCAAG TACGCCCCCTATTGACGTCAATGACGGTAAATGGCCCGCCTGGCATTATGCCCAGT ACATGACCTTATGGGACTTTCCTACTTGGCAGTACATCTACGTATTAGTCATCGCTA TTACCATGGTGATGCGGTTTTGGCAGTACATCAATGGGCGTGGATAGCGGTTTGAC TCACGGGGATTTCCAAGTCTCCACCCCATTGACGTCAATGGGAGTTTGTTTTGGCAC CAAAATCAACGGGACTTTCCAAAATGTCGTAACAACTCCGCCCCATTGACGCAAAT GGGCGGTAGGCGTGTACGGTGGGAGGTCTATATAAGCAGAGCTCTCCCTATCAGTG ATAGAGATCTCCCTATCAGTGATAGAGATCGTCGACGAGCTCGTTTAGTGAACCGT CAGATCGCCTGGAGACGCCATCCACGCTGTTTTGACCTCCATAGAAGACACCGGGA CCGATCCAGCCTCCGCGGCCGGGAACGGTGCATTGGATCTAGAGCCACCATGGCAT GCCCAGGCTTCCTGTGGGCCCTGGTCATCAGCACCTGTCTGGAGTTTTCCATGGCCA TGAAGGACAAGCAGGATGAGGAGCAGCGGACCCGGAGAATGATGAGGACAAAGA TGCGCATGAGGCGCATGCGGAGAACAAGGCGCAAGATGCGGAGAAAGATGTCTCC AGCAAGGCCTAGAACCAGCTGCAGGGAGGCATGTCTGCAGGGATGGACAGAGGCA GCATACGAGGAGGCAGAGGACAACTGCAGGCGCATGATGAGGACCAAGGCCGCCT ACGTGCTGAATTATGGCGTGTGCTTCTGTGCCGCCTATTTTTGTGGCGATGAGAACA TCCTGGTGTGATAAGGTACCATCCGAACTTGTTTATTGCAGCTTATAATGGTTACAA ATAAAGCAATAGCATCACAAATTTCACAAATAAAGCATTTTTTTCACTGCATTCTAG TTGTGGTTTGTCCAAACTCATCAATGTATCTTATCATGTCT |
| 25 | HCalJ-9.9 (TCE_CALR JAK 2-2x9mer) Full insert DNA for expression in MVA and Gad20 | GATCACTAATTCCAAACCCACCCGCTTTTTATAGTAAGTTTTTCACCCATAAATAAT AAATACAATAATTAATTTCTCGTAAAAGTAGAAAATATATTCTAATTTATTGCACG GTAAGGAAGTAGAATCATAAAGAACAGTGACGGATCCCGCGACTTCGCCGCCATG GGCCAGAAGGAACAGATTCATACGCTTCAGAAAAATTCTGAACGAATGTCAAAGC AATTGACACGAAGTTCTCAGGCAGTAATGAAGGACAAACAAGACGAAGAACAACG AACTAGGCGGATGATGAGGACTAAGATGAGGATGCGGAGGATGAGACGGACGCGA CGCAAGATGCGCCGGAAAATGTCTCCCGCCCGGCCAAGGACGTCTTGTCGGGAAGC CTGTTTGCAGGGCTGGACCGAAGCAGCTTACGAAGAAGCAGAAGACAATTGTCGG CGAATGATGAGAACGAAGGCTGCTTACGTGCTTAACTATGGAGTGTGCTTCTGCGC TGCCTATTTCTGCGGAGATGAGAACATTCTGGTGTAGTAAAGGCGCGCC |
| 26 | HCalJ-9.9 (TCE_CALR JAK 2-2x9mer) Transgene only with leader sequence for expression in MVA and Gad20 | ATGGGCCAGAAGGAACAGATTCATACGCTTCAGAAAAATTCTGAACGAATGTCAA AGCAATTGACACGAAGTTCTCAGGCAGTAATGAAGGACAAACAAGACGAAGAACA ACGAACTAGGCGGATGATGAGGACTAAGATGAGGATGCGGAGGATGAGACGGACG CGACGCAAGATGCGCCGGAAAATGTCTCCCGCCCGGCCAAGGACGTCTTGTCGGGA AGCCTGTTTGCAGGGCTGGACCGAAGCAGCTTACGAAGAAGCAGAAGACAATTGT CGGCGAATGATGAGAACGAAGGCTGCTTACGTGCTTAACTATGGAGTGTGCTTCTG CGCTGCCTATTTCTGCGGAGATGAGAACATTCTGGTG |
| 27 | CALR JAK2-2x9mer Transgene only without leader sequence DNA for expression in MVA and Gad20 | ATGAAGGACAAACAAGACGAAGAACAACGAACTAGGCGGATGATGAGGACTAAG ATGAGGATGCGGAGGATGAGACGGACGCGACGCAAGATGCGCCGGAAAATGTCTC CCGCCCGGCCAAGGACGTCTTGTCGGGAAGCCTGTTTGCAGGGCTGGACCGAAGCA GCTTACGAAGAAGCAGAAGACAATTGTCGGCGAATGATGAGAACGAAGGCTGCTT ACGTGCTTAACTATGGAGTGTGCTTCTGCGCTGCCTATTTCTGCGGAGATGAGAAC ATTCTGGT |
| 28 | JAK2 Epitope2-AAY-JAK2 Epitope 2 | FCGDENILVAAYFCGDENILV |
| 29 | TCE | MGQKEQIHTLQKNSERMSKQLTRSSQAV |
| 30 | TCE polynucleotide | ATGGGCCAGAAGGAACAGATTCATACGCTTCAGAAAAATTCTGAACGAATGTCAA AGCAATTGACACGAAGTTCTCAGGCAGTA |
| 31 | TCE_CALR_JAK 2-2x9mer | MGQKEQIHTLQKNSERMSKQLTRSSQAVMKDKQDEEQRTRRMMRTKMRMRRMRRT RRKMRRKMSPARPRTSCREACLQGWTEAAYEEAEDNCRRMMRTKAAYVLNYGVCFC AAYFCGDENILV |
| 32 | P7.5 promoter | GATCACTAATTCCAAACCCACCCGCTTTTTATAGTAAGTTTTTCACCCATAAATAAT AAATACAATAATTAATTTCTCGTAAAAGTAGAAAATATATTCTAATTTATTGCACG GTAAGGAAGTAGAATCATAAAGAACAGTGACGGATC |

-continued

SEQUENCE LISTING

| SEQ ID NO: | Epitope | Sequence |
|---|---|---|
| 33 | Polynucleotide sequence of the full self-replicating RNA plasmid | TAATACGACTCACTATAGATAGGCGGCGCATGAGAGAAGCCCAGACCAATTACCTA<br>CCCAAATAGGAGAAAGTTCACGTTGACATCGAGGAAGACAGCCCATTCCTCAGAG<br>CTTTGCAGCGGAGCTTCCCGCAGTTTGAGGTAGAAGCCAAGCAGGTCACTGATAAT<br>GACCATGCTAATGCCAGAGCGTTTTCGCATCTGGCTTCAAAACTGATCGAAACGGA<br>GGTGGACCCATCCGACACGATCCTTGACATTGGAATAGTCAGCATAGTACATTTCA<br>TCTGACTAATACTACAACACCACCACCATGAATAGAGGATTCTTTAACATGCTCGG<br>CCGCCGCCCCTTCCCGGCCCCCACTGCCATGTGGAGGCCGCGGAGAAGGAGGCAG<br>GCGGCCCCGGGAAGCGGAGCTACTAACTTCAGCCTGCTGAAGCAGGCTGGAGACG<br>TGGAGGAGAACCCTGGACCTGAGAAAGTTCACGTTGACATCGAGGAAGACAGCCC<br>ATTCCTCAGAGCTTTGCAGCGGAGCTTCCCGCAGTTTGAGGTAGAAGCCAAGCAGG<br>TCACTGATAATGACCATGCTAATGCCAGAGCGTTTTCGCATCTGGCTTCAAAACTG<br>ATCGAAACGGAGGTGGACCCATCCGACACGATCCTTGACATTGGAAGTGCGCCCGC<br>CCGCAGAATGTATTCTAAGCACAAGTATCATTGTATCTGTCCGATGAGATGTGCGG<br>AAGATCCGGACAGATTGTATAAGTATGCAACTAAGCTGAAGAAAAACTGTAAGGA<br>AATAACTGATAAGGAATTGGACAAGAAAATGAAGGAGCTCGCCGCCGTCATGAGC<br>GACCCTGACCTGGAAACTGAGACTATGTGCCTCCACGACGACGAGTCGTGTCGCTA<br>CGAAGGGCAAGTCGCTGTTTACCAGGATGTATACGCGGTTGACGGACCGACAAGTC<br>TCTATCACCAAGCCAATAAGGGAGTTAGAGTCGCCTACTGGATAGGCTTTGACACC<br>ACCCCTTTTATGTTTAAGAACTTGGCTGGAGCATATCCATCATACTCTACCAACTGG<br>GCCGACGAAACCGTGTTAACGGCTCGTAACATAGGCCTATGCAGCTCTGACGTTAT<br>GGAGCGGTCACGTAGAGGGATGTCCATTCTTAGAAAGAAGTATTTGAAACCATCCA<br>ACAATGTTCTATTCTCTGTTGGCTCGACCATCTACCACGAGAAGAGGGACTTACTG<br>AGGAGCTGGCACCTGCCGTCTGTATTTCACTTACGTGGCAAGCAAAATTACACATG<br>TCGGTGTGAGACTATAGTTAGTTGCGACGGGTACGTCGTTAAAAGAATAGCTATCA<br>GTCCAGGCCTGTATGGGAAGCCTTCAGGCTATGCTGCTACGATGCACCGCGAGGGA<br>TTCTTGTGCTGCAAAGTGACAGACACATTGAACGGGGAGAGGGTCTCTTTTCCCGT<br>GTGCACGTATGTGCCAGCTACATTGTGTGACCAAATGACTGGCATACTGGCAACAG<br>ATGTCAGTGCGGACGACGCGCAAAAACTGCTGGTTGGGCTCAACCAGCGTATAGTC<br>GTCAACGGTCGCACCCAGAGAAACACCAATACCATGAAAAATTACCTTTTGCCCGT<br>AGTGGCCCAGGCATTTGCTAGGTGGGCAAAGGAATATAAGGAAGATCAAGAAGAT<br>GAAAGGCCACTAGGACTACGAGATAGACAGTTAGTCATGGGGTGTTGTTGGGCTTT<br>TAGAAGGCACAAGATAACATCTATTTATAAGCGCCCGGATACCCAAACCATCATCA<br>AAGTGAACAGCGATTTCCACTCATTCGTGCTGCCCAGGATAGGCAGTAACACATTG<br>GAGATCGGGCTGAGAACAAGAATCAGGAAAATGTTAGAGGAGCACAAGGAGCCGT<br>CACCTCTCATTACCGCCGAGGACGTACAAGAAGCTAAGTGCGCAGCCGATGAGGCT<br>AAGGAGGTGCGTGAAGCCGAGGAGTTGCGCGCAGCTCTACCACCTTTGGCAGCTGA<br>TGTTGAGGAGCCCACTCTGGAAGCCGATGTCGACTTGATGTTACAAGAGGCTGGGG<br>CCGGCTCAGTGGAGACACCTCGTGGCTTGATAAAGGTTACCAGCTACGATGGCGAG<br>GACAAGATCGGCTCTTACGCTGTGCTTTCTCCGCAGGCTGTACTCAAGAGTGAAAA<br>ATTATCTTGCATCCACCCTCTCGCTGAACAAGTCATAGTGATAACACACTCTGGCCG<br>AAAAGGGCGTTATGCCGTGGAACCATACCATGGTAAAGTAGTGGTGCCAGAGGGA<br>CATGCAATACCCGTCCAGGACTTTCAAGCTCTGAGTGAAAGTGCCACCATTGTGTA<br>CAACGAACGTGAGTTCGTAAACAGGTACCTGCACCATATTGCCACACATGGAGGAG<br>CGCTGAACACTGATGAAGAATATTACAAAACTGTCAAGCCCAGCGAGCACGACGG<br>CGAATACCTGTACGACATCGACAGGAAACAGTGCGTCAAGAAAGAACTAGTCACT<br>GGGCTAGGGCTCACAGGCGAGCTGGTGGATCCTCCCTTCCATGAATTCGCCTACGA<br>GAGTCTGAGAACACGACCAGCCGCTCCTTACCAAGTACCAACCATAGGGGTGTATG<br>GCGTGCCAGGATCAGGCAAGTCTGGCATCATTAAAAGCGCAGTCACCAAAAAAGA<br>TCTAGTGGTGAGCGCCAAGAAAGAAAACTGTGCAGAAATTATAAGGGACGTCAAG<br>AAAATGAAAGGGCTGGACGTCAATGCCAGAACTGTGGACTCAGTGCTCTTGAATGG<br>ATGCAAACACCCCGTAGAGACCCTGTATATTGACGAAGCTTTTGCTTGTCATGCAG<br>GTACTCTCAGAGCGCTCATAGCCATTATAAGACCTAAAAAGGCAGTGCTCTGCGGG<br>GATCCCAAACAGTGCGGTTTTTTTAACATGATGTGCCTGAAAGTGCATTTTAACCAC<br>GAGATTTGCACACAAGTCTTCCACAAAAGCATCTCTCGCCGTTGCACTAAATCTGT<br>GACTTCGGTCGTCTCAACCTTGTTTTACGACAAAAAAATGAGAACGACGAATCCGA<br>AAGAGACTAAGATTGTGATTGACACTACCGGCAGTACCAAACCTAAGCAGGACGA<br>TCTCATTCTCACTTGTTTCAGAGGGTGGGTGAAGCAGTTGCAAATAGATTACAAAG<br>GCAACGAAATAATGACGGCAGCTGCCTCTCAAGGGCTGACCCGTAAAGGTGTGTAT<br>GCCGTTCGGTACAAGGTGAATGAAAATCCTCTGTACGCACCCACCTCTGAACATGT<br>GAACGTCCTACTGACCCGCACGGAGGACCGCATCGTGTGGAAAACACTAGCCGGC<br>GACCCATGGATAAAAACACTGACTGCCAAGTACCCTGGGAATTTCACTGCCACGAT<br>AGAGGAGTGGCAAGCAGAGCATGATGCCATCATGAGGCACATCTTGGAGAGACCG<br>GACCCTACCGACGTCTTCCAGAATAAGGCAAACGTGTGTTGGGCCAAGGCTTTAGT<br>GCCGGTGCTGAAGACCGCTGGCATAGACATGACCACTGAACAATGGAACACTGTG<br>GATTATTTTGAAACGGACAAAGCTCACTCAGCAGAGATAGTATTGAACCAACTATG<br>CGTGAGGTTCTTTGGACTCGATCTGGACTCCGGTCTATTTTCTGCACCCACTGTTCC<br>GTTATCCATTAGGAATAATCACTGGGATAACTCCCCGTCGCCTAACATGTACGGGC<br>TGAATAAAGAAGTGGTCCGTCAGCTCTCTCGCAGGTACCCACAACTGCCTCGGGCA<br>GTTGCCACTGGAAGAGTCTATGACATGAACACTGGTACACTGCGCAATTATGATCC<br>GCGCATAAACCTAGTACCTGTAAACAGAAGACTGCCTCATGCTTTAGTCCTCCACC<br>ATAATGAACACCCACAGAGTGACTTTTCTTCATTCGTCAGCAAATTGAAGGGCAGA<br>ACTGTCCTGGTGGTCGGGGAAAAGTTGTCCGTCCCAGGCAAAATGGTTGACTGGTT<br>GTCAGACCGGCCTGAGGCTACCTTCAGAGCTCGGCTGGATTTAGGCATCCCAGGTG |

-continued

SEQUENCE LISTING

| SEQ ID NO: | Epitope | Sequence |
|---|---|---|
| | | ATGTGCCCAAATATGACATAATATTTGTTAATGTGAGGACCCCATATAAATACCAT |
| | | CACTATCAGCAGTGTGAAGACCATGCCATTAAGCTTAGCATGTTGACCAAGAAAGC |
| | | TTGTCTGCATCTGAATCCCGGCGGAACCTGTGTCAGCATAGGTTATGGTTACGCTGA |
| | | CAGGGCCAGCGAAAGCATCATTGGTGCTATAGCGCGGCAGTTCAAGTTTTCCCGGG |
| | | TATGCAAACCGAAATCCTCACTTGAAGAGACGGAAGTTCTGTTTGTATTCATTGGG |
| | | TACGATCGCAAGGCCCGTACGCACAATCCTTACAAGCTTTCATCAACCTTGACCAA |
| | | CATTTATACAGGTTCCAGACTCCACGAAGCCGGATGTGCACCCTCATATCATGTGG |
| | | TGCGAGGGGATATTGCCACGGCCACCGAAGGAGTGATTATAAATGCTGCTAACAGC |
| | | AAAGGACAACCTGGCGGAGGGGTGTGCGGAGCGCTGTATAAGAAATTCCCGGAAA |
| | | GCTTCGATTTACAGCCGATCGAAGTAGGAAAAGCGCGACTGGTCAAAGGTGCAGCT |
| | | AAACATATCATTCATGCCGTAGGACCAAACTTCAACAAAGTTTCGGAGGTTGAAGG |
| | | TGACAAACAGTTGGCAGAGGCTTATGAGTCCATCGCTAAGATTGTCAACGATAACA |
| | | ATTACAAGTCAGTAGCGATTCCACTGTTGTCCACCGGCATCTTTTCCGGGAACAAA |
| | | GATCGACTAACCCAATCATTGAACCATTTGCTGACAGCTTTAGACACCACTGATGC |
| | | AGATGTAGCCATATACTGCAGGGACAAGAAATGGGAAATGACTCTCAAGGAAGCA |
| | | GTGGCTAGGAGAGAAGCAGTGGAGGAGATATGCATATCCGACGACTCTTCAGTGA |
| | | CAGAACCTGATGCAGAGCTGGTGAGGGTGCATCCGAAGAGTTCTTTGGCTGGAAGG |
| | | AAGGGCTACAGCACAAGCGATGGCAAAACTTTCTCATATTTGGAAGGGACCAAGTT |
| | | TCACCAGGCGGCCAAGGATATAGCAGAAATTAATGCCATGTGGCCCGTTGCAACGG |
| | | AGGCCAATGAGCAGGTATGCATGTATATCCTCGGAGAAAGCATGAGCAGTATTAG |
| | | GTCGAAATGCCCCGTCGAAGAGTCGGAAGCCTCCACACCACCTAGCACGCTGCCTT |
| | | GCTTGTGCATCCATGCCATGACTCCAGAAAGAGTACAGCGCCTAAAAGCCTCACGT |
| | | CCAGAACAAATTACTGTGTGCTCATCCTTTCCATTGCCGAAGTATAGAATCACTGGT |
| | | GTGCAGAAGATCCAATGCTCCCAGCCTATATTGTTCTCACCGAAAGTGCCTGCGTA |
| | | TATTCATCCAAGGAAGTATCTCGTGGAAACACCACCGGTAGACGAGACTCCGGAGC |
| | | CATCGGCAGAGAACCAATCCACAGAGGGGACACCTGAACAACCACCACTTATAAC |
| | | CGAGGATGAGACCAGGACTAGAACGCCTGAGCCGATCATCATCGAAGAGGAAGAA |
| | | GAGGATAGCATAAGTTTGCTGTCAGATGGCCCGACCCACCAGGTGCTGCAAGTCGA |
| | | GGCAGACATTCACGGGCCGCCCTCTGTATCTAGCTCATCCTGGTCCATTCCTCATGC |
| | | ATCCGACTTTGATGTGGACAGTTTATCCATACTTGACACCCTGGAGGGAGCTAGCG |
| | | TGACCAGCGGGGCAACGTCAGCCGAGACTAACTCTTACTTCGCAAAGAGTATGGAG |
| | | TTTCTGGCGCGACCGGTGCCTGCGCCTCGAACAGTATTCAGGAACCCTCCACATCC |
| | | CGCTCCGCGCACAAGAACACCGTCACTTGCACCCAGCAGGGCCTGCTCGAGAACCA |
| | | GCCTAGTTTCCACCCCGCCAGGCGTGAATAGGGTGATCACTAGAGAGGAGCTCGAG |
| | | GCGCTTACCCCGTCACGCACTCCTAGCAGGTCGGTCTCGAGAACCAGCCTGGTCTC |
| | | CAACCCGCCAGGCGTAAATAGGGTGATTACAAGAGAGGAGTTTGAGGCGTTCGTA |
| | | GCACAACAACAATGACGGTTTGATGCGGGTGCATACATCTTTTCCTCCGACACCGG |
| | | TCAAGGGCATTTACAACAAAAATCAGTAAGGCAAACGGTGCTATCCGAAGTGGTGT |
| | | TGGAGAGGACCGAATTGGAGATTTCGTATGCCCCGCGCCTCGACCAAGAAAAAGA |
| | | AGAATTACTACGCAAGAAATTACAGTTAAATCCCACACCTGCTAACAGAAGCAGAT |
| | | ACCAGTCCAGGAAGGTGGAGAACATGAAAGCCATAACAGCTAGACGTATTCTGCA |
| | | AGGCCTAGGGCATTATTTGAAGGCAGAAGGAAAAGTGGAGTGCTACCGAACCCTG |
| | | CATCCTGTTCCTTTGTATTCATCTAGTGTGAACCGTGCCTTTTCAAGCCCCAAGGTC |
| | | GCAGTGGAAGCCTGTAACGCCATGTTGAAAGAGAACTTTCCGACTGTGGCTTCTTA |
| | | CTGTATTATTCCAGAGTACGATGCCTATTTGGACATGGTTGACGGAGCTTCATGCTG |
| | | CTTAGACACTGCCAGTTTTTGCCCTGCAAAGCTGCGCAGCTTTCCAAAGAAACACT |
| | | CCTATTTGGAACCCACAATACGATCGGCAGTGCCTTCAGCGATCCAGAACACGCTC |
| | | CAGAACGTCCTGGCAGCTGCCACAAAAAGAAATTGCAATGTCACGCAAATGAGAG |
| | | AATTGCCCGTATTGGATTCGGCGGCCTTTAATGTGGAATGCTTCAAGAAATATGCG |
| | | TGTAATAATGAATATTGGGAAACGTTTAAAGAAAACCCCATCAGGCTTACTGAAGA |
| | | AAACGTGGTAAATTACATTACCAAATTAAAAGGACCAAAAGCTGCTGCTCTTTTTG |
| | | CGAAGACACATAATTTGAATATGTTGCAGGACATACCAATGGACAGGTTTGTAATG |
| | | GACTTAAAGAGAGACGTGAAAGTGACTCCAGGAACAAAACATACTGAAGAACGGC |
| | | CCAAGGTACAGGTGATCCAGGCTGCCGATCCGCTAGCAACAGCGTATCTGTGCGGA |
| | | ATCCACCGAGAGCTGGTTAGGAGATTAAATGCGGTCCTGCTTCCGAACATTCATAC |
| | | ACTGTTTGATATGTCGGCTGAAGACTTTGACGCTATTATAGCCGAGCACTTCCAGCC |
| | | TGGGGATTGTGTTCTGGAAACTGACATCGCGTCGTTTGATAAAAGTGAGGACGACG |
| | | CCATGGCTCTGACCGCGTTAATGATTCTGGAAGACTTAGGTGTGGACGCAGAGCTG |
| | | TTGACGCTGATTGAGGCGGCTTTCGGCGAAATTTCATCAATACATTTGCCCACTAAA |
| | | ACTAAATTTAAATTCGGAGCCATGATGAAATCTGGAATGTTCCTCACACTGTTTGTG |
| | | AACACAGTCATTAACATTGTAATCGCAAGCAGAGTGTTGAGAGAACGGCTAACCG |
| | | GATCACCATGTGCAGCATTCATTGGAGATGACAATATCGTGAAAGGAGTCAAATCG |
| | | GACAAATTAATGGCAGACAGGTGCGCCACCTGGTTGAATATGGAAGTCAAGATTAT |
| | | AGATGCTGTGGTGGGCGAGAAAGCGCCTTATTTCTGTGGAGGGTTTATTTTGTGTG |
| | | ACTCCGTGACCGGCACAGCGTGCCGTGTGGCAGACCCCCTAAAAAGGCTGTTTAAG |
| | | CTTGGCAAACCTCTGGCAGCAGACGATGAACATGATGATGACAGGAGAAGGGCAT |
| | | TGCATGAAGAGTCAACACGCTGGAACCGAGTGGGTATTCTTTCAGAGCTGTGCAAG |
| | | GCAGTAGAATCAAGGTATGAAACCGTAGGAACTTCCATCATAGTTATGGCCATGAC |
| | | TACTCTAGCTAGCAGTGTTAAATCATTCAGCTACCTGAGAGGGGCCCCTATAACTCT |
| | | CTACGGCTAACCTGAATGGACTACGACATAGTCTAGTCCGCCAAGATATCGGCGCG |
| | | CCGTTTAAACGGCCGGCCTTAATTAAGTAACGATACAGCAGCAATTGGCAAGCTGC |
| | | TTACATAGAACTCGCGGCGATTGGCATGCCGCTTTAAAATTTTTATTTTATTTTTCTT |
| | | TTCTTTTCCGAATCGGATTTTGTTTTTAATATTTCAAAAAAAAAAAAAAAAAAAAA |
| | | AAAAAAAAAAAAAAAAAACCCCTCTCTAAACGGAGGGGTTTTTTTCAGCGTAACTG |

-continued

SEQUENCE LISTING

| SEQ ID NO: | Epitope | Sequence |
|---|---|---|
| | | GACTGGCCACAGTTAGGCGGCCGCGCATGTTCATCATCAGTAACCCGTATCGTGAG CATCCTCTCTCGTTTCATCGGTATCATTACCTCCATGAACAGAAATCCCCCTTACAC GGAGGCATCAGTGACCAAACAGGAAAAAACCGCCCTTAACATGGCCCGCTTTATCA GAAGCCAGACATTAACGCTTCTGGAGAAACTCAACGAGCTGGACGCGGATGAACA GGCAGACATCTGTGAATCGCTTCACGACCACGCTGATGAGCTTTACCGCAGCTGCC TCGCGCGTTTCGGTGATGACGGTGAAAACCTCTGACACATGCAGCTCCCGGAGACG GTCACAGCTTGTCTGTAAGCGGATGCCGGGAGCAGACAAGCCCGTCAGGGCGCGTC AGCGGGTGTTGGCGGGTGTCGGGGCGCAGCCATGACCCAGTCACGTAGCGATAGC GGAGTGTATACTGGCTTAACTATGCGGCATCAGAGCAGATTGTACTGAGAGTGCAC CATATGCGGTGTGAAATACCGCACAGATGCGTAAGGAGAAAATACCGCATCAGGC GCTCGCTTCCTCGCTCACTGACTCGCTGCGCTCGGTCGTTCGGCTGCGGCGAGCGGT ATCAGCTCACTCAAAGGCGGTAATACGGTTATCCACAGAATCAGGGGATAACGCA GGAAAGAACATGTGAGCAAAAGGCCAGCAAAAGGCCAGGAACCGTAAAAAGGCC GCGTTGCTGGCGTTTTTCCATAGGCTCCGCCCCCCTGACGAGCATCACAAAAATCG ACGCTCAAGTCAGAGGTGGCGAAACCCGACAGGACTATAAAGATACCAGGCGTTT CCCCCTGGAAGCTCCCTCGTGCGCTCTCCTGTTCCGACCCTGCCGCTTACCGGATAC CTGTCCGCCTTTCTCCCTTCGGGAAGCGTGGCGCTTTCTCATAGCTCACGCTGTAGG TATCTCAGTTCGGTGTAGGTCGTTCGCTCCAAGCTGGGCTGTGTGCACGAACCCCCC GTTCAGCCCGACCGCTGCGCCTTATCCGGTAACTATCGTCTTGAGTCCAACCCGGTA AGACACGACTTATCGCCACTGGCAGCAGCCACTGGTAACAGGATTAGCAGAGCGA GGTATGTAGGCGGTGCTACAGAGTTCTTGAAGTGGTGGCCTAACTACGGCTACACT AGAAGGACAGTATTTGGTATCTGCGCTCTGCTGAAGCCAGTTACCTTCGGAAAAAG AGTTGGTAGCTCTTGATCCGGCAAACAAACCACCGCTGGTAGCGGTGGTTTTTTTGT TTGCAAGCAGCAGATTACGCGCAGAAAAAAAGGATCTCAAGAAGATCCTTTGATCT TTTCTACGGGGTCTGACGCTCAGTGGAACGAAAACTCACGTTAAGGGATTTTGGTC ATGAGATTATCAAAAAGGATCTTCACCTAGATCCTTTTAAATTAAAAATGAAGTTTT AAATCAATCTAAAGTATATATGAGTAAACTTGGTCTGACAGTTATTAGAAAAATTC ATCCAGCAGACGATAAAACGCAATACGCTGGCTATCCGGTGCCGCAATGCCATACA GCACCAGAAAACGATCCGCCCATTCGCCGCCCAGTTCTTCCGCAATATCACGGGTG GCCAGCGCAATATCCTGATAACGATCCGCCACGCCCAGACGGCCGCAATCAATAAA GCCGCTAAAACGGCCATTTTCCACCATAATGTTCGGCAGGCACGCATCACCATGGG TCACCACCAGATCTTCGCCATCCGGCATGCTCGCTTTCAGACGCGCAAACAGCTCT GCCGGTGCCAGGCCCTGATGTTCTTCATCCAGATCATCCTGATCCACCAGGCCCGCT TCCATACGGGTACGCGCACGTTCAATACGATGTTTCGCCTGATGATCAAACGGACA GGTCGCCGGGTCCAGGGTATGCAGACGACGCATGGCATCCGCCATAATGCTCACTT TTTCTGCCGGCGCCAGATGGCTAGACAGCAGATCCTGACCCGGCACTTCGCCCAGC AGCAGCCAATCACGGCCCGCTTCGGTCACCACATCCAGCACCGCCGCACACGGAAC ACCGGTGGTGGCCAGCCAGCTCAGACGCGCCGCTTCATCCTGCAGCTCGTTCAGCG CACCGCTCAGATCGGTTTTCACAAACAGCACCGGACGACCCTGCGCGCTCAGACGA AACACCGCCGCATCAGAGCAGCCAATGGTCTGCTGCGCCCAATCATAGCCAAACAG ACGTTCCACCCACGCTGCCGGGCTACCCGCATGCAGGCCATCCTGTTCAATCATACT CTTCCTTTTTCAATATTATTGAAGCATTTATCAGGGTTATTGTCTCATGAGCGGATA CATATTTGAATGTATTTAGAAAAATAAACAAATAGGGGTTCCGCGCACATTTCCCC GAAAAGTGCCACCTGACGTCTAAGAAACCATTATTATCATGACATTAAGCATCCGC CTTTCGTTTTATTTGACCATGTTGGTATG |
| 34 | T7 terminator | AACCCCTCTCTAAACGGAGGGGTTTTTTT |
| 35 | AmpR promoter | CGCGGAACCCCTATTTGTTTATTTTTCTAAATACATTCAAATATGTATCCGCTCATG AGACAATAACCCTGATAAATGCTTCAATAATATTGAAAAAGGAAGAGT |
| 36 | 26S promoter | CTCTCTACGGCTAACCTGAATGGA |
| 37 | T7 promoter | TAATACGACTCACTATAG |
| 38 | Poly A site | AAAAAAAAAAAAAAAAAAAAAAAAAAAAAAAAAAAAAAAA |
| 39 | Alpha 5' replication sequence from nsP1 | TAGGAGAAAGTTCACGTTGACATCGAGGAAGACAGCCCATTCCTCAGAGCTTTGCA GCGGAGCTTCCCGCAGTTTGAGGTAGAAGCCAAGCAGGTCACTGATAATGACCATG CTAATGCCAGAGCGTTTTCGCATCTGGCTTCAAAACTGATCGAAACGGAGGTGGAC CCATCCGACACGATCCTTGACATTGGA |
| 40 | DLP | ATAGTCAGCATAGTACATTTCATCTGACTAATACTACAACACCACCACCATGAATA GAGGATTCTTTAACATGCTCGGCCGCCGCCCCTTCCCGGCCCCCACTGCCATGTGGA GGCCGCGGAGAAGGAGGCAGGCGGCCCCG |
| 41 | P2A | GGAAGCGGAGCTACTAACTTCAGCCTGCTGAAGCAGGCTGGAGACGTGGAGGAGA ACCCTGGACCT |
| 42 | Bon | CGCAGCCATGACCCAGTCACGTAGCGATAGCGGAGTGTATACTGGCTTAACTATGC GGCATCAGAGCAGATTGTACTGAGAGTGCACCATATGCGGTGTGAAATACCGCACA GATGCGTAAGGAGAAAATACCGCATCAGG |

-continued

SEQUENCE LISTING

| SEQ ID NO: | Epitope | Sequence |
|---|---|---|
| 43 | DLP nsp ORF | ATGAATAGAGGATTCTTTAACATGCTCGGCCGCCGCCCCTTCCCGGCCCCCACTGCC |
| | | ATGTGGAGGCCGCGGAGAAGGAGGCAGGCGGCCCCGGGAAGCGGAGCTACTAACT |
| | | TCAGCCTGCTGAAGCAGGCTGGAGACGTGGAGGAGAACCCTGGACCTGAGAAAGT |
| | | TCACGTTGACATCGAGGAAGACAGCCCATTCCTCAGAGCTTTGCAGCGGAGCTTCC |
| | | CGCAGTTTGAGGTAGAAGCCAAGCAGGTCACTGATAATGACCATGCTAATGCCAGA |
| | | GCGTTTTCGCATCTGGCTTCAAAACTGATCGAAACGGAGGTGGACCCATCCGACAC |
| | | GATCCTTGACATTGGAAGTGCGCCCGCCCGCAGAATGTATTCTAAGCACAAGTATC |
| | | ATTGTATCTGTCCGATGAGATGTGCGGAAGATCCGGACAGATTGTATAAGTATGCA |
| | | ACTAAGCTGAAGAAAAACTGTAAGGAAATAACTGATAAGGAATTGGACAAGAAAA |
| | | TGAAGGAGCTCGCCGCCGTCATGAGCGACCCTGACCTGGAAACTGAGACTATGTGC |
| | | CTCCACGACGACGAGTCGTGTCGCTACGAAGGGCAAGTCGCTGTTTACCAGGATGT |
| | | ATACGCGGTTGACGGACCGACAAGTCTCTATCACCAAGCCAATAAGGGAGTTAGA |
| | | GTCGCCTACTGGATAGGCTTTGACACCACCCCTTTTATGTTTAAGAACTTGGCTGGA |
| | | GCATATCCATCATACTCTACCAACTGGGCCGACGAAACCGTGTTAACGGCTCGTAA |
| | | CATAGGCCTATGCAGCTCTGACGTTATGGAGCGGTCACGTAGAGGGATGTCCATTC |
| | | TTAGAAAGAAGTATTTGAAACCATCCAACAATGTTCTATTCTCTGTTGGCTCGACCA |
| | | TCTACCACGAGAAGAGGGACTTACTGAGGAGCTGGCACCTGCCGTCTGTATTTCAC |
| | | TTACGTGGCAAGCAAAATTACACATGTCGGTGTGAGACTATAGTTAGTTGCGACGG |
| | | GTACGTCGTTAAAAGAATAGCTATCAGTCCAGGCCTGTATGGGAAGCCTTCAGGCT |
| | | ATGCTGCTACGATGCACCGCGAGGGATTCTTGTGCTGCAAAGTGACAGACACATTG |
| | | AACGGGGAGAGGGTCTCTTTTCCCGTGTGCACGTATGTGCCAGCTACATTGTGTGA |
| | | CCAAATGACTGGCATACTGGCAACAGATGTCAGTGCGGACGACGCGCAAAAACTG |
| | | CTGGTTGGGCTCAACCAGCGTATAGTCGTCAACGGTCGCACCCAGAGAAACACCAA |
| | | TACCATGAAAAATTACCTTTTGCCCGTAGTGGCCCAGGCATTTGCTAGGTGGGCAA |
| | | AGGAATATAAGGAAGATCAAGAAGATGAAAGGCCACTAGGACTACGAGATAGACA |
| | | GTTAGTCATGGGGTGTTGTTGGGCTTTTAGAAGGCACAAGATAACATCTATTTATA |
| | | AGCGCCCGGATACCCAAACCATCATCAAAGTGAACAGCGATTTCCACTCATTCGTG |
| | | CTGCCCAGGATAGGCAGTAACACATTGGAGATCGGGCTGAGAACAAGAATCAGGA |
| | | AAATGTTAGAGGAGCACAAGGAGCCGTCACCTCTCATTACCGCCGAGGACGTACA |
| | | AGAAGCTAAGTGCGCAGCCGATGAGGCTAAGGAGGTGCGTGAAGCCGAGGAGTTG |
| | | CGCGCAGCTCTACCACCTTTGGCAGCTGATGTTGAGGAGCCCACTCTGGAAGCCGA |
| | | TGTCGACTTGATGTTACAAGAGGCTGGGGCCGGCTCAGTGGAGACACCTCGTGGCT |
| | | TGATAAAGGTTACCAGCTACGATGGCGAGGACAAGATCGGCTCTTACGCTGTGCTT |
| | | TCTCCGCAGGCTGTACTCAAGAGTGAAAAATTATCTTGCATCCACCCTCTCGCTGAA |
| | | CAAGTCATAGTGATAACACACTCTGGCCGAAAAGGGCGTTATGCCGTGGAACCATA |
| | | CCATGGTAAAGTAGTGGTGCCAGAGGGACATGCAATACCCGTCCAGGACTTTCAAG |
| | | CTCTGAGTGAAAGTGCCACCATTGTGTACAACGAACGTGAGTTCGTAAACAGGTAC |
| | | CTGCACCATATTGCCACACATGGAGGAGCGCTGAACACTGATGAAGAATATTACAA |
| | | AACTGTCAAGCCCAGCGAGCACGACGGCGAATACCTGTACGACATCGACAGGAAA |
| | | CAGTGCGTCAAGAAAGAACTAGTCACTGGGCTAGGGCTCACAGGCGAGCTGGTGG |
| | | ATCCTCCCTTCCATGAATTCGCCTACGAGAGTCTGAGAACACGACCAGCCGCTCCTT |
| | | ACCAAGTACCAACCATAGGGGTGTATGGCGTGCCAGGATCAGGCAAGTCTGGCATC |
| | | ATTAAAAGCGCAGTCACCAAAAAAGATCTAGTGGTGAGCGCCAAGAAAGAAAACT |
| | | GTGCAGAAATTATAAGGGACGTCAAGAAAATGAAAGGGCTGGACGTCAATGCCAG |
| | | AACTGTGGACTCAGTGCTCTTGAATGGATGCAAACACCCCGTAGAGACCCTGTATA |
| | | TTGACGAAGCTTTTGCTTGTCATGCAGGTACTCTCAGAGCGCTCATAGCCATTATAA |
| | | GACCTAAAAAGGCAGTGCTCTGCGGGGATCCCAAACAGTGCGGTTTTTTTAACATG |
| | | ATGTGCCTGAAAGTGCATTTTAACCACGAGATTTGCACACAAGTCTTCCACAAAAG |
| | | CATCTCTCGCCGTTGCACTAAATCTGTGACTTCGGTCGTCTCAACCTTGTTTTACGA |
| | | CAAAAAAATGAGAACGACGAATCCGAAAGAGACTAAGATTGTGATTGACACTACC |
| | | GGCAGTACCAAACCTAAGCAGGACGATCTCATTCTCACTTGTTTCAGAGGGTGGGT |
| | | GAAGCAGTTGCAAATAGATTACAAAGGCAACGAAATAATGACGGCAGCTGCCTCT |
| | | CAAGGGCTGACCCGTAAAGGTGTGTATGCCGTTCGGTACAAGGTGAATGAAAATCC |
| | | TCTGTACGCACCCACCTCTGAACATGTGAACGTCCTACTGACCCGCACGGAGGACC |
| | | GCATCGTGTGGAAAACACTAGCCGGCGACCCATGGATAAAAACACTGACTGCCAA |
| | | GTACCCTGGGAATTTCACTGCCACGATAGAGGAGTGGCAAGCAGAGCATGATGCC |
| | | ATCATGAGGCACATCTTGGAGAGACCGGACCCTACCGACGTCTTCCAGAATAAGGC |
| | | AAACGTGTGTTGGGCCAAGGCTTTAGTGCCGGTGCTGAAGACCGCTGGCATAGACA |
| | | TGACCACTGAACAATGGAACACTGTGGATTATTTTGAAACGGACAAAGCTCACTCA |
| | | GCAGAGATAGTATTGAACCAACTATGCGTGAGGTTCTTTGGACTCGATCTGGACTC |
| | | CGGTCTATTTTCTGCACCCACTGTTCCGTTATCCATTAGGAATAATCACTGGGATAA |
| | | CTCCCCGTCGCCTAACATGTACGGGCTGAATAAAGAAGTGGTCCGTCAGCTCTCTC |
| | | GCAGGTACCCACAACTGCCTCGGGCAGTTGCCACTGGAAGAGTCTATGACATGAAC |
| | | ACTGGTACACTGCGCAATTATGATCCGCGCATAAACCTAGTACCTGTAAACAGAAG |
| | | ACTGCCTCATGCTTTAGTCCTCCACCATAATGAACACCCACAGAGTGACTTTTCTTC |
| | | ATTCGTCAGCAAATTGAAGGGCAGAACTGTCCTGGTGGTCGGGGAAAAGTTGTCCG |
| | | TCCCAGGCAAAATGGTTGACTGGTTGTCAGACCGGCCTGAGGCTACCTTCAGAGCT |
| | | CGGCTGGATTTAGGCATCCCAGGTGATGTGCCCAAATATGACATAATATTTGTTAA |
| | | TGTGAGGACCCCATATAAATACCATCACTATCAGCAGTGTGAAGACCATGCCATTA |
| | | AGCTTAGCATGTTGACCAAGAAAGCTTGTCTGCATCTGAATCCCGGCGGAACCTGT |
| | | GTCAGCATAGGTTATGGTTACGCTGACAGGGCCAGCGAAAGCATCATTGGTGCTAT |
| | | AGCGCGGCAGTTCAAGTTTTCCCGGGTATGCAAACCGAAATCCTCACTTGAAGAGA |
| | | CGGAAGTTCTGTTTGTATTCATTGGGTACGATCGCAAGGCCCGTACGCACAATCCTT |
| | | ACAAGCTTTCATCAACCTTGACCAACATTTATACAGGTTCCAGACTCCACGAAGCC |

-continued

SEQUENCE LISTING

| SEQ ID NO: | Epitope | Sequence |
|---|---|---|
| | | GGATGTGCACCCTCATATCATGTGGTGCGAGGGGATATTGCCACGGCCACCGAAGG<br>AGTGATTATAAATGCTGCTAACAGCAAAGGACAACCTGGCGGAGGGGTGTGCGGA<br>GCGCTGTATAAGAAATTCCCGGAAAGCTTCGATTTACAGCCGATCGAAGTAGGAAA<br>AGCGCGACTGGTCAAAGGTGCAGCTAAACATATCATTCATGCCGTAGGACCAAACT<br>TCAACAAAGTTTCGGAGGTTGAAGGTGACAAACAGTTGGCAGAGGCTTATGAGTCC<br>ATCGCTAAGATTGTCAACGATAACAATTACAAGTCAGTAGCGATTCCACTGTTGTC<br>CACCGGCATCTTTTCCGGGAACAAAGATCGACTAACCCAATCATTGAACCATTTGC<br>TGACAGCTTTAGACACCACTGATGCAGATGTAGCCATATACTGCAGGGACAAGAAA<br>TGGGAAATGACTCTCAAGGAAGCAGTGGCTAGGAGAGAAGCAGTGGAGGAGATAT<br>GCATATCCGACGACTCTTCAGTGACAGAACCTGATGCAGAGCTGGTGAGGGTGCAT<br>CCGAAGAGTTCTTTGGCTGGAAGGAAGGGCTACAGCACAAGCGATGGCAAAACTT<br>TCTCATATTTGGAAGGGACCAAGTTTCACCAGGCGGCCAAGGATATAGCAGAAATT<br>AATGCCATGTGGCCCGTTGCAACGGAGGCCAATGAGCAGGTATGCATGTATATCCT<br>CGGAGAAAGCATGAGCAGTATTAGGTCGAAATGCCCCGTCGAAGAGTCGGAAGCC<br>TCCACACCACCTAGCACGCTGCCTTGCTTGTGCATCCATGCCATGACTCCAGAAAG<br>AGTACAGCGCCTAAAAGCCTCACGTCCAGAACAAATTACTGTGTGCTCATCCTTTC<br>CATTGCCGAAGTATAGAATCACTGGTGTGCAGAAGATCCAATGCTCCCAGCCTATA<br>TTGTTCTCACCGAAAGTGCCTGCGTATATTCATCCAAGGAAGTATCTCGTGGAAAC<br>ACCACCGGTAGACGAGACTCCGGAGCCATCGGCAGAGAACCAATCCACAGAGGGG<br>ACACCTGAACAACCACCACTTATAACCGAGGATGAGACCAGGACTAGAACGCCTG<br>AGCCGATCATCATCGAAGAGGAAGAAGAGGATAGCATAAGTTTGCTGTCAGATGG<br>CCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCA<br>TACTTGACACCCTGGAGGGAGCTAGCGTGACCAGCGGGGCAACGTCAGCCGAGAC<br>TAACTCTTACTTCGCAAAGAGTATGGAGTTTCTGGCGCGACCGGTGCCTGCGCCTC<br>GAACAGTATTCAGGAACCCTCCACATCCCGCTCCGCGCACAAGAACACCGTCACTT<br>GCACCCAGCAGGGCCTGCTCGAGAACCAGCCTAGTTTCCACCCCGCCAGGCGTGAA<br>TAGGGTGATCACTAGAGAGGAGCTCGAGGCGCTTACCCCGTCACGCACTCCTAGCA<br>GGTCGGTCTCGAGAACCAGCCTGGTCTCCAACCCGCCAGGCGTAAATAGGGTGATT<br>ACAAGAGAGGAGTTTGAGGCGTTCGTAGCACAACAACAATGA |
| 44 | nsP2 | GGCTCAGTGGAGACACCTCGTGGCTTGATAAAGGTTACCAGCTACGATGGCGAGGA<br>CAAGATCGGCTCTTACGCTGTGCTTTCTCCGCAGGCTGTACTCAAGAGTGAAAAAT<br>TATCTTGCATCCACCCTCTCGCTGAACAAGTCATAGTGATAACACACTCTGGCCGA<br>AAAGGGCGTTATGCCGTGGAACCATACCATGGTAAAGTAGTGGTGCCAGAGGGAC<br>ATGCAATACCCGTCCAGGACTTTCAAGCTCTGAGTGAAAGTGCCACCATTGTGTAC<br>AACGAACGTGAGTTCGTAAACAGGTACCTGCACCATATTGCCACACATGGAGGAGC<br>GCTGAACACTGATGAAGAATATTACAAAACTGTCAAGCCCAGCGAGCACGACGGC<br>GAATACCTGTACGACATCGACAGGAAACAGTGCGTCAAGAAAGAACTAGTCACTG<br>GGCTAGGGCTCACAGGCGAGCTGGTGGATCCTCCCTTCCATGAATTCGCCTACGAG<br>AGTCTGAGAACACGACCAGCCGCTCCTTACCAAGTACCAACCATAGGGGTGTATGG<br>CGTGCCAGGATCAGGCAAGTCTGGCATCATTAAAAGCGCAGTCACCAAAAAAGAT<br>CTAGTGGTGAGCGCCAAGAAAGAAAACTGTGCAGAAATTATAAGGGACGTCAAGA<br>AAATGAAAGGGCTGGACGTCAATGCCAGAACTGTGGACTCAGTGCTCTTGAATGGA<br>TGCAAACACCCCGTAGAGACCCTGTATATTGACGAAGCTTTTGCTTGTCATGCAGG<br>TACTCTCAGAGCGCTCATAGCCATTATAAGACCTAAAAAGGCAGTGCTCTGCGGGG<br>ATCCCAAACAGTGCGGTTTTTTAACATGATGTGCCTGAAAGTGCATTTTAACCACG<br>AGATTTGCACACAAGTCTTCCACAAAAGCATCTCTCGCCGTTGCACTAAATCTGTG<br>ACTTCGGTCGTCTCAACCTTGTTTTACGACAAAAAAATGAGAACGACGAATCCGAA<br>AGAGACTAAGATTGTGATTGACACTACCGGCAGTACCAAACCTAAGCAGGACGAT<br>CTCATTCTCACTTGTTTCAGAGGGTGGGTGAAGCAGTTGCAAATAGATTACAAAGG<br>CAACGAAATAATGACGGCAGCTGCCTCTCAAGGGCTGACCCGTAAAGGTGTGTATG<br>CCGTTCGGTACAAGGTGAATGAAAATCCTCTGTACGCACCCACCTCTGAACATGTG<br>AACGTCCTACTGACCCGCACGGAGGACCGCATCGTGTGGAAAACACTAGCCGGCG<br>ACCCATGGATAAAAACACTGACTGCCAAGTACCCTGGGAATTTCACTGCCACGATA<br>GAGGAGTGGCAAGCAGAGCATGATGCCATCATGAGGCACATCTTGGAGAGACCGG<br>ACCCTACCGACGTCTTCCAGAATAAGGCAAACGTGTGTTGGGCCAAGGCTTTAGTG<br>CCGGTGCTGAAGACCGCTGGCATAGACATGACCACTGAACAATGGAACACTGTGG<br>ATTATTTTGAAACGGACAAAGCTCACTCAGCAGAGATAGTATTGAACCAACTATGC<br>GTGAGGTTCTTTGGACTCGATCTGGACTCCGGTCTATTTTCTGCACCCACTGTTCCG<br>TTATCCATTAGGAATAATCACTGGGATAACTCCCCGTCGCCTAACATGTACGGGCT<br>GAATAAAGAAGTGGTCCGTCAGCTCTCTCGCAGGTACCCACAACTGCCTCGGGCAG<br>TTGCCACTGGAAGAGTCTATGACATGAACACTGGTACACTGCGCAATTATGATCCG<br>CGCATAAACCTAGTACCTGTAAACAGAAGACTGCCTCATGCTTTAGTCCTCCACCA<br>TAATGAACACCCACAGAGTGACTTTTCTTCATTCGTCAGCAAATTGAAGGGCAGAA<br>CTGTCCTGGTGGTCGGGGAAAAGTTGTCCGTCCCAGGCAAAATGGTTGACTGGTTG<br>TCAGACCGGCCTGAGGCTACCTTCAGAGCTCGGCTGGATTTAGGCATCCCAGGTGA<br>TGTGCCCAAATATGACATAATATTTGTTAATGTGAGGACCCCATATAAATACCATC<br>ACTATCAGCAGTGTGAAGACCATGCCATTAAGCTTAGCATGTTGACCAAGAAAGCT<br>TGTCTGCATCTGAATCCCGGCGGAACCTGTGTCAGCATAGGTTATGGTTACGCTGA<br>CAGGGCCAGCGAAAGCATCATTGGTGCTATAGCGCGGCAGTTCAAGTTTTCCCGGG<br>TATGCAAACCGAAATCCTCACTTGAAGAGACGGAAGTTCTGTTTGTATTCATTGGG<br>TACGATCGCAAGGCCCGTACGCACAATCCTTACAAGCTTTCATCAACCTTGACCAA<br>CATTTATACAGGTTCCAGACTCCACGAAGCCGGATGT |

-continued

SEQUENCE LISTING

| SEQ ID NO: | Epitope | Sequence |
|---|---|---|
| 45 | nsP4 | TACATCTTTTCCTCCGACACCGGTCAAGGGCATTTACAACAAAAATCAGTAAGGCA<br>AACGGTGCTATCCGAAGTGGTGTTGGAGAGGACCGAATTGGAGATTTCGTATGCCC<br>CGCGCCTCGACCAAGAAAAAGAAGAATTACTACGCAAGAAATTACAGTTAAATCC<br>CACACCTGCTAACAGAAGCAGATACCAGTCCAGGAAGGTGGAGAACATGAAAGCC<br>ATAACAGCTAGACGTATTCTGCAAGGCCTAGGGCATTATTTGAAGGCAGAAGGAA<br>AAGTGGAGTGCTACCGAACCCTGCATCCTGTTCCTTTGTATTCATCTAGTGTGAACC<br>GTGCCTTTTCAAGCCCCAAGGTCGCAGTGGAAGCCTGTAACGCCATGTTGAAAGAG<br>AACTTTCCGACTGTGGCTTCTTACTGTATTATTCCAGAGTACGATGCCTATTTGGAC<br>ATGGTTGACGGAGCTTCATGCTGCTTAGACACTGCCAGTTTTTGCCCTGCAAAGCTG<br>CGCAGCTTTCCAAAGAAACACTCCTATTTGGAACCCACAATACGATCGGCAGTGCC<br>TTCAGCGATCCAGAACACGCTCCAGAACGTCCTGGCAGCTGCCACAAAAAGAAATT<br>GCAATGTCACGCAAATGAGAGAATTGCCCGTATTGGATTCGGCGGCCTTTAATGTG<br>GAATGCTTCAAGAAATATGCGTGTAATAATGAATATTGGGAAACGTTTAAAGAAAA<br>CCCCATCAGGCTTACTGAAGAAAACGTGGTAAATTACATTACCAAATTAAAAGGAC<br>CAAAAGCTGCTGCTCTTTTTGCGAAGACACATAATTTGAATATGTTGCAGGACATA<br>CCAATGGACAGGTTTGTAATGGACTTAAAGAGAGACGTGAAAGTGACTCCAGGAA<br>CAAAACATACTGAAGAACGGCCCAAGGTACAGGTGATCCAGGCTGCCGATCCGCT<br>AGCAACAGCGTATCTGTGCGGAATCCACCGAGAGCTGGTTAGGAGATTAAATGCG<br>GTCCTGCTTCCGAACATTCATACACTGTTTGATATGTCGGCTGAAGACTTTGACGCT<br>ATTATAGCCGAGCACTTCCAGCCTGGGGATTGTGTTCTGGAAACTGACATCGCGTC<br>GTTTGATAAAAGTGAGGACGACGCCATGGCTCTGACCGCGTTAATGATTCTGGAAG<br>ACTTAGGTGTGGACGCAGAGCTGTTGACGCTGATTGAGGCGGCTTTCGGCGAAATT<br>TCATCAATACATTTGCCCACTAAAACTAAATTTAAATTCGGAGCCATGATGAAATC<br>TGGAATGTTCCTCACACTGTTTGTGAACACAGTCATTAACATTGTAATCGCAAGCA<br>GAGTGTTGAGAGAACGGCTAACCGGATCACCATGTGCAGCATTCATTGGAGATGAC<br>AATATCGTGAAAGGAGTCAAATCGGACAAATTAATGGCAGACAGGTGCGCCACCT<br>GGTTGAATATGGAAGTCAAGATTATAGATGCTGTGGTGGGCGAGAAAGCGCCTTAT<br>TTCTGTGGAGGGTTTATTTGTGTGACTCCGTGACCGGCACAGCGTGCCGTGTGGCA<br>GACCCCCTAAAAAGGCTGTTTAAGCTTGGCAAACCTCTGGCAGCAGACGATGAACA<br>TGATGATGACAGGAGAAGGGCATTGCATGAAGAGTCAACACGCTGGAACCGAGTG<br>GGTATTCTTTCAGAGCTGTGCAAGGCAGTAGAATCAAGGTATGAAACCGTAGGAAC<br>TTCCATCATAGTTATGGCCATGACTACTCTAGCTAGCAGTGTTAAATCATTCAGCTA<br>CCTGAGAGGGGCCCCTATAACTCTCTACGGC |
| 46 | nsP3 | GCACCCTCATATCATGTGGTGCGAGGGGATATTGCCACGGCCACCGAAGGAGTGAT<br>TATAAATGCTGCTAACAGCAAAGGACAACCTGGCGGAGGGGTGTGCGGAGCGCTG<br>TATAAGAAATTCCCGGAAAGCTTCGATTTACAGCCGATCGAAGTAGGAAAAGCGC<br>GACTGGTCAAAGGTGCAGCTAAACATATCATTCATGCCGTAGGACCAAACTTCAAC<br>AAAGTTTCGGAGGTTGAAGGTGACAAACAGTTGGCAGAGGCTTATGAGTCCATCGC<br>TAAGATTGTCAACGATAACAATTACAAGTCAGTAGCGATTCCACTGTTGTCCACCG<br>GCATCTTTTCCGGGAACAAAGATCGACTAACCCAATCATTGAACCATTTGCTGACA<br>GCTTTAGACACCACTGATGCAGATGTAGCCATATACTGCAGGGACAAGAAATGGG<br>AAATGACTCTCAAGGAAGCAGTGGCTAGGAGAGAAGCAGTGGAGGAGATATGCAT<br>ATCCGACGACTCTTCAGTGACAGAACCTGATGCAGAGCTGGTGAGGGTGCATCCGA<br>AGAGTTCTTTGGCTGGAAGGAAGGGCTACAGCACAAGCGATGGCAAAACTTTCTCA<br>TATTTGGAAGGGACCAAGTTTCACCAGGCGGCCAAGGATATAGCAGAAATTAATGC<br>CATGTGGCCCGTTGCAACGGAGGCCAATGAGCAGGTATGCATGTATATCCTCGGAG<br>AAAGCATGAGCAGTATTAGGTCGAAATGCCCCGTCGAAGAGTCGGAAGCCTCCAC<br>ACCACCTAGCACGCTGCCTTGCTTGTGCATCCATGCCATGACTCCAGAAAGAGTAC<br>AGCGCCTAAAAGCCTCACGTCCAGAACAAATTACTGTGTGCTCATCCTTTCCATTGC<br>CGAAGTATAGAATCACTGGTGTGCAGAAGATCCAATGCTCCCAGCCTATATTGTTC<br>TCACCGAAAGTGCCTGCGTATATTCATCCAAGGAAGTATCTCGTGGAAACACCACC<br>GGTAGACGAGACTCCGGAGCCATCGGCAGAGAACCAATCCACAGAGGGGACACCT<br>GAACAACCACCACTTATAACCGAGGATGAGACCAGGACTAGAACGCCTGAGCCGA<br>TCATCATCGAAGAGGAAGAAGAGGATAGCATAAGTTTGCTGTCAGATGGCCCGAC<br>CCACCAGGTGCTGCAAGTCGAGGCAGACATTCACGGGCCGCCCTCTGTATCTAGCT<br>CATCCTGGTCCATTCCTCATGCATCCGACTTTGATGTGGACAGTTTATCCATACTTG<br>ACACCCTGGAGGGAGCTAGCGTGACCAGCGGGGCAACGTCAGCCGAGACTAACTC<br>TTACTTCGCAAAGAGTATGGAGTTTCTGGCGCGACCGGTGCCTGCGCCTCGAACAG<br>TATTCAGGAACCCTCCACATCCCGCTCCGCGCACAAGAACACCGTCACTTGCACCC<br>AGCAGGGCCTGCTCGAGAACCAGCCTAGTTTCCACCCCGCCAGGCGTGAATAGGGT<br>GATCACTAGAGAGGAGCTCGAGGCGCTTACCCCGTCACGCACTCCTAGCAGGTCGG<br>TCTCGAGAACCAGCCTGGTCTCCAACCCGCCAGGCGTAAATAGGGTGATTACAAGA<br>GAGGAGTTTGAGGCGTTCGTAGCACAACAACAATGACGGTTTGATGCGGGTGCA |
| 47 | nsP1 | GAGAAAGTTCACGTTGACATCGAGGAAGACAGCCCATTCCTCAGAGCTTTGCAGCG<br>GAGCTTCCCGCAGTTTGAGGTAGAAGCCAAGCAGGTCACTGATAATGACCATGCTA<br>ATGCCAGAGCGTTTTCGCATCTGGCTTCAAAACTGATCGAAACGGAGGTGGACCCA<br>TCCGACACGATCCTTGACATTGGAAGTGCGCCCGCCCGCAGAATGTATTCTAAGCA<br>CAAGTATCATTGTATCTGTCCGATGAGATGTGCGGAAGATCCGGACAGATTGTATA<br>AGTATGCAACTAAGCTGAAGAAAAACTGTAAGGAAATAACTGATAAGGAATTGGA<br>CAAGAAAATGAAGGAGCTCGCCGCCGTCATGAGCGACCCTGACCTGGAAACTGAG<br>ACTATGTGCCTCCACGACGACGAGTCGTGTCGCTACGAAGGGCAAGTCGCTGTTTA |

-continued

SEQUENCE LISTING

| SEQ ID NO: | Epitope | Sequence |
|---|---|---|
| | | CCAGGATGTATACGCGGTTGACGGACCGACAAGTCTCTATCACCAAGCCAATAAGG GAGTTAGAGTCGCCTACTGGATAGGCTTTGACACCACCCCTTTTATGTTTAAGAACT TGGCTGGAGCATATCCATCATACTCTACCAACTGGGCCGACGAAACCGTGTTAACG GCTCGTAACATAGGCCTATGCAGCTCTGACGTTATGGAGCGGTCACGTAGAGGGAT GTCCATTCTTAGAAAGAAGTATTTGAAACCATCCAACAATGTTCTATTCTCTGTTGG CTCGACCATCTACCACGAGAAGAGGGACTTACTGAGGAGCTGGCACCTGCCGTCTG TATTTCACTTACGTGGCAAGCAAAATTACACATGTCGGTGTGAGACTATAGTTAGTT GCGACGGGTACGTCGTTAAAAGAATAGCTATCAGTCCAGGCCTGTATGGGAAGCCT TCAGGCTATGCTGCTACGATGCACCGCGAGGGATTCTTGTGCTGCAAAGTGACAGA CACATTGAACGGGGAGAGGGTCTCTTTTCCCGTGTGCACGTATGTGCCAGCTACAT TGTGTGACCAAATGACTGGCATACTGGCAACAGATGTCAGTGCGGACGACGCGCA AAAACTGCTGGTTGGGCTCAACCAGCGTATAGTCGTCAACGGTCGCACCCAGAGAA ACACCAATACCATGAAAAATTACCTTTTGCCCGTAGTGGCCCAGGCATTTGCTAGG TGGGCAAAGGAATATAAGGAAGATCAAGAAGATGAAAGGCCACTAGGACTACGAG ATAGACAGTTAGTCATGGGGTGTTGTTGGGCTTTTAGAAGGCACAAGATAACATCT ATTTATAAGCGCCCGGATACCCAAACCATCATCAAAGTGAACAGCGATTTCCACTC ATTCGTGCTGCCCAGGATAGGCAGTAACACATTGGAGATCGGGCTGAGAACAAGA ATCAGGAAAATGTTAGAGGAGCACAAGGAGCCGTCACCTCTCATTACCGCCGAGG ACGTACAAGAAGCTAAGTGCGCAGCCGATGAGGCTAAGGAGGTGCGTGAAGCCGA GGAGTTGCGCGCAGCTCTACCACCTTTGGCAGCTGATGTTGAGGAGCCCACTCTGG AAGCCGATGTCGACTTGATGTTACAAGAGGCTGGGGCC |
| 48 | KanR | ATGATTGAACAGGATGGCCTGCATGCGGGTAGCCCGGCAGCGTGGGTGGAACGTCT GTTTGGCTATGATTGGGCGCAGCAGACCATTGGCTGCTCTGATGCGGCGGTGTTTC GTCTGAGCGCGCAGGGTCGTCCGGTGCTGTTTGTGAAAACCGATCTGAGCGGTGCG CTGAACGAGCTGCAGGATGAAGCGGCGCGTCTGAGCTGGCTGGCCACCACCGGTGT TCCGTGTGCGGCGGTGCTGGATGTGGTGACCGAAGCGGGCCGTGATTGGCTGCTGC TGGGCGAAGTGCCGGGTCAGGATCTGCTGTCTAGCCATCTGGCGCCGGCAGAAAAA GTGAGCATTATGGCGGATGCCATGCGTCGTCTGCATACCCTGGACCCGGCGACCTG TCCGTTTGATCATCAGGCGAAACATCGTATTGAACGTGCGCGTACCCGTATGGAAG CGGGCCTGGTGGATCAGGATGATCTGGATGAAGAACATCAGGGCCTGGCACCGGC AGAGCTGTTTGCGCGTCTGAAAGCGAGCATGCCGGATGGCGAAGATCTGGTGGTGA CCCATGGTGATGCGTGCCTGCCGAACATTATGGTGGAAAATGGCCGTTTTAGCGGC TTTATTGATTGCGGCCGTCTGGGCGTGGCGGATCGTTATCAGGATATTGCGCTGGCC ACCCGTGATATTGCGGAAGAACTGGGCGGCGAATGGGCGGATCGTTTTCTGGTGCT GTATGGCATTGCGGCACCGGATAGCCAGCGTATTGCGTTTTATCGTCTGCTGGATG AATTTTTCTAATAA |
| 49 | Rop | GTGACCAAACAGGAAAAAACCGCCCTTAACATGGCCCGCTTTATCAGAAGCCAGA CATTAACGCTTCTGGAGAAACTCAACGAGCTGGACGCGGATGAACAGGCAGACAT CTGTGAATCGCTTCACGACCACGCTGATGAGCTTTACCGCAGCTGCCTCGCGCGTTT CGGTGATGACGGTGAAAACCTCTGA |
| 50 | 5' UTR | ATAGGCGGCGCATGAGAGAAGCCCAGACCAATTACCTACCCAAA |
| 51 | 3' UTR | ATACAGCAGCAATTGGCAAGCTGCTTACATAGAACTCGCGGCGATTGGCATGCCGC TTTAAAATTTTTATTTTATTTTTCTTTTCTTTTCCGAATCGGATTTTGTTTTTAATATT TC |
| 52 | CVM promoter with TetO sites | CCATTGCATACGTTGTATCCATATCATAATATGTACATTTATATTGGCTCATGTCCA ACATTACCGCCATGTTGACATTGATTATTGACTAGTTATTAATAGTAATCAATTACG GGGTCATTAGTTCATAGCCCATATATGGAGTTCCGCGTTACATAACTTACGGTAAAT GGCCCGCCTGGCTGACCGCCCAACGACCCCCGCCCATTGACGTCAATAATGACGTA TGTTCCCATAGTAACGCCAATAGGGACTTTCCATTGACGTCAATGGGTGGAGTATTT ACGGTAAACTGCCCACTTGGCAGTACATCAAGTGTATCATATGCCAAGTACGCCCC CTATTGACGTCAATGACGGTAAATGGCCCGCCTGGCATTATGCCCAGTACATGACC TTATGGGACTTTCCTACTTGGCAGTACATCTACGTATTAGTCATCGCTATTACCATG GTGATGCGGTTTTGGCAGTACATCAATGGGCGTGGATAGCGGTTTGACTCACGGGG ATTTCCAAGTCTCCACCCCATTGACGTCAATGGGAGTTTGTTTTGGCACCAAAATCA ACGGGACTTTCCAAAATGTCGTAACAACTCCGCCCCATTGACGCAAATGGGCGGTA GGCGTGTACGGTGGGAGGTCTATATAAGCAGAGCTCTCCCTATCAGTGATAGAGAT CTCCCTATCAGTGATAGAGATCGTCGACGAGCTCGTTTAGTGAACCGTCAGATCGC CTGGAGACGCCATCCACGCTGTTTTGACCTCCATAGAAGACACCGGGACCGATCCA GCCTCCGCGGCCGGGAACGGTGCATTGGAACGCGGATTCCCCGTGCCAAGAGTGA |
| 53 | BGH polyA | CTGTGCCTTCTAGTTGCCAGCCATCTGTTGTTTGCCCCTCCCCCGTGCCTTCCTTGAC CCTGGAAGGTGCCACTCCCACTGTCCTTTCCTAATAAAATGAGGAAATTGCATCGC ATTGTCTGAGTAGGTGTCATTCTATTCTGGGGGGTGGGGTGGGGCAGGACAGCAAG GGGGAGGATTGGGAAGACAATAGCAGGCATGCTGGGGATGCGGTGGGCTCTATGG CC |
| 54 | Ubiquitin leader seq | MQIFVKTLTGKTITLEVEPSDTIENVKAKIQDKEGIPPDQQRLIFAGKQLEDGRTLSDYNI QKESTLHLVLRLRGV |

SEQUENCE LISTING

```
Sequence total quantity: 59
SEQ ID NO: 1            moltype = AA  length = 54
FEATURE                 Location/Qualifiers
REGION                  1..54
                        note = Description of Artificial Sequence: Synthetic
                         polypeptide
source                  1..54
                        mol_type = protein
                        organism = synthetic construct
SEQUENCE: 1
MKDKQDEEQR TRRMMRTKMR MRRMRRTRRK MRRKMSPARP RTSCREACLQ GWTE        54

SEQ ID NO: 2            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 2
EEAEDNCRRM MRTK                                                    14

SEQ ID NO: 3            moltype = AA  length = 71
FEATURE                 Location/Qualifiers
REGION                  1..71
                        note = Description of Artificial Sequence: Synthetic
                         polypeptide
source                  1..71
                        mol_type = protein
                        organism = synthetic construct
SEQUENCE: 3
MKDKQDEEQR TRRMMRTKMR MRRMRRTRRK MRRKMSPARP RTSCREACLQ GWTEAAYEEA  60
EDNCRRMMRT K                                                       71

SEQ ID NO: 4            moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 4
KLSHKHLVLN YGVCFCGDEN ILVQEFVKFG                                   30

SEQ ID NO: 5            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 5
VLNYGVCFC                                                          9

SEQ ID NO: 6            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
FCGDENILV                                                          9

SEQ ID NO: 7            moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 7
VLNYGVCFCA AYFCGDENIL V                                            21

SEQ ID NO: 8            moltype = AA  length = 21
FEATURE                 Location/Qualifiers
REGION                  1..21
```

```
                        note = Description of Artificial Sequence: Synthetic peptide
source                  1..21
                        mol_type = protein
                        organism = synthetic construct
SEQUENCE: 8
MACPGFLWAL VISTCLEFSM A                                               21

SEQ ID NO: 9            moltype = AA  length = 92
FEATURE                 Location/Qualifiers
REGION                  1..92
                        note = Description of Artificial Sequence: Synthetic
                         polypeptide
source                  1..92
                        mol_type = protein
                        organism = synthetic construct
SEQUENCE: 9
MACPGFLWAL VISTCLEFSM AMKDKQDEEQ RTRRMMRTKM RMRRMRRTRR KMRRKMSPAR  60
PRTSCREACL QGWTEAAYEE AEDNCRRMMR TK                                92

SEQ ID NO: 10           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 10
MACPGFLWAL VISTCLEFSM AMKDKQDEEQ RTRRMMRTKM RMRRMRRTRR KMRRKMSPAR  60
PRTSCREACL QGWTEAAYEE AEDNCRRMMR TKAAYVLNYG VCFCAAYFCG DENILV      116

SEQ ID NO: 11           moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 11
MACPGFLWAL VISTCLEFSM AMKDKQDEEQ RTRRMMRTKM RMRRMRRTRR KMRRKMSPAR  60
PRTSCREACL QGWTEAAYEE AEDNCRRMMR TKAAYKLSHK HLVLNYGVCF CGDENILVQE  120
FVKFG                                                              125

SEQ ID NO: 12           moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 12
MKDKQDEEQR TRRMMRTKMR MRRMRRTRRK MRRKMSPARP RTSCREACLQ GWTEAAYEEA  60
EDNCRRMMRT KAAYVLNYGV CFCAAYFCGD ENILV                             95

SEQ ID NO: 13           moltype = AA  length = 104
FEATURE                 Location/Qualifiers
REGION                  1..104
                        note = Description of Artificial Sequence: Synthetic
                         polypeptide
source                  1..104
                        mol_type = protein
                        organism = synthetic construct
SEQUENCE: 13
MKDKQDEEQR TRRMMRTKMR MRRMRRTRRK MRRKMSPARP RTSCREACLQ GWTEAAYEEA  60
EDNCRRMMRT KAAYKLSHKH LVLNYGVCFC GDENILVQEF VKFG                   104

SEQ ID NO: 14           moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 14
MQIFVKTLTG KTITLEVEPS DTIENVKAKI QDKEGIPPDQ QRLIFAGKQL EDGRTLSDYN  60
IQKESTLHLV LRLRGVRKDK QDEEQRTRRM MRTKMRMRRM RRTRRKMRRK MSPARPRTSC  120
```

```
REACLQGWTE AAYEEAEDNC RRMMRTKAAY VLNYGVCFCA AYFCGDENIL V          171

SEQ ID NO: 15          moltype = AA  length = 180
FEATURE                Location/Qualifiers
REGION                 1..180
                       note = Description of Artificial Sequence: Synthetic
                        polypeptide
source                 1..180
                       mol_type = protein
                       organism = synthetic construct
SEQUENCE: 15
MQIFVKTLTG KTITLEVEPS DTIENVKAKI QDKEGIPPDQ QRLIFAGKQL EDGRTLSDYN  60
IQKESTLHLV LRLRGVRKDK QDEEQRTRRM MRTKMRMRRM RRTRRKMRRK MSPARPRTSC  120
REACLQGWTE AAYEEAEDNC RRMMRTKAAY KLSHKHLVLN YGVCFCGDEN ILVQEFVKFG  180

SEQ ID NO: 16          moltype = DNA  length = 276
FEATURE                Location/Qualifiers
misc_feature           1..276
                       note = Description of Artificial Sequence: Synthetic
                        polynucleotide
source                 1..276
                       mol_type = other DNA
                       organism = synthetic construct
SEQUENCE: 16
atggcatgcc caggcttcct gtgggccctg gtcatcagca cctgtctgga gttttccatg  60
gccatgaagg acaagcagga tgaggagcag cggacccgga gaatgatgag gacaaagatg  120
cgcatgaggc gcatgcggag aacaaggcgc aagatgcgga gaaagatgtc tccagcaagg  180
cctagaacca gctgcaggga ggcatgtctg cagggatgga cagaggcagc atacgaggag  240
gcagaggaca actgcaggcg catgatgagg accaag                          276

SEQ ID NO: 17          moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 17
atggcatgcc caggcttcct gtgggccctg gtcatcagca cctgtctgga gttttccatg  60
gccatgaagg acaagcagga tgaggagcag cggacccgga gaatgatgag gacaaagatg  120
cgcatgaggc gcatgcggag aacaaggcgc aagatgcgga gaaagatgtc tccagcaagg  180
cctagaacca gctgcaggga ggcatgtctg cagggatgga cagaggcagc atacgaggag  240
gcagaggaca actgcaggcg catgatgagg accaaggccg cctacgtgct gaattatggc  300
gtgtgcttct gtgccgccta tttttgtggc gatgagaaca tcctggtg            348

SEQ ID NO: 18          moltype = DNA  length = 375
FEATURE                Location/Qualifiers
misc_feature           1..375
                       note = Description of Artificial Sequence: Synthetic
                        polynucleotide
source                 1..375
                       mol_type = other DNA
                       organism = synthetic construct
SEQUENCE: 18
atggcatgcc caggcttcct gtgggccctg gtcatcagca cctgtctgga gttttccatg  60
gccatgaagg acaagcagga tgaggagcag cggacccgga gaatgatgag gacaaagatg  120
cgcatgaggc gcatgcggag aacaaggcgc aagatgcgga gaaagatgtc tccagcaagg  180
cctagaacca gctgcaggga ggcatgtctg cagggatgga cagaggcagc atacgaggag  240
gcagaggaca actgcaggcg catgatgagg accaaggccg cctacaagct gagccacaag  300
cacctggtgc tgaactatgg cgtgtgcttc tgtggcgatg agaatatcct ggtgcaggag  360
ttcgtgaagt ttggc                                                 375

SEQ ID NO: 19          moltype = DNA  length = 285
FEATURE                Location/Qualifiers
misc_feature           1..285
                       note = Description of Artificial Sequence: Synthetic
                        polynucleotide
source                 1..285
                       mol_type = other DNA
                       organism = synthetic construct
SEQUENCE: 19
atgaaggaca agcaggatga ggagcagcgg acccggagaa tgatgaggac aaagatgcgc  60
atgaggcgca tgcggagaac aaggcgcaag atgcggagaa agatgtctcc agcaaggcct  120
agaaccagct gcagggaggc atgtctgcag ggatggacag aggcagcata cgaggaggca  180
gaggacaact gcaggcgcat gatgaggacc aaggccgcct acgtgctgaa ttatggcgtg  240
tgcttctgtg ccgcctattt ttgtggcgat gagaacatcc tggtg                285

SEQ ID NO: 20          moltype = DNA  length = 312
```

```
FEATURE                Location/Qualifiers
misc_feature           1..312
                       note = Description of Artificial Sequence: Synthetic
                        polynucleotide
source                 1..312
                       mol_type = other DNA
                       organism = synthetic construct
SEQUENCE: 20
atgaaggaca agcaggatga ggagcagcgg acccggagaa tgatgaggac aaagatgcgc  60
atgaggcgca tgcggagaac aaggcgcaag atgcggagaa agatgtctcc agcaaggcct  120
agaaccagct gcagggaggc atgtctgcag ggatggacag aggcagcata cgaggaggca  180
gaggacaact gcaggcgcat gatgaggacc aaggccgcct acaagctgag ccacaagcac  240
ctggtgctga actatggcgt gtgcttctgt ggcgatgaga atatcctggt gcaggagttc  300
gtgaagtttg gc                                                    312

SEQ ID NO: 21          moltype = DNA  length = 513
FEATURE                Location/Qualifiers
misc_feature           1..513
                       note = Description of Artificial Sequence: Synthetic
                        polynucleotide
source                 1..513
                       mol_type = other DNA
                       organism = synthetic construct
SEQUENCE: 21
atgcagatct tcgtgaagac cctgacaggc aagaccatca cactggaggt ggagccctcc  60
gacaccatcg agaacgtgaa ggccaagatc caggacaagg agggcatccc ccctgatcag  120
cagcggctga tctttgccgg caagcagctg gaggacggca gaaccctgtc tgattacaat  180
atccagaagg agagcacact gcacctggtg ctgcggctga gaggcgtgag gaaggacaag  240
caggatgagg agcagcgcac ccggagaatg atgcggacaa agatgagaat gaggcgcatg  300
cggagaacca ggcgcaagat gcggagaaag atgagcccag caaggccacg cacctcctgc  360
agggaggcat gtctgcaggg atggacagag gcagcctatg aggaggccga ggacaactgc  420
aggcgcatga tgcggacaaa ggccgcctac gtgctgaatt atggcgtgtg cttctgtgcc  480
gcctattttt gtggcgatga gaacatcctg gtg                             513

SEQ ID NO: 22          moltype = DNA  length = 546
FEATURE                Location/Qualifiers
misc_feature           1..546
                       note = Description of Artificial Sequence: Synthetic
                        polynucleotide
source                 1..546
                       mol_type = other DNA
                       organism = synthetic construct
SEQUENCE: 22
atgcagatct tcgtgaagac cctgacaggc aagaccatca cactggaggt ggagccctcc  60
gacaccatcg agaacgtgaa ggccaagatc caggacaagg agggcatccc ccctgatcag  120
cagcggctga tctttgccgg caagcagctg gaggacggca gaaccctgtc tgattacaat  180
atccagaagg agagcacact gcacctggtg ctgcggctga gaggcgtgag gaaggacaag  240
caggatgagg agcagcgcac ccggagaatg atgcggacaa agatgagaat gaggcgcatg  300
cggagaacca ggcgcaagat gcggagaaag atgagcccag caaggccacg cacctcctgc  360
agggaggcat gtctgcaggg atggacagag gcagcctatg aggaggccga ggacaactgc  420
aggcgcatga tgcggacaaa ggccgcctac aagctgtctc acaagcacct ggtgctgaac  480
tatggcgtgt gcttctgtgg cgatgagaat atcctggtgc aggagttcgt gaagtttggc  540
tgataa                                                           546

SEQ ID NO: 23          moltype = DNA  length = 1417
FEATURE                Location/Qualifiers
misc_feature           1..1417
                       note = Description of Artificial Sequence: Synthetic
                        polynucleotide
source                 1..1417
                       mol_type = other DNA
                       organism = synthetic construct
SEQUENCE: 23
tcaatattgg ccattagcca tattattcat tggttatata gcataaatca atattggcta  60
ttggccattg catacgttgt atccatatca taatatgtac atttatattg gctcatgtcc  120
aacattaccg ccatgttgac attgattatt gactagttat taatagtaat caattacggg  180
gtcattagtt catagcccat atatggagtt ccgcgttaca taacttacgg taaatggccc  240
gcctggctga ccgcccaacg acccccgccc attgacgtca ataatgacgt atgttcccat  300
agtaacgcca atagggactt tccattgacg tcaatgggtg gagtatttac ggtaaactgc  360
ccacttggca gtacatcaag tgtatcatat gccaagtacg ccccctattg acgtcaatga  420
cggtaaatgg cccgcctggc attatgccca gtacatgacc ttatgggact ttcctacttg  480
gcagtacatc tacgtattag tcatcgctat taccatggtg atgcggtttt ggcagtacat  540
caatgggcgt ggatagcggt ttgactcacg gggatttcca agtctccacc ccattgacgt  600
caatgggagt ttgttttggc accaaaatca acgggacttt ccaaaatgtc gtaacaactc  660
cgccccattg acgcaaatgg gcggtaggcg tgtacggtgg gaggtctata taagcagagc  720
tctccctatc agtgatagag atctccctat cagtgataga gatcgtcgac gagctcgttt  780
agtgaaccgt cagatcgcct ggagacgcca tccacgctgt tttgacctcc atagaagaca  840
ccgggaccga tccagcctcc gcggccggga acggtgcatt ggatctagag ccaccatggc  900
atgcccaggc ttcctgtggg ccctggtcat cagcacctgt ctggagtttt ccatggccat  960
```

```
gaaggacaag caggatgagg agcagcggac ccggagaatg atgaggacaa agatgcgcat  1020
gaggcgcatg cggagaacaa ggcgcaagat gcggagaaag atgtctccag caaggcctag  1080
aaccagctgc agggaggcat gtctgcaggg atggacagag gcagcatacg aggaggcaga  1140
ggacaactgc aggcgcatga tgaggaccaa ggccgcctac aagctgagcc acaagcacct  1200
ggtgctgaac tatggcgtgt gcttctgtgg cgatgagaat atcctggtgc aggagttcgt  1260
gaagtttggc tgataaggta ccatccgaac ttgtttattg cagcttataa tggttacaaa  1320
taaagcaata gcatcacaaa tttcacaaat aaagcatttt tttcactgca ttctagttgt  1380
ggtttgtcca aactcatcaa tgtatcttat catgtct                           1417

SEQ ID NO: 24          moltype = DNA  length = 1390
FEATURE                Location/Qualifiers
misc_feature           1..1390
                       note = Description of Artificial Sequence: Synthetic
                        polynucleotide
source                 1..1390
                       mol_type = other DNA
                       organism = synthetic construct
SEQUENCE: 24
tcaatattgg ccattagcca tattattcat tggttatata gcataaatca atattggcta  60
ttggccattg catacgttgt atccatatca taatatgtac atttatattg gctcatgtcc  120
aacattaccg ccatgttgac attgattatt gactagttat taatagtaat caattacggg  180
gtcattagtt catagcccat atatggagtt ccgcgttaca taacttacgg taaatggccc  240
gcctggctga ccgcccaacg acccccgccc attgacgtca ataatgacgt atgttcccat  300
agtaacgcca atagggactt tccattgacg tcaatgggtg gagtatttac ggtaaactgc  360
ccacttggca gtacatcaag tgtatcatat gccaagtacg ccccctattg acgtcaatga  420
cggtaaatgg cccgcctggc attatgccca gtacatgacc ttatgggact ttcctacttg  480
gcagtacatc tacgtattag tcatcgctat taccatggtg atgcggtttt ggcagtacat  540
caatgggcgt ggatagcggt ttgactcacg gggatttcca agtctccacc ccattgacgt  600
caatgggagt ttgttttggc accaaaatca acgggacttt ccaaaatgtc gtaacaactc  660
cgccccattg acgcaaatgg gcggtaggcg tgtacggtgg gaggtctata taagcagagc  720
tctccctatc agtgatagag atctccctat cagtgataga gatcgtcgac gagctcgttt  780
agtgaaccgt cagatcgcct ggagacgcca tccacgctgt tttgacctcc atagaagaca  840
ccgggaccga tccagcctcc gcggccggga acggtgcatt ggatctagag ccaccatggc  900
atgcccaggc ttcctgtggg ccctggtcat cagcacctgt ctggagtttt ccatggccat  960
gaaggacaag caggatgagg agcagcggac ccggagaatg atgaggacaa agatgcgcat  1020
gaggcgcatg cggagaacaa ggcgcaagat gcggagaaag atgtctccag caaggcctag  1080
aaccagctgc agggaggcat gtctgcaggg atggacagag gcagcatacg aggaggcaga  1140
ggacaactgc aggcgcatga tgaggaccaa ggccgcctac gtgctgaatt atggcgtgtg  1200
cttctgtgcc gcctattttt gtggcgatga gaacatcctg gtgtgataag gtaccatccg  1260
aacttgttta ttgcagctta taatggttac aaataaagca atagcatcac aaatttcaca  1320
aataaagcat ttttttcact gcattctagt tgtggtttgt ccaaactcat caatgtatct  1380
tatcatgtct                                                         1390

SEQ ID NO: 25          moltype = DNA  length = 549
FEATURE                Location/Qualifiers
misc_feature           1..549
                       note = Description of Artificial Sequence: Synthetic
                        polynucleotide
source                 1..549
                       mol_type = other DNA
                       organism = synthetic construct
SEQUENCE: 25
gatcactaat tccaaaccca cccgcttttt atagtaagtt tttcacccat aaataataaa  60
tacaataatt aatttctcgt aaaagtagaa aatatattct aatttattgc acggtaagga  120
agtagaatca taaagaacag tgacggatcc cgcgacttcg ccgccatggg ccagaaggaa  180
cagattcata cgcttcagaa aaattctgaa cgaatgtcaa agcaattgac acgaagttct  240
caggcagtaa tgaaggacaa acaagacgaa gaacaacgaa ctaggcggat gatgaggact  300
aagatgagga tgcggaggat gagacggacg cgacgcaaga tgcgccggaa aatgtctccc  360
gcccggccaa ggacgtcttg tcgggaagcc tgtttgcagg gctggaccga agcagcttac  420
gaagaagcag aagacaattg tcggcgaatg atgagaacga aggctgctta cgtgcttaac  480
tatggagtgt gcttctgcgc tgcctatttc tgcggagatg agaacattct ggtgtagtaa  540
aggcgcgcc                                                          549

SEQ ID NO: 26          moltype = DNA  length = 369
FEATURE                Location/Qualifiers
misc_feature           1..369
                       note = Description of Artificial Sequence: Synthetic
                        polynucleotide
source                 1..369
                       mol_type = other DNA
                       organism = synthetic construct
SEQUENCE: 26
atgggccaga aggaacagat tcatacgctt cagaaaaatt ctgaacgaat gtcaaagcaa  60
ttgacacgaa gttctcaggc agtaatgaag gacaaacaag acgaagaaca acgaactagg  120
cggatgatga ggactaagat gaggatgcgg aggatgagac ggacgcgacg caagatgcgc  180
cggaaaatgt ctcccgcccg gccaaggacg tcttgtcggg aagcctgttt gcagggctgg  240
accgaagcag cttacgaaga agcagaagac aattgtcggc gaatgatgag aacgaaggct  300
gcttacgtgc ttaactatgg agtgtgcttc tgcgctgcct atttctgcgg agatgagaac  360
attctggtg                                                          369
```

```
SEQ ID NO: 27          moltype = DNA  length = 285
FEATURE                Location/Qualifiers
misc_feature           1..285
                       note = Description of Artificial Sequence: Synthetic
                        polynucleotide
source                 1..285
                       mol_type = other DNA
                       organism = synthetic construct
SEQUENCE: 27
atgaaggaca aacaagacga agaacaacga actaggcgga tgatgaggac taagatgagg  60
atgcggagga tgagacggac gcgacgcaag atgcgccgga aaatgtctcc cgcccggcca  120
aggacgtctt gtcgggaagc ctgtttgcag ggctggaccg aagcagctta cgaagaagca  180
gaagacaatt gtcggcgaat gatgagaacg aaggctgctt acgtgcttaa ctatggagtg  240
tgcttctgcg ctgcctattt ctgcggagat gagaacattc tggtg                285

SEQ ID NO: 28          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 28
FCGDENILVA AYFCGDENIL V                                          21

SEQ ID NO: 29          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 29
MGQKEQIHTL QKNSERMSKQ LTRSSQAV                                   28

SEQ ID NO: 30          moltype = DNA  length = 84
FEATURE                Location/Qualifiers
misc_feature           1..84
                       note = Description of Artificial Sequence: Synthetic
                        oligonucleotide
source                 1..84
                       mol_type = other DNA
                       organism = synthetic construct
SEQUENCE: 30
atgggccaga aggaacagat tcatacgctt cagaaaaatt ctgaacgaat gtcaaagcaa  60
ttgacacgaa gttctcaggc agta                                       84

SEQ ID NO: 31          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 31
MGQKEQIHTL QKNSERMSKQ LTRSSQAVMK DKQDEEQRTR RMMRTKMRMR RMRRTRRKMR  60
RKMSPARPRT SCREACLQGW TEAAYEEAED NCRRMMRTKA AYVLNYGVCF CAAYFCGDEN  120
ILV                                                              123

SEQ ID NO: 32          moltype = DNA  length = 149
FEATURE                Location/Qualifiers
misc_feature           1..149
                       note = Description of Artificial Sequence: Synthetic
                        polynucleotide
source                 1..149
                       mol_type = other DNA
                       organism = synthetic construct
SEQUENCE: 32
gatcactaat tccaaaccca cccgcttttt atagtaagtt tttcacccat aaataataaa  60
tacaataatt aatttctcgt aaaagtagaa aatatattct aatttattgc acggtaagga  120
agtagaatca taaagaacag tgacggatc                                  149

SEQ ID NO: 33          moltype = DNA  length = 10712
FEATURE                Location/Qualifiers
misc_feature           1..10712
                       note = Description of Artificial Sequence: Synthetic
                        polynucleotide
```

```
source                  1..10712
                        mol_type = other DNA
                        organism = synthetic construct
SEQUENCE: 33
taatacgact cactatagat aggcggcgca tgagagaagc ccagaccaat tacctaccca  60
aataggagaa agttcacgtt gacatcgagg aagacagccc attcctcaga gctttgcagc  120
ggagcttccc gcagtttgag gtagaagcca agcaggtcac tgataatgac catgctaatg  180
ccagagcgtt ttcgcatctg gcttcaaaac tgatcgaaac ggaggtggac ccatccgaca  240
cgatccttga cattggaata gtcagcatag tacatttcat ctgactaata ctacaacacc  300
accaccatga atagaggatt ctttaacatg ctcggccgcc gccccttccc ggccccccact  360
gccatgtgga ggccgcggag aaggaggcag gcggccccgg gaagcggagc tactaacttc  420
agcctgctga agcaggctgg agacgtggag gagaaccctg gacctgagaa agttcacgtt  480
gacatcgagg aagacagccc attcctcaga gctttgcagc ggagcttccc gcagtttgag  540
gtagaagcca agcaggtcac tgataatgac catgctaatg ccagagcgtt ttcgcatctg  600
gcttcaaaac tgatcgaaac ggaggtggac ccatccgaca cgatccttga cattggaagt  660
gcgcccgccc gcagaatgta ttctaagcac aagtatcatt gtatctgtcc gatgagatgt  720
gcggaagatc cggacagatt gtataagtat gcaactaagc tgaagaaaaa ctgtaaggaa  780
ataactgata aggaattgga caagaaaatg aaggagctcg ccgccgtcat gagcgaccct  840
gacctggaaa ctgagactat gtgcctccac gacgacgagt cgtgtcgcta cgaagggcaa  900
gtcgctgttt accaggatgt atacgcggtt gacggaccga caagtctcta tcaccaagcc  960
aataagggag ttagagtcgc ctactggata ggctttgaca ccaccccttt tatgtttaag  1020
aacttggctg gagcatatcc atcatactct accaactggg ccgacgaaac cgtgttaacg  1080
gctcgtaaca taggcctatg cagctctgac gttatggagc ggtcacgtag agggatgtcc  1140
attcttagaa agaagtattt gaaaccatcc aacaatgttc tattctctgt tggctcgacc  1200
atctaccacg agaagaggga cttactgagg agctggcacc tgccgtctgt atttcactta  1260
cgtggcaagc aaaattacac atgtcggtgt gagactatag ttagttgcga cgggtacgtc  1320
gttaaaagaa tagctatcag tccaggcctg tatgggaagc cttcaggcta tgctgctacg  1380
atgcaccgcg agggattctt gtgctgcaaa gtgacagaca cattgaacgg ggagagggtc  1440
tcttttcccg tgtgcacgta tgtgccagct acattgtgtg accaaatgac tggcatactg  1500
gcaacagatg tcagtgcgga cgacgcgcaa aaactgctgg ttgggctcaa ccagcgtata  1560
gtcgtcaacg gtcgcaccca gagaaacacc aataccatga aaaattacct tttgcccgta  1620
gtggcccagg catttgctag gtgggcaaag gaatataagg aagatcaaga agatgaaagg  1680
ccactaggac tacgagatag acagttagtc atggggtgtt gttgggcttt tagaaggcac  1740
aagataacat ctatttataa gcgcccggat acccaaacca tcatcaaagt gaacagcgat  1800
ttccactcat tcgtgctgcc caggatagac agtaacacat tggagatcgg gctgagaaca  1860
agaatcagga aaatgttaga ggagcacaag gagccgtcac ctctcattac cgccgaggac  1920
gtacaagaag ctaagtgcgc agccgatgag gctaaggagg tgcgtgaagc cgaggagttg  1980
cgcgcagctc taccaccttt ggcagctgat gttgaggagc ccactctgga agccgatgtc  2040
gacttgatgt tacaagaggc tggggccggc tcagtggaga cacctcgtgg cttgataaag  2100
gttaccagct acgatggcga ggacaagatc ggctcttacg ctgtgctttc tccgcaggct  2160
gtactcaaga gtgaaaaatt atcttgcatc caccctctcg ctgaacaagt catagtgata  2220
acacactctg gccgaaaagg gcgttatgcc gtggaaccat accatggtaa agtagtggtg  2280
ccagagggac atgcaatacc cgtccaggac tttcaagctc tgagtgaaag tgccaccatt  2340
gtgtacaacg aacgtgagtt cgtaaacagg tacctgcacc atattgccac acatggagga  2400
gcgctgaaca ctgatgaaga atattacaaa actgtcaagc ccagcgagca cgacggcgaa  2460
tacctgtacg acatcgacag gaaacagtgc gtcaagaaag aactagtcac tgggctaggg  2520
ctcacaggcg agctggtgga tcctcccttc catgaattcg cctacgagag tctgagaaca  2580
cgaccagccg ctccttacca agtaccaacc ataggggtgt atggcgtgcc aggatcaggc  2640
aagtctggca tcattaaaag cgcagtcacc aaaaaagatc tagtggtgag cgccaagaaa  2700
gaaaactgtg cagaaattat aagggacgtc aagaaaatga aagggctgga cgtcaatgcc  2760
agaactgtgg actcagtgct cttgaatgga tgcaaacacc ccgtagagac cctgtatatt  2820
gacgaagctt ttgcttgtca tgcaggtact ctcagagcgc tcatagccat tataagacct  2880
aaaaaggcag tgctctgcgg ggatcccaaa cagtgcggtt tttttaacat gatgtgcctg  2940
aaagtgcatt ttaaccacga gatttgcaca caagtcttcc acaaaagcat ctctcgccgt  3000
tgcactaaat ctgtgacttc ggtcgtctca acctttgttt acgacaaaaa aatgagaacg  3060
acgaatccga aagagactaa gattgtgatt gacactaccg gcagtaccaa acctaagcag  3120
gacgatctca ttctcacttg tttcagaggg tgggtgaagc agttgcaaat agattacaaa  3180
ggcaacgaaa taatgacggc agctgcctct caagggctga cccgtaaagg tgtgtatgcc  3240
gttcggtaca aggtgaatga aaatcctctg tacgcaccca cctctgaaca tgtgaacgtc  3300
ctactgaccc gcacggagga ccgcatcgtg tggaaaacac tagccggcga cccatggata  3360
aaaacactga ctgccaagta ccctgggaat ttcactgcca cgatagagga gtggcaagca  3420
gagcatgatg ccatcatgag gcacatcttg gagagaccgg accctaccga cgtcttccag  3480
aataaggcaa acgtgtgttg ggccaaggct ttagtgccgg tgctgaagac cgctggcata  3540
gacatgacca ctgaacaatg gaacactgtg gattattttg aaacggacaa agctcactca  3600
gcagagatag tattgaacca actatgcgtg aggttctttg gactcgatct ggactccggt  3660
ctattttctg cacccactgt tccgttatcc attaggaata atcactggga taactccccg  3720
tcgcctaaca tgtacgggct gaataaagaa gtggtccgtc agctctctcg caggtaccca  3780
caactgcctc gggcagttgc cactggaaga gtctatgaca tgaacactgg tacactgcgc  3840
aattatgatc cgcgcataaa cctagtacct gtaaacagaa gactgcctca tgctttagtc  3900
ctccaccata atgaacaccc acagagtgac ttttcttcat tcgtcagcaa attgaagggc  3960
agaactgtcc tggtggtcgg ggaaaagttg tccgtcccag gcaaaatggt tgactggttg  4020
tcagaccggc ctgaggctac cttcagagct cggctggatt taggcatccc aggtgatgtg  4080
cccaaatatg acataatatt tgttaatgtg aggaccccat ataaatacca tcactatcag  4140
cagtgtgaag accatgccat taagcttagc atgttgacca agaaagcttg tctgcatctg  4200
aatcccggcg gaacctgtgt cagcataggt tatggttacg ctgacagggc cagcgaaagc  4260
atcattggtg ctatagcgcg gcagttcaag ttttcccggg tatgcaaacc gaaatcctca  4320
cttgaagaga cggaagttct gtttgtattc attgggtacg atcgcaaggc ccgtacgcac  4380
aatccttaca agctttcatc aaccttgacc aacatttata caggttccag actccacgaa  4440
gccggatgtg caccctcata tcatgtggtg cgaggggata ttgccacggc caccgaagga  4500
```

```
gtgattataa atgctgctaa cagcaaagga caacctggcg gaggggtgtg cggagcgctg  4560
tataagaaat tcccggaaag cttcgattta cagccgatcg aagtaggaaa agcgcgactg  4620
gtcaaaggtg cagctaaaca tatcattcat gccgtaggac caaacttcaa caaagtttcg  4680
gaggttgaag gtgacaaaca gttggcagag gcttatgagt ccatcgctaa gattgtcaac  4740
gataacaatt acaagtcagt agcgattcca ctgttgtcca ccggcatctt ttccgggaac  4800
aaagatcgac taacccaatc attgaaccat ttgctgacag ctttagacac cactgatgca  4860
gatgtagcca tatactgcag ggacaagaaa tgggaaatga ctctcaagga agcagtggct  4920
aggagagaag cagtggagga gatatgcata tccgacgact cttcagtgac agaacctgat  4980
gcagagctgg tgagggtgca tccgaagagt tctttggctg gaaggaaggg ctacagcaca  5040
agcgatggca aaactttctc atatttggaa gggaccaagt ttcaccaggc ggccaaggat  5100
atagcagaaa ttaatgccat gtggcccgtt gcaacggagg ccaatgagca ggtatgcatg  5160
tatatcctcg gagaaagcat gagcagtatt aggtcgaaat gccccgtcga agagtcggaa  5220
gcctccacac cacctagcac gctgccttgc ttgtgcatcc atgccatgac tccagaaaga  5280
gtacagcgcc taaaagcctc acgtccagaa caaattactg tgtgctcatc ctttccattg  5340
ccgaagtata gaatcactgg tgtgcagaag atccaatgct cccagcctat attgttctca  5400
ccgaaagtgc ctgcgtatat tcatccaagg aagtatctcg tggaaacacc accggtagac  5460
gagactccgg agccatcggc agagaaccaa tccacagagg ggacacctga acaaccacca  5520
cttataaccg aggatgagac caggactaga acgcctgagc cgatcatcat cgaagaggaa  5580
gaagaggata gcataagttt gctgtcagat ggcccgaccc accaggtgct gcaagtcgag  5640
gcagacattc acgggccgcc ctctgtatct agctcatcct ggtccattcc tcatgcatcc  5700
gactttgatg tggacagttt atccatactt gacaccctgg agggagctag cgtgaccagc  5760
ggggcaacgt cagccgagac taactcttac ttcgcaaaga gtatggagtt tctggcgcga  5820
ccggtgcctg cgcctcgaac agtattcagg aaccctccac atcccgctcc gcgcacaaga  5880
acaccgtcac ttgcacccag cagggcctgc tcgagaacca gcctagtttc caccccgcca  5940
ggcgtgaata gggtgatcac tagagaggag ctcgaggcgc ttaccccgtc acgcactcct  6000
agcaggtcgg tctcgagaac cagcctggtc tccaacccgc caggcgtaaa tagggtgatt  6060
acaagagagg agtttgaggc gttcgtagca caacaacaat gacggtttga tgcgggtgca  6120
tacatctttt cctccgacac cggtcaaggg catttacaac aaaaatcagt aaggcaaacg  6180
gtgctatccg aagtggtgtt ggagaggacc gaattggaga tttcgtatgc cccgcgcctc  6240
gaccaagaaa aagaagaatt actacgcaag aaattacagt taaatcccac acctgctaac  6300
agaagcagat accagtccag gaaggtggag aacatgaaag ccataacagc tagacgtatt  6360
ctgcaaggcc tagggcatta tttgaaggca gaaggaaaag tggagtgcta ccgaaccctg  6420
catcctgttc ctttgtattc atctagtgtg aaccgtgcct tttcaagccc caaggtcgca  6480
gtggaagcct gtaacgccat gttgaaagag aactttccga ctgtggcttc ttactgtatt  6540
attccagagt acgatgccta tttggacatg gttgacggag cttcatgctg cttagacact  6600
gccagttttt gccctgcaaa gctgcgcagc tttccaaaga aacactccta tttggaaccc  6660
acaatacgat cggcagtgcc ttcagcgatc cagaacacgc tccagaacgt cctggcagct  6720
gccacaaaaa gaaattgcaa tgtcacgcaa atgagagaat tgcccgtatt ggattcggcg  6780
gcctttaatg tggaatgctt caagaaatat gcgtgtaata atgaatattg ggaaacgttt  6840
aaagaaaacc ccatcaggct tactgaagaa aacgtggtaa attacattac caaattaaaa  6900
ggaccaaaag ctgctgctct tttgcgaag acacataatt tgaatatgtt gcaggacata  6960
ccaatggaca ggtttgtaat ggacttaaag agagacgtga aagtgactcc aggaacaaaa  7020
catactgaag aacggcccaa ggtacaggtg atccaggctg ccgatccgct agcaacagcg  7080
tatctgtgcg gaatccaccg agagctggtt aggagattaa atgcggtcct gcttccgaac  7140
attcatacac tgtttgatat gtcggctgaa gactttgacg ctattatagc cgagcacttc  7200
cagcctgggg attgtgttct ggaaactgac atcgcgtcgt ttgataaaag tgaggacgac  7260
gccatggctc tgaccgcgtt aatgattctg gaagacttag gtgtggacgc agagctgttg  7320
acgctgattg aggcggcttt cggcgaaatt tcatcaatac atttgcccac taaaactaaa  7380
tttaaattcg gagccatgat gaaatctgga atgttcctca cactgtttgt gaacacagtc  7440
attaacattg taatcgcaag cagagtgttg agagaacggc taaccggatc accatgtgca  7500
gcattcattg gagatgacaa tatcgtgaaa ggagtcaaat cggacaaatt aatggcagac  7560
aggtgcgcca cctggttgaa tatggaagtc aagattatag atgctgtggt gggcgagaaa  7620
gcgccttatt tctgtggagg gtttattttg tgtgactccg tgaccggcac agcgtgccgt  7680
gtggcagacc ccctaaaaag gctgtttaag cttggcaaac ctctggcagc agacgatgaa  7740
catgatgatg acaggagaag ggcattgcat gaagagtcaa cacgctggaa ccgagtgggt  7800
attctttcag agctgtgcaa ggcagtagaa tcaaggtatg aaaccgtagg aacttccatc  7860
atagttatgg ccatgactac tctagctagc agtgttaaat cattcagcta cctgagaggg  7920
gcccctataa ctctctacgg ctaacctgaa tggactacga catagtctag tccgccaaga  7980
tatcggcgcg ccgtttaaac ggccggcctt aattaagtaa cgatacagca gcaattggca  8040
agctgcttac atagaactcg cggcgattgg catgccgctt taaaattttt attttatttt  8100
tcttttcttt tccgaatcgg attttgtttt taatatttca aaaaaaaaaa aaaaaaaaaa  8160
aaaaaaaaaa aaaaaaaacc cctctctaaa cggaggggtt tttttcagcg taactggact  8220
ggccacagtt aggcggccgc gcatgttcat catcagtaac ccgtatcgtg agcatcctct  8280
ctcgtttcat cggtatcatt acctccatga acagaaatcc cccttacacg gaggcatcag  8340
tgaccaaaca ggaaaaaacc gcccttaaca tggcccgctt tatcagaagc cagacattaa  8400
cgcttctgga gaaactcaac gagctggacg cggatgaaca ggcagacatc tgtgaatcgc  8460
ttcacgacca cgctgatgag ctttaccgca gctgcctcgc gcgtttcggt gatgacggtg  8520
aaaacctctg acacatgcag ctcccggaga cggtcacagc ttgtctgtaa gcggatgccg  8580
ggagcagaca agcccgtcag ggcgcgtcag cgggtgttgg cgggtgtcgg ggcgcagcca  8640
tgacccagtc acgtagcgat agcggagtgt atactggctt aactatgcgg catcagagca  8700
gattgtactg agagtgcacc atatgcggtg tgaaataccg cacagatgcg taaggagaaa  8760
ataccgcatc aggcgctcgc ttcctcgctc actgactcgc tgcgctcggt cgttcggctg  8820
cggcgagcgg tatcagctca ctcaaaggcg gtaatacggt tatccacaga atcaggggat  8880
aacgcaggaa agaacatgtg agcaaaaggc cagcaaaagg ccaggaaccg taaaaaggcc  8940
gcgttgctgg cgtttttcca taggctccgc ccccctgacg agcatcacaa aaatcgacgc  9000
tcaagtcaga ggtggcgaaa cccgacagga ctataaagat accaggcgtt tccccctgga  9060
agctccctcg tgcgctctcc tgttccgacc ctgccgctta ccggatacct gtccgccttt  9120
ctcccttcgg gaagcgtggc gctttctcat agctcacgct gtaggtatct cagttcggtg  9180
taggtcgttc gctccaagct gggctgtgtg cacgaacccc ccgttcagcc cgaccgctgc  9240
```

```
gccttatccg gtaactatcg tcttgagtcc aacccggtaa gacacgactt atcgccactg  9300
gcagcagcca ctggtaacag gattagcaga gcgaggtatg taggcggtgc tacagagttc  9360
ttgaagtggt ggcctaacta cggctacact agaaggacag tatttggtat ctgcgctctg  9420
ctgaagccag ttaccttcgg aaaaagagtt ggtagctctt gatccggcaa acaaaccacc  9480
gctggtagcg gtggtttttt tgtttgcaag cagcagatta cgcgcagaaa aaaaggatct  9540
caagaagatc ctttgatctt ttctacgggg tctgacgctc agtggaacga aaactcacgt  9600
taagggattt tggtcatgag attatcaaaa aggatcttca cctagatcct tttaaattaa  9660
aaatgaagtt ttaaatcaat ctaaagtata tatgagtaaa cttggtctga cagttattag  9720
aaaaattcat ccagcagacg ataaaacgca atacgctggc tatccggtgc cgcaatgcca  9780
tacagcacca gaaaacgatc cgcccattcg ccgcccagtt cttccgcaat atcacgggtg  9840
gccagcgcaa tatcctgata acgatccgcc acgcccagac ggccgcaatc aataaagccg  9900
ctaaaacggc cattttccac cataatgttc ggcaggcacg catcaccatg ggtcaccacc  9960
agatcttcgc catccggcat gctcgctttc agacgcgcaa acagctctgc cggtgccagg  10020
ccctgatgtt cttcatccag atcatcctga tccaccaggc ccgcttccat acgggtacgc  10080
gcacgttcaa tacgatgttt cgcctgatga tcaaacggac aggtcgccgg gtccagggta  10140
tgcagacgac gcatggcatc cgccataatg ctcacttttt ctgccggcgc cagatggcta  10200
gacagcagat cctgacccgg cacttcgccc agcagcagcc aatcacggcc cgcttcggtc  10260
accacatcca gcaccgccgc acacggaaca ccggtggtgg ccagccagct cagacgcgcc  10320
gcttcatcct gcagctcgtt cagcgcaccg ctcagatcgg ttttcacaaa cagcaccgga  10380
cgaccctgcg cgctcagacg aaacaccgcc gcatcagagc agccaatggt ctgctgcgcc  10440
caatcatagc caaacagacg ttccacccac gctgccgggc tacccgcatg caggccatcc  10500
tgttcaatca tactcttcct ttttcaatat tattgaagca tttatcaggg ttattgtctc  10560
atgagcggat acatatttga atgtatttag aaaaataaac aaataggggt tccgcgcaca  10620
tttccccgaa aagtgccacc tgacgtctaa gaaaccatta ttatcatgac attaagcatc  10680
cgcctttcgt tttatttgac catgttggta tg                                 10712

SEQ ID NO: 34          moltype = DNA  length = 29
FEATURE                Location/Qualifiers
misc_feature           1..29
                       note = Description of Artificial Sequence: Synthetic
                        oligonucleotide
source                 1..29
                       mol_type = other DNA
                       organism = synthetic construct
SEQUENCE: 34
aacccctctc taaacggagg ggtttttt                                     29

SEQ ID NO: 35          moltype = DNA  length = 105
FEATURE                Location/Qualifiers
misc_feature           1..105
                       note = Description of Artificial Sequence: Synthetic
                        polynucleotide
source                 1..105
                       mol_type = other DNA
                       organism = synthetic construct
SEQUENCE: 35
cgcggaaccc ctatttgttt atttttctaa atacattcaa atatgtatcc gctcatgaga  60
caataaccct gataaatgct tcaataatat tgaaaaagga agagt                  105

SEQ ID NO: 36          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 36
ctctctacgg ctaacctgaa tgga                                         24

SEQ ID NO: 37          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 37
taatacgact cactatag                                                18

SEQ ID NO: 38          moltype = RNA  length = 39
FEATURE                Location/Qualifiers
misc_feature           1..39
                       note = Description of Artificial Sequence: Synthetic
                        oligonucleotide
source                 1..39
                       mol_type = other RNA
                       organism = synthetic construct
```

```
SEQUENCE: 38
aaaaaaaaaa aaaaaaaaaa aaaaaaaaaa aaaaaaaaa                        39

SEQ ID NO: 39          moltype = DNA  length = 195
FEATURE                Location/Qualifiers
misc_feature           1..195
                       note = Description of Artificial Sequence: Synthetic
                        polynucleotide
source                 1..195
                       mol_type = other DNA
                       organism = synthetic construct
SEQUENCE: 39
taggagaaag ttcacgttga catcgaggaa gacagcccat tcctcagagc tttgcagcgg  60
agcttcccgc agtttgaggt agaagccaag caggtcactg ataatgacca tgctaatgcc  120
agagcgtttt cgcatctggc ttcaaaactg atcgaaacgg aggtggaccc atccgacacg  180
atccttgaca ttgga                                                  195

SEQ ID NO: 40          moltype = DNA  length = 142
FEATURE                Location/Qualifiers
misc_feature           1..142
                       note = Description of Artificial Sequence: Synthetic
                        polynucleotide
source                 1..142
                       mol_type = other DNA
                       organism = synthetic construct
SEQUENCE: 40
atagtcagca tagtacattt catctgacta atactacaac accaccacca tgaatagagg  60
attctttaac atgctcggcc gccgcccctt cccggccccc actgccatgt ggaggccgcg  120
gagaaggagg caggcggccc cg                                          142

SEQ ID NO: 41          moltype = DNA  length = 66
FEATURE                Location/Qualifiers
misc_feature           1..66
                       note = Description of Artificial Sequence: Synthetic
                        oligonucleotide
source                 1..66
                       mol_type = other DNA
                       organism = synthetic construct
SEQUENCE: 41
ggaagcggag ctactaactt cagcctgctg aagcaggctg gagacgtgga ggagaaccct  60
ggacct                                                            66

SEQ ID NO: 42          moltype = DNA  length = 141
FEATURE                Location/Qualifiers
misc_feature           1..141
                       note = Description of Artificial Sequence: Synthetic
                        polynucleotide
source                 1..141
                       mol_type = other DNA
                       organism = synthetic construct
SEQUENCE: 42
cgcagccatg acccagtcac gtagcgatag cggagtgtat actggcttaa ctatgcggca  60
tcagagcaga ttgtactgag agtgcaccat atgcggtgtg aaataccgca cagatgcgta  120
aggagaaaat accgcatcag g                                           141

SEQ ID NO: 43          moltype = DNA  length = 5796
FEATURE                Location/Qualifiers
misc_feature           1..5796
                       note = Description of Artificial Sequence: Synthetic
                        polynucleotide
source                 1..5796
                       mol_type = other DNA
                       organism = synthetic construct
SEQUENCE: 43
atgaatagag gattctttaa catgctcggc cgccgcccct tcccggcccc cactgccatg  60
tggaggccgc ggagaaggag gcaggcggcc ccgggaagcg gagctactaa cttcagcctg  120
ctgaagcagg ctggagacgt ggaggagaac cctggacctg agaaagttca cgttgacatc  180
gaggaagaca gcccattcct cagagctttg cagcggagct tcccgcagtt tgaggtagaa  240
gccaagcagg tcactgataa tgaccatgct aatgccagag cgttttcgca tctggcttca  300
aaactgatcg aaacggaggt ggacccatcc gacacgatcc ttgacattgg aagtgcgccc  360
gcccgcagaa tgtattctaa gcacaagtat cattgtatct gtccgatgag atgtgcggaa  420
gatccggaca gattgtataa gtatgcaact aagctgaaga aaaactgtaa ggaaataact  480
gataaggaat tggacaagaa aatgaaggag ctcgccgccg tcatgagcga ccctgacctg  540
gaaactgaga ctatgtgcct ccacgacgac gagtcgtgtc gctacgaagg gcaagtcgct  600
gtttaccagg atgtatacgc ggttgacgga ccgacaagtc tctatcacca agccaataag  660
ggagttagag tcgcctactg gataggcttt gacaccaccc cttttatgtt taagaacttg  720
gctggagcat atccatcata ctctaccaac tgggccgacg aaaccgtgtt aacggctcgt  780
aacataggcc tatgcagctc tgacgttatg gagcggtcac gtagagggat gtccattctt  840
agaaagaagt atttgaaacc atccaacaat gttctattct ctgttggctc gaccatctac  900
```

-continued

```
cacgagaaga gggacttact gaggagctgg cacctgccgt ctgtatttca cttacgtggc  960
aagcaaaatt acacatgtcg gtgtgagact atagttagtt gcgacgggta cgtcgttaaa  1020
agaatagcta tcagtccagg cctgtatggg aagccttcag gctatgctgc tacgatgcac  1080
cgcgagggat tcttgtgctg caaagtgaca gacacattga acggggagag ggtctctttt  1140
cccgtgtgca cgtatgtgcc agctacattg tgtgaccaaa tgactggcat actggcaaca  1200
gatgtcagtg cggacgacgc gcaaaaactg ctggttgggc tcaaccagcg tatagtcgtc  1260
aacggtcgca cccagagaaa caccaatacc atgaaaaatt accttttgcc cgtagtggcc  1320
caggcatttg ctaggtgggc aaaggaatat aaggaagatc aagaagatga aaggccacta  1380
ggactacgag atagacagtt agtcatgggg tgttgttggg cttttagaag gcacaagata  1440
acatctattt ataagcgccc ggatacccaa accatcatca aagtgaacag cgatttccac  1500
tcattcgtgc tgcccaggat aggcagtaac acattggaga tcgggctgag aacaagaatc  1560
aggaaaatgt tagaggagca caaggagccg tcacctctca ttaccgccga ggacgtacaa  1620
gaagctaagt gcgcagccga tgaggctaag gaggtgcgtg aagccgagga gttgcgcgca  1680
gctctaccac ctttggcagc tgatgttgag gagcccactc tggaagccga tgtcgacttg  1740
atgttacaag aggctggggc cggctcagtg gagacacctc gtggcttgat aaaggttacc  1800
agctacgatg gcgaggacaa gatcggctct tacgctgtgc tttctccgca ggctgtactc  1860
aagagtgaaa aattatcttg catccaccct ctcgctgaac aagtcatagt gataacacac  1920
tctggccgaa aagggcgtta tgccgtggaa ccataccatg gtaaagtagt ggtgccagag  1980
ggacatgcaa tacccgtcca ggactttcaa gctctgagtg aaagtgccac cattgtgtac  2040
aacgaacgtg agttcgtaaa caggtacctg caccatattg ccacacatgg aggagcgctg  2100
aacactgatg aagaatatta caaaactgtc aagcccagcg agcacgacgg cgaatacctg  2160
tacgacatcg acaggaaaca gtgcgtcaag aaagaactag tcactgggct agggctcaca  2220
ggcgagctgg tggatcctcc cttccatgaa ttcgcctacg agagtctgag aacacgacca  2280
gccgctcctt accaagtacc aaccataggg gtgtatggcg tgccaggatc aggcaagtct  2340
ggcatcatta aaagcgcagt caccaaaaaa gatctagtgg tgagcgccaa gaaagaaaac  2400
tgtgcagaaa ttataaggga cgtcaagaaa atgaaagggc tggacgtcaa tgccagaact  2460
gtggactcag tgctcttgaa tggatgcaaa caccccgtag agaccctgta tattgacgaa  2520
gcttttgctt gtcatgcagg tactctcaga gcgctcatag ccattataag acctaaaaag  2580
gcagtgctct gcggggatcc caaacagtgc ggttttttta acatgatgtg cctgaaagtg  2640
cattttaacc acgagatttg cacacaagtc ttccacaaaa gcatctctcg ccgttgcact  2700
aaatctgtga cttcggtcgt ctcaaccttg ttttacgaca aaaaaatgag aacgacgaat  2760
ccgaaagaga ctaagattgt gattgacact accggcagta ccaaacctaa gcaggacgat  2820
ctcattctca cttgtttcag agggtgggtg aagcagttgc aaatagatta caaaggcaac  2880
gaaataatga cggcagctgc ctctcaaggg ctgacccgta aaggtgtgta tgccgttcgg  2940
tacaaggtga atgaaaatcc tctgtacgca cccacctctg aacatgtgaa cgtcctactg  3000
acccgcacgg aggaccgcat cgtgtggaaa acactagccg gcgacccatg gataaaaaca  3060
ctgactgcca agtaccctgg gaatttcact gccacgatag aggagtggca agcagagcat  3120
gatgccatca tgaggcacat cttggagaga ccggacccta ccgacgtctt ccagaataag  3180
gcaaacgtgt gttgggccaa ggctttagtg ccggtgctga agaccgctgg catagacatg  3240
accactgaac aatggaacac tgtggattat tttgaaacgg acaaagctca ctcagcagag  3300
atagtattga accaactatg cgtgaggttc tttggactcg atctggactc cggtctattt  3360
tctgcaccca ctgttccgtt atccattagg aataatcact gggataactc cccgtcgcct  3420
aacatgtacg ggctgaataa agaagtggtc cgtcagctct ctcgcaggta cccacaactg  3480
cctcgggcag ttgccactgg aagagtctat gacatgaaca ctggtacact gcgcaattat  3540
gatccgcgca taaacctagt acctgtaaac agaagactgc ctcatgcttt agtcctccac  3600
cataatgaac acccacagag tgacttttct tcattcgtca gcaaattgaa gggcagaact  3660
gtcctggtgg tcggggaaaa gttgtccgtc ccaggcaaaa tggttgactg gttgtcagac  3720
cggcctgagg ctaccttcag agctcggctg gatttaggca tcccaggtga tgtgcccaaa  3780
tatgacataa tatttgttaa tgtgaggacc ccatataaat accatcacta tcagcagtgt  3840
gaagaccatg ccattaagct tagcatgttg accaagaaag cttgtctgca tctgaatccc  3900
ggcggaacct gtgtcagcat aggttatggt tacgctgaca gggccagcga aagcatcatt  3960
ggtgctatag cgcggcagtt caagttttcc cgggtatgca aaccgaaatc ctcacttgaa  4020
gagacggaag ttctgtttgt attcattggg tacgatcgca aggcccgtac gcacaatcct  4080
tacaagcttt catcaacctt gaccaacatt tatacaggtt ccagactcca cgaagccgga  4140
tgtgcacccct catatcatgt ggtgcgaggg gatattgcca cggccaccga aggagtgatt  4200
ataaatgctg ctaacagcaa aggacaacct ggcggagggg tgtgcggagc gctgtataag  4260
aaattcccgg aaagcttcga tttacagccg atcgaagtag gaaaagcgcg actggtcaaa  4320
ggtgcagcta aacatatcat tcatgccgta ggaccaaact tcaacaaagt ttcggaggtt  4380
gaaggtgaca aacagttggc agaggcttat gagtccatcg ctaagattgt caacgataac  4440
aattacaagt cagtagcgat tccactgttg tccaccggca tcttttccgg gaacaaagat  4500
cgactaaccc aatcattgaa ccatttgctg acagctttag acaccactga tgcagatgta  4560
gccatatact gcagggacaa gaaatgggaa atgactctca aggaagcagt ggctaggaga  4620
gaagcagtgg aggagatatg catatccgac gactcttcag tgacagaacc tgatgcagag  4680
ctggtgaggg tgcatccgaa gagttctttg gctggaagga agggctacag cacaagcgat  4740
ggcaaaactt tctcatattt ggaagggacc aagtttcacc aggcggccaa ggatatagca  4800
gaaattaatg ccatgtggcc cgttgcaacg gaggccaatg agcaggtatg catgtatatc  4860
ctcggagaaa gcatgagcag tattaggtcg aaatgccccg tcgaagagtc ggaagcctcc  4920
acaccaccta gcacgctgcc ttgcttgtgc atccatgcca tgactccaga aagagtacag  4980
cgcctaaaag cctcacgtcc agaacaaatt actgtgtgct catcctttcc attgccgaag  5040
tatagaatca ctggtgtgca gaagatccaa tgctcccagc ctatattgtt ctcaccgaaa  5100
gtgcctgcgt atattcatcc aaggaagtat ctcgtggaaa caccaccggt agacgagact  5160
ccggagccat cggcagagaa ccaatccaca gaggggacac ctgaacaacc accacttata  5220
accgaggatg agaccaggac tagaacgcct gagccgatca tcatcgaaga ggaagaagag  5280
gatagcataa gtttgctgtc agatggcccg acccaccagg tgctgcaagt cgaggcagac  5340
attcacgggc cgccctctgt atctagctca tcctggtcca ttcctcatgc atccgacttt  5400
gatgtggaca gtttatccat acttgacacc ctggagggag ctagcgtgac cagcggggca  5460
acgtcagccg agactaactc ttacttcgca aagagtatgg agtttctggc gcgaccggtg  5520
cctgcgcctc gaacagtatt caggaaccct ccacatcccg ctccgcgcac aagaacaccg  5580
tcacttgcac ccagcagggc ctgctcgaga accagcctag tttccacccc gccaggcgtg  5640
```

```
aatagggtga tcactagaga ggagctcgag gcgcttaccc cgtcacgcac tcctagcagg  5700
tcggtctcga gaaccagcct ggtctccaac ccgccaggcg taaatagggt gattacaaga  5760
gaggagtttg aggcgttcgt agcacaacaa caatga                            5796

SEQ ID NO: 44          moltype = DNA  length = 2382
FEATURE                Location/Qualifiers
misc_feature           1..2382
                       note = Description of Artificial Sequence: Synthetic
                        polynucleotide
source                 1..2382
                       mol_type = other DNA
                       organism = synthetic construct
SEQUENCE: 44
ggctcagtgg agacacctcg tggcttgata aaggttacca gctacgatgg cgaggacaag  60
atcggctctt acgctgtgct ttctccgcag gctgtactca agagtgaaaa attatcttgc  120
atccaccctc tcgctgaaca agtcatagtg ataacacact ctggccgaaa agggcgttat  180
gccgtggaac cataccatgg taaagtagtg gtgccagagg gacatgcaat acccgtccag  240
gactttcaag ctctgagtga aagtgccacc attgtgtaca acgaacgtga gttcgtaaac  300
aggtacctgc accatattgc cacacatgga ggagcgctga acactgatga agaatattac  360
aaaactgtca agcccagcga gcacgacggc gaatacctgt acgacatcga caggaaacag  420
tgcgtcaaga aagaactagt cactgggcta gggctcacag gcgagctggt ggatcctccc  480
ttccatgaat tcgcctacga gagtctgaga acacgaccag ccgctcctta ccaagtacca  540
accatagggg tgtatggcgt gccaggatca ggcaagtctg gcatcattaa aagcgcagtc  600
accaaaaaag atctagtggt gagcgccaag aaagaaaact gtgcagaaat tataagggac  660
gtcaagaaaa tgaaagggct ggacgtcaat gccagaactg tggactcagt gctcttgaat  720
ggatgcaaac accccgtaga gaccctgtat attgacgaag cttttgcttg tcatgcaggt  780
actctcagag cgctcatagc cattataaga cctaaaaagg cagtgctctg cggggatccc  840
aaacagtgcg gttttttaa catgatgtgc ctgaaagtgc attttaacca cgagatttgc  900
acacaagtct tccacaaaag catctctcgc cgttgcacta aatctgtgac ttcggtcgtc  960
tcaaccttgt tttacgacaa aaaaatgaga acgacgaatc cgaaagagac taagattgtg  1020
attgacacta ccggcagtac caaacctaag caggacgatc tcattctcac ttgtttcaga  1080
gggtgggtga agcagttgca aatagattac aaaggcaacg aaataatgac ggcagctgcc  1140
tctcaagggc tgacccgtaa aggtgtgtat gccgttcggt acaaggtgaa tgaaaatcct  1200
ctgtacgcac ccacctctga acatgtgaac gtcctactga cccgcacgga ggaccgcatc  1260
gtgtggaaaa cactagccgg cgacccatgg ataaaaacac tgactgccaa gtaccctggg  1320
aatttcactg ccacgataga ggagtggcaa gcagagcatg atgccatcat gaggcacatc  1380
ttggagagac cggaccctac cgacgtcttc cagaataagg caaacgtgtg ttgggccaag  1440
gctttagtgc cggtgctgaa gaccgctggc atagacatga ccactgaaca atggaacact  1500
gtggattatt ttgaaacgga caaagctcac tcagcagaga tagtattgaa ccaactatgc  1560
gtgaggttct ttggactcga tctggactcc ggtctattt ctgcacccac tgttccgtta  1620
tccattagga ataatcactg ggataactcc ccgtcgccta acatgtacgg gctgaataaa  1680
gaagtggtcc gtcagctctc tcgcaggtac ccacaactgc ctcgggcagt tgccactgga  1740
agagtctatg acatgaacac tggtacactg cgcaattatg atccgcgcat aaacctagta  1800
cctgtaaaca gaagactgcc tcatgcttta gtcctccacc ataatgaaca cccacagagt  1860
gacttttctt cattcgtcag caaattgaag ggcagaactg tcctggtggt cggggaaaag  1920
ttgtccgtcc caggcaaaat ggttgactgg ttgtcagacc ggcctgaggc taccttcaga  1980
gctcggctgg atttaggcat cccaggtgat gtgcccaaat atgacataat atttgttaat  2040
gtgaggaccc catataaata ccatcactat cagcagtgtg aagaccatgc cattaagctt  2100
agcatgttga ccaagaaagc ttgtctgcat ctgaatcccg gcggaacctg tgtcagcata  2160
ggttatggtt acgctgacag ggccagcgaa agcatcattg gtgctatagc gcggcagttc  2220
aagttttccc gggtatgcaa accgaaatcc tcacttgaag agacggaagt tctgtttgta  2280
ttcattgggt acgatcgcaa ggcccgtacg cacaatcctt acaagctttc atcaaccttg  2340
accaacattt atacaggttc cagactccac gaagccggat gt                    2382

SEQ ID NO: 45          moltype = DNA  length = 1821
FEATURE                Location/Qualifiers
misc_feature           1..1821
                       note = Description of Artificial Sequence: Synthetic
                        polynucleotide
source                 1..1821
                       mol_type = other DNA
                       organism = synthetic construct
SEQUENCE: 45
tacatctttt cctccgacac cggtcaaggg catttacaac aaaaatcagt aaggcaaacg  60
gtgctatccg aagtggtgtt ggagaggacc gaattggaga tttcgtatgc cccgcgcctc  120
gaccaagaaa aagaagaatt actacgcaag aaattacagt taaatcccac acctgctaac  180
agaagcagat accagtccag gaaggtggag aacatgaaag ccataacagc tagacgtatt  240
ctgcaaggcc tagggcatta tttgaaggca gaaggaaaag tggagtgcta ccgaaccctg  300
catcctgttc ctttgtattc atctagtgtg aaccgtgcct tttcaagccc caaggtcgca  360
gtggaagcct gtaacgccat gttgaaagag aactttccga ctgtggcttc ttactgtatt  420
attccagagt acgatgccta tttggacatg gttgacggag cttcatgctg cttagacact  480
gccagttttt gccctgcaaa gctgcgcagc tttccaaaga aacactccta tttggaaccc  540
acaatacgat cggcagtgcc ttcagcgatc cagaacacgc tccagaacgt cctggcagct  600
gccacaaaaa gaaattgcaa tgtcacgcaa atgagagaat tgcccgtatt ggattcggcg  660
gcctttaatg tggaatgctt caagaaatat gcgtgtaata atgaatattg ggaaacgttt  720
aaagaaaacc ccatcaggct tactgaagaa aacgtggtaa attacattac caaattaaaa  780
ggaccaaaag ctgctgctct tttgcgaag acacataatt tgaatatgtt gcaggacata  840
ccaatggaca ggtttgtaat ggacttaaag agagacgtga aagtgactcc aggaacaaaa  900
catactgaag aacggcccaa ggtacaggtg atccaggctg ccgatccgct agcaacagcg  960
```

```
tatctgtgcg gaatccaccg agagctggtt aggagattaa atgcggtcct gcttccgaac  1020
attcatacac tgtttgatat gtcggctgaa gactttgacg ctattatagc cgagcacttc  1080
cagcctgggg attgtgttct ggaaactgac atcgcgtcgt ttgataaaag tgaggacgac  1140
gccatggctc tgaccgcgtt aatgattctg gaagacttag gtgtggacgc agagctgttg  1200
acgctgattg aggcggcttt cggcgaaatt tcatcaatac atttgcccac taaaactaaa  1260
tttaaattcg gagccatgat gaaatctgga atgttcctca cactgtttgt gaacacagtc  1320
attaacattg taatcgcaag cagagtgttg agagaacggc taaccggatc accatgtgca  1380
gcattcattg gagatgacaa tatcgtgaaa ggagtcaaat cggacaaatt aatggcagac  1440
aggtgcgcca cctggttgaa tatggaagtc aagattatag atgctgtggt gggcgagaaa  1500
gcgccttatt tctgtggagg gtttattttg tgtgactccg tgaccggcac agcgtgccgt  1560
gtggcagacc ccctaaaaag gctgtttaag cttggcaaac ctctggcagc agacgatgaa  1620
catgatgatg acaggagaag ggcattgcat gaagagtcaa cacgctggaa ccgagtgggt  1680
attctttcag agctgtgcaa ggcagtagaa tcaaggtatg aaaccgtagg aacttccatc  1740
atagttatgg ccatgactac tctagctagc agtgttaaat cattcagcta cctgagaggg  1800
gcccctataa ctctctacgg c                                           1821

SEQ ID NO: 46          moltype = DNA  length = 1671
FEATURE                Location/Qualifiers
misc_feature           1..1671
                       note = Description of Artificial Sequence: Synthetic
                        polynucleotide
source                 1..1671
                       mol_type = other DNA
                       organism = synthetic construct
SEQUENCE: 46
gcaccctcat atcatgtggt gcgaggggat attgccacgg ccaccgaagg agtgattata  60
aatgctgcta acagcaaagg acaacctggc ggaggggtgt gcggagcgct gtataagaaa  120
ttcccggaaa gcttcgattt acagccgatc gaagtaggaa aagcgcgact ggtcaaaggt  180
gcagctaaac atatcattca tgccgtagga ccaaacttca acaaagtttc ggaggttgaa  240
ggtgacaaac agttggcaga ggcttatgag tccatcgcta agattgtcaa cgataacaat  300
tacaagtcag tagcgattcc actgttgtcc accggcatct tttccgggaa caaagatcga  360
ctaacccaat cattgaacca tttgctgaca gctttagaca ccactgatgc agatgtagcc  420
atatactgca gggacaagaa atgggaaatg actctcaagg aagcagtggc taggagagaa  480
gcagtggagg agatatgcat atccgacgac tcttcagtga cagaacctga tgcagagctg  540
gtgagggtgc atccgaagag ttctttggct ggaaggaagg gctacagcac aagcgatggc  600
aaaactttct catatttgga agggaccaag tttcaccagg cggccaagga tatagcagaa  660
attaatgcca tgtggcccgt tgcaacggag gccaatgagc aggtatgcat gtatatcctc  720
ggagaaagca tgagcagtat taggtcgaaa tgccccgtcg aagagtcgga agcctccaca  780
ccacctagca cgctgccttg cttgtgcatc catgccatga ctccagaaag agtacagcgc  840
ctaaaagcct cacgtccaga acaaattact gtgtgctcat cctttccatt gccgaagtat  900
agaatcactg gtgtgcagaa gatccaatgc tcccagccta tattgttctc accgaaagtg  960
cctgcgtata ttcatccaag gaagtatctc gtggaaacac caccggtaga cgagactccg  1020
gagccatcgg cagagaacca atccacagag ggacacctg aacaaccacc acttataacc  1080
gaggatgaga ccaggactag aacgcctgag ccgatcatca tcgaagagga agaagaggat  1140
agcataagtt tgctgtcaga tggcccgacc caccaggtgc tgcaagtcga ggcagacatt  1200
cacgggccgc cctctgtatc tagctcatcc tggtccattc ctcatgcatc cgactttgat  1260
gtggacagtt tatccatact tgacaccctg gagggagcta gcgtgaccag cggggcaacg  1320
tcagccgaga ctaactctta cttcgcaaag agtatggagt ttctggcgcg accggtgcct  1380
gcgcctcgaa cagtattcag gaaccctcca catcccgctc cgcgcacaag aacaccgtca  1440
cttgcaccca gcagggcctg ctcgagaacc agcctagttt ccaccccgcc aggcgtgaat  1500
agggtgatca ctagagagga gctcgaggcg cttaccccgt cacgcactcc tagcaggtcg  1560
gtctcgagaa ccagcctggt ctccaacccg ccaggcgtaa atagggtgat tacaagagag  1620
gagtttgagg cgttcgtagc acaacaacaa tgacggtttg atgcgggtgc a          1671

SEQ ID NO: 47          moltype = DNA  length = 1602
FEATURE                Location/Qualifiers
misc_feature           1..1602
                       note = Description of Artificial Sequence: Synthetic
                        polynucleotide
source                 1..1602
                       mol_type = other DNA
                       organism = synthetic construct
SEQUENCE: 47
gagaaagttc acgttgacat cgaggaagac agcccattcc tcagagcttt gcagcggagc  60
ttcccgcagt ttgaggtaga agccaagcag gtcactgata atgaccatgc taatgccaga  120
gcgttttcgc atctggcttc aaaactgatc gaaacggagg tggacccatc cgacacgatc  180
cttgacattg gaagtgcgcc cgcccgcaga atgtattcta agcacaagta tcattgtatc  240
tgtccgatga gatgtgcgga agatccggac agattgtata agtatgcaac taagctgaag  300
aaaaactgta aggaaataac tgataaggaa ttggacaaga aaatgaagga gctcgccgcc  360
gtcatgagcg accctgacct ggaaactgag actatgtgcc tccacgacga cgagtcgtgt  420
cgctacgaag ggcaagtcgc tgtttaccag gatgtatacg cggttgacgg accgacaagt  480
ctctatcacc aagccaataa gggagttaga gtcgcctact ggataggctt tgacaccacc  540
ccttttatgt ttaagaactt ggctggagca tatccatcat actctaccaa ctgggccgac  600
gaaaccgtgt taacggctcg taacataggc ctatgcagct ctgacgttat ggagcggtca  660
cgtagaggga tgtccattct tagaaagaag tatttgaaac catccaacaa tgttctattc  720
tctgttggct cgaccatcta ccacgagaag agggacttac tgaggagctg gcacctgccg  780
tctgtatttc acttacgtgg caagcaaaat tacacatgtc ggtgtgagac tatagttagt  840
tgcgacgggt acgtcgttaa aagaatagct atcagtccag gcctgtatgg gaagccttca  900
ggctatgctg ctacgatgca ccgcgaggga ttcttgtgct gcaaagtgac agacacattg  960
```

-continued

```
aacggggaga gggtctcttt tcccgtgtgc acgtatgtgc cagctacatt gtgtgaccaa  1020
atgactggca tactggcaac agatgtcagt gcggacgacg cgcaaaaact gctggttggg  1080
ctcaaccagc gtatagtcgt caacggtcgc acccagagaa acaccaatac catgaaaaat  1140
taccttttgc ccgtagtggc ccaggcattt gctaggtggg caaaggaata taaggaagat  1200
caagaagatg aaaggccact aggactacga gatagacagt tagtcatggg gtgttgttgg  1260
gcttttagaa ggcacaagat aacatctatt tataagcgcc cggataccca aaccatcatc  1320
aaagtgaaca gcgatttcca ctcattcgtg ctgcccagga taggcagtaa cacattggag  1380
atcgggctga gaacaagaat caggaaaatg ttagaggagc acaaggagcc gtcacctctc  1440
attaccgccg aggacgtaca agaagctaag tgcgcagccg atgaggctaa ggaggtgcgt  1500
gaagccgagg agttgcgcgc agctctacca ccctttggcag ctgatgttga ggagcccact  1560
ctggaagccg atgtcgactt gatgttacaa gaggctgggg cc                    1602

SEQ ID NO: 48          moltype = DNA  length = 798
FEATURE                Location/Qualifiers
misc_feature           1..798
                       note = Description of Artificial Sequence: Synthetic
                        polynucleotide
source                 1..798
                       mol_type = other DNA
                       organism = synthetic construct
SEQUENCE: 48
atgattgaac aggatggcct gcatgcgggt agcccggcag cgtgggtgga acgtctgttt  60
ggctatgatt gggcgcagca gaccattggc tgctctgatg cggcggtgtt tcgtctgagc  120
gcgcagggtc gtccggtgct gtttgtgaaa accgatctga gcggtgcgct gaacgagctg  180
caggatgaag cggcgcgtct gagctggctg gccaccaccg gtgttccgtg tgcggcggtg  240
ctggatgtgg tgaccgaagc gggccgtgat tggctgctgc tgggcgaagt gccgggtcag  300
gatctgctgt ctagccatct ggcgccggca gaaaaagtga gcattatggc ggatgccatg  360
cgtcgtctgc ataccctgga cccggcgacc tgtccgtttg atcatcaggc gaaacatcgt  420
attgaacgtg cgcgtacccg tatggaagcg ggcctggtgg atcaggatga tctggatgaa  480
gaacatcagg gcctggcacc ggcagagctg tttgcgcgtc tgaaagcgag catgccggat  540
ggcgaagatc tggtggtgac ccatggtgat gcgtgcctgc cgaacattat ggtggaaaat  600
ggccgtttta gcggctttat tgattgcggc cgtctgggcg tggcggatcg ttatcaggat  660
attgcgctgg ccacccgtga tattgcggaa gaactgggcg gcgaatgggc ggatcgtttt  720
ctggtgctgt atggcattgc ggcaccggat agccagcgta ttgcgtttta tcgtctgctg  780
gatgaatttt tctaataa                                                798

SEQ ID NO: 49          moltype = DNA  length = 192
FEATURE                Location/Qualifiers
misc_feature           1..192
                       note = Description of Artificial Sequence: Synthetic
                        polynucleotide
source                 1..192
                       mol_type = other DNA
                       organism = synthetic construct
SEQUENCE: 49
gtgaccaaac aggaaaaaac cgcccttaac atggcccgct ttatcagaag ccagacatta  60
acgcttctgg agaaactcaa cgagctggac gcggatgaac aggcagacat ctgtgaatcg  120
cttcacgacc acgctgatga gctttaccgc agctgcctcg cgcgtttcgg tgatgacggt  180
gaaaacctct ga                                                      192

SEQ ID NO: 50          moltype = DNA  length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 50
ataggcggcg catgagagaa gcccagacca attacctacc caaa                  44

SEQ ID NO: 51          moltype = DNA  length = 117
FEATURE                Location/Qualifiers
misc_feature           1..117
                       note = Description of Artificial Sequence: Synthetic
                        polynucleotide
source                 1..117
                       mol_type = other DNA
                       organism = synthetic construct
SEQUENCE: 51
atacagcagc aattggcaag ctgcttacat agaactcgcg gcgattggca tgccgcttta  60
aaatttttat tttatttttc ttttcttttc cgaatcggat tttgttttta atatttc     117

SEQ ID NO: 52          moltype = DNA  length = 845
FEATURE                Location/Qualifiers
misc_feature           1..845
                       note = Description of Artificial Sequence: Synthetic
                        polynucleotide
source                 1..845
```

```
                        mol_type = other DNA
                        organism = synthetic construct
SEQUENCE: 52
ccattgcata cgttgtatcc atatcataat atgtacattt atattggctc atgtccaaca  60
ttaccgccat gttgacattg attattgact agttattaat agtaatcaat tacggggtca  120
ttagttcata gcccatatat ggagttccgc gttacataac ttacggtaaa tggcccgcct  180
ggctgaccgc ccaacgaccc ccgcccattg acgtcaataa tgacgtatgt tcccatagta  240
acgccaatag ggactttcca ttgacgtcaa tgggtggagt atttacggta aactgcccac  300
ttggcagtac atcaagtgta tcatatgcca agtacgcccc ctattgacgt caatgacggt  360
aaatggcccg cctggcatta tgcccagtac atgaccttat gggactttcc tacttggcag  420
tacatctacg tattagtcat cgctattacc atggtgatgc ggttttggca gtacatcaat  480
gggcgtggat agcggtttga ctcacgggga tttccaagtc tccaccccat tgacgtcaat  540
gggagtttgt tttggcacca aaatcaacgg gactttccaa aatgtcgtaa caactccgcc  600
ccattgacgc aaatgggcgg taggcgtgta cggtgggagg tctatataag cagagctctc  660
cctatcagtg atagagatct ccctatcagt gatagagatc gtcgacgagc tcgtttagtg  720
aaccgtcaga tcgcctggag acgccatcca cgctgttttg acctccatag aagacaccgg  780
gaccgatcca gcctccgcgg ccgggaacgg tgcattggaa cgcggattcc ccgtgccaag  840
agtga                                                             845

SEQ ID NO: 53           moltype = DNA  length = 227
FEATURE                 Location/Qualifiers
misc_feature            1..227
                        note = Description of Artificial Sequence: Synthetic
                         polynucleotide
source                  1..227
                        mol_type = other DNA
                        organism = synthetic construct
SEQUENCE: 53
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatggcc               227

SEQ ID NO: 54           moltype = AA  length = 76
FEATURE                 Location/Qualifiers
REGION                  1..76
                        note = Description of Artificial Sequence: Synthetic
                         polypeptide
source                  1..76
                        mol_type = protein
                        organism = synthetic construct
SEQUENCE: 54
MQIFVKTLTG KTITLEVEPS DTIENVKAKI QDKEGIPPDQ QRLIFAGKQL EDGRTLSDYN  60
IQKESTLHLV LRLRGV                                                 76

SEQ ID NO: 55           moltype = AA  length = 4
FEATURE                 Location/Qualifiers
REGION                  1..4
                        note = Description of Unknown: "KDEL" motif peptide
source                  1..4
                        mol_type = protein
                        organism = unidentified
SEQUENCE: 55
KDEL                                                              4

SEQ ID NO: 56           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 56
HHAA                                                              4

SEQ ID NO: 57           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 57
RKSYL                                                             5

SEQ ID NO: 58           moltype = AA  length = 4
FEATURE                 Location/Qualifiers
REGION                  1..4
                        note = Description of Artificial Sequence: Synthetic peptide
```

-continued

```
source                  1..4
                        mol_type = protein
                        organism = synthetic construct
SEQUENCE: 58
RKSY                                                                  4

SEQ ID NO: 59           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 59
REKR                                                                  4
```

The invention claimed is:

1. A method of treating or preventing a myeloproliferative disease in a subject, the method comprising administering to the subject in need thereof a composition comprising a polynucleotide encoding a polypeptide comprising the epitope sequences of:

CALR epitope of SEQ ID NO: 1;

CALR epitope of SEQ ID NO: 2;

JAK2 epitope of SEQ ID NO: 5; and

JAK2 epitope of SEQ ID NO: 6, wherein the administration comprises one or more administrations of the composition.

2. The method of claim 1, wherein the polynucleotide further encodes one or more linker sequences, wherein the epitope sequences are connected to each other by the one or more linker sequences.

3. The method of claim 2, wherein the one or more linker sequences are selected from AAY, RR, DPP, HHAA (SEQ ID NO: 56), HHA, HHL, RKSYL (SEQ ID NO: 57), RKSY (SEQ ID NO: 58), SSL, and REKR (SEQ ID NO: 59).

4. The method of claim 3, wherein the one or more linker sequences comprise a protease cleavage site.

5. The method of claim 4, wherein the polynucleotide encodes a polypeptide comprising the amino acid sequence of SEQ ID NO: 12.

6. The method of claim 5, wherein the polynucleotide comprises the nucleic acid sequence of SEQ ID NO: 27.

7. The method of claim 5, wherein the polynucleotide further encodes a leader sequence at the N terminus of SEQ ID NO: 12, wherein the leader sequence is selected from the group consisting of:

```
                                       (SEQ ID NO: 8)
MACPGFLWALVISTCLEFSMA;

                                       (SEQ ID NO: 54)
MQIFVKTLTGKTITLEVEPSDTIENVKAKIQDKEGIPPDQQRLIFAGKQL

EDGRTLSDYNIQKESTLHLVLRLRGV;
and

                                       (SEQ ID NO: 29)
MGQKEQIHTLQKNSERMSKQLTRSSQAV.
```

8. The method of claim 7, wherein the polynucleotide encodes a polypeptide comprising:

the amino acid sequence of SEQ ID NO: 10;

the amino acid sequence of SEQ ID NO: 31.

9. The method of claim 8, wherein the polynucleotide comprises the nucleic acid sequence of SEQ ID NO: 17;

the nucleic acid sequence of SEQ ID NO: 26.

10. The method of claim 1, wherein the polynucleotide comprises:

nucleotides 1-162 of SEQ ID NO: 27;

nucleotides 172-213 of SEQ ID NO: 27;

nucleotides 223-249 of SEQ ID NO: 27; and nucleotides 259-285 of SEQ ID NO: 27.

11. The method of claim 1, wherein the myeloproliferative disease is selected from the group consisting of primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

12. The method of claim 1, wherein the composition comprises a vector comprising the polynucleotide.

13. The method of claim 12, wherein the vector is a recombinant virus or a self-replicating RNA molecule.

14. The method of claim 12, wherein the recombinant virus is an adenovirus vector, an alphaviral vector, a poxvirus vector, an adeno-associated virus vector, or a retrovirus vector.

15. The method of claim 14, wherein the adenovirus vector is selected from the group consisting of hAd5, hAd7, hAd11, hAd26, hAd34, hAd35, hAd48, hAd49, hAd50, GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

16. The method of claim 15, wherein the vector is the GAd20 vector and wherein the polynucleotide encodes the polypeptide of SEQ ID NO: 31.

17. The method of claim 14, wherein the poxvirus vector is selected from the group consisting of smallpox virus vector, vaccinia virus vector, cowpox virus vector, monkeypox virus vector, Copenhagen vaccinia virus vector, New York Attenuated Vaccinia Virus (NYVAC) vector, and Modified Vaccinia Ankara (MVA) vector.

18. The method of claim 17, wherein the vector is the MVA vector and wherein the polynucleotide encodes the polypeptide of SEQ ID NO: 31.

19. The method of claim 13, wherein the vector is the self-replicating RNA molecule.

20. The method of claim 19, wherein the vector is the self-replicating RNA molecule and wherein the polynucleotide encodes the polypeptide of SEQ ID NO: 12.

21. The method of claim 14, wherein the vector is the adenovirus vector.

22. The method of claim 14, wherein the vector is an Ad26 vector and wherein the polynucleotide encodes the polypeptide of SEQ ID NO: 12.

23. The method of claim 14, wherein the vector is a GAd20 vector or an MVA vector and wherein the polynucleotide comprises the nucleic acid sequence of SEQ ID NO: 27.

24. The method of claim 14, wherein the vector is an Ad26 vector and wherein the polynucleotide comprises the nucleic acid sequence of SEQ ID NO: 19.

25. The method of claim 12, wherein the method comprises:

a first administration comprising a first composition comprising a vector comprising a polynucleotide encoding the CALR epitope of SEQ ID NO: 1, the CALR epitope of SEQ ID NO: 2, the JAK2 epitope of SEQ ID NO: 5, and the JAK2 epitope of SEQ ID NO: 6, wherein the vector is selected from the group consisting of an Ad26 vector, an MVA vector, a GAd20 vector, and a self-replicating RNA molecule; and a second administration comprising a second composition comprising a vector comprising a polynucleotide encoding the CALR epitope of SEQ ID NO: 1, the CALR epitope of SEQ ID NO: 2, the JAK2 epitope of SEQ ID NO: 5, and the JAK2 epitope of SEQ ID NO: 6, wherein the vector is selected from the group consisting of an Ad26 vector, an MVA vector, a GAd20 vector, and a self-replicating RNA molecule.

* * * * *